US009740100B2

(12) United States Patent
Hasegawa et al.

(10) Patent No.: US 9,740,100 B2
(45) Date of Patent: Aug. 22, 2017

(54) HEMIACETAL COMPOUND, POLYMER, RESIST COMPOSITION, AND PATTERNING PROCESS

(71) Applicant: Shin-Etsu Chemical Co., Ltd., Tokyo (JP)

(72) Inventors: Koji Hasegawa, Joetsu (JP); Masayoshi Sagehashi, Joetsu (JP); Masahiro Fukushima, Joetsu (JP); Ryosuke Taniguchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/041,498

(22) Filed: Feb. 11, 2016

(65) Prior Publication Data

US 2016/0238930 A1 Aug. 18, 2016

(30) Foreign Application Priority Data

Feb. 13, 2015 (JP) ................................ 2015-026066

(51) Int. Cl.
*G03F 7/038* (2006.01)
*G03F 7/039* (2006.01)
(Continued)

(52) U.S. Cl.
CPC .......... *G03F 7/038* (2013.01); *C07D 307/04* (2013.01); *C07D 307/93* (2013.01);
(Continued)

(58) Field of Classification Search
None
See application file for complete search history.

(56) References Cited

U.S. PATENT DOCUMENTS

| | | | |
|---|---|---|---|
| 6,280,898 | B1 | 8/2001 | Hasegawa et al. |
| 7,186,495 | B2 | 3/2007 | Maeda et al. |

(Continued)

FOREIGN PATENT DOCUMENTS

| | | | |
|---|---|---|---|
| JP | 09-050126 | * | 2/1997 |
| JP | 3042618 B2 | | 5/2000 |

(Continued)

OTHER PUBLICATIONS

Office Action dated Oct. 6, 2016, issued in counterpart Taiwanese Application No. 105103903. (5 pages).

*Primary Examiner* — Martin Angebranndt
(74) *Attorney, Agent, or Firm* — Westerman, Hattori, Daniels & Adrian, LLP

(57) ABSTRACT

A polymer for resist use is obtainable from a hemiacetal compound having formula (1*a*) wherein $R^1$ is H, $CH_3$ or $CF_3$, $R^2$ to $R^4$ each are H or a monovalent hydrocarbon group, $X^1$ is a divalent hydrocarbon group, ZZ designates a non-aromatic mono- or polycyclic ring of 4 to 20 carbon atoms having a hemiacetal structure, $k^1$=0 or 1, and $k^2$=0 to 3. A resist composition comprising the polymer displays controlled acid diffusion and low roughness during both positive and negative tone developments.

(Continued)

PHOTORESIST EXPOSURE

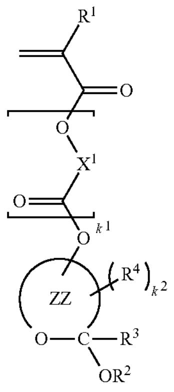

(1a)

11 Claims, 1 Drawing Sheet

(51) Int. Cl.

| | |
|---|---|
| ***C08F 224/00*** | (2006.01) |
| ***C08F 228/06*** | (2006.01) |
| ***C07D 307/04*** | (2006.01) |
| ***C07D 493/18*** | (2006.01) |
| ***C07D 307/93*** | (2006.01) |
| ***G03F 7/32*** | (2006.01) |

(52) U.S. Cl.
CPC .......... *C07D 493/18* (2013.01); *C08F 224/00* (2013.01); *C08F 228/06* (2013.01); *G03F 7/039* (2013.01); *G03F 7/325* (2013.01)

(56) References Cited

U.S. PATENT DOCUMENTS

| | | | | |
|---|---|---|---|---|
| 7,371,505 | B2 | 5/2008 | Kodama | |
| RE41,580 | E | 8/2010 | Hasegawa et al. | |
| 8,034,547 | B2 | 10/2011 | Tsubaki et al. | |
| 8,241,840 | B2 | 8/2012 | Tsubaki et al. | |
| 2003/0017415 | A1 | 1/2003 | Kodama et al. | |
| 2006/0093960 | A1* | 5/2006 | Kinsho ................ | C07D 307/20 430/270.1 |
| 2010/0112482 | A1* | 5/2010 | Watanabe ............ | C07D 307/04 430/286.1 |
| 2011/0236826 | A1* | 9/2011 | Hatakeyama ........... | C07C 69/54 430/270.1 |
| 2013/0017492 | A1* | 1/2013 | Hatakeyama ......... | G03F 7/0045 430/285.1 |
| 2013/0052587 | A1 | 2/2013 | Hatakeyama et al. | |

FOREIGN PATENT DOCUMENTS

| | | | |
|---|---|---|---|
| JP | 2006-146143 | A | 6/2006 |
| JP | 4131062 | B2 | 8/2008 |
| JP | 2008-281974 | A | 11/2008 |
| JP | 2009-158144 | | 7/2009 |
| TW | 548523 | B | 8/2003 |
| TW | 201319742 | A1 | 5/2013 |

* cited by examiner

PHOTORESIST COATING

PHOTORESIST EXPOSURE

ORGANIC SOLVENT DEVELOPMENT

HEMIACETAL COMPOUND, POLYMER, RESIST COMPOSITION, AND PATTERNING PROCESS

CROSS-REFERENCE TO RELATED APPLICATION

This non-provisional application claims priority under 35 U.S.C. §119(a) on Patent Application Ser. No. 2015-026066 filed in Japan on Feb. 13, 2015, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a resist composition comprising the polymer, and a pattern forming process using the resist composition. The monomer is useful for the preparation of a polymer which is used as a base resin to formulate a radiation-sensitive resist composition having high transparency to radiation of wavelength 500 nm or less, especially 300 nm or less, typically KrF, ArF or $F_2$ laser radiation, and improved development properties.

BACKGROUND ART

To meet the demand for higher integration density and operating speed of LSIs, the effort to reduce the pattern rule is in rapid progress. As the advanced miniaturization technology, manufacturing of microelectronic devices at the 45 to 32 nm node by the ArF immersion lithography has been implemented in a mass scale. The candidates for the next generation 32 nm or finer node include ultra-high NA lens immersion lithography using a liquid having a higher refractive index than water in combination with a high refractive index lens and a high refractive index resist film, extreme ultraviolet (EUV) lithography of 13.5 nm wavelength, and double patterning version of the ArF lithography, on which active research efforts have been made.

Besides the positive tone resist by alkaline development, a highlight is recently put on the negative tone resist by organic solvent development. It would be desirable if a very fine hole pattern, which is not achievable with the positive tone, is resolvable through negative tone exposure. To this end, a positive resist composition featuring a high resolution is subjected to organic solvent development to form a negative pattern.

As the ArF resist composition for negative tone development with organic solvent, positive ArF resist compositions of the prior art design may be used. Such a pattern forming process is described in Patent Document 1.

Independent of whether the resist material is subject to positive or negative tone development, the resist material must have a high sensitivity and resolution and form a resist pattern tenaciously adhered to the substrate, referred to as substrate adhesion, hereinafter. As the unit capable of providing substrate adhesion, heretofore, methacrylate units of monocyclic lactone type such as butyrolactone or valerolactone ring and methacrylate units of fused ring lactone as typified by norbornane lactone have been proposed (see Patent Documents 2 to 4). Sultone units having a cyclic sulfonic acid ester structure are also used for the same purpose as the lactone units (see Patent Document 5).

To meet the further miniaturization requirement, there is a desire to have a base resin unit capable of displaying improved properties including sensitivity, resolution, control of acid diffusion length, and substrate adhesion.

CITATION LIST

Patent Document 1: JP-A 2008-281974
Patent Document 2: JP 3042618
Patent Document 3: JP 4131062
Patent Document 4: JP-A 2006-146143
Patent Document 5: JP-A 2009-158144

DISCLOSURE OF INVENTION

In the current lithography for which further miniaturization is required, it is desired to meet controlled diffusion of acid generated upon exposure, good pattern profile, and low roughness. To this end, further collaboration must be made on the formulation of a base resin, typically composed of acid labile units and adhesive units, and the structure and function of additives including a photoacid generator and sensitivity adjustors such as a basic compound or quencher. In the negative tone development process under the recent study, the region which is retained after exposure and organic solvent development is the portion where acid labile units accounting for a large proportion in the base resin are deprotected so that the carbon density is reduced from that prior to the exposure. Then resistance during the etching step and the retention of pattern profile after etching become outstanding issues.

An object of the invention is to provide a resist composition which displays improved performance properties such as controlled acid diffusion and low roughness so that the negative tone development process is applicable thereto. Specifically, an object of the invention is to provide a monomer, a polymer prepared from the monomer and suited for use in photoresist compositions, a resist composition comprising the polymer as a base resin, and a pattern forming process using the resist composition.

The inventors have found that a hemiacetal compound having the general formula (1a) defined below can be readily synthesized, and that a resist composition comprising a polymer resulting from the monomer as base resin is improved in performance properties such as acid diffusion control when used in the negative tone development process, and exhibits etch resistance.

A first embodiment of the invention provides a hemiacetal compound having the general formula (1a).

(1a)

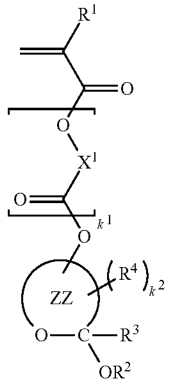

Herein $R^1$ is hydrogen, methyl or trifluoromethyl, $R^2$ to $R^4$ are each independently hydrogen or a straight, branched or cyclic, $C_1$-$C_{15}$ monovalent hydrocarbon group in which a constituent —$CH_2$— may be replaced by —O— or —C(=O)—, $X^1$ is a straight, branched or cyclic, $C_1$-$C_{15}$ divalent hydrocarbon group in which a constituent —$C_2$— may be replaced by —O— or —C(=O)—, the ring ZZ designates a non-aromatic mono- or polycyclic ring of 4 to 20 carbon atoms having a hemiacetal structure, $k^4$ is 0 or 1, and $k^2$ is an integer of 0 to 3.

A preferred embodiment is a hemiacetal compound having the general formula (1b), (1c) or (1d).

(1b)

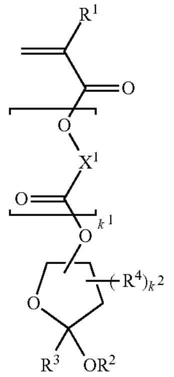

(1c)

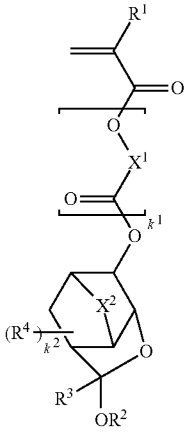

(1d)

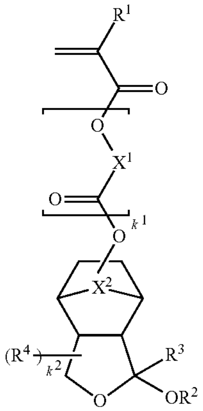

Herein $R^1$ to $R^4$, $X^1$, $k^1$, and $k^2$ are as defined above, and $X^2$ is —$CH_2$— or —O—.

A second embodiment of the invention provides a polymer comprising recurring units of at least one type selected from the general formulae (2a) to (2d).

(2a)

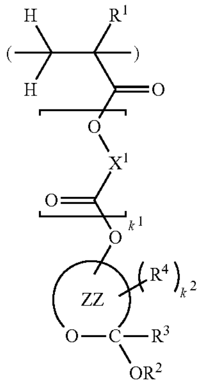

(2b)

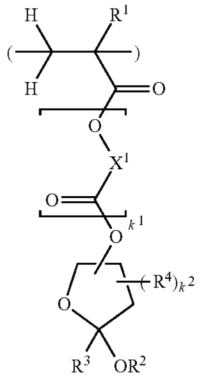

(2c)

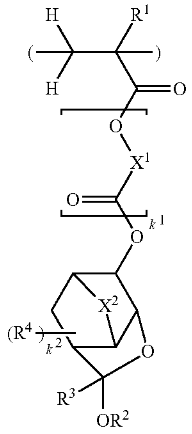

-continued (2d)

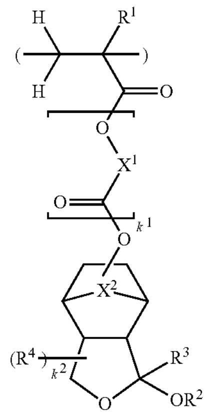

Herein $R^1$ to $R^4$, $X^1$, $X^2$, ZZ, $k^1$, and $k^2$ are as defined above.

In a preferred embodiment, the polymer further comprises recurring units of at least one type selected from the general formulae (4A) to (4E).

(4A)

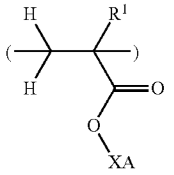

(4B)

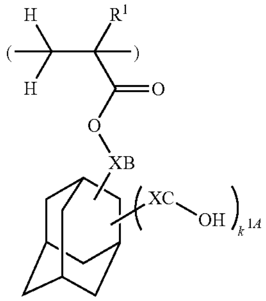

(4C)

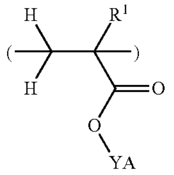

(4D)

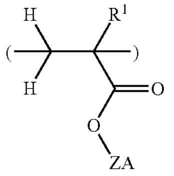

-continued (4E)

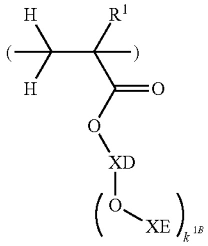

Herein $R^1$ is as defined above, XA is an acid labile group, XB and XC are each independently a single bond or a straight or branched, $C_1$-$C_4$ divalent hydrocarbon group, XD is a straight, branched or cyclic, $C_1$-$C_{16}$ di- to pentavalent aliphatic hydrocarbon group in which a constituent —$CH_2$— may be replaced by —O— or —C(═O)—, XE is an acid labile group, YA is a substituent group of lactone, sultone or carbonate structure, ZA is hydrogen, a $C_1$-$C_{15}$ fluoroalkyl group or a $C_1$-$C_{15}$ fluoroalcohol-containing group, $k^{1A}$ is an integer of 1 to 3, and $k^{1B}$ is an integer of 1 to 4.

In a preferred embodiment, the polymer further comprises recurring units of at least one type selected from sulfonium salt units (f1) to (f3) represented by the following general formula.

(f1)

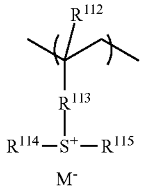

(f2)

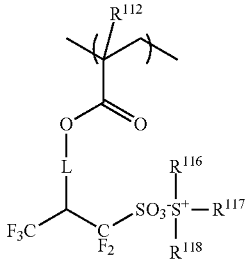

(f3)

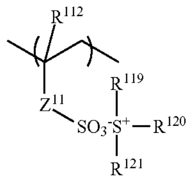

Herein $R^{112}$ is hydrogen or methyl; $R^{113}$ is a single bond, phenylene, or —O—$R^{122}$—, or —C(═O)—$Z^{22}$—$R^{122}$—, $Z^{22}$ is oxygen or NH, $R^{122}$ is a straight $C_1$-$C_6$ or branched or cyclic $C_3$-$C_6$ alkylene group, $C_2$-$C_6$ alkenylene group or phenylene group, which may contain a carbonyl (—CO—), ester (—COO—), ether (—O—), or hydroxyl moiety; L is a single bond or —$Z^{33}$—C(═O)—O—, $Z^{33}$ is a straight $C_1$-$C_{20}$ or branched or cyclic $C_3$-$C_{20}$ divalent hydrocarbon group which may be substituted with or separated by a heteroatom, $Z^{11}$ is a single bond, methylene, ethylene, phenylene, fluorinated phenylene, —O—$R^{123}$— or —C(═O)—$Z^{44}$—$R^{123}$—, $Z^{44}$ is oxygen or NH, $R^{123}$ is a straight $C_1$-$C_6$ or branched or cyclic $C_3$-$C_6$ alkylene group, $C_2$-$C_6$ alkenylene group or phenylene group, which may contain a carbonyl, ester, ether, or hydroxyl moiety; M is a non-nucleophilic counter ion; $R^{114}$, $R^{113}$, $R^{116}$, $R^{117}$, $R^{118}$, $R^{119}$, $R^{120}$, and $R^{121}$ are each independently a straight $C_1$-$C_{20}$ or branched or cyclic $C_3$-$C_{20}$ hydrocarbon group which may be substituted with or separated by a heteroatom.

A third embodiment of the invention provides a resist composition comprising a base resin containing the polymer defined above, an acid generator, and an organic solvent; or a resist composition comprising a base resin containing the polymer defined above and an organic solvent.

A fourth embodiment of the invention provides a pattern forming process comprising the steps of applying the resist composition onto a substrate, prebaking to form a resist film, exposing the resist film to high-energy radiation, baking, and developing the exposed resist film in a developer.

In one preferred embodiment, an aqueous alkaline solution is used as the developer in the developing step to form a positive pattern wherein the exposed region of resist film is dissolved away and the unexposed region of resist film is not dissolved.

In another preferred embodiment, an organic solvent is used as the developer in the developing step to form a negative pattern wherein the unexposed region of resist film is dissolved away and the exposed region of resist film is not dissolved.

Typically, the developer comprises at least one organic solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the step of exposing the resist film to high-energy radiation includes KrF excimer laser lithography of wavelength 248 nm, ArF excimer laser lithography of wavelength 193 nm, EUV lithography of wavelength 13.5 nm or EB lithography.

Advantageous Effects of Invention

When a polymer comprising recurring units derived from the inventive monomer or hemiacetal compound is used as base resin in a resist composition, the resulting resist composition is improved in acid diffusion control and roughness performance in either of positive tone development and negative tone development and is thus capable of forming a fine line-and-space pattern which is resistant to collapse during pattern formation and has improved etch resistance.

BRIEF DESCRIPTION OF DRAWINGS

FIG. 1(A) shows a photoresist film formed on a substrate, FIG. 1(B) shows the photoresist film being exposed, and FIG. 1(C) shows the photoresist film being developed in organic solvent.

DESCRIPTION OF EMBODIMENTS

Figure 1A:
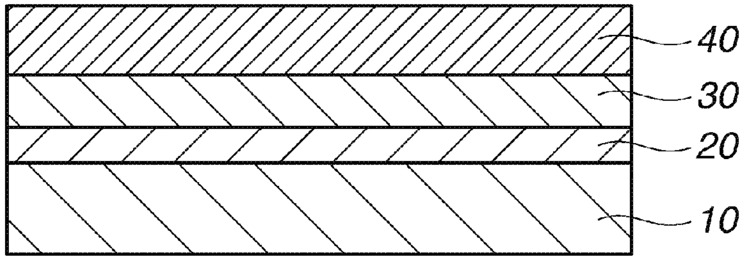
FIGS. 1(A) to 1(C) schematically illustrate in cross-sectional views the pattern forming process of the invention.

In the disclosure, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In the chemical formulae, the broken line denotes a valence bond; Me stands for methyl, Ph for phenyl, and Ac for acetyl.

The abbreviations and acronyms have the following meaning.

EB: electron beam
EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake It is understood that for some structures represented by chemical formulae, there can exist enantiomers and diastereomers because of the presence of asymmetric carbon atoms. In such a case, a single formula collectively represents all such isomers. The isomers may be used alone or in admixture.

Hemiacetal Compound

In the first embodiment, the invention provides a hemiacetal compound having the general formula (1a).

(1a)

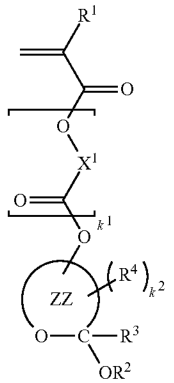

Herein $R^1$ is hydrogen, methyl or trifluoromethyl. $R^2$ to $R^4$ are each independently hydrogen or a straight, branched or cyclic, $C_1$-$C_{15}$ monovalent hydrocarbon group in which a constituent —$CH_2$— may be replaced by —O— or —C(═O)—. $X^1$ is a straight, branched or cyclic, $C_1$-$C_{15}$ divalent hydrocarbon group in which a constituent —$CH_2$— may be replaced by —O— or —C(═O)—. The ring ZZ designates a non-aromatic mono- or polycyclic ring of 4 to 20 carbon atoms having a hemiacetal structure, $k^1$ is 0 or 1, and $k^2$ is an integer of 0 to 3.

Typical examples of the straight, branched or cyclic $C_1$-$C_{15}$ monovalent hydrocarbon group represented by $R^2$ to $R^4$ are alkyl groups including methyl, ethyl, propyl, isopropyl, n-butyl, sec-butyl, tert-butyl, cyclopentyl, cyclohexyl, 2-ethylhexyl, n-octyl, norbornyl, tricyclodecanyl, and adamantyl.

The straight, branched or cyclic $C_1$-$C_{15}$, preferably $C_1$-$C_{10}$, divalent hydrocarbon group represented by $X^1$ is typically alkylene. Examples thereof are shown below.

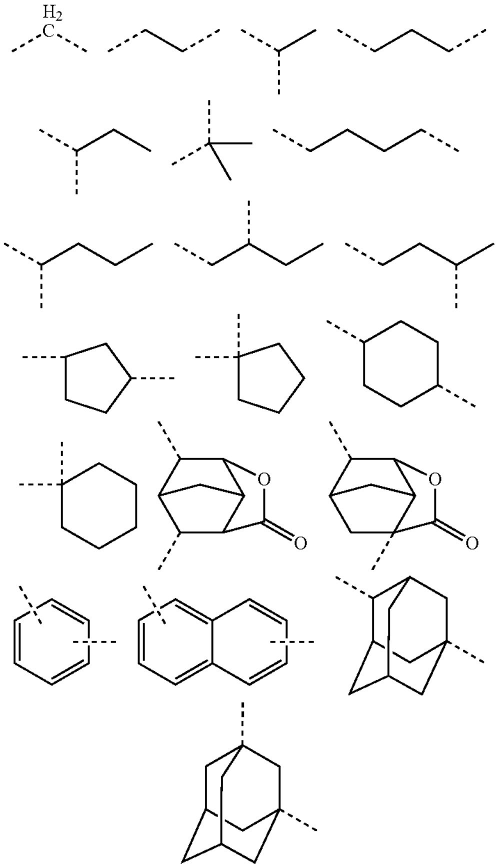

The ring ZZ designates a non-aromatic mono- or polycyclic ring of 4 to 20 carbon atoms having a hemiacetal structure, examples of which are shown below.

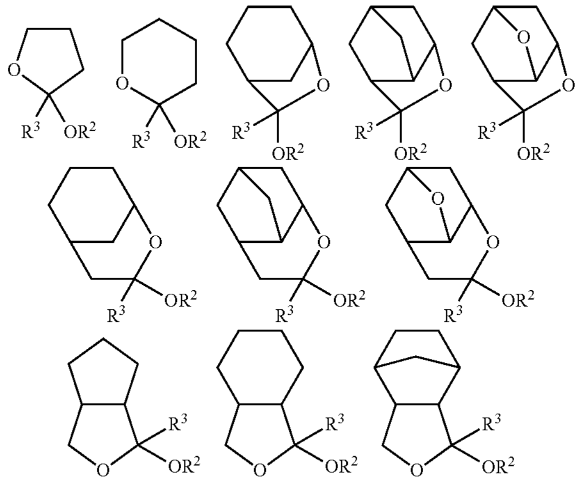

-continued

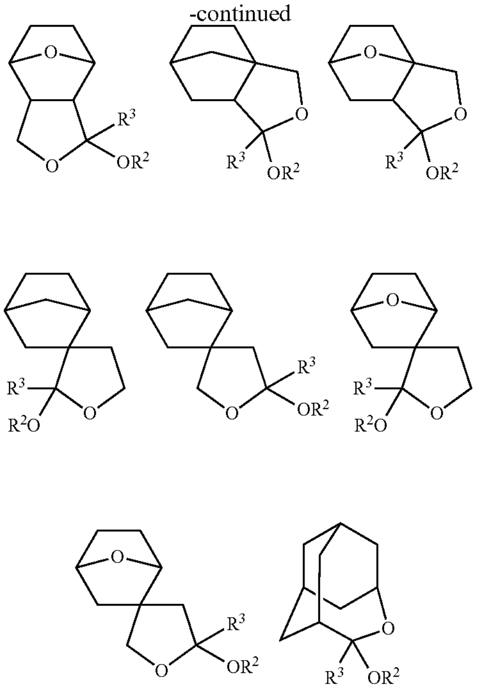

Herein $R^2$ and $R^3$ are as defined and exemplified above.

In a preferred embodiment, the hemiacetal compound having formula (1a) is a hemiacetal compound having the general formula (1b), (1c) or (1d).

(1b)

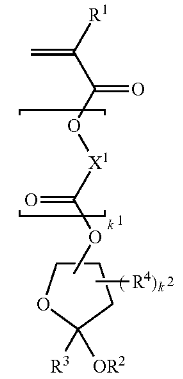

(1c)

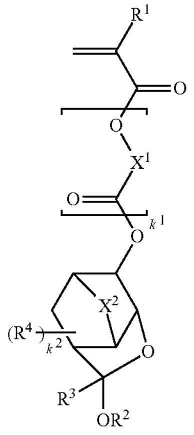

-continued (1d)

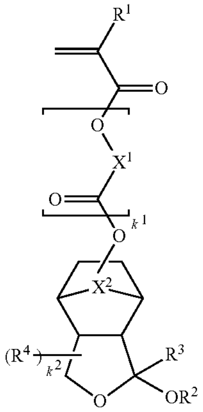

Herein $R^1$ is hydrogen, methyl or trifluoromethyl. $R^2$ to $R^4$ are each independently hydrogen or a straight, branched or cyclic, $C_1$-$C_{15}$ monovalent hydrocarbon group in which a constituent —$CH_2$— may be replaced by —O— or —C(═O)—. $X^1$ is a straight, branched or cyclic, $C_1$-$C_{15}$ divalent hydrocarbon group in which a constituent —$CH_2$— may be replaced by —O— or —C(═O)—. $X^2$ is —$CH_2$— or —O—, $k^1$ is 0 or 1, and $k^2$ is an integer of 0 to 3.

Illustrative, non-limiting examples of the compounds having formulae (1a) to (1d) are shown below.

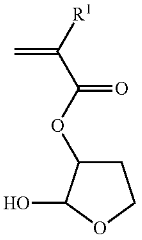
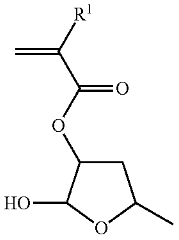
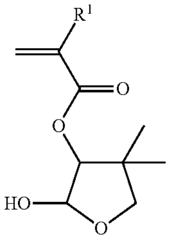
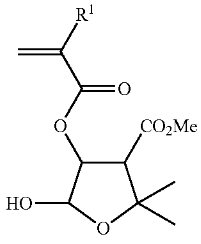
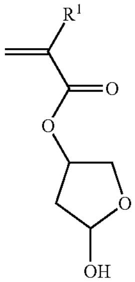
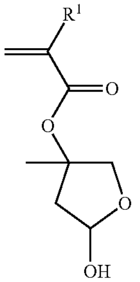
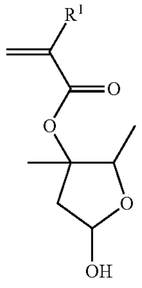
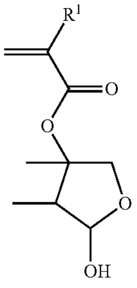
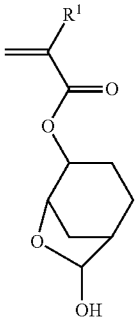
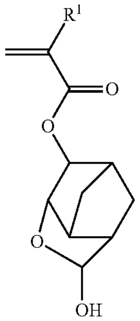

-continued

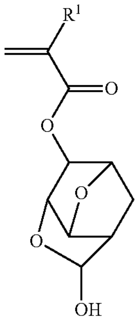
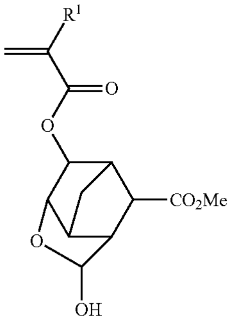
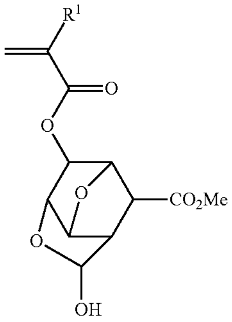
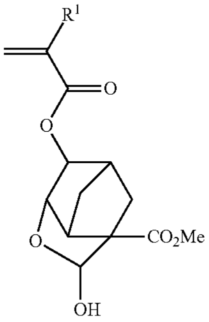
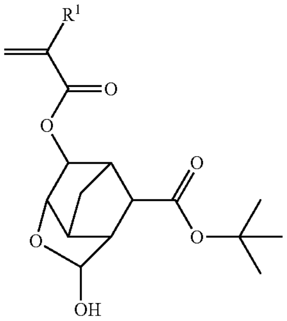
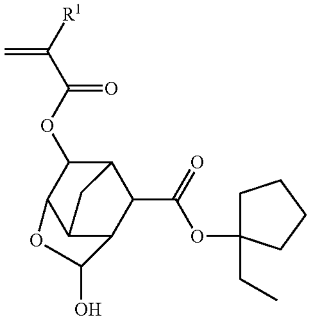
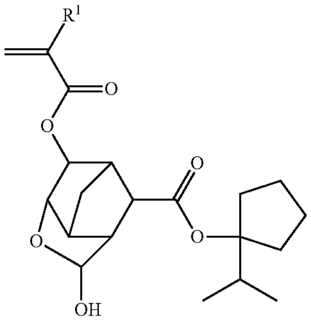

-continued
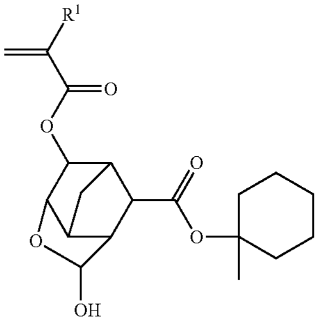
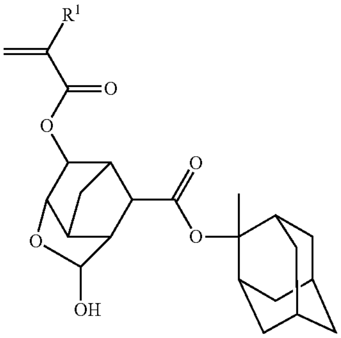
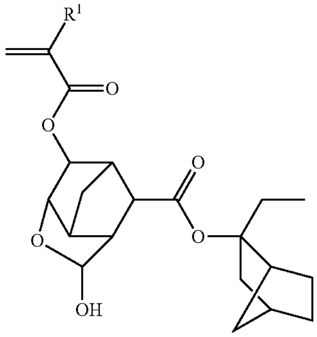
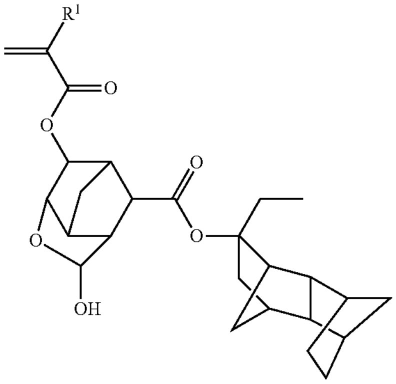
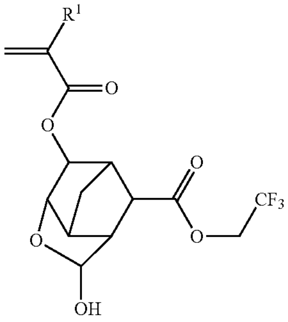
-continued
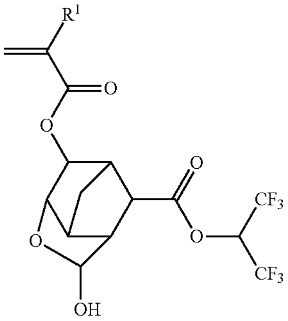
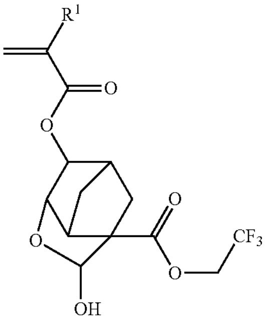
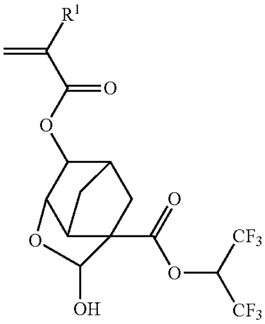
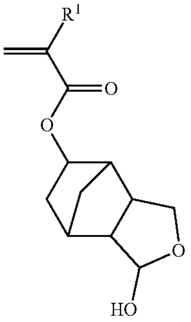
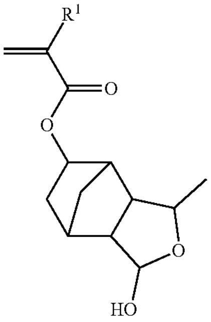
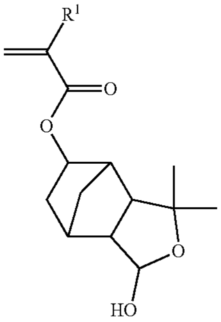
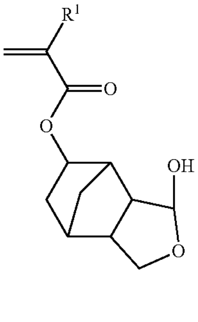
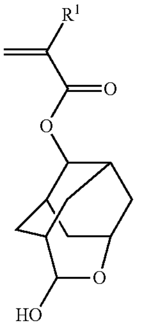
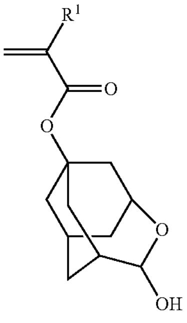

-continued
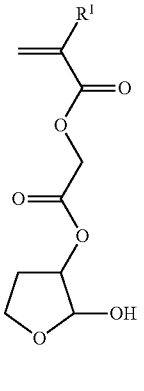
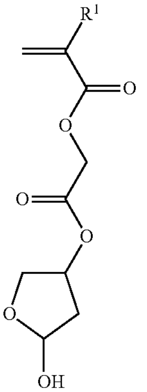
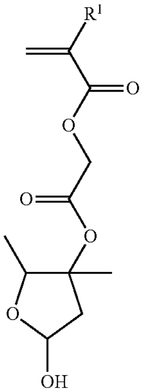
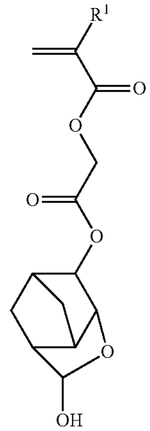
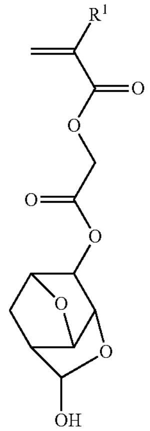
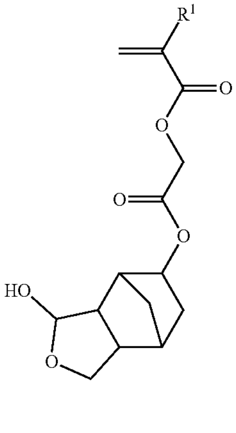
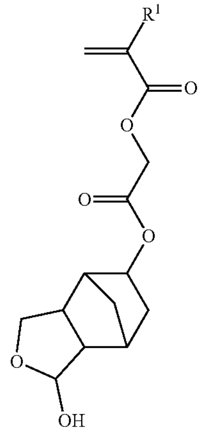
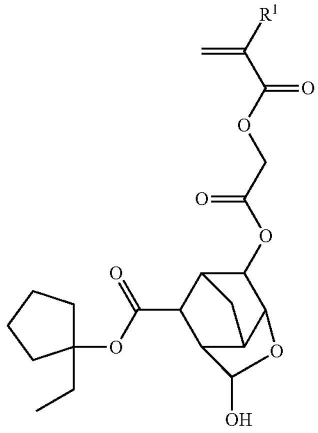
-continued
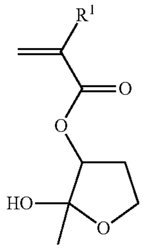
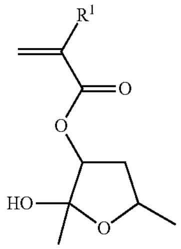
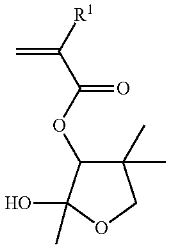
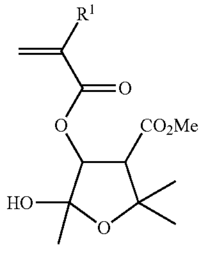
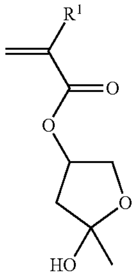
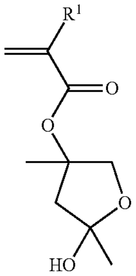
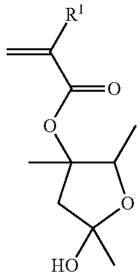
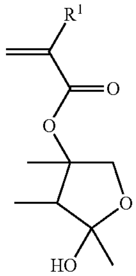
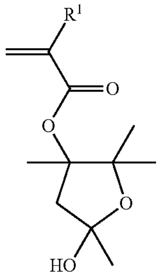
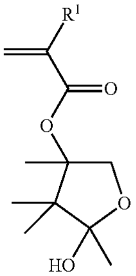
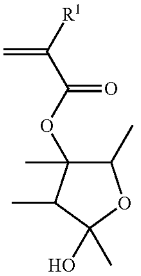
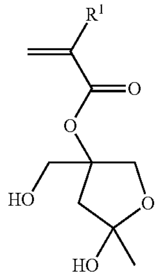
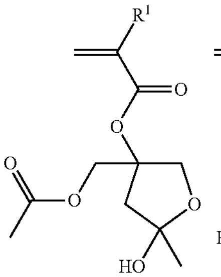
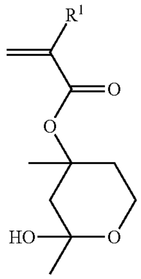
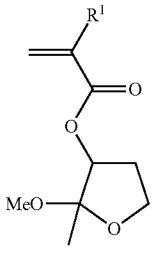
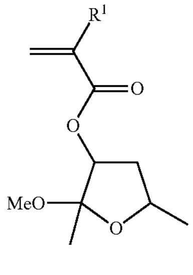
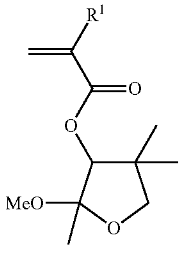
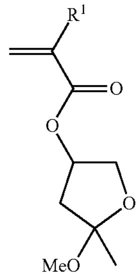

-continued
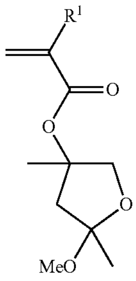
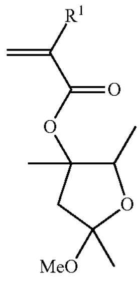
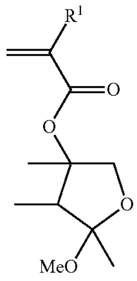
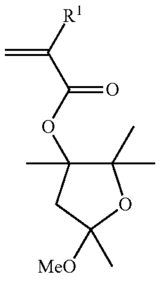
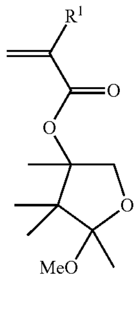
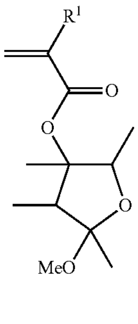
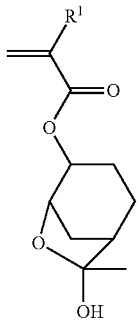
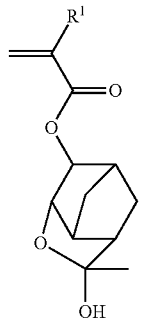
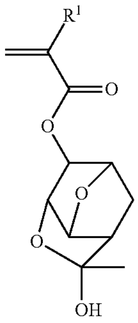
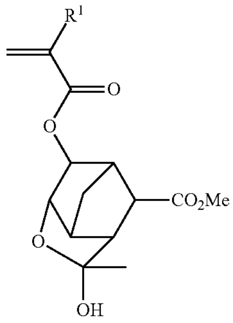
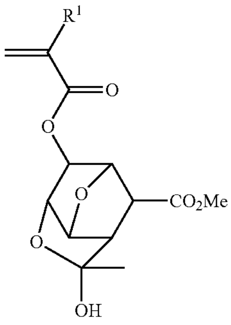
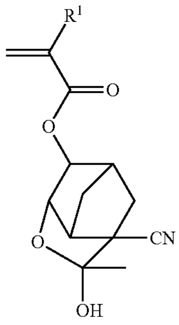
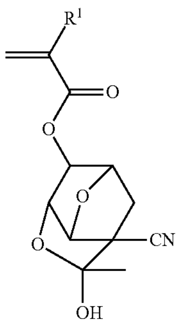
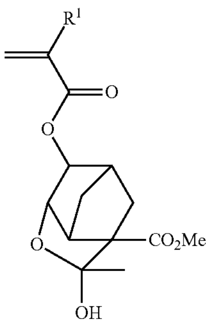
-continued
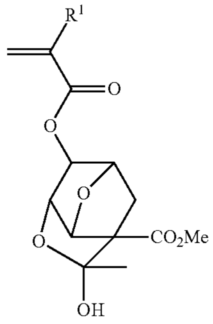
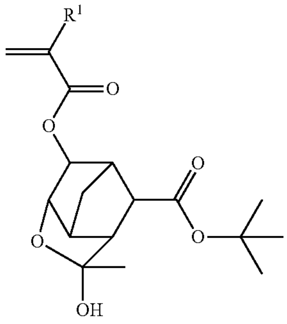
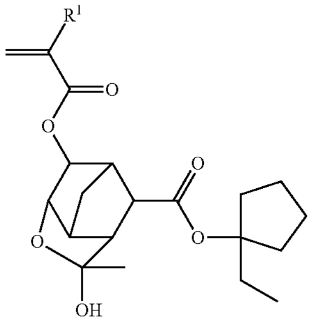
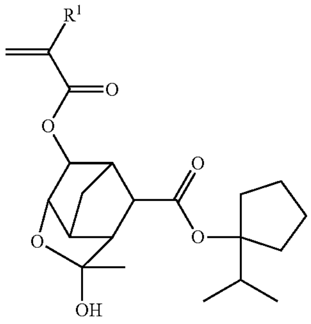
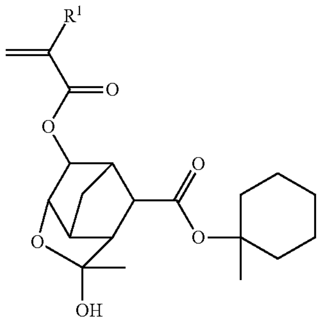
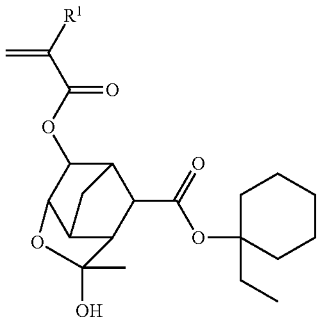

-continued
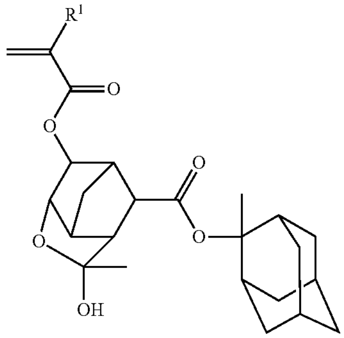
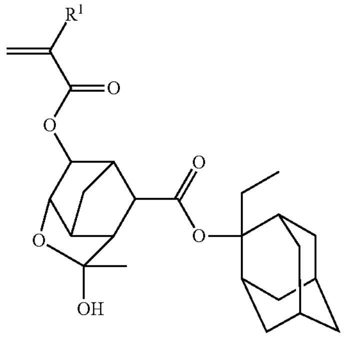
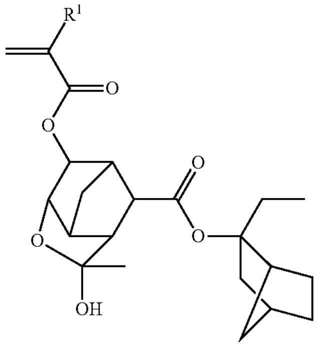
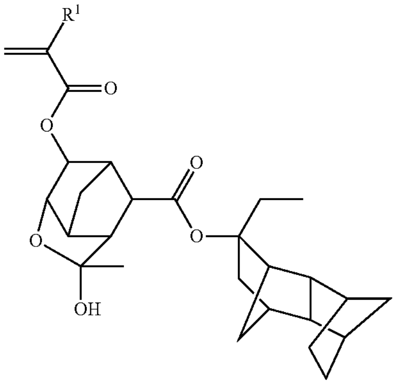
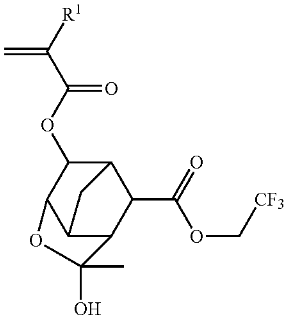
-continued
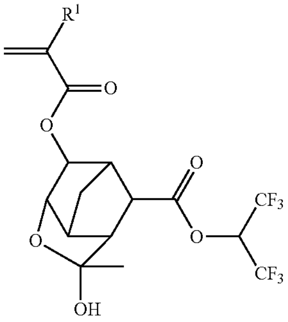
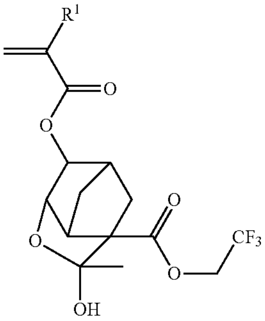
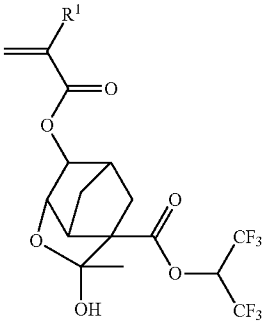
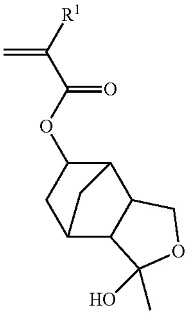
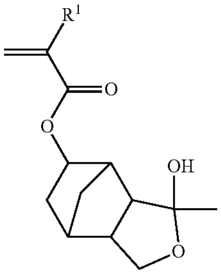
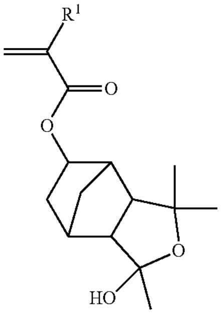
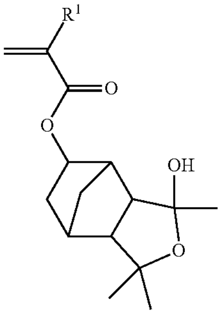
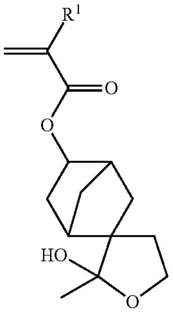

-continued
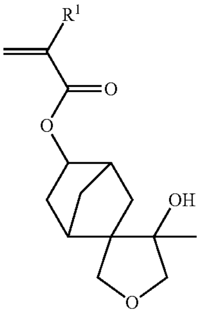
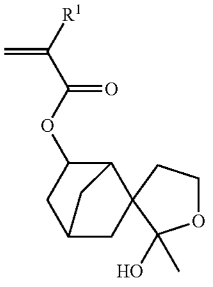
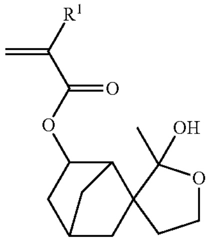
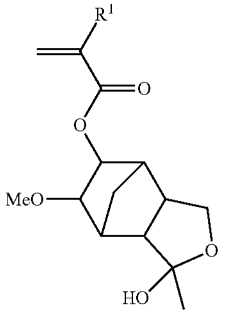
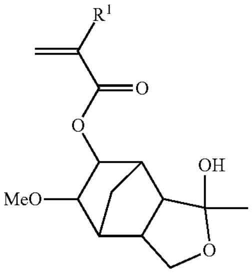
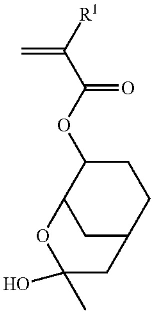
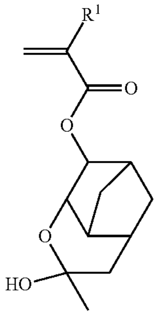
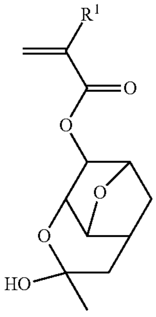
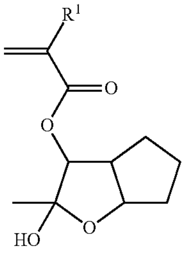
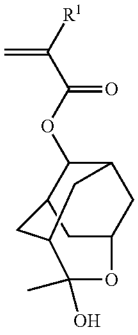
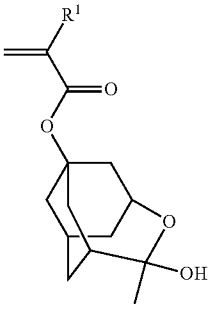
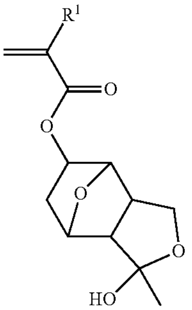
-continued
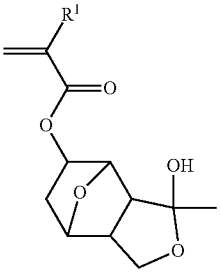
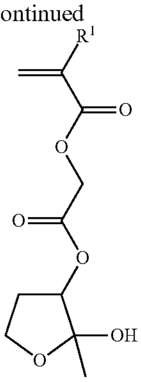
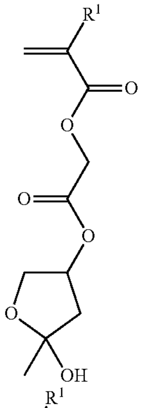
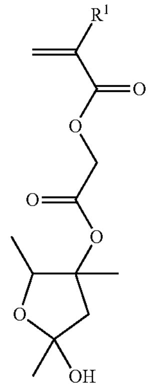
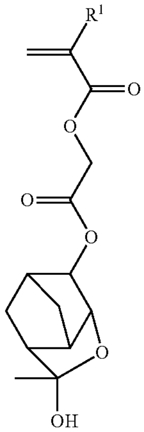
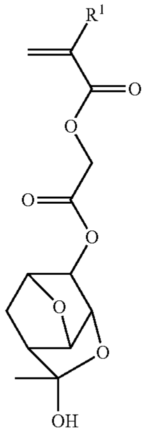
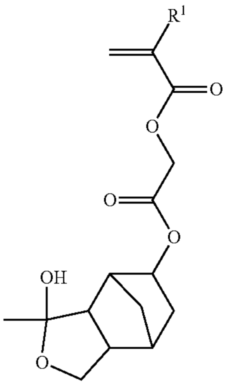
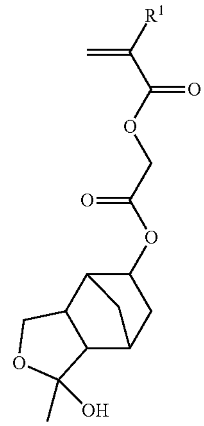
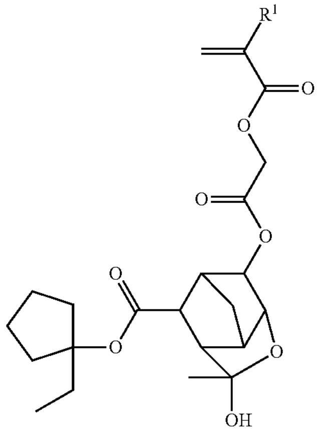

-continued
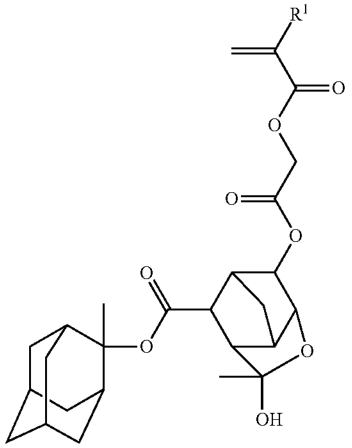
-continued
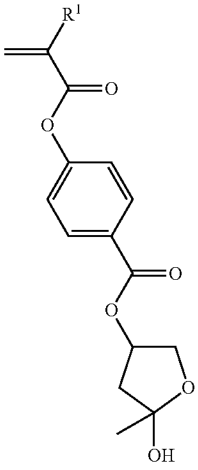
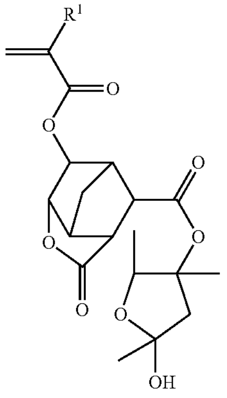
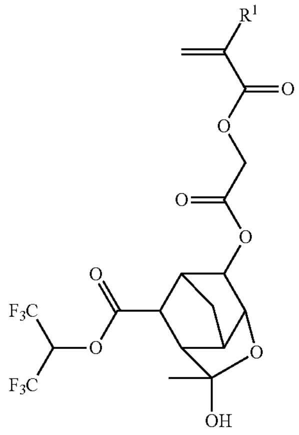
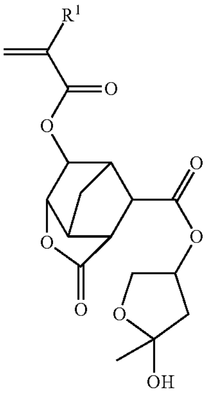
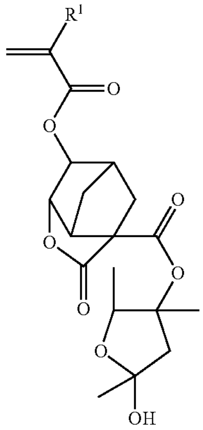
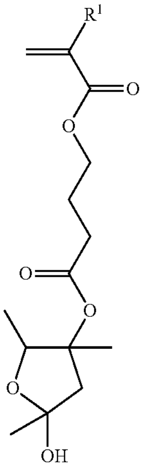
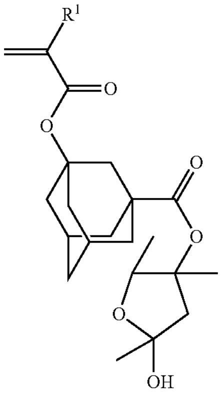
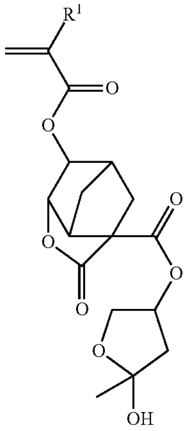
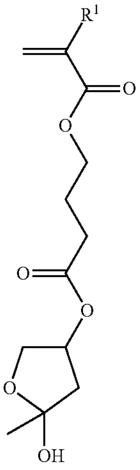
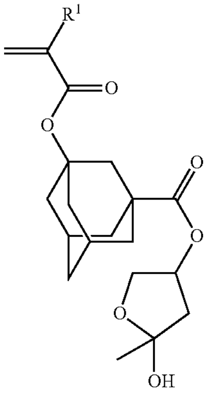
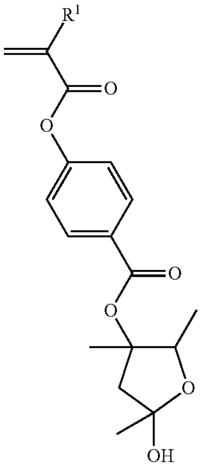
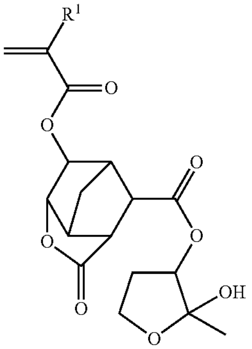

-continued
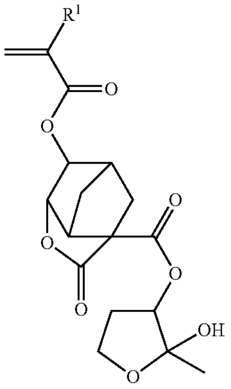
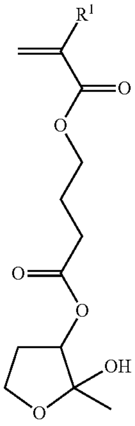
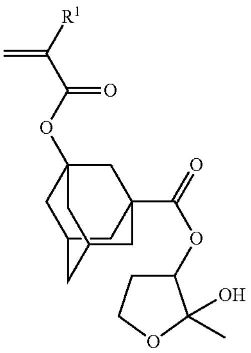
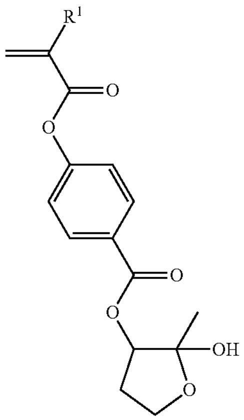
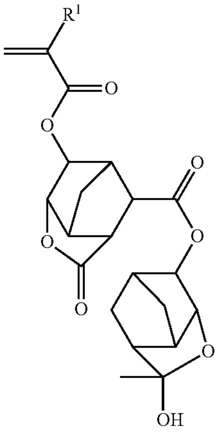
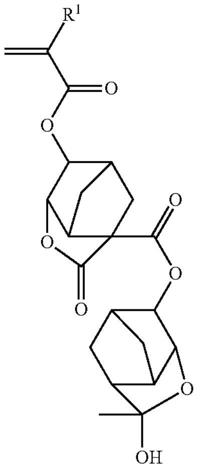
-continued
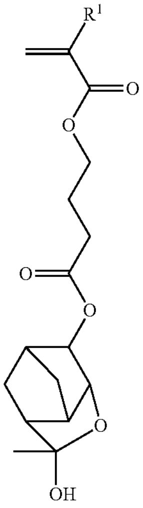
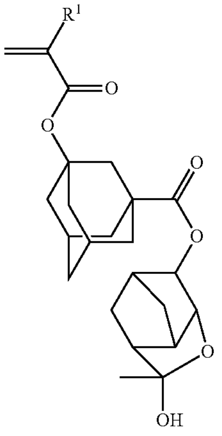
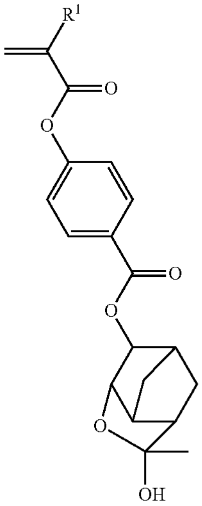
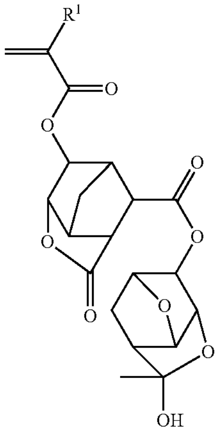
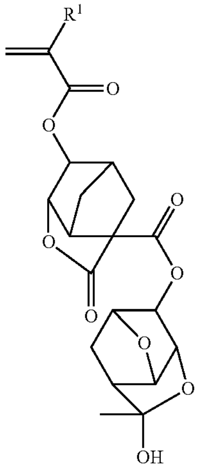
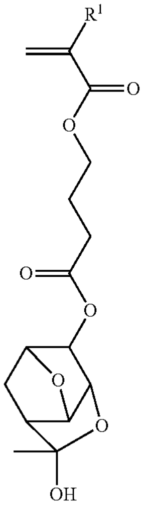

-continued
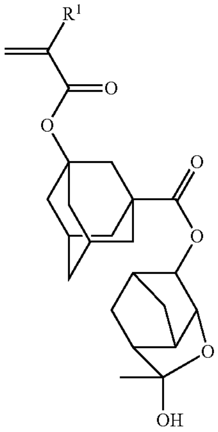
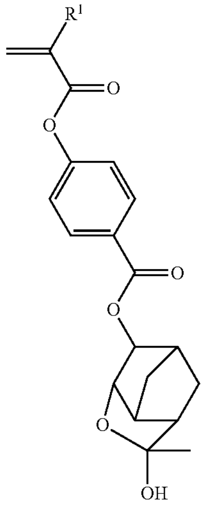
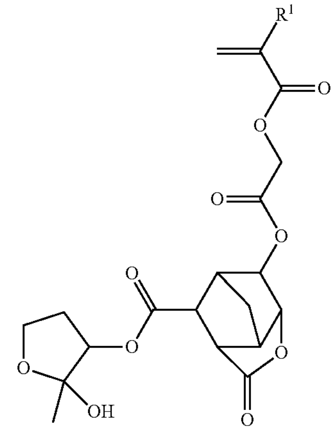
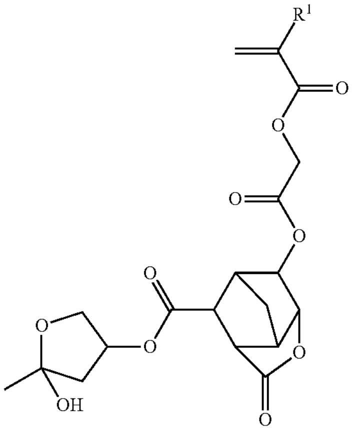
-continued
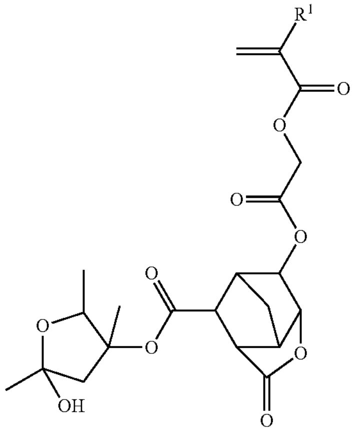
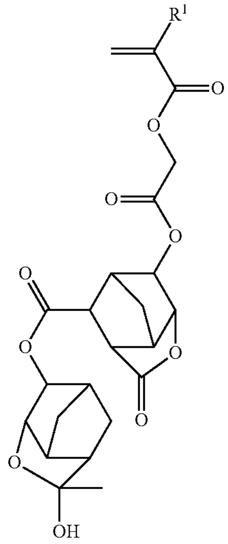
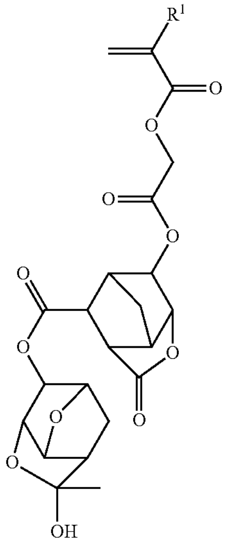
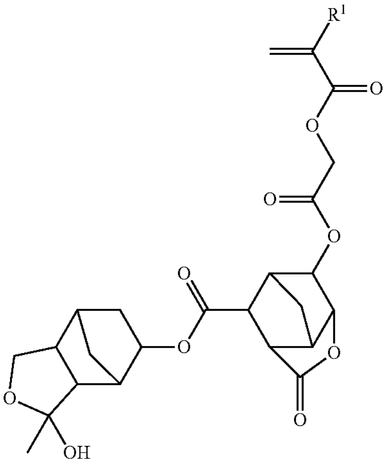

-continued
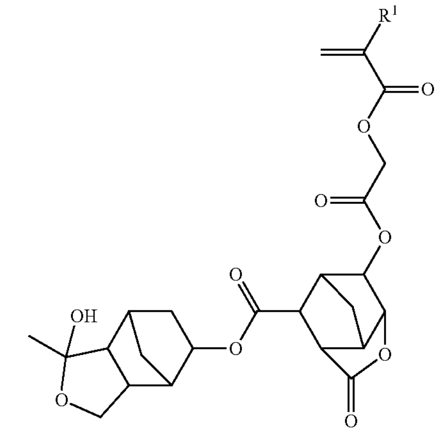
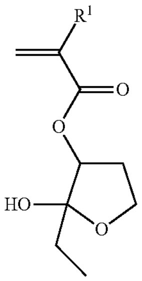
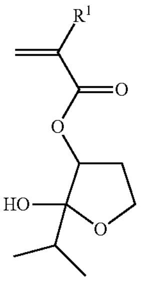
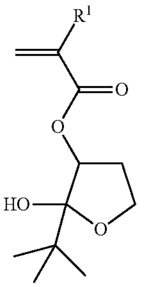
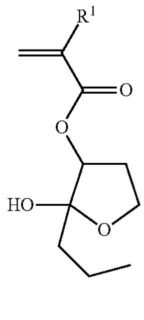
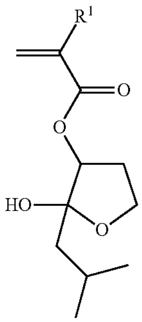
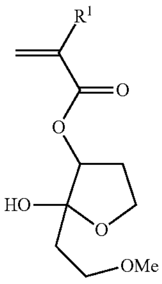
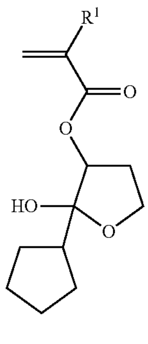
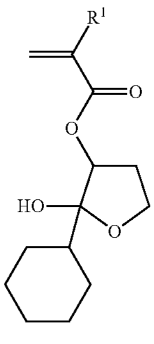
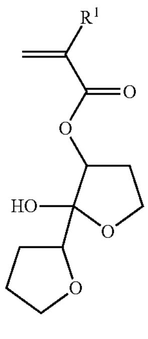
-continued
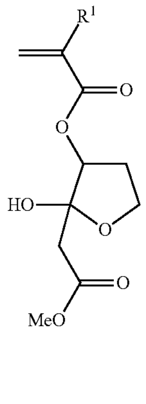
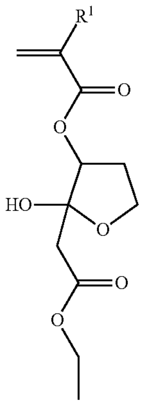
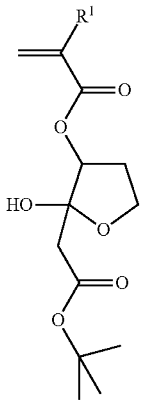
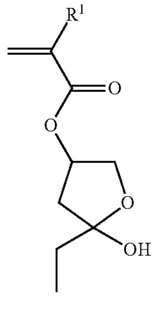
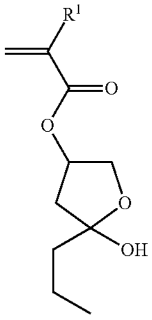
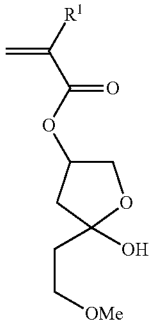
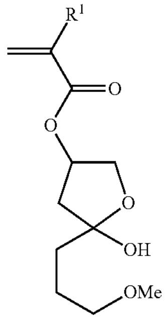
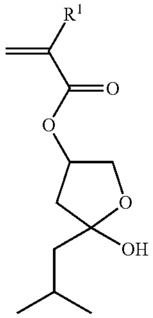
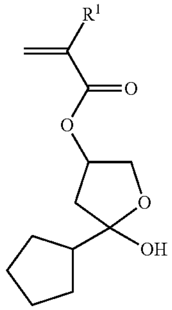
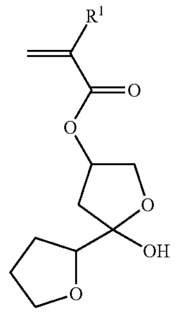
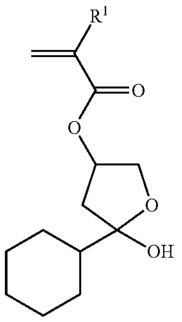
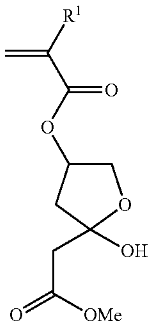

-continued
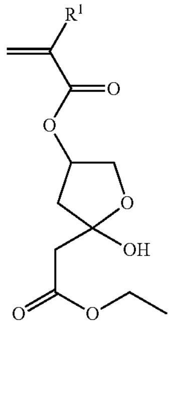
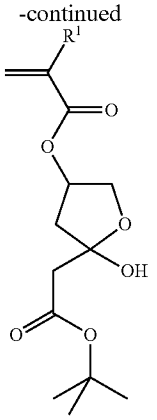
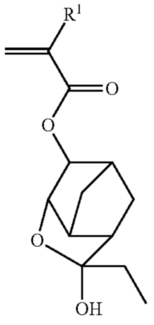
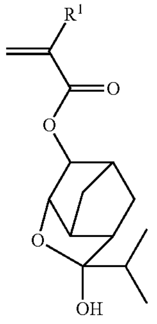
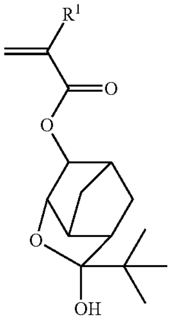
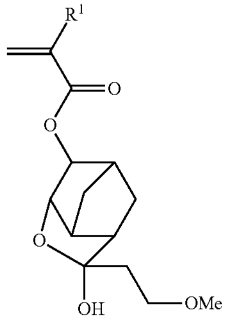
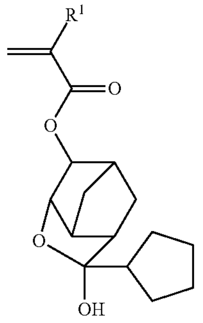
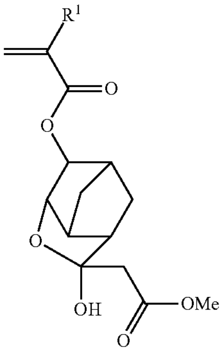
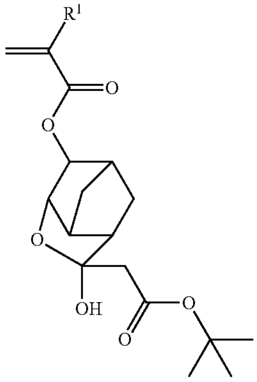
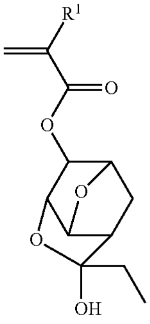
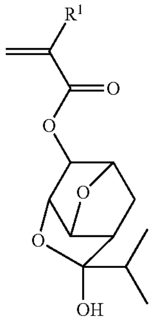
-continued
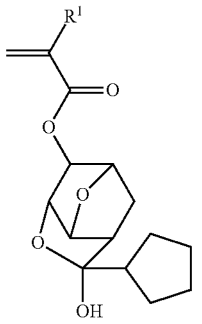
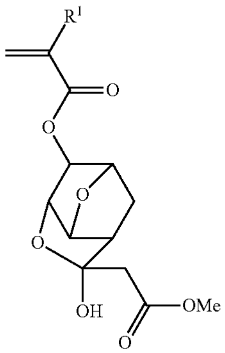
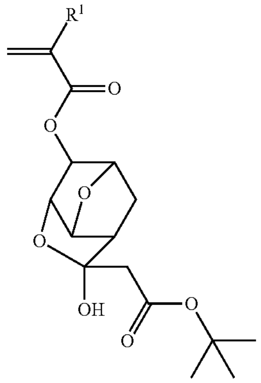
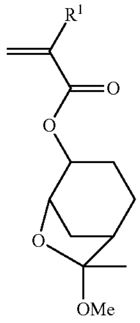
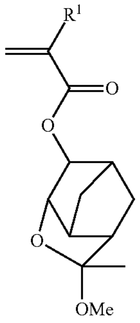
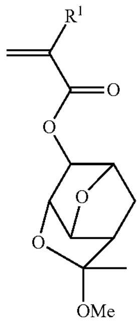
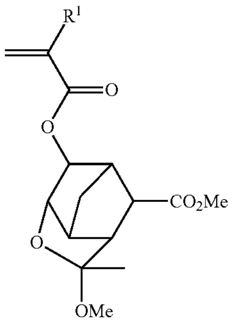
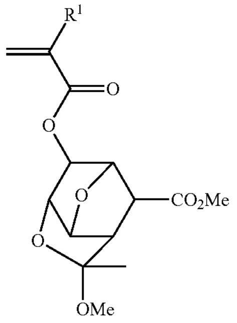
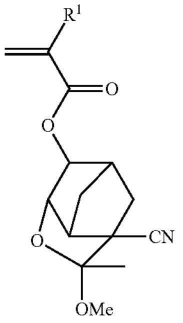
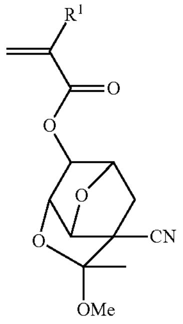
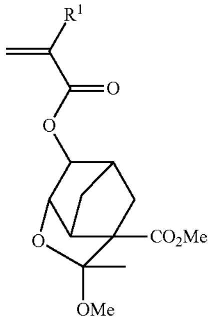

-continued
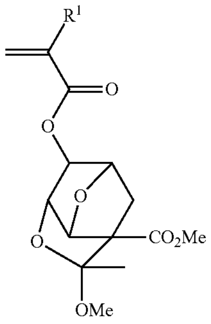
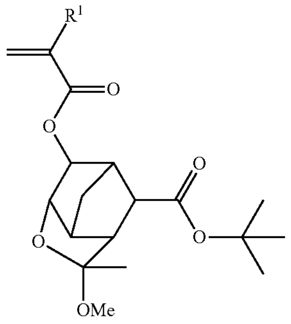
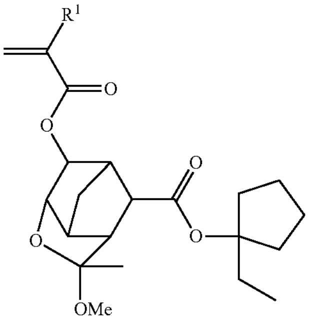
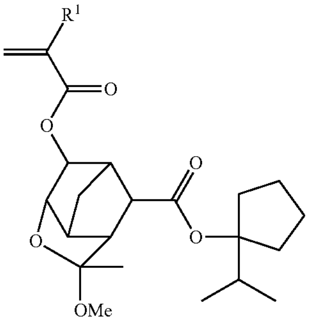
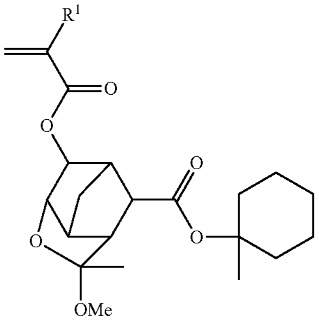
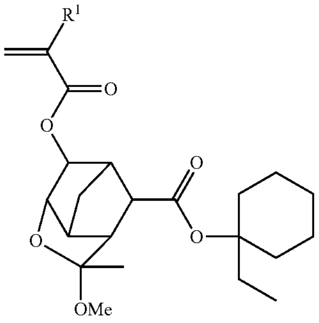
-continued
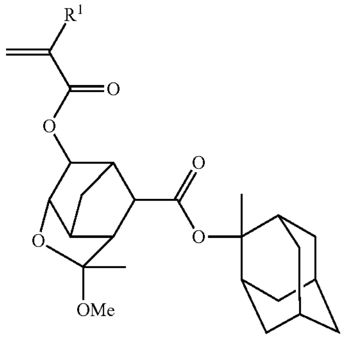
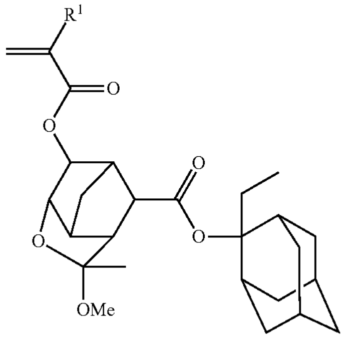
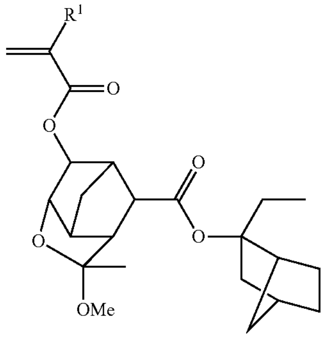
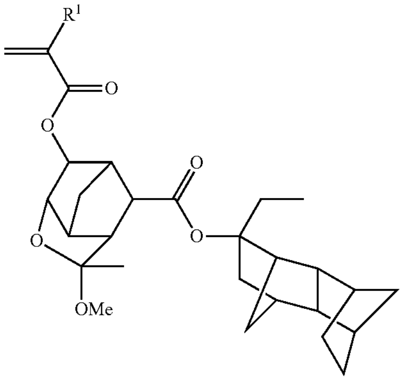
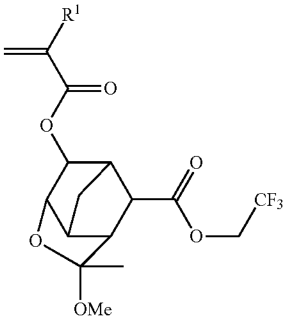

-continued
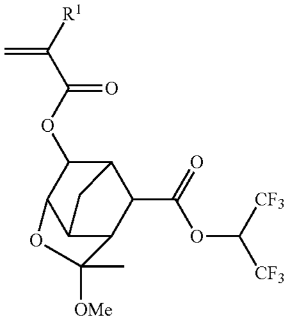
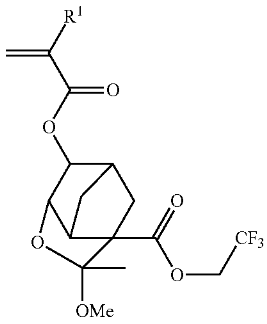
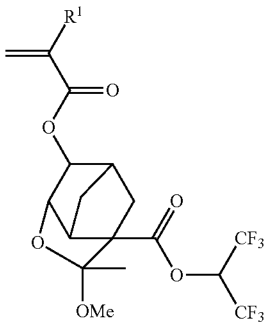
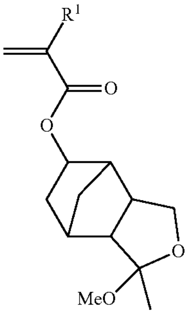
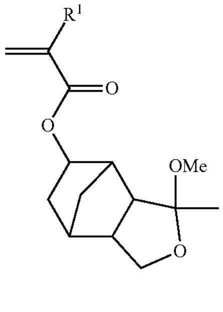
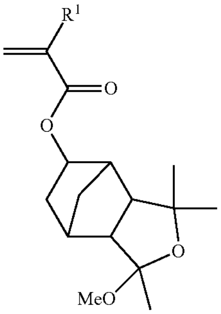
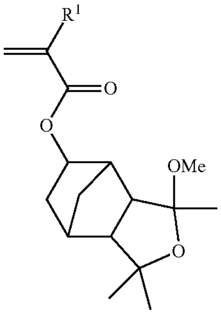
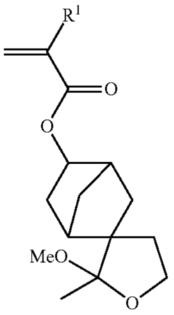
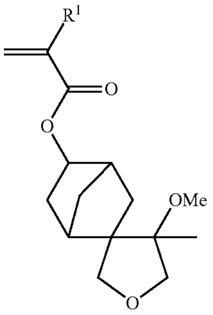
-continued
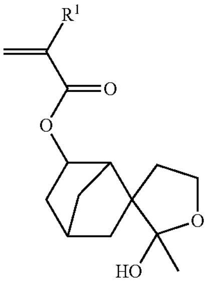
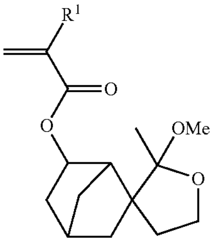
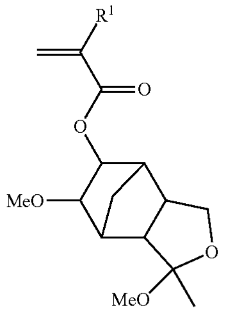
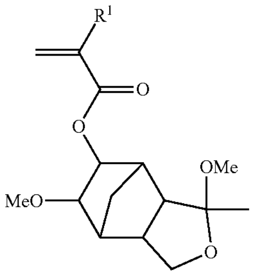
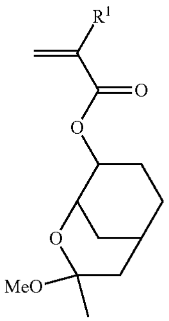
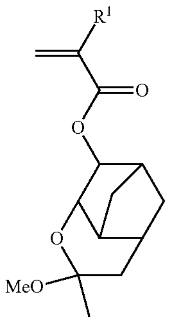
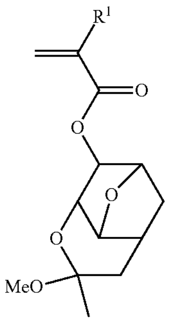
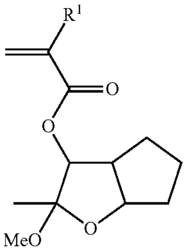
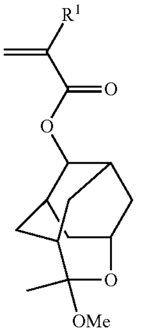
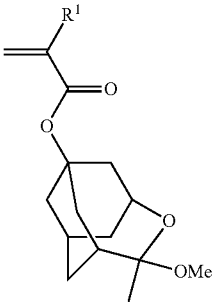
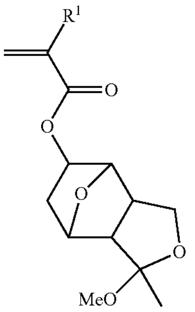
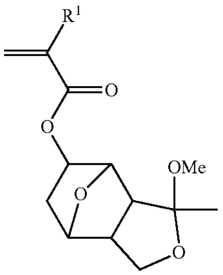

-continued
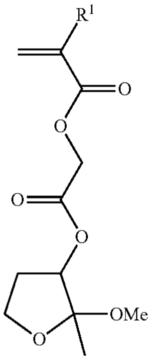
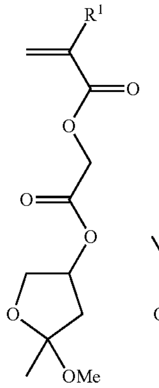
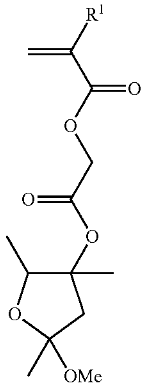
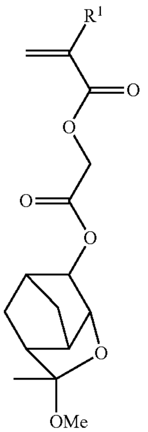
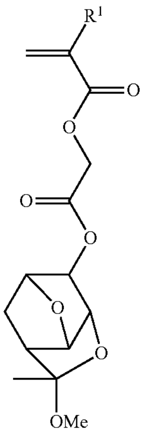
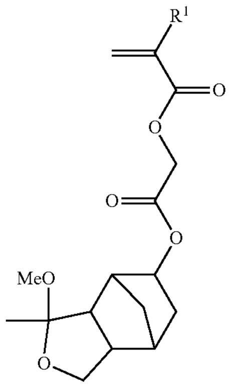
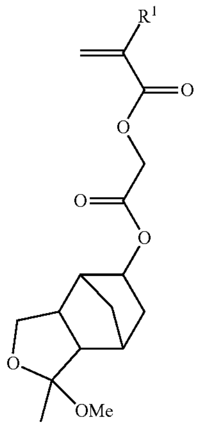
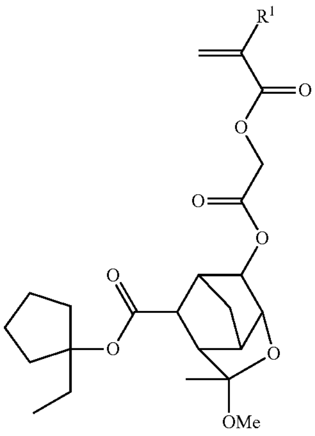
-continued
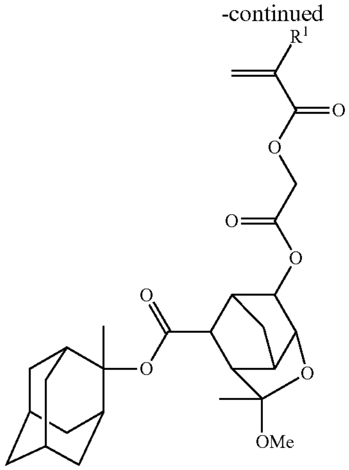
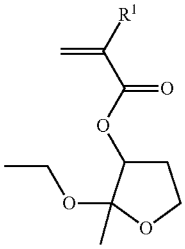
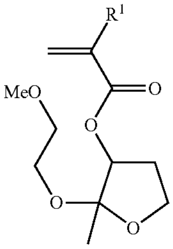
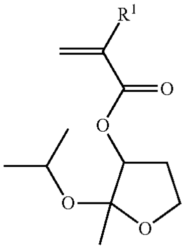
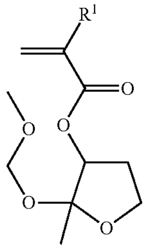
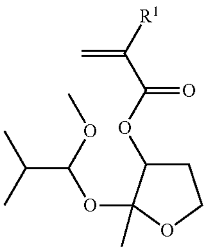
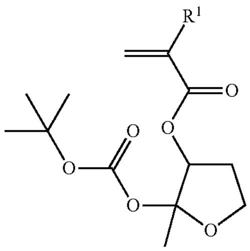
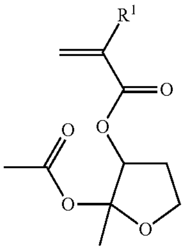
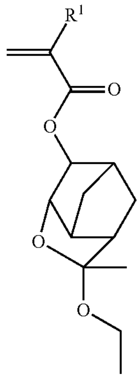
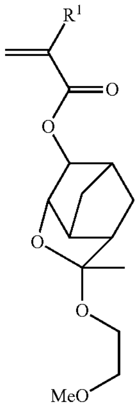

-continued

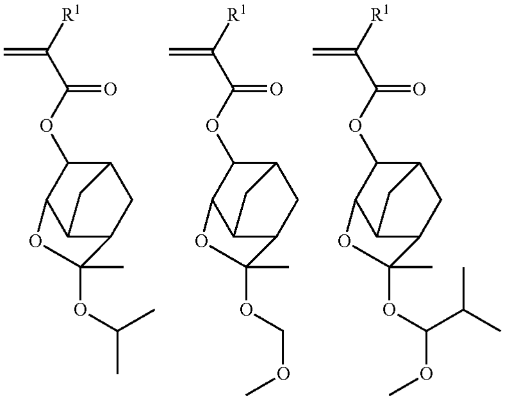

-continued

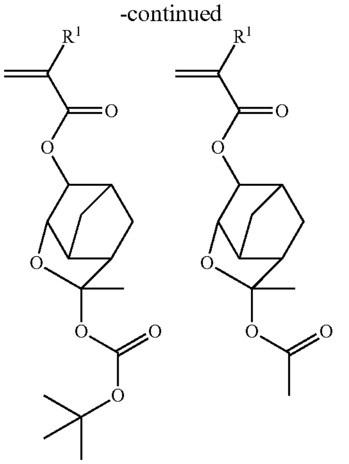

Herein $R^1$ is as defined above.

The method for synthesizing the hemiacetal compound having any one of formulae (1a) to (1d) is not particularly limited. An optimum method may be selected depending on the structure of the desired hemiacetal compound. For example, a hemiacetal compound of formula (1a) wherein $R^2$ is hydrogen, i.e., formula (1aa) may be synthesized by reactions according to the following scheme.

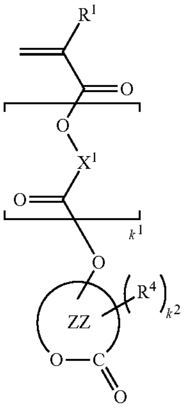

(5)

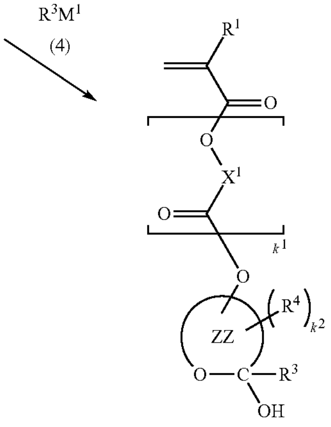

(Iaa)

-continued

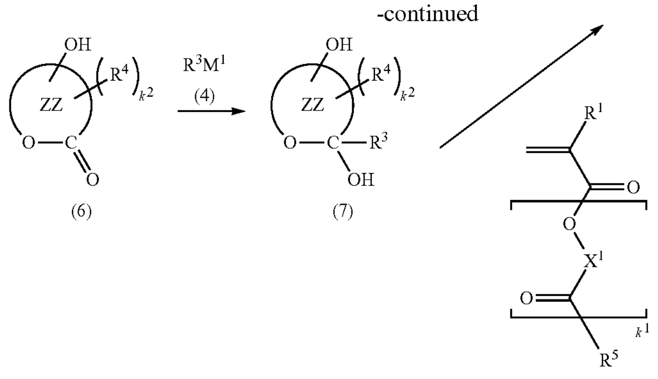

(6) (7)

(8)

Herein $R^1$, $R^3$, $R^4$, $X^1$, $k^2$, and ZZ are as defined above. $R^5$ is halogen, hydroxyl or —$OR^6$ wherein $R^6$ is methyl, ethyl or a group of the following formula (9).

(9)

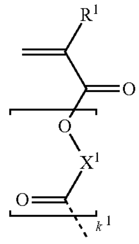

$M^1$ is Li, Na, K, MgY or ZnY wherein Y is halogen.

One route for forming the desired hemiacetal compound (1aa) is nucleophilic addition reaction of an organometallic reagent (4) to a corresponding lactone compound (5).

The reaction may be performed by a standard procedure. For example, the desired hemiacetal compound (1aa) may be obtained by dissolving the lactone compound (5) in an ether solvent (e.g., tetrahydrofuran or diethyl ether), and adding the organometallic reagent (4) corresponding to the substituent $R^3$, for example, a Grignard reagent (e.g., methylmagnesium chloride or ethylmagnesium chloride) or alkyl lithium reagent (e.g., methyllithium). An appropriate amount of organometallic reagent (4) used is 0.5 to 5.0 moles, more preferably 0.8 to 3.0 moles per mole of lactone compound (5). If organometallic reagent (4) is less than 0.5 mole, the addition reaction may not be driven to completion. More than 5.0 moles of the reagent may be uneconomical because of the increased expense of the reagent. The addition reaction may be carried out while cooling or heating the reaction system if desired, preferably at a temperature in the range from −30° C. to approximately the boiling point of a particular solvent used. It is desired for higher yields that the reaction time be determined by monitoring the progress of reaction by gas chromatography (GC) or thin-layer chromatography (TLC). The reaction time is usually about 0.5 to about 24 hours. The hemiacetal compound (1aa) may be recovered from the reaction mixture by ordinary aqueous work-up. If necessary, it can be purified by any standard technique such as distillation, chromatography or recrystallization.

The other route includes nucleophilic addition reaction of an organometallic reagent (4) to a corresponding hydroxy-lactone compound (6) to form a hydroxy-hemiacetal compound (7) and subsequent esterifying reaction to form the desired hemiacetal compound (1aa).

The first step is addition reaction of organometallic reagent (4) to hydroxy-lactone compound (6) to form hydroxy-hemiacetal compound (7). The reaction may be performed by a standard procedure. For example, the hydroxy-hemiacetal compound (7) may be obtained by dissolving the hydroxy-lactone compound (6) in an ether solvent (e.g., tetrahydrofuran or diethyl ether), and adding the organometallic reagent (4) corresponding to the substituent $R^3$, for example, a Grignard reagent (e.g., methylmagnesium chloride or ethylmagnesium chloride) or alkyl lithium reagent (e.g., methyllithium). An appropriate amount of organometallic reagent (4) used is 1.0 to 6.0 moles, more preferably 1.5 to 4.0 moles per mole of hydroxy-lactone compound (6). If organometallic reagent (4) is less than 1.0 mole, the addition reaction may not be driven to completion. More than 6.0 moles of the reagent may be uneconomical because of the increased expense of the reagent. The addition reaction may be carried out while cooling or heating the reaction system if desired, preferably at a temperature in the range from −30° C. to approximately the boiling point of a particular solvent used. It is desired for higher yields that the reaction time be determined by monitoring the progress of reaction by GC or TLC. The reaction time is usually about 0.5 to about 24 hours. The hydroxy-hemiacetal compound (7) may be recovered from the reaction mixture by ordinary aqueous work-up. If necessary, it can be purified by any standard technique such as distillation, chromatography or recrystallization.

The second step is a reaction of hydroxy-hemiacetal compound (7) with an esterifying agent (8), that is, esterifying the hydroxyl group on hydroxy-hemiacetal compound (7) to form hemiacetal compound (1aa).

The esterifying reaction may readily run by a well-known procedure. The preferred esterifying agent (8) is an acid chloride of formula (8) wherein $R^5$ is chlorine or a carboxylic anhydride of formula (8) wherein $R^5$ is —$OR^6$ wherein $R^6$ is a group of the following formula (9).

(9)

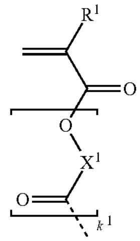

When an acid chloride such as methacrylic chloride is used as esterifying agent (8), the reaction may be conducted in a solventless system or in a solvent (e.g., methylene chloride, acetonitrile, toluene or hexane) by adding hydroxy-hemiacetal compound (7), acid chloride, and a base (e.g., triethylamine, pyridine or 4-dimethylaminopyridine) in sequence or at the same time, and optional cooling or heating. When a carboxylic anhydride such as methacrylic anhydride is used as esterifying agent (8), the reaction may be conducted in a solventless system or in a solvent (e.g., methylene chloride, acetonitrile, toluene or hexane) by adding hydroxy-hemiacetal compound (7), carboxylic anhydride, and a base (e.g., triethylamine, pyridine or 4-dimethylaminopyridine) in sequence or at the same time, and optional cooling or heating.

An appropriate amount of esterifying agent (8) used is 1 to 10 moles, more preferably 1 to 5 moles per mole of hydroxy-hemiacetal compound (7). If esterifying agent (8) is less than 1 mole, the reaction takes place insufficiently and a large fraction of hydroxy-hemiacetal compound (7) is left unreacted, with a substantial drop of yield. More than 10 moles of esterifying agent (8) may be uneconomical because of an increase expense of the agent and a lowering of pot yield.

The reaction time of second step is determined as appropriate by monitoring the reaction process by thin-layer chromatography (TLC) or gas chromatography (GC) because it is desirable from the yield aspect to drive the reaction to completion. Usually the reaction time is about 30 minutes to about 40 hours. The hemiacetal compound (1aa) may be recovered from the reaction mixture by ordinary aqueous work-up. If necessary, it can be purified by any standard technique such as distillation, recrystallization or chromatography.

Alternatively, hemiacetal compound (1a) may be synthesized by reacting a hemiacetal compound (1aa) with a protecting agent (10) as depicted by the following scheme.

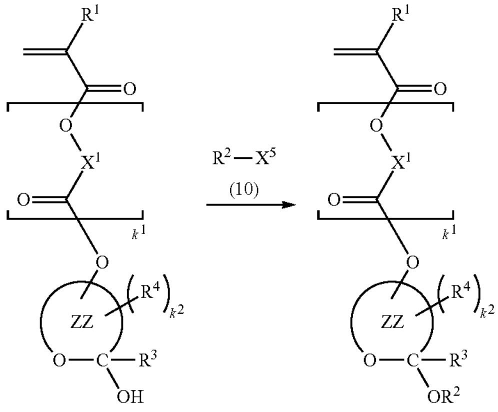

(Iaa) (Ia)

Herein $R^1$ to $R^4$, $X^1$, $k^1$, $k^2$, and ZZ are as defined above. $X^5$ is halogen, hydroxyl or sulfonyl.

Typical of the halogen represented by $X^5$ are chlorine, bromine and iodine. Inter alia, chlorine is most preferred because of ease of handling.

The reaction may readily run by a well-known procedure. When it is desired to obtain a hemiacetal compound of formula (1a) wherein $R^2$ is methoxymethyl, the reaction may be conducted in a solventless system or in a solvent by adding hemiacetal compound (1aa), protecting agent (10) (e.g., chloromethyl methyl ether), and a base (e.g., triethylamine, pyridine, N,N-diisopropylethylamine or 4-dimethylaminopyridine) in sequence or at the same time, and optional cooling or heating. An appropriate amount of protecting agent (10) used is 0.5 to 10 moles, more preferably 1.0 to 3.0 moles per mole of hemiacetal compound (1aa). If the protecting agent is less than 0.5 mole, a large fraction of the reactant is left unreacted, with a substantial drop of yield. More than 10 moles of the protecting agent may be uneconomical because of the increased amount of the agent and a lowering of pot yield. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. To the reaction system, a phase transfer catalyst such as tetrabutylammonium hydrogensulfate may be added. An appropriate amount of the phase transfer catalyst added is 0.0001 to 1.0 mole, more preferably 0.001 to 0.5 mole per mole of hemiacetal compound (1aa). Less than 0.0001 mole of the phase transfer catalyst may fail to exert catalytic effect whereas more than 1.0 mole may be uneconomical because of the increased catalyst cost.

It is desired for higher yields that the reaction time be determined by monitoring the progress of reaction by TLC or GC. The reaction time is usually about 30 minutes to about 40 hours. The hemiacetal compound (1a) may be recovered from the reaction mixture by ordinary aqueous work-up. If necessary, it can be purified by any standard technique such as distillation, recrystallization or chromatography.

When a protecting agent of formula (10) wherein $X^5$ is hydroxyl is used, the reaction of hemiacetal compound (1aa) with the corresponding alcohol (e.g., methanol or ethanol) may be conducted in a solventless system or in a solvent (e.g., toluene or hexane) in the presence of an acid catalyst at a temperature of 0 to 100° C. Suitable acid catalysts include mineral acids such as hydrochloric acid, sulfuric acid, nitric acid and perchloric acid and organic acids such as methanesulfonic acid, trifluoromethanesulfonic acid, p-toluenesulfonic acid and benzenesulfonic acid.

Polymer

A second embodiment of the invention is a polymer or high-molecular-weight compound comprising recurring units of at least one type selected from the general formulae (2a), (2b), (2c) and (2d).

(2a)

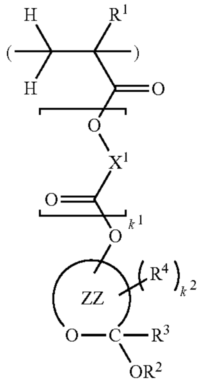

-continued (2b)

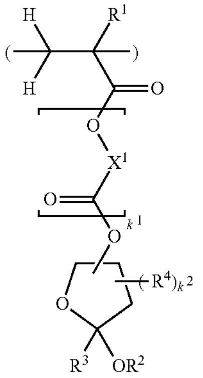

(2c)

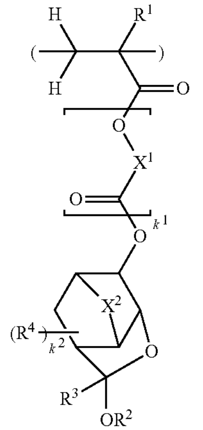

(2d)

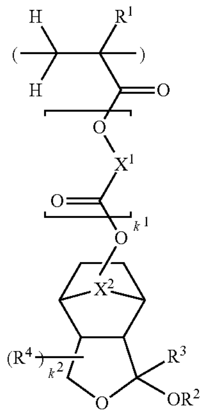

Herein $R^1$ is hydrogen, methyl or trifluoromethyl. $R^2$ to $R^4$ are each independently hydrogen or a straight, branched or cyclic, $C_1$-$C_{15}$ monovalent hydrocarbon group in which any constituent —$CH_2$— may be replaced by —O— or —C(═O)—. $X^1$ is a straight, branched or cyclic, $C_1$-$C_{15}$ divalent hydrocarbon group in which any constituent —$CH_2$— may be replaced by —O— or —C(═O)—. $X^2$ is —$CH_2$— or —O—. The ring ZZ designates a non-aromatic mono- or polycyclic ring of 4 to 20 carbon atoms having a hemiacetal structure, $k^1$ is 0 or 1, and $k^2$ is an integer of 0 to 3.

The polymer comprising recurring units (2a) to (2d) has a chemically active hemiacetal structure. Reference is made to a polymer comprising recurring units (2ca) of formula (2c) wherein $k^1$=$k^2$=0 as a typical example. When the polymer (2ca) is used as a base resin in a resist composition, an acetal exchange readily takes place under the action of the acid generated in the exposed region whereby the polymer is converted to a polymer comprising recurring units (2cb) or (2cc) as shown below. This brings about a substantial molecular weight buildup after exposure. It is thus believed that particularly in image formation via positive/negative reversal by organic solvent development, the solubility of the polymer in the developer is remarkably reduced, and the contrast is improved. Since only $R^2OH$ is lost by the acetal exchange reaction, a high carbon density and a resin film thickness are maintained. The resin film maintains satisfactory etch resistance, which is a pending problem with conventional negative tone resist by organic solvent development. Thus, a finer size pattern can be resolved.

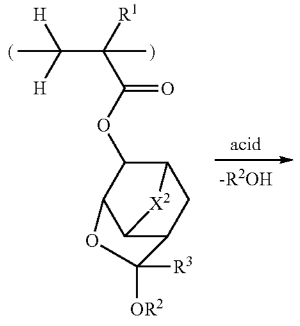

(2ca)

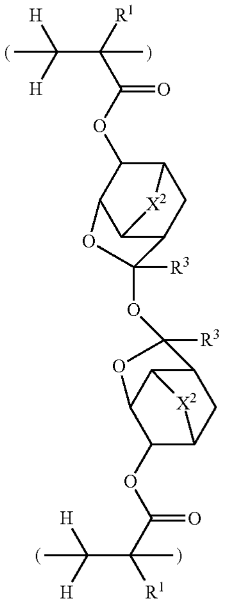

or

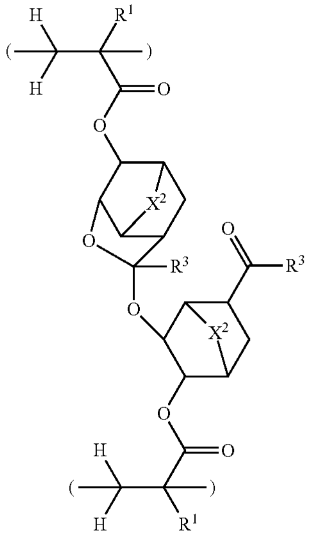

(2cb)

(2cc)

Herein $R^1$ to $R^3$ and $X^2$ are as defined above.

In addition to the units having formulae (2a) to (2d), the preferred polymer may further comprise recurring units of at least one type selected from recurring units having the general formulae (4A) to (4E).

(4A)

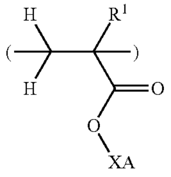

(4B)

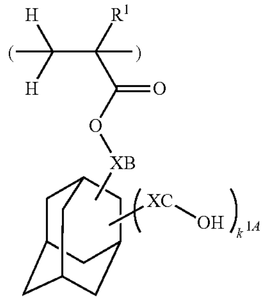

(4C)

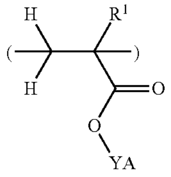

(4D)

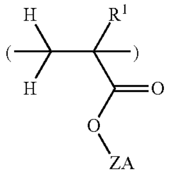

(4E)

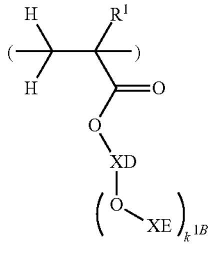

Herein $R^1$ is as defined above. XA is an acid labile group. XB and XC are each independently a single bond or a straight or branched, $C_1$-$C_4$ divalent hydrocarbon group. XD is a straight, branched or cyclic, $C_1$-$C_{16}$ di- to pentavalent aliphatic hydrocarbon group in which a constituent —$CH_2$— may be replaced by —O— or —C(═O)—. XE is an acid labile group. YA is a substituent group of lactone, sultone or carbonate structure. ZA is hydrogen, a $C_1$-$C_{15}$ fluoroalkyl group or a $C_1$-$C_{15}$ fluoroalcohol-containing group, $k^{1A}$ is an integer of 1 to 3, and $k^{1B}$ is an integer of 1 to 4.

A polymer comprising recurring units of formula (4A) is decomposed under the action of acid to generate carboxylic acid so that it may turn alkali soluble. The acid labile group XA may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

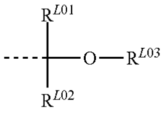

(L2)

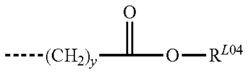

(L3)

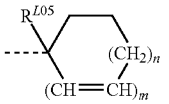

(L4)

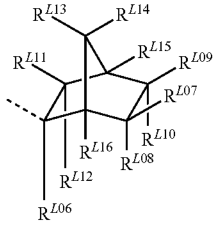

Herein $R^{L01}$ and $R^{L02}$ are each independently hydrogen or a straight, branched or cyclic alkyl group of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is an optionally substituted, straight, branched or cyclic $C_1$-$C_{10}$ alkyl group or an optionally substituted $C_6$-$C_{20}$ aryl group. $R^{L06}$ is an optionally substituted, straight, branched or cyclic $C_1$-$C_{10}$ alkyl group or an optionally substituted $C_6$-$C_{20}$ aryl group. $R^{L07}$ to $R^{L16}$ independently represent hydrogen or an optionally substituted monovalent hydrocarbon group of 1 to 15 carbon atoms. Letter y is an integer of 0 to 6, m is equal to 0 or 1, n is equal to 0, 1, 2 or 3, and 2m+n is equal to 2 or 3. The broken line denotes a valence bond.

In formula (L1), exemplary groups of $R^{L01}$ and $R^{L02}$ include methyl, ethyl, propyl, isopropyl, n-butyl, sec-butyl, tert-butyl, cyclopentyl, cyclohexyl, 2-ethylhexyl, n-octyl, and adamantyl.

$R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. Illustrative examples of the straight, branched or cyclic alkyl groups are as exemplified above for $R^{L01}$ and $R^{L02}$, and examples of the substituted alkyl groups are as shown below.

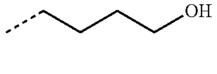

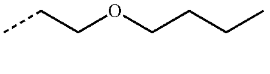

-continued

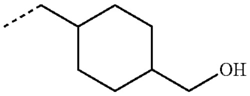
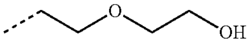
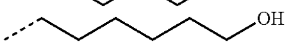
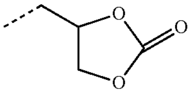

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of ring-forming $R^{L01}$, $R^{L02}$ and $R^{L03}$ is a straight or branched alkylene group of 1 to 18 carbon atoms, preferably 1 to 10 carbon atoms when they form a ring.

In formula (L2), exemplary tertiary alkyl groups of $R^{L04}$ are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), examples of the optionally substituted $C_1$-$C_{10}$ alkyl groups of $R^{L05}$ include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxyl, alkoxycarbonyl, oxo, amino, alkylamino, cyano, mercapto, alkylthio, sulfo or other groups or in which a methylene moiety is replaced by an oxygen or sulfur atom. Examples of optionally substituted $C_6$-$C_{20}$ aryl groups include phenyl, methylphenyl, naphthyl, anthryl, phenanthryl, and pyrenyl.

In formula (L4), examples of optionally substituted, straight, branched or cyclic $C_1$-$C_{10}$ alkyl groups and optionally substituted $C_6$-$C_{20}$ aryl groups of $R^{L06}$ are the same as exemplified for $R^{L05}$. Exemplary $C_1$-$C_{15}$ monovalent hydrocarbon groups of $R^{L07}$ to $R^{L16}$ include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom(s) to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, or $R^{L13}$ and $R^{L14}$ form a ring). Each of $R^{L07}$ to $R^{L16}$ represents a $C_1$-$C_{15}$ divalent hydrocarbon group, typically alkylene, when they form a ring, examples of which are those exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, or $R^{L13}$ and $R^{L15}$).

Of the acid labile groups of formula (L1), the straight and branched ones are exemplified by the following groups.

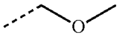
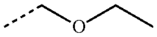
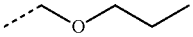
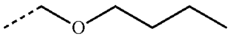
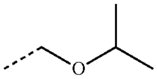
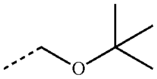
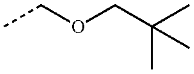
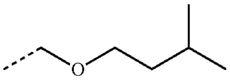
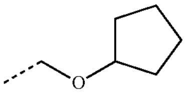
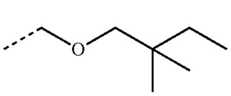
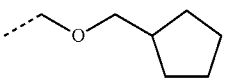
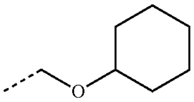
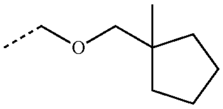
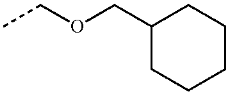
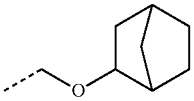
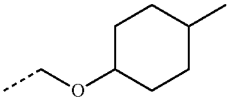
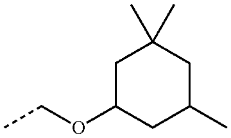
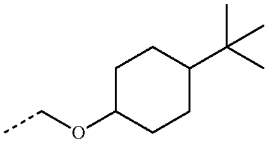
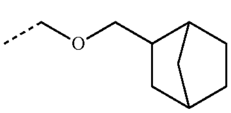
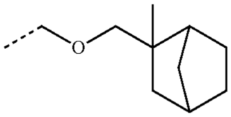
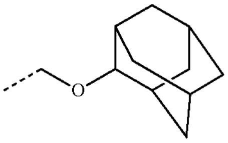
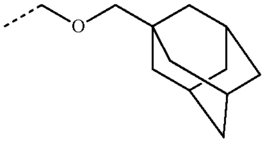
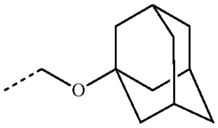
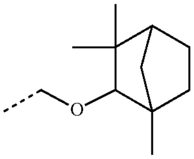
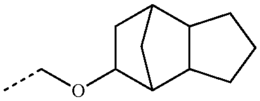
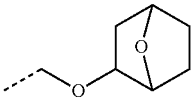
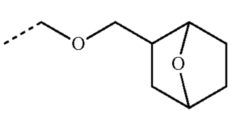
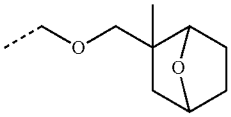
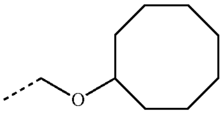
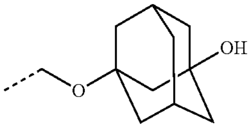
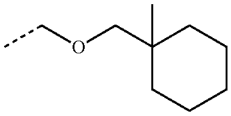
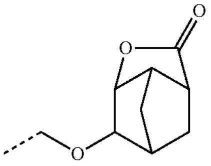

-continued

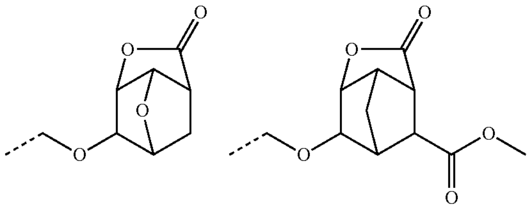

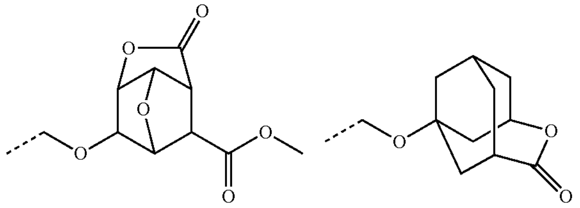

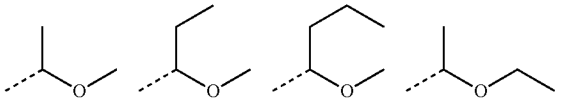

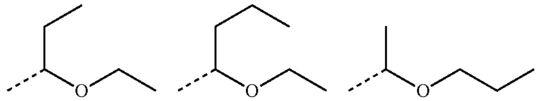

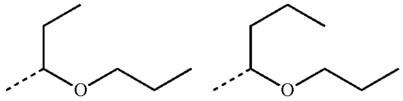

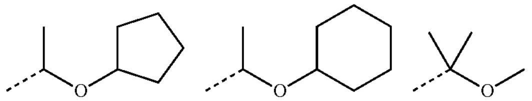

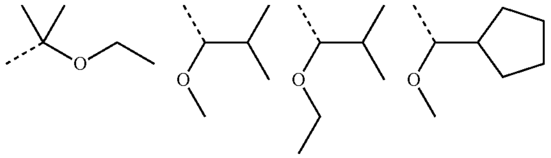

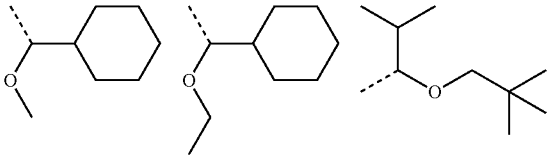

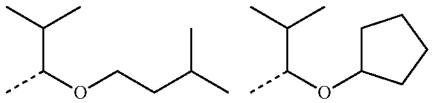

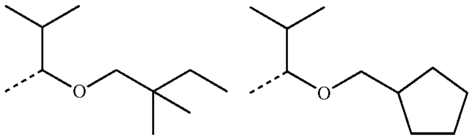

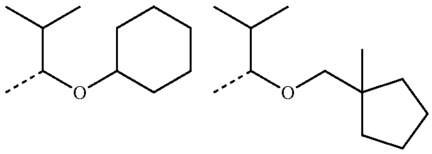

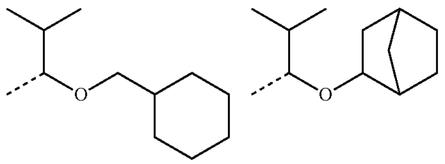

-continued

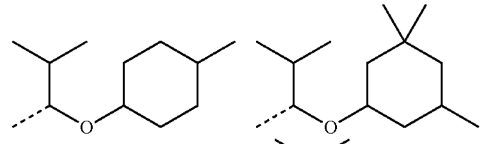

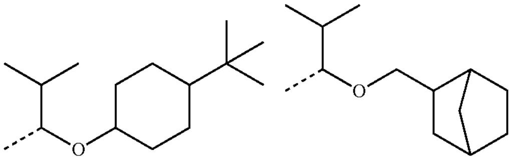

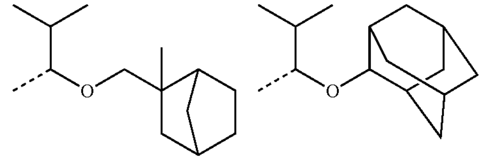

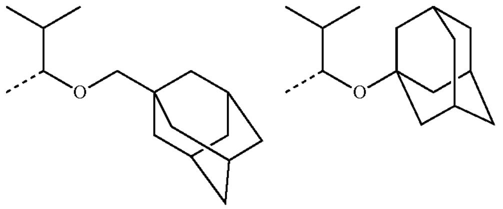

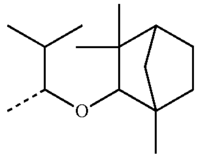

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethyl cyclopentyloxycarbonyl, 1-ethyl cyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

(L4-1)

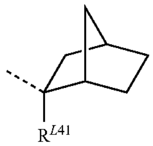

$R^{L41}$

-continued (L4-2)

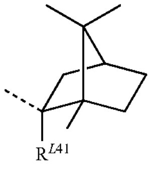

(L4-3)

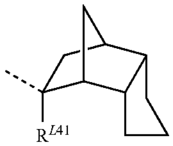

(L4-4)

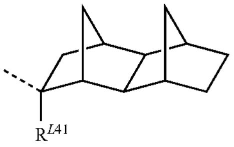

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

(L4-3-1)

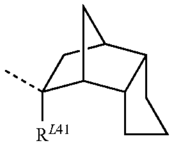

(L4-3-2)

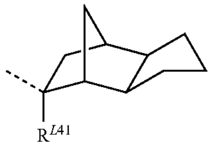

Note that $R^{L41}$ is as defined above.

Similarly, the general formula (L4-4) represents one or a mixture of two or more selected from groups having the following general formulas (L4-4-1) to (L4-4-4).

(L4-4-1)

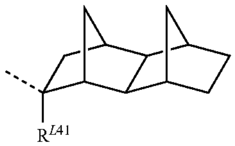

-continued (L4-4-2)

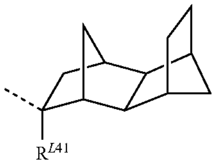

(L4-4-3)

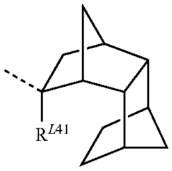

(L4-4-4)

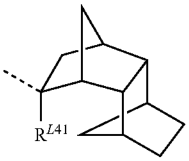

Note that $R^{41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

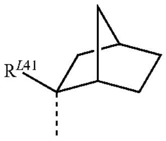

(L4-2-endo)

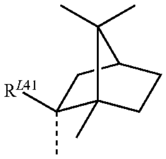

(L4-3-endo)

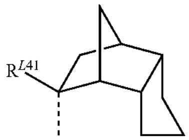

-continued (L4-4-endo)

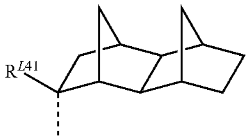

Note that $R^{L41}$ is as defined above.

Illustrative examples of the acid labile group of formula (L4) are given below

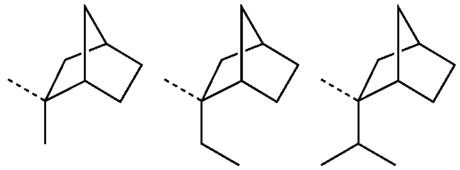

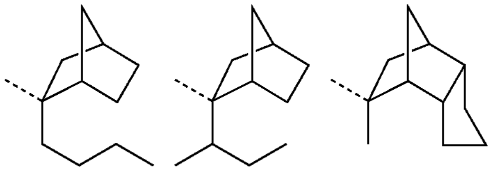

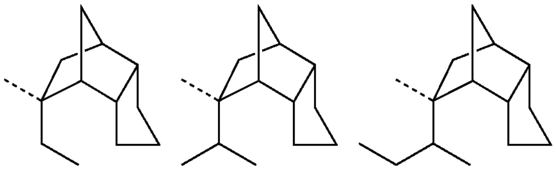

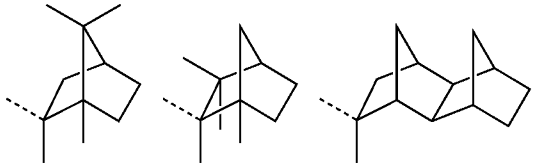

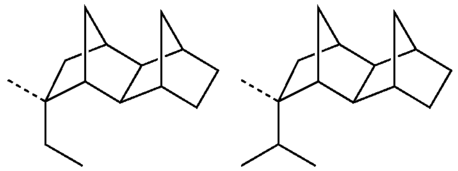

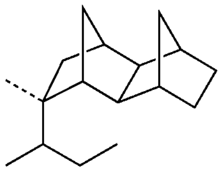

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups, represented by XA, are as exemplified for $R^{L04}$ and the like.

Illustrative examples of the recurring units having formula (4A) are given below, but not limited thereto.

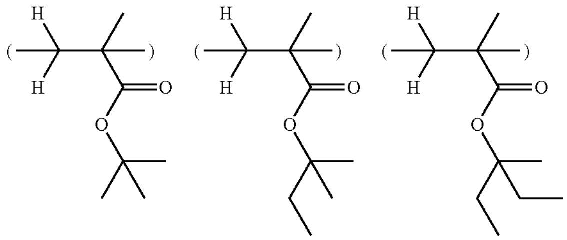

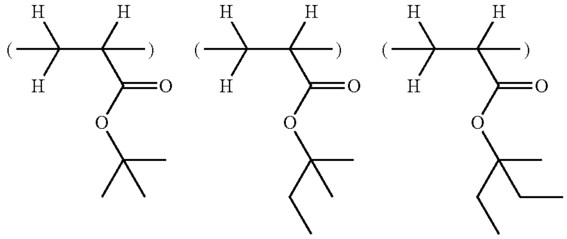

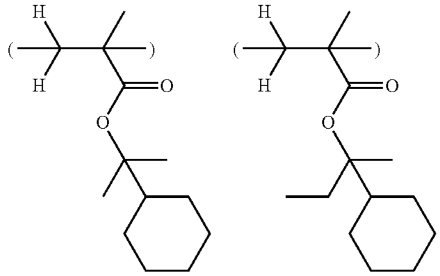

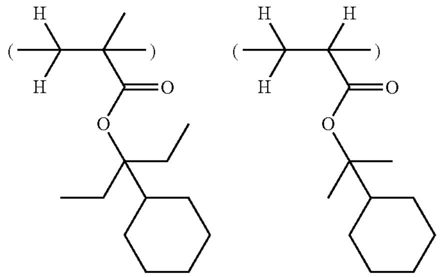

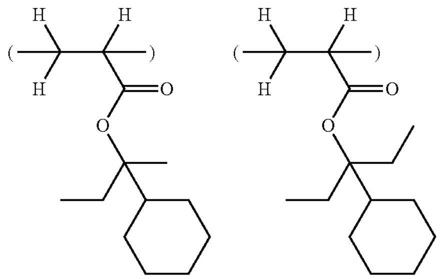

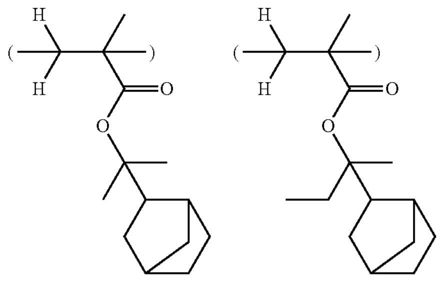

-continued
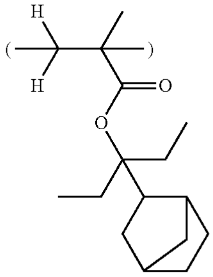
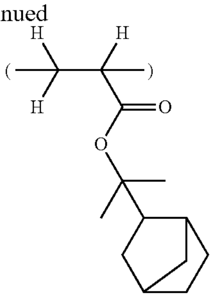
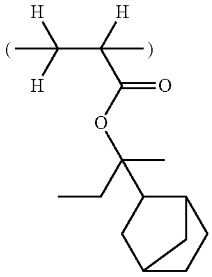
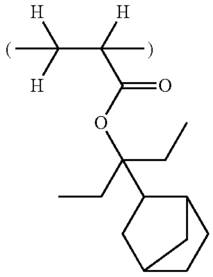
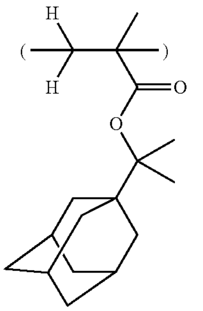
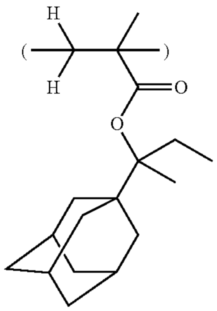
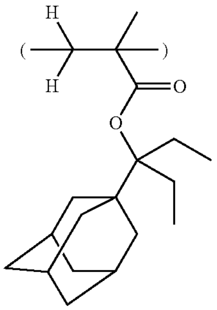
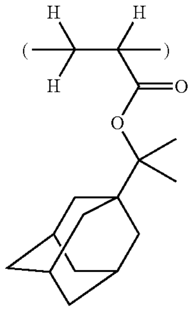
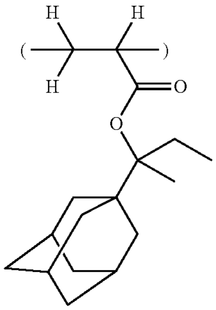
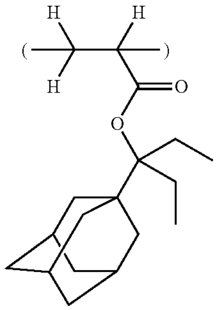
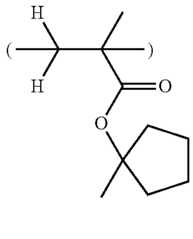
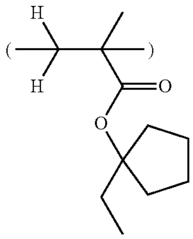
-continued
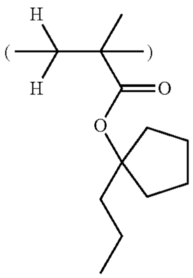
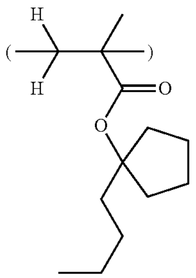
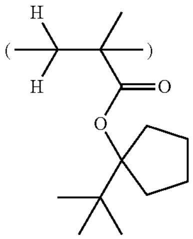
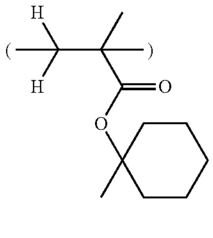
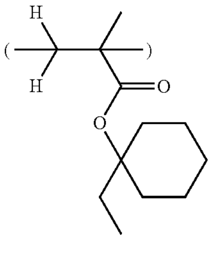
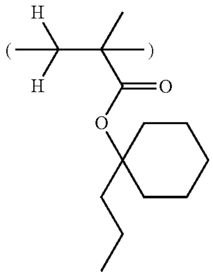
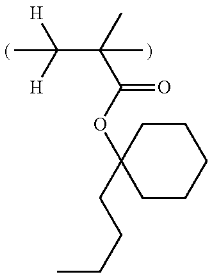
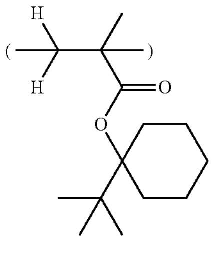
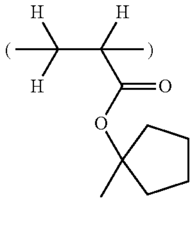
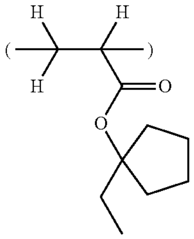
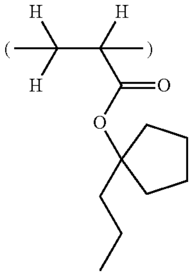
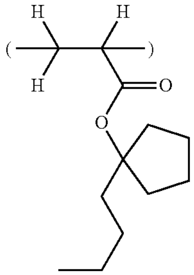

-continued
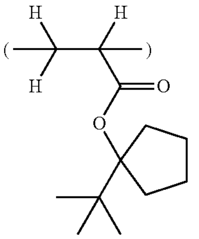
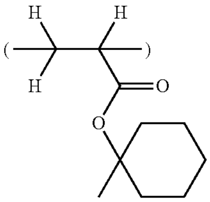
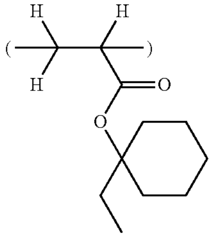
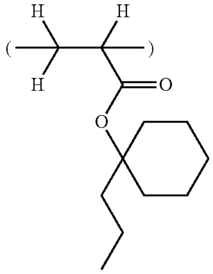
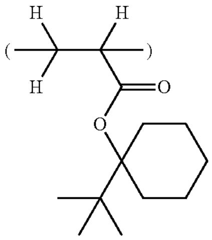
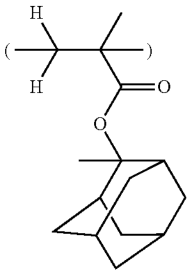
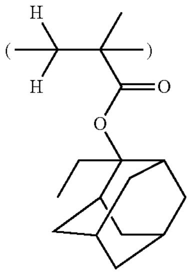
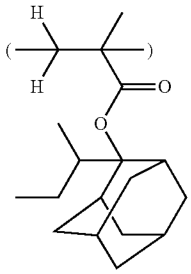
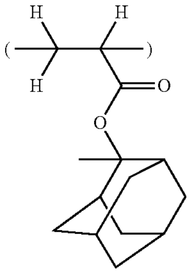
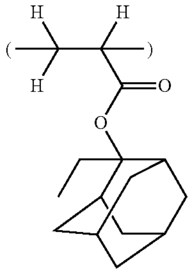
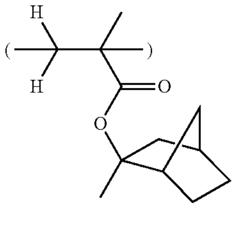
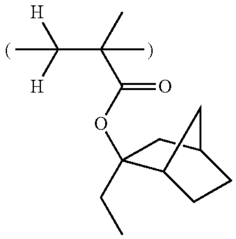
-continued
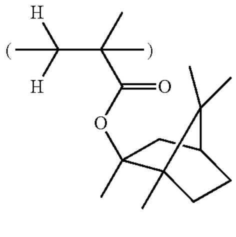
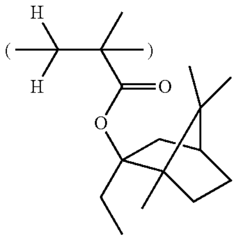
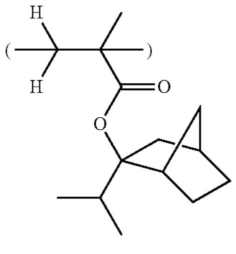
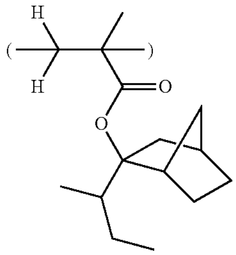
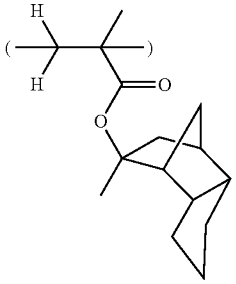
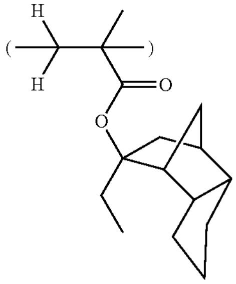
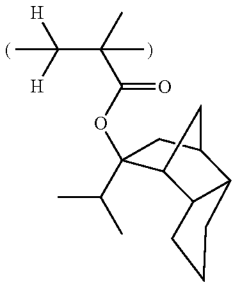
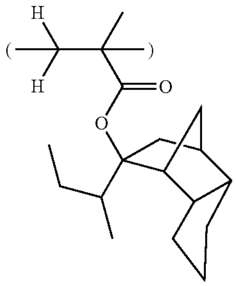
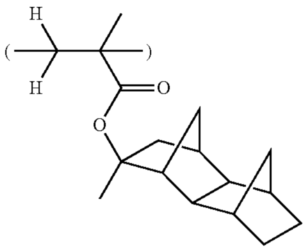
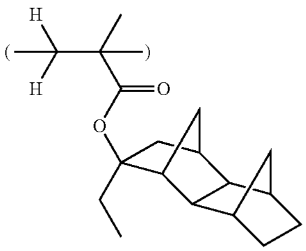

-continued
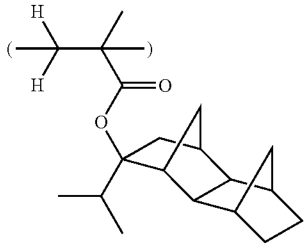
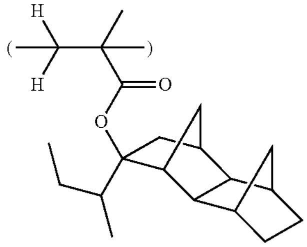
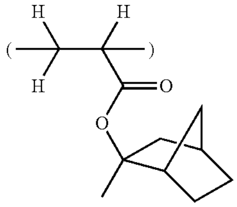
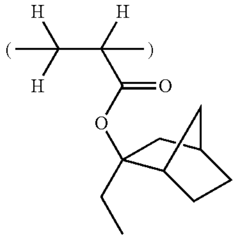
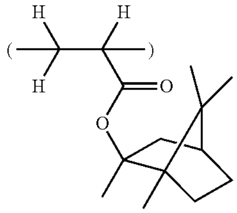
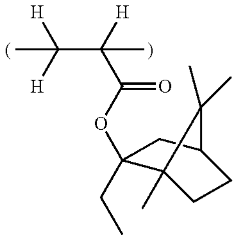
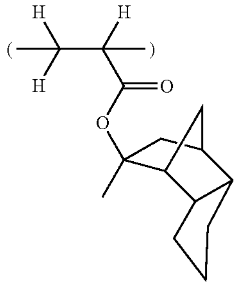
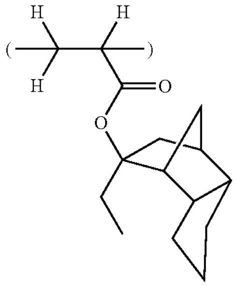
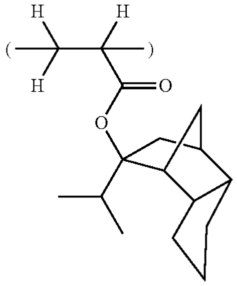
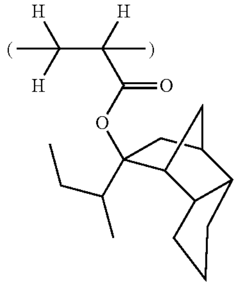
-continued
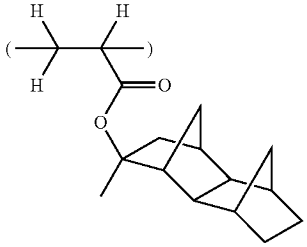
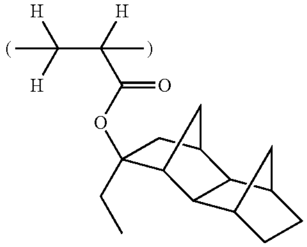
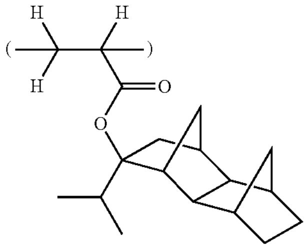
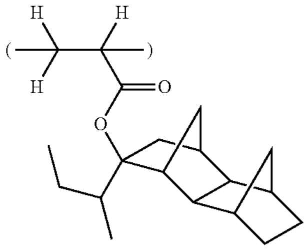
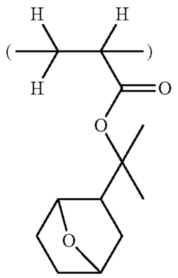
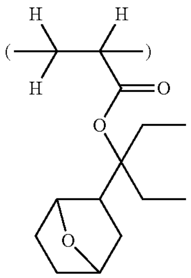
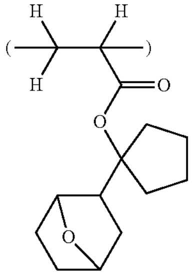
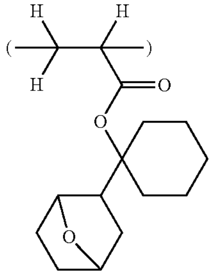

-continued
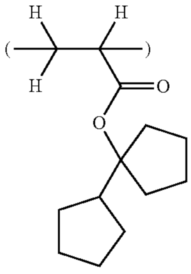
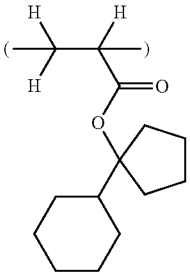
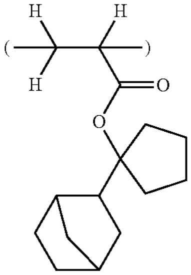
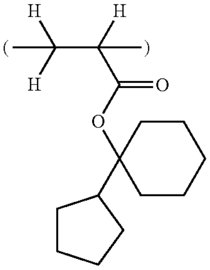
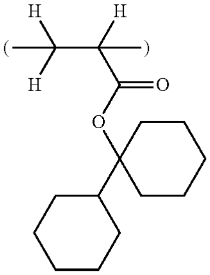
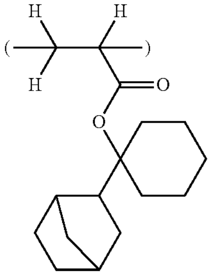
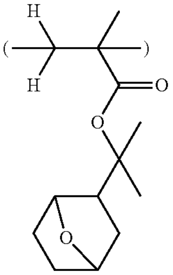
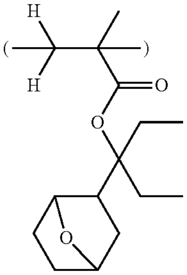
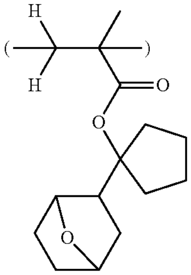
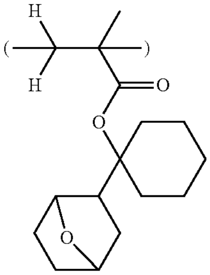
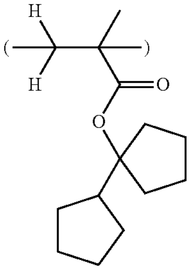
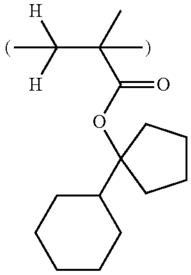
-continued
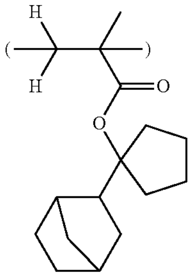
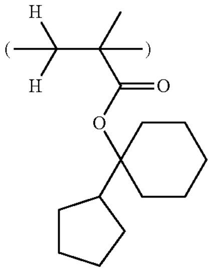
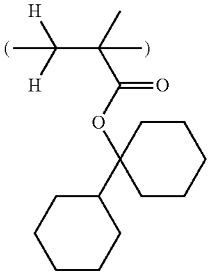
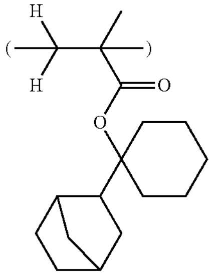
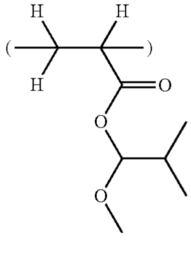
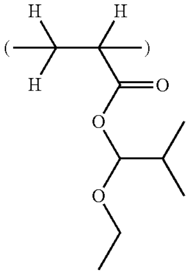
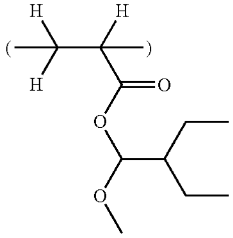
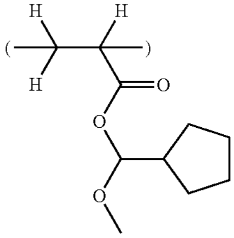
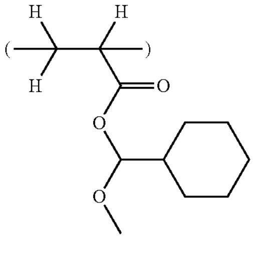
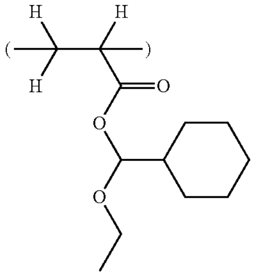
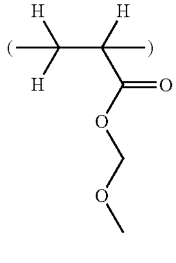
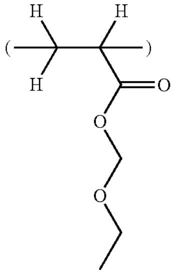

-continued
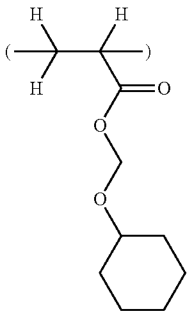
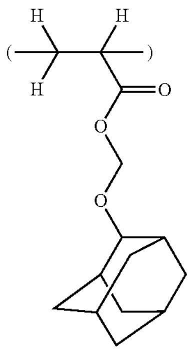
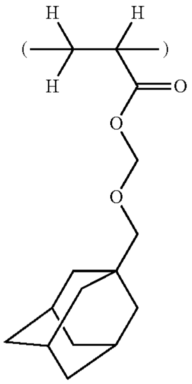
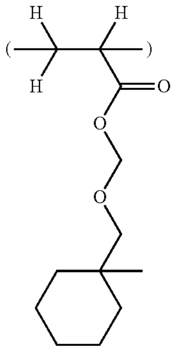
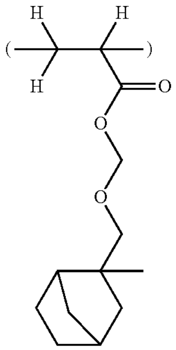
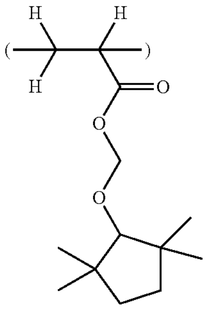
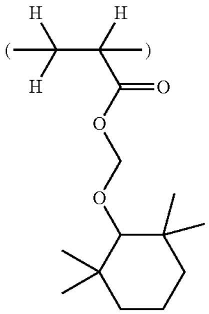
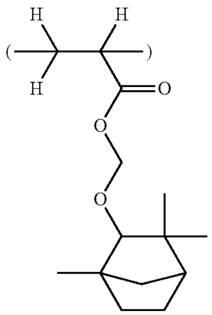
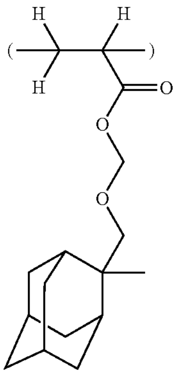
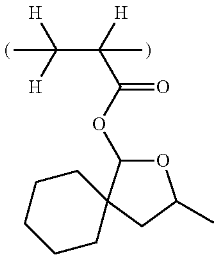
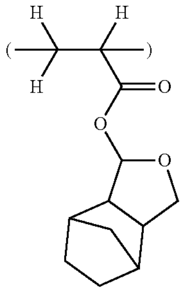
-continued
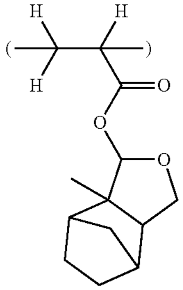
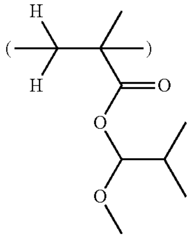
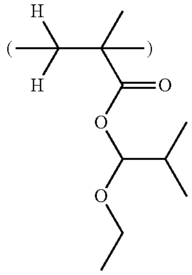
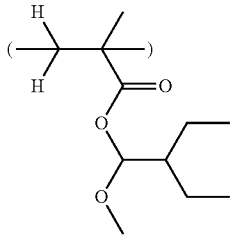
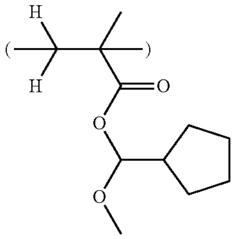
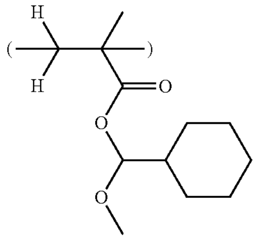
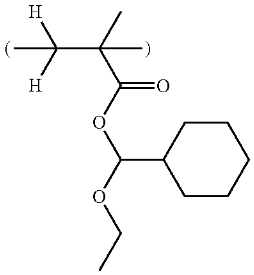
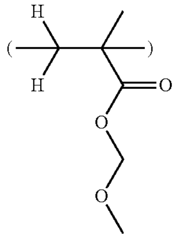
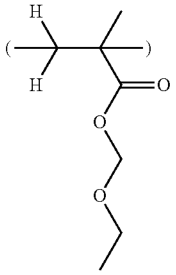
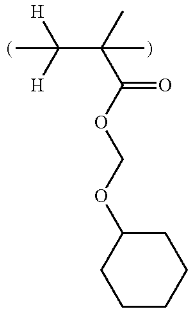
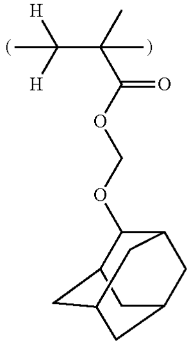
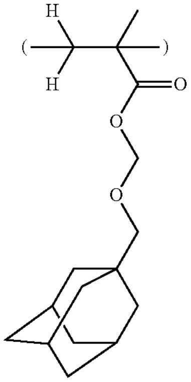
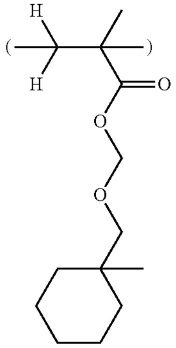

-continued
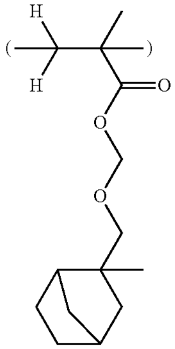
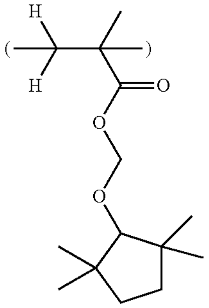
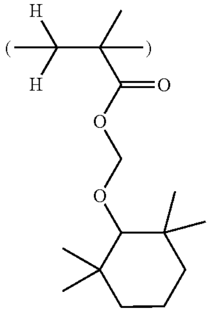
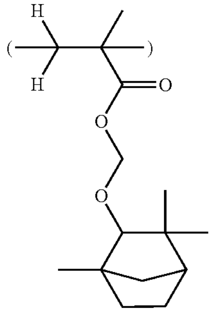
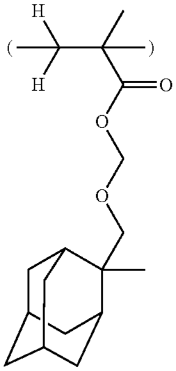
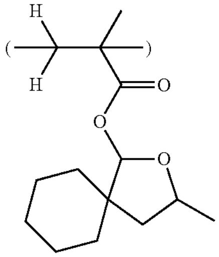
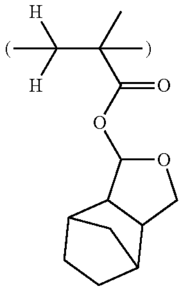
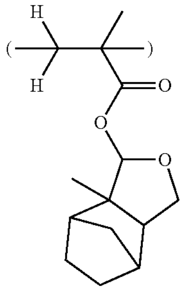
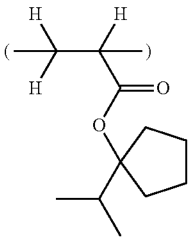
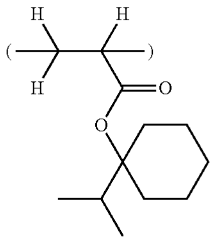
-continued
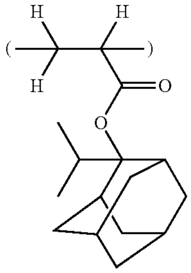
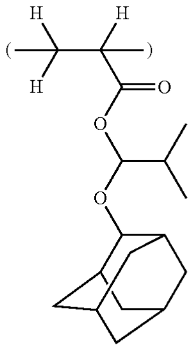
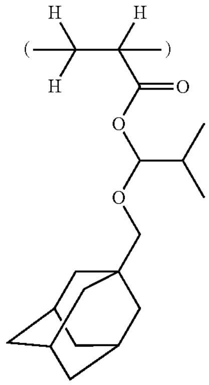
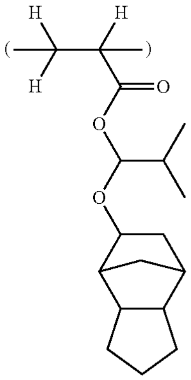
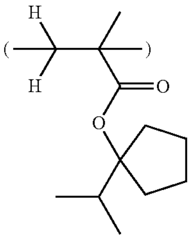
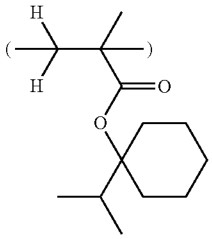
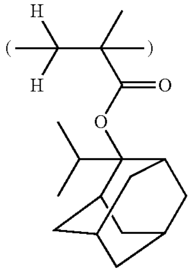
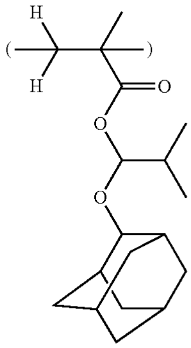
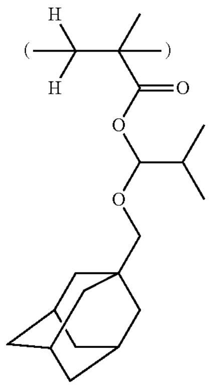
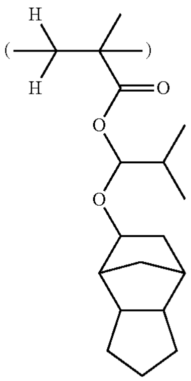

-continued
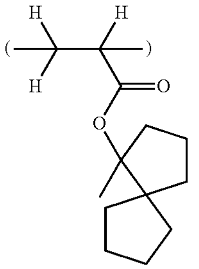
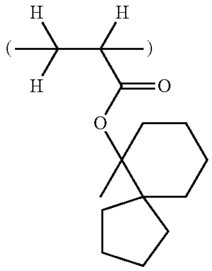
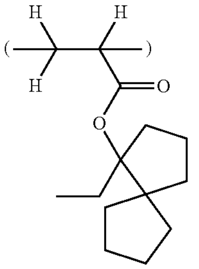
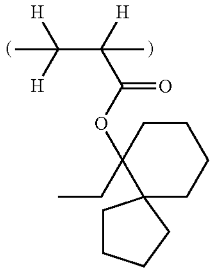
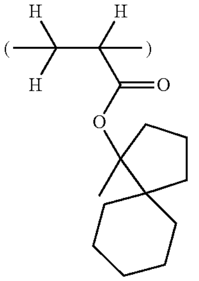
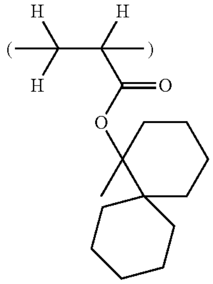
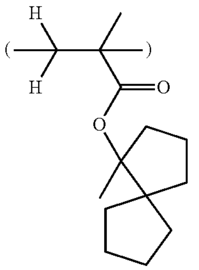
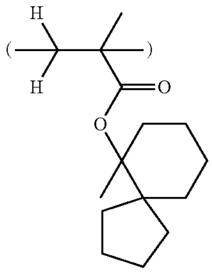
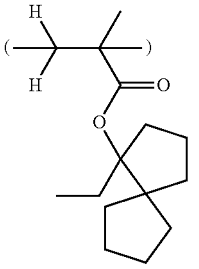
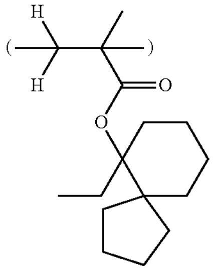
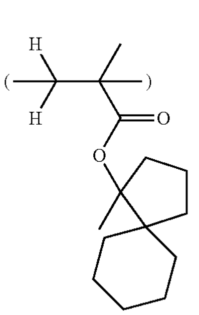
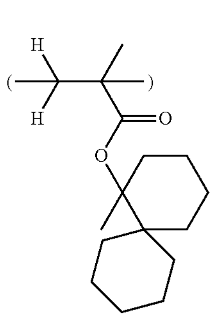
-continued
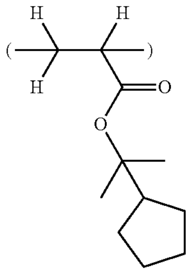
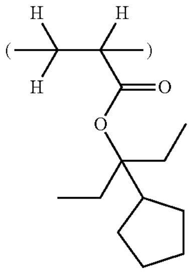
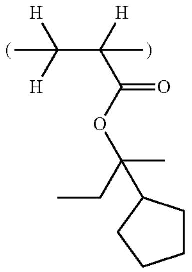
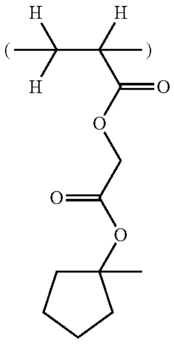
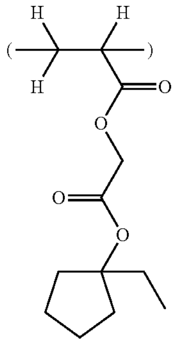
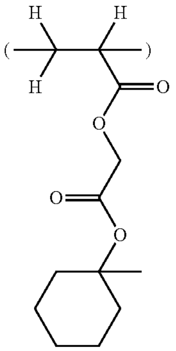
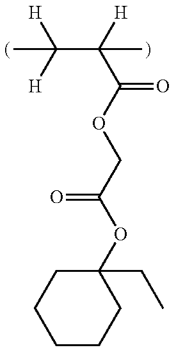
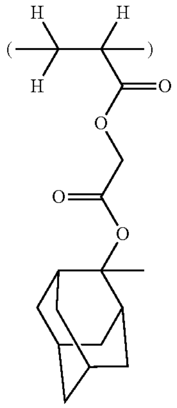
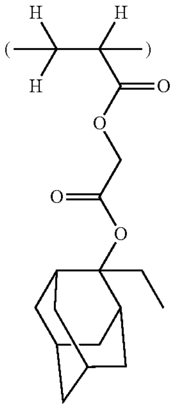
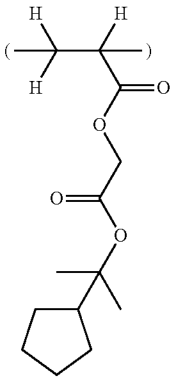
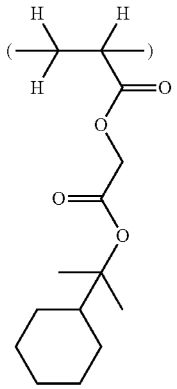
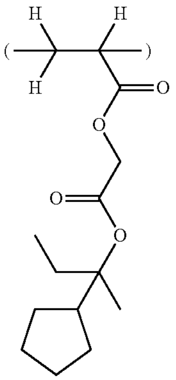

-continued
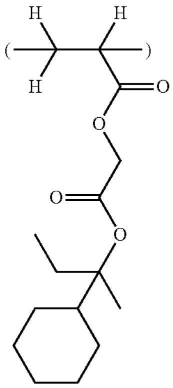
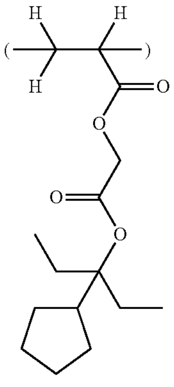
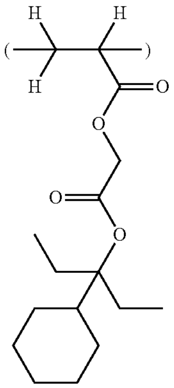
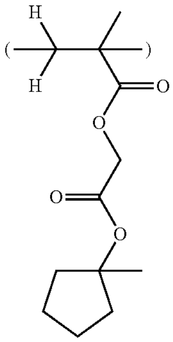
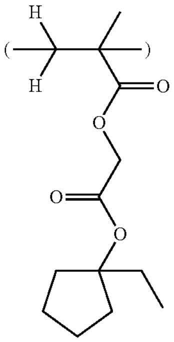
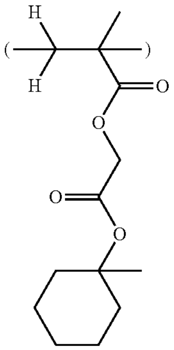
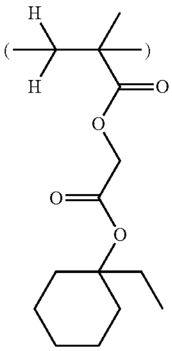
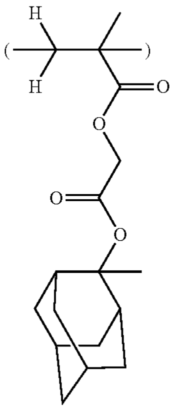
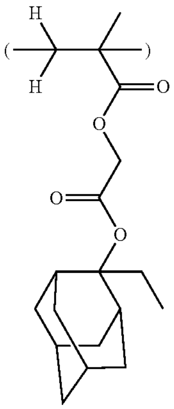
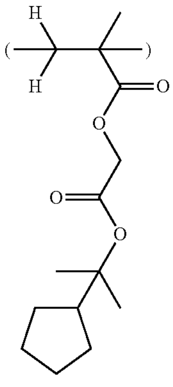
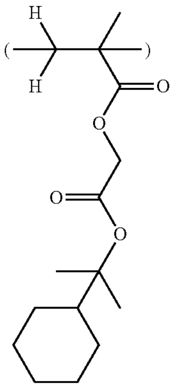
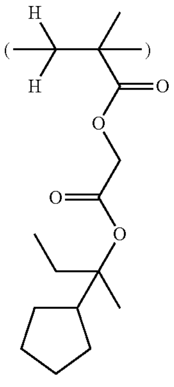
-continued
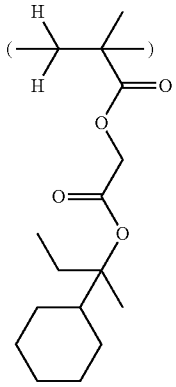
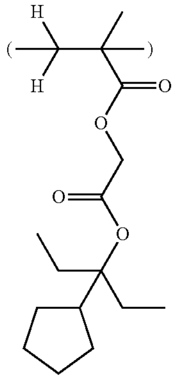
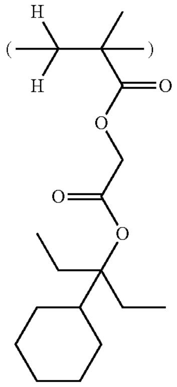
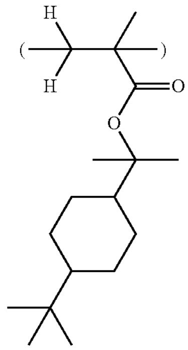
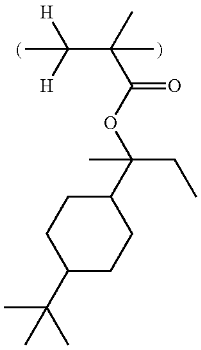
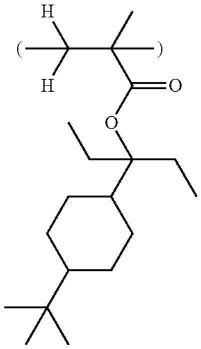
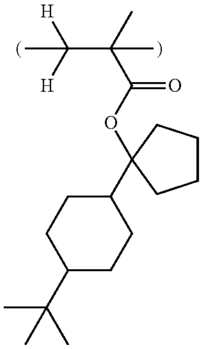
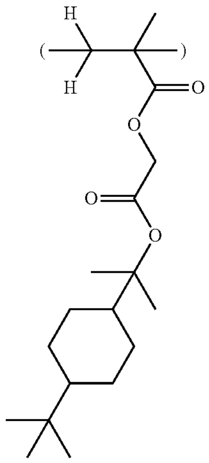
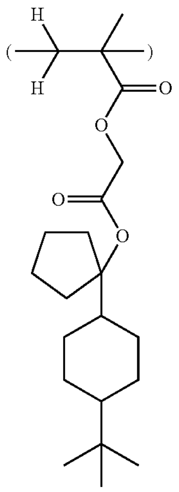
Illustrative examples of the recurring units having formula (4B) are given below, but not limited thereto.

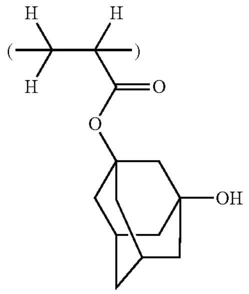
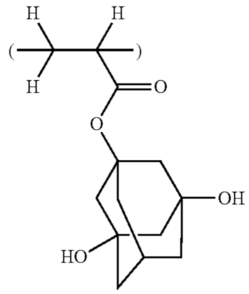
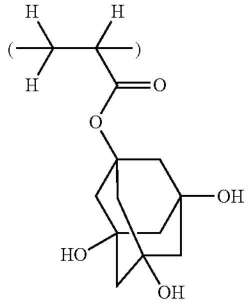
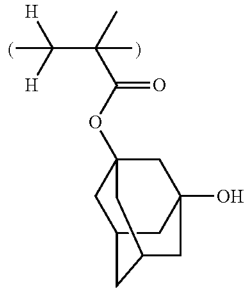
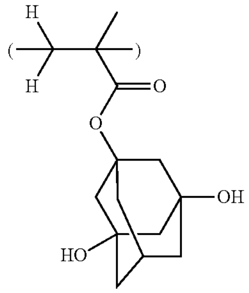
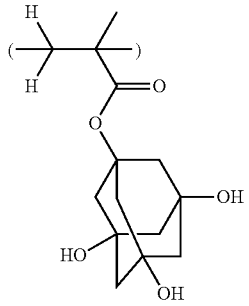
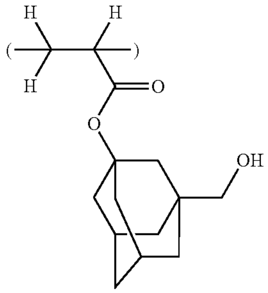
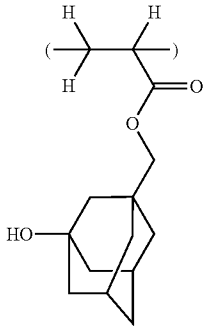
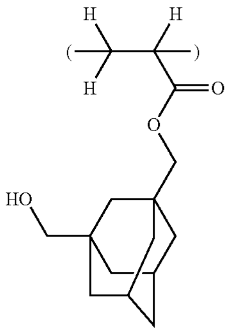
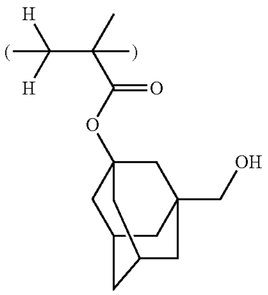
-continued
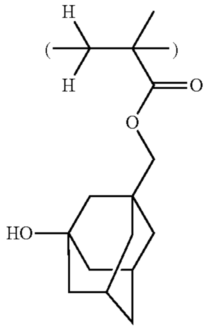
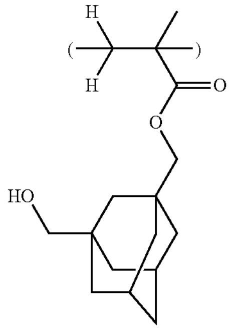
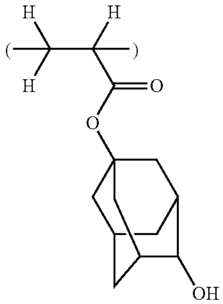
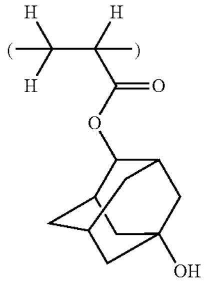
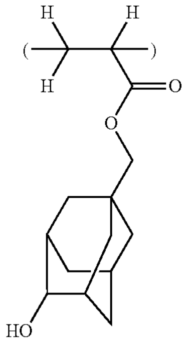
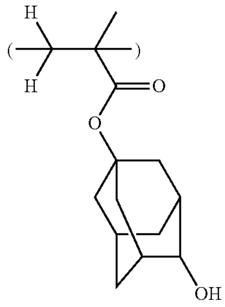
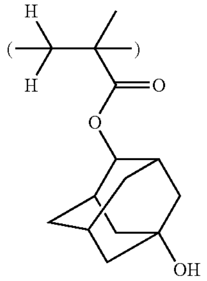
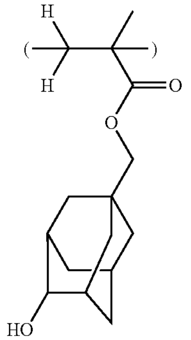
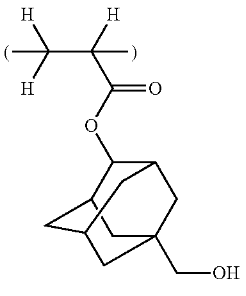
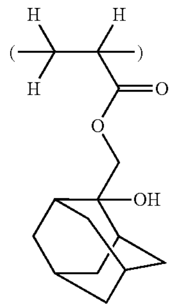

-continued
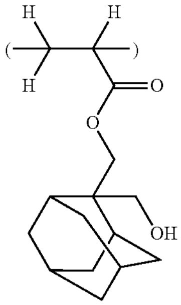
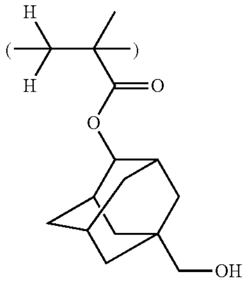
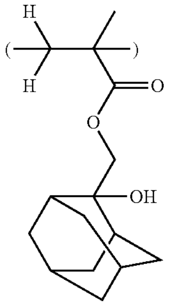
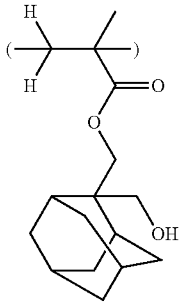
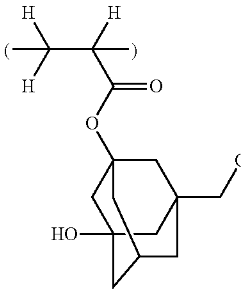
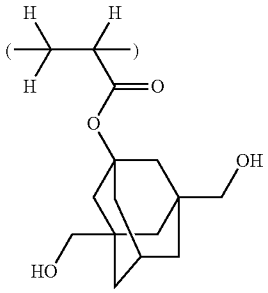
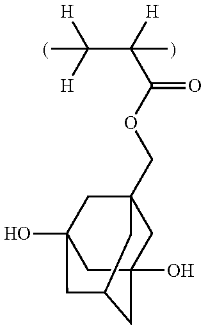
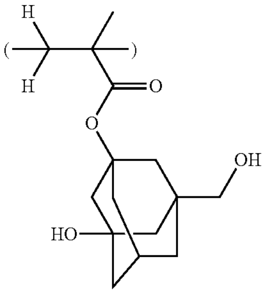
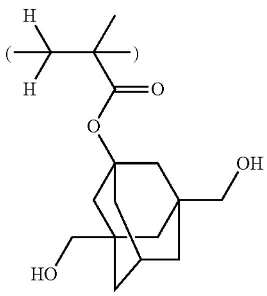
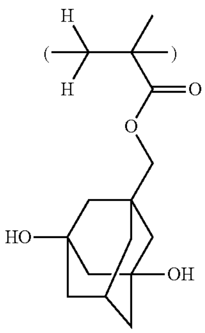
-continued
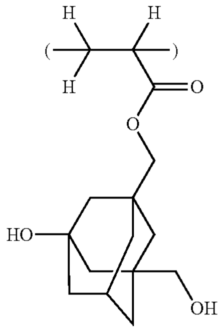
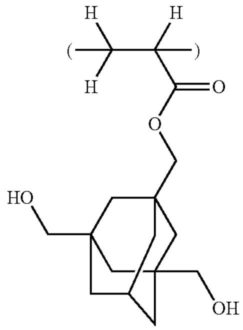
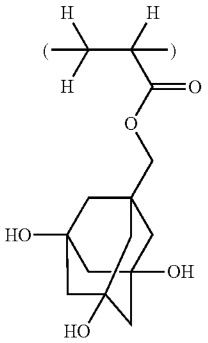
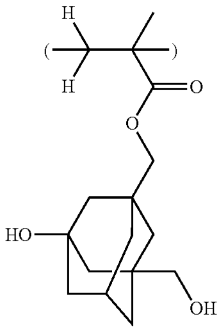
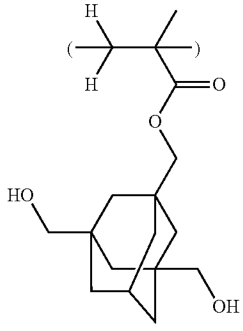
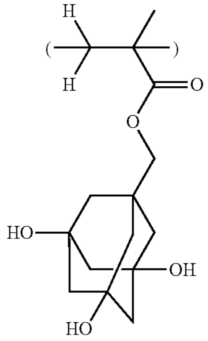
Illustrative examples of the recurring units having formula (4C) are given below, but not limited thereto.
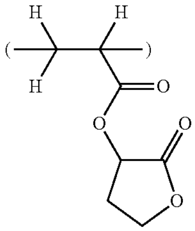
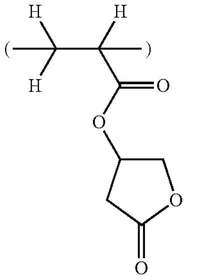
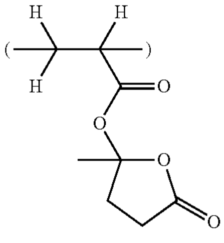
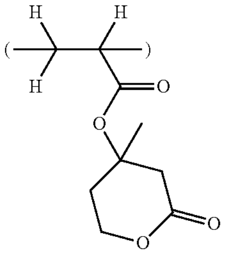

-continued
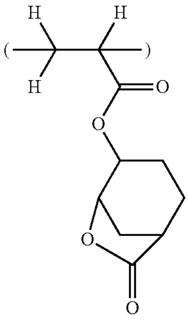
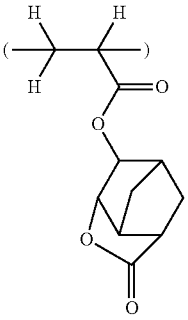
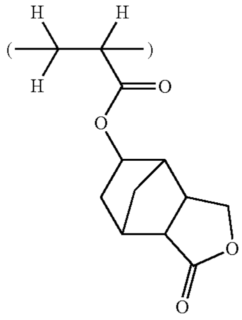
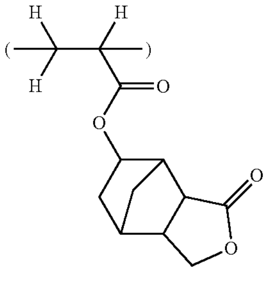
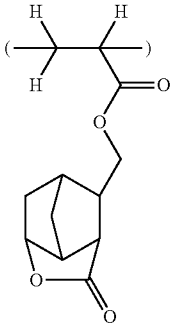
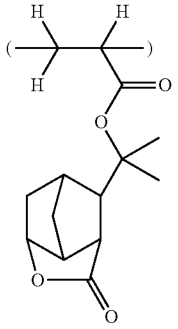
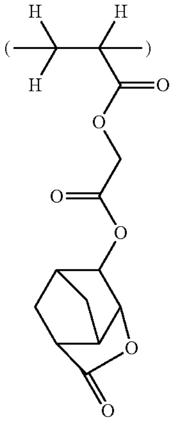
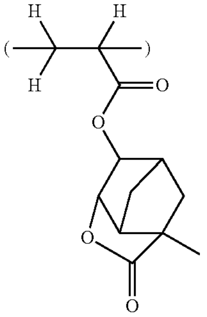
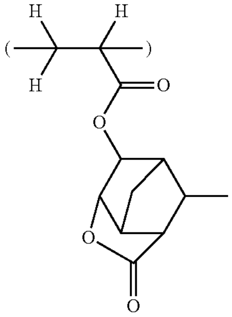
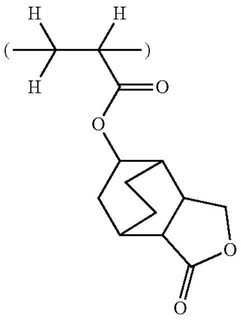
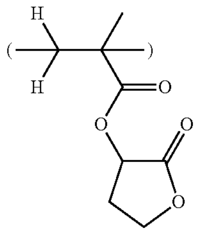
-continued
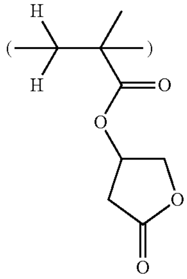
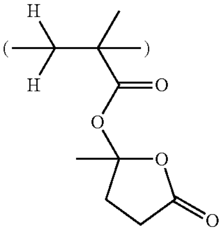
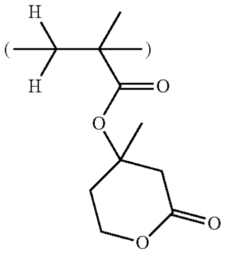
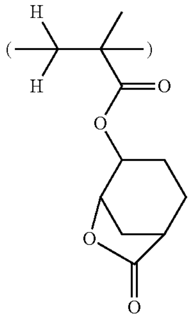
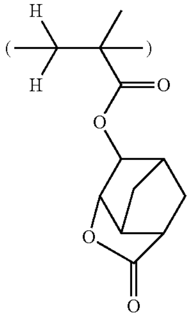
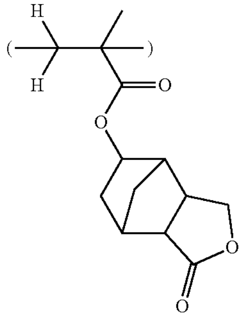
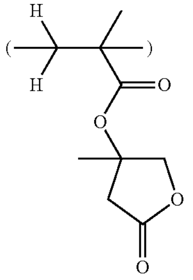
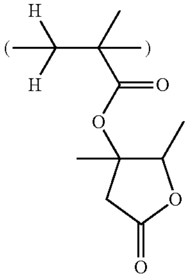
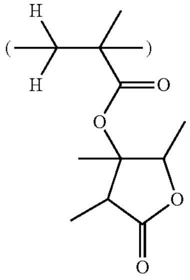
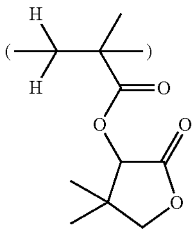
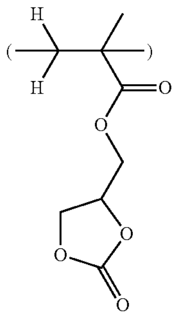
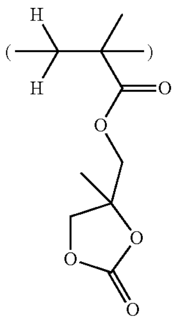

-continued
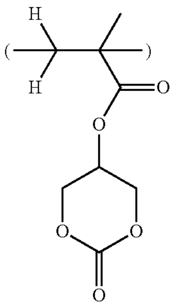
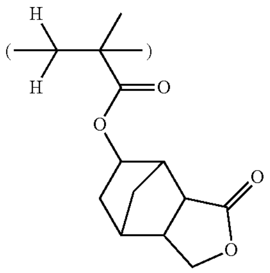
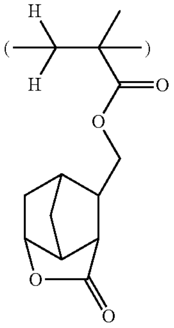
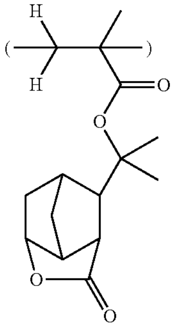
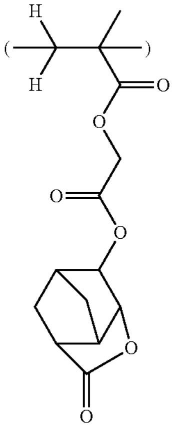
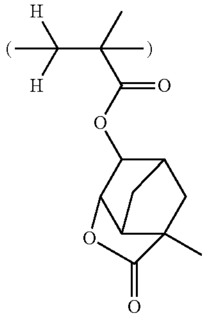
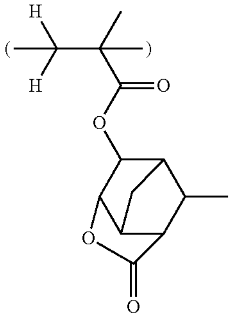
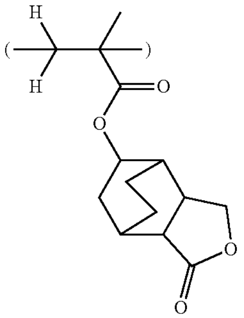
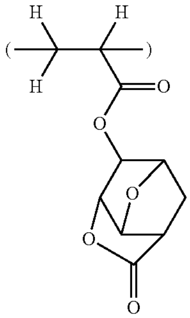
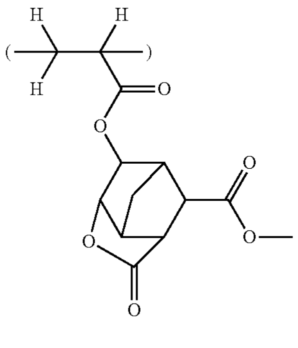
-continued
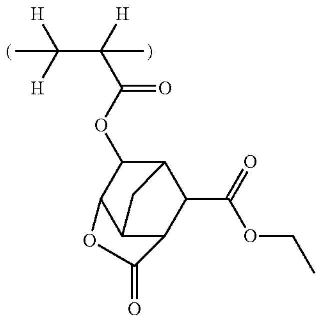
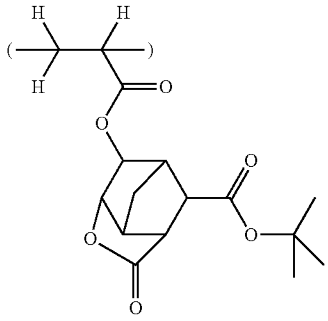
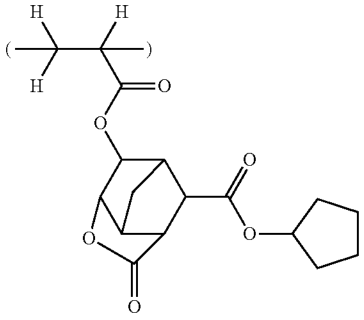
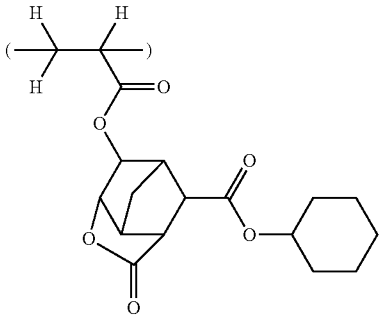
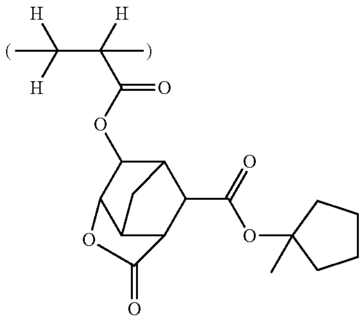

-continued
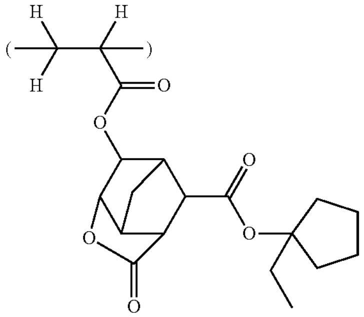
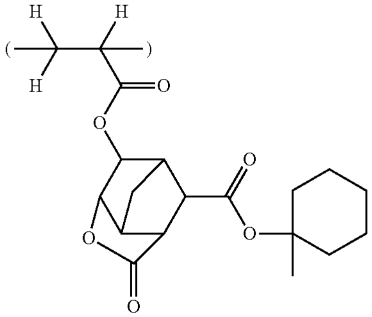
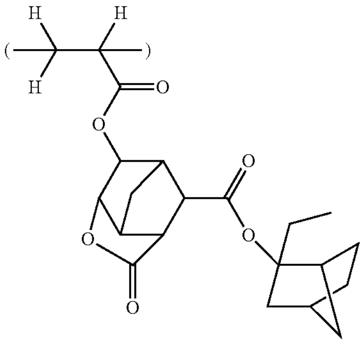
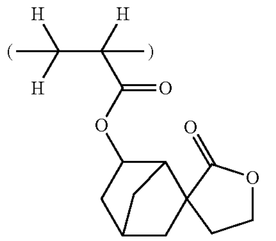
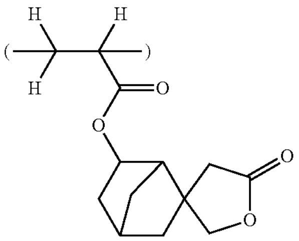
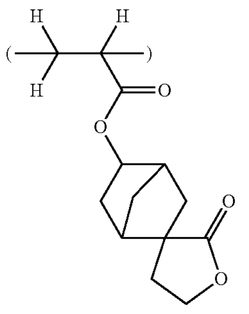
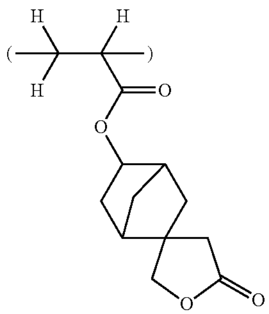
-continued
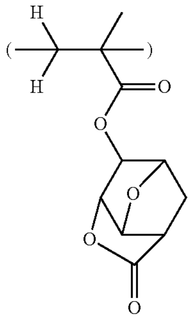
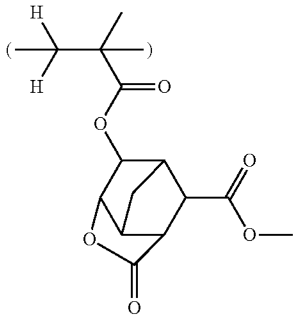
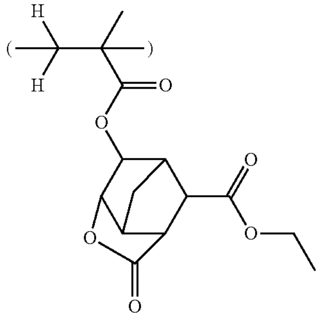
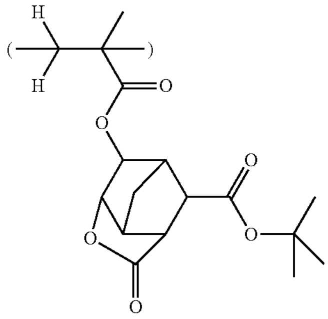
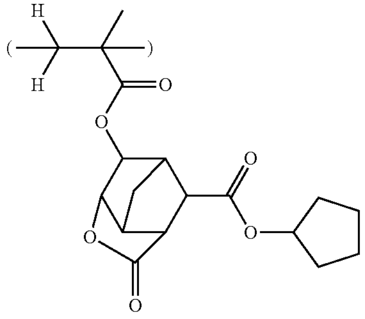
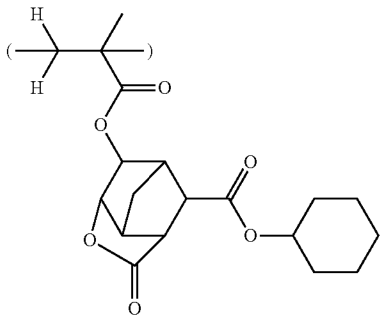

-continued
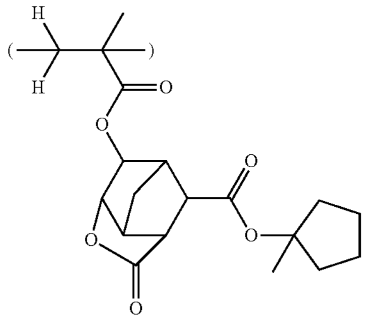
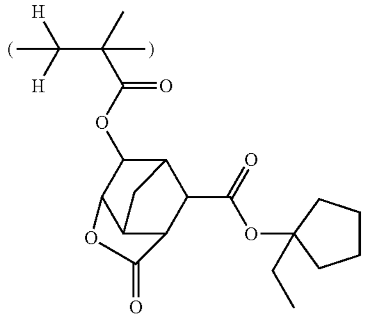
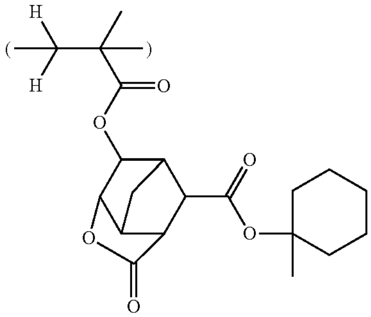
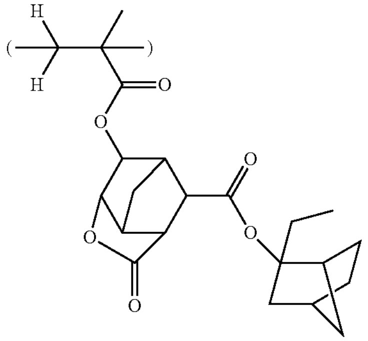
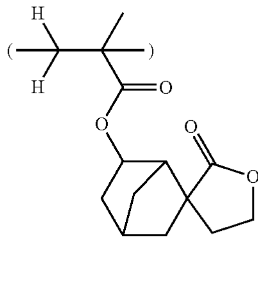
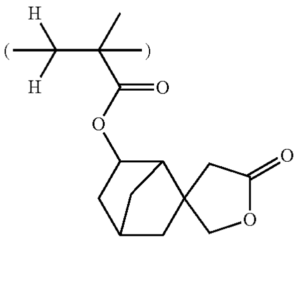
-continued
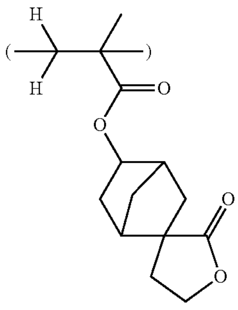
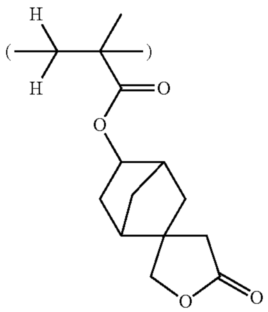
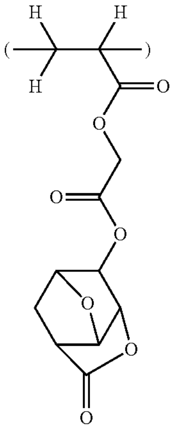
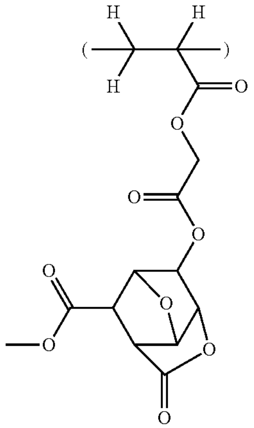
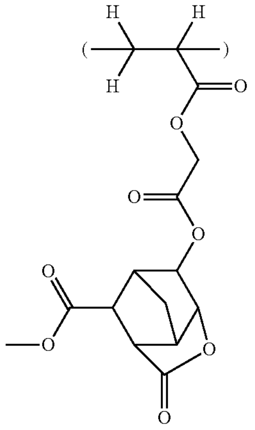
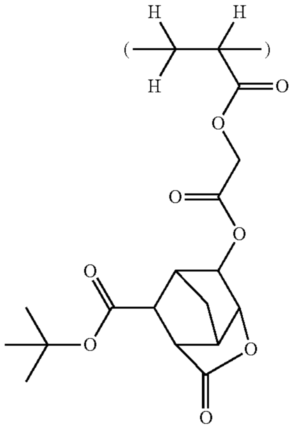
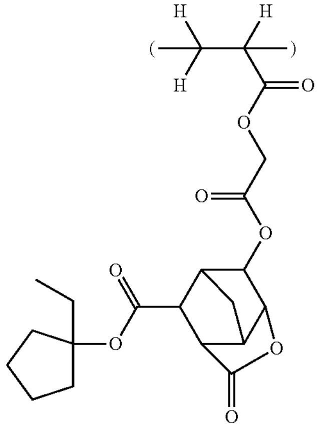

-continued
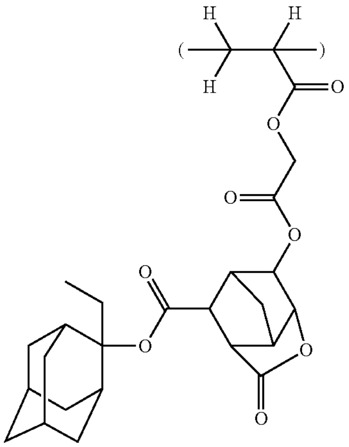
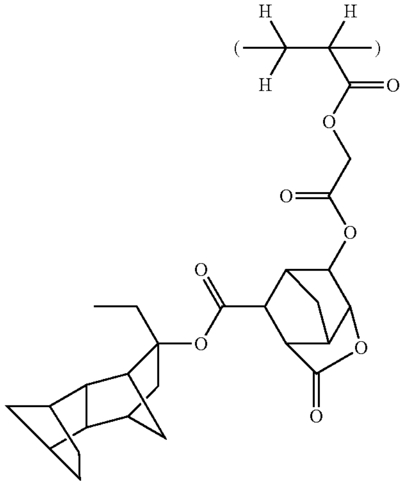
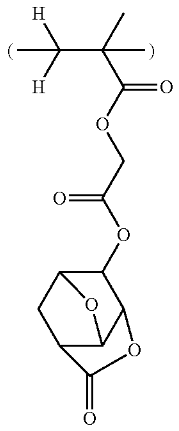
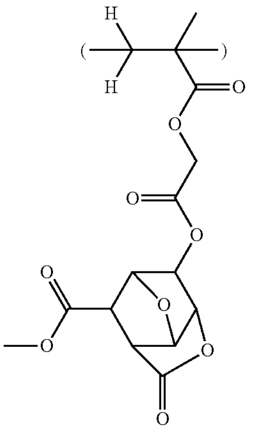
-continued
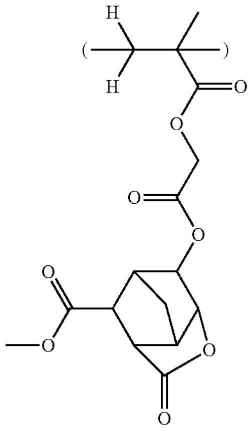
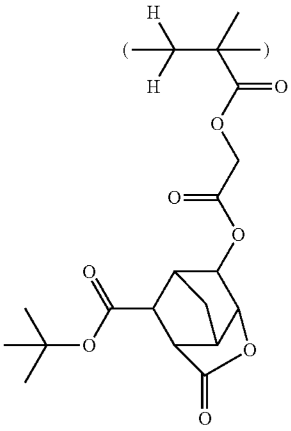
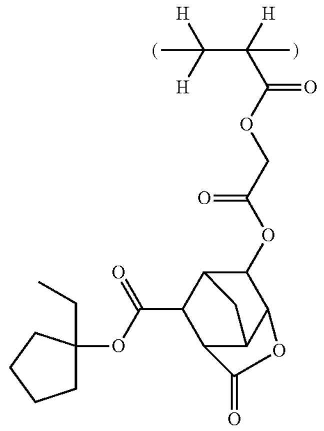
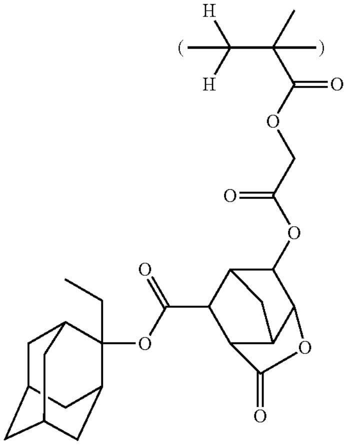

-continued
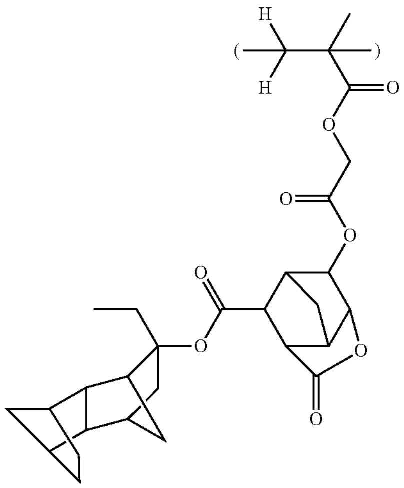
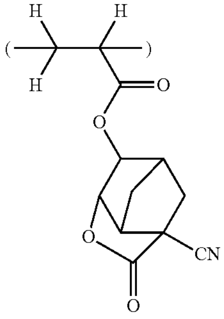
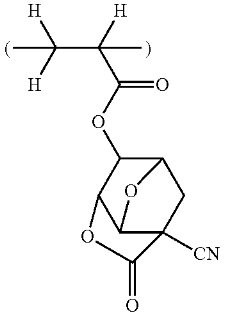
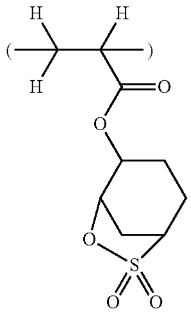
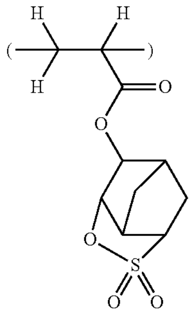
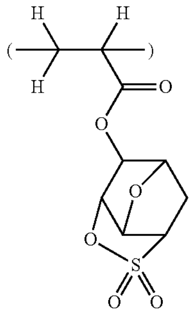
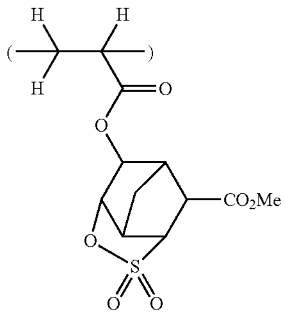
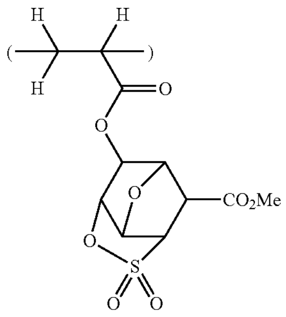
-continued
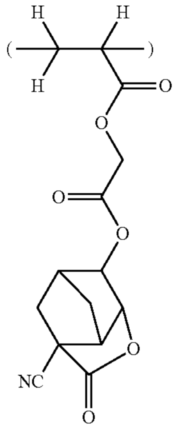
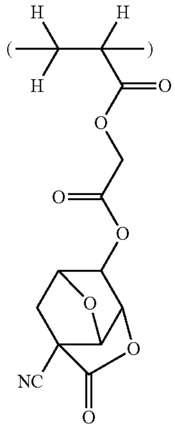
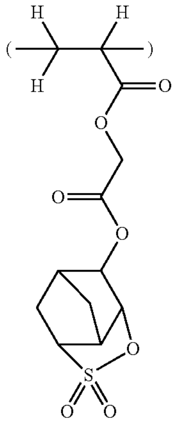
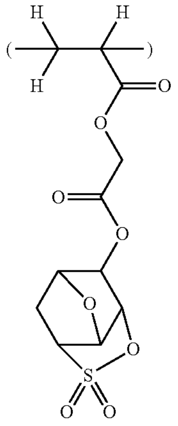
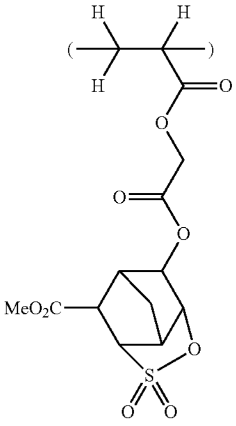
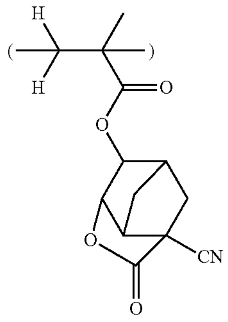
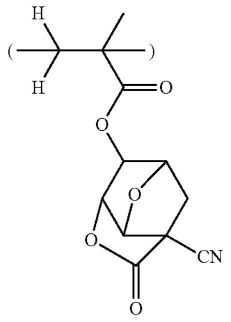
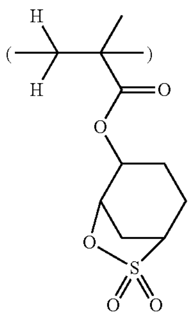
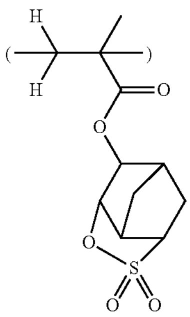
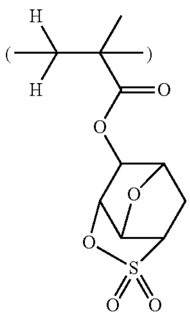

-continued
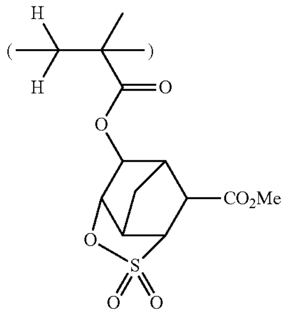
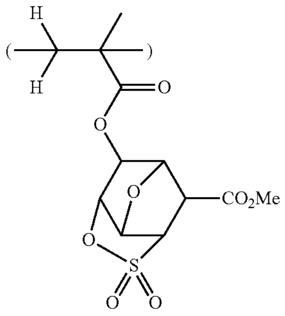
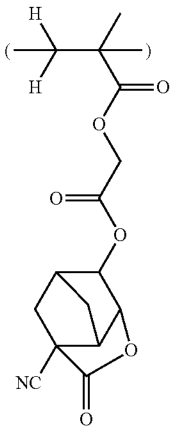
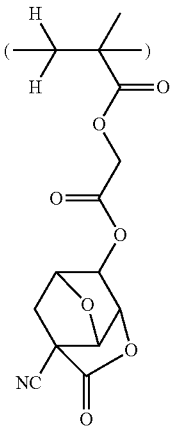
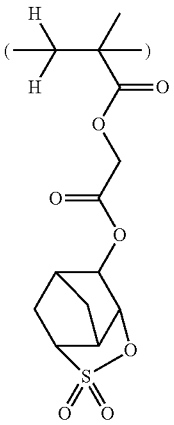
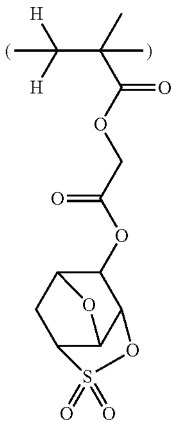
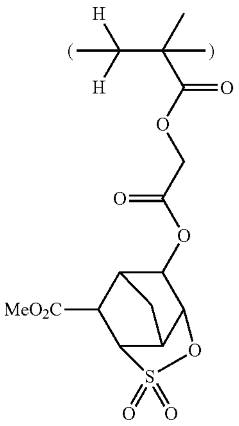
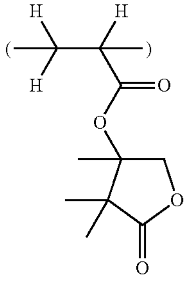
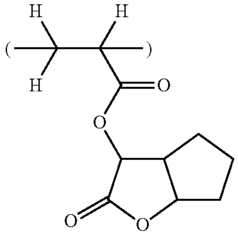
-continued
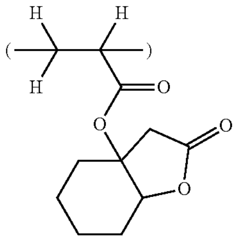
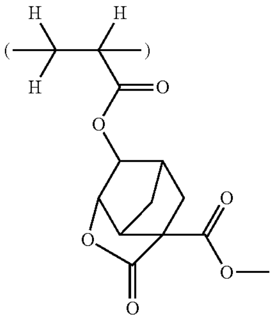
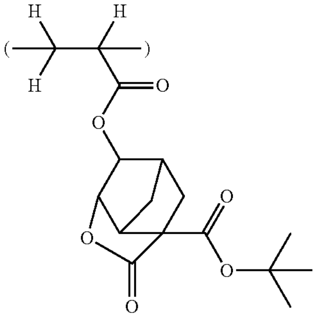
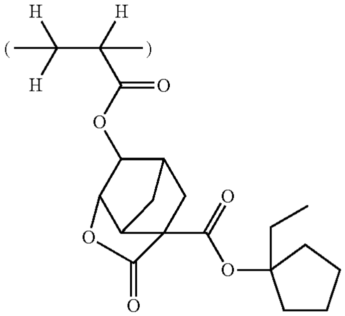
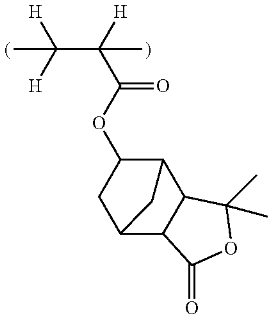
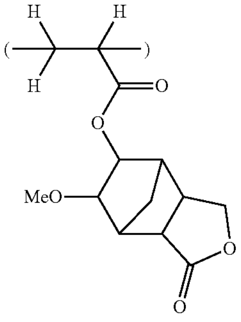
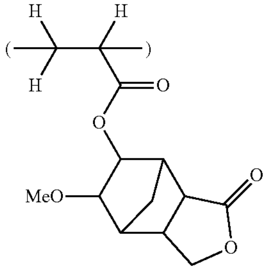
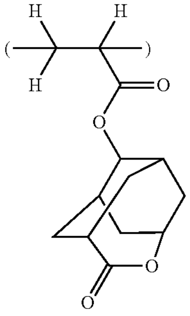

-continued
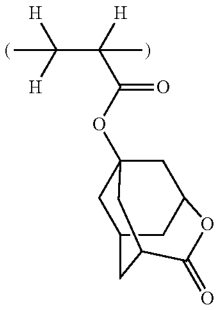
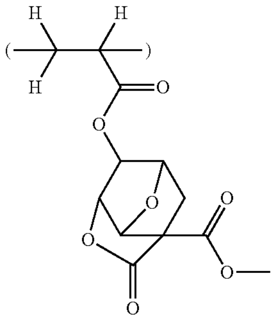
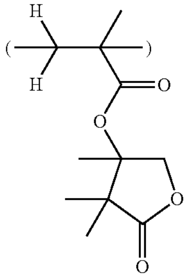
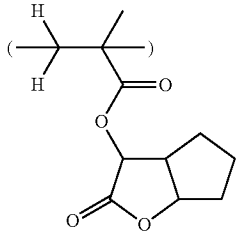
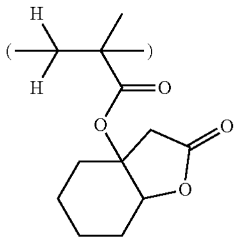
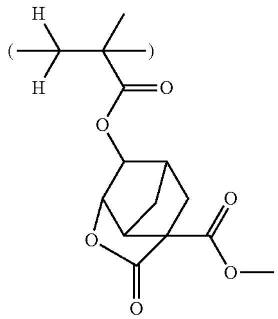
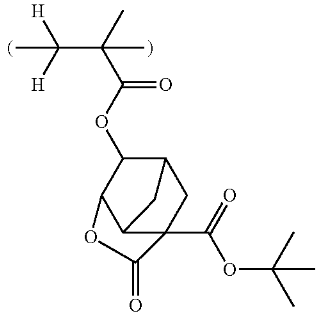
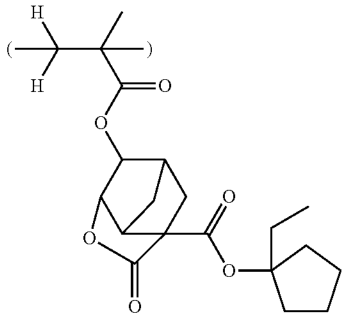
-continued
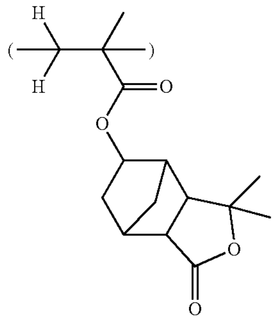
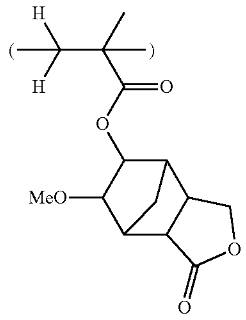
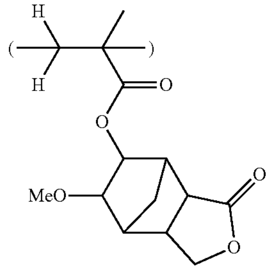
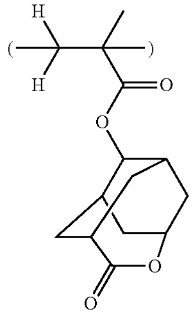
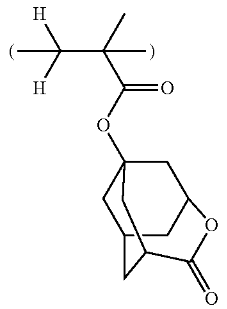
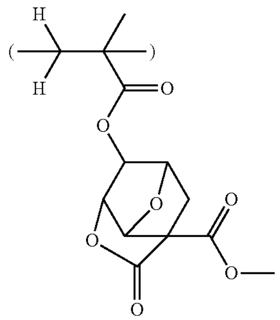
Illustrative examples of the recurring units having formula (4D) are given below, but not limited thereto.
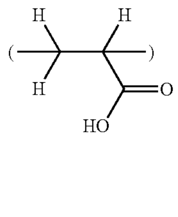
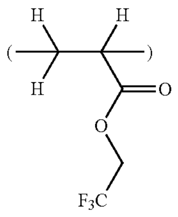
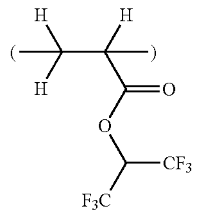
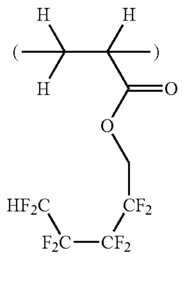
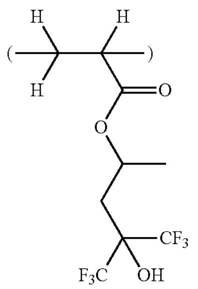

-continued
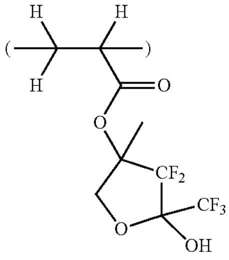
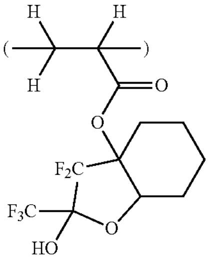
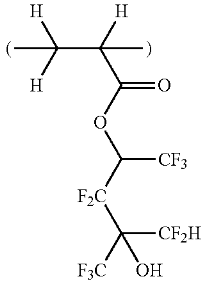
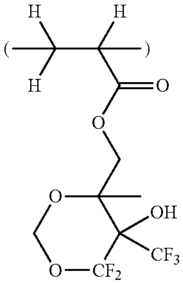
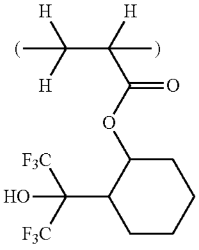
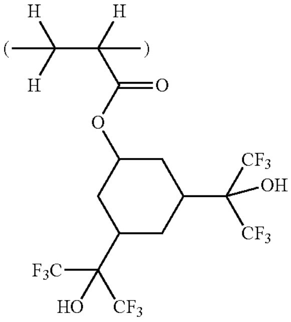
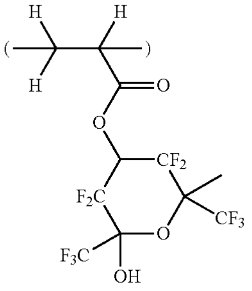
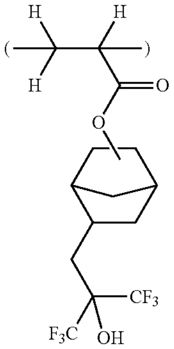
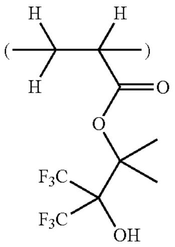
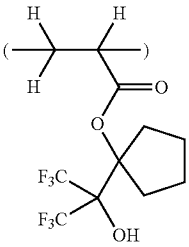
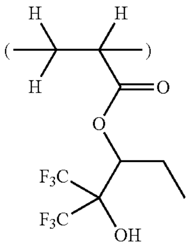
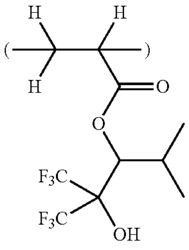
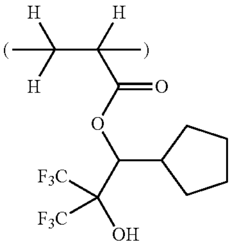
-continued
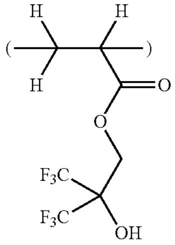
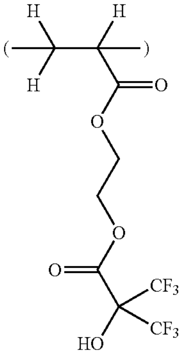
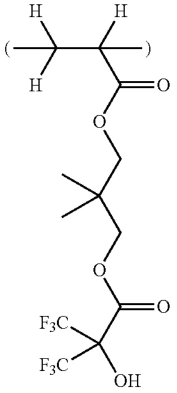
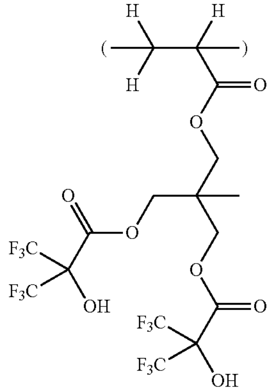
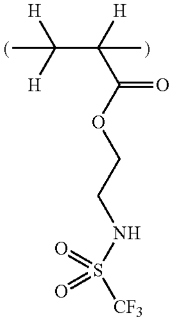
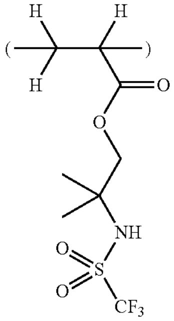
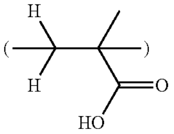
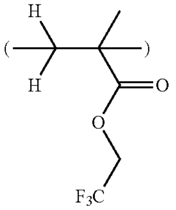
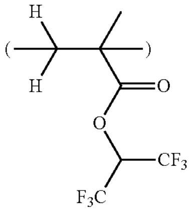
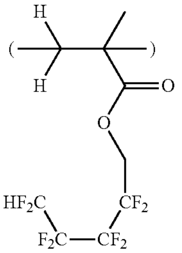
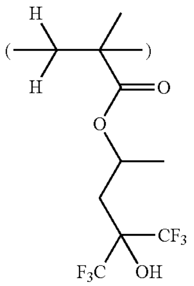
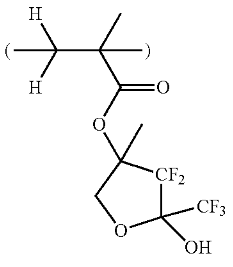
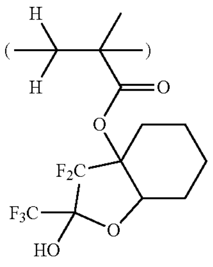

-continued

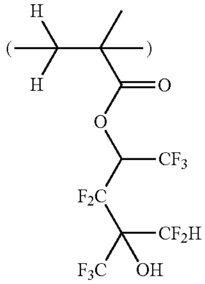
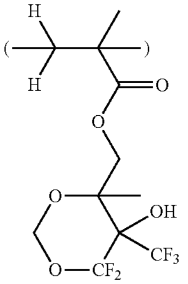
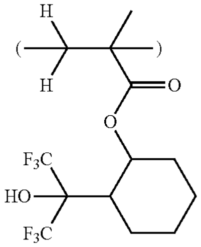
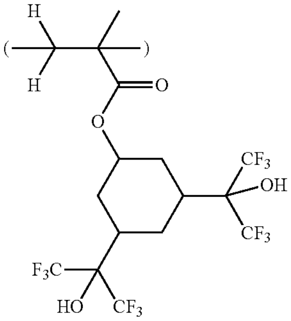
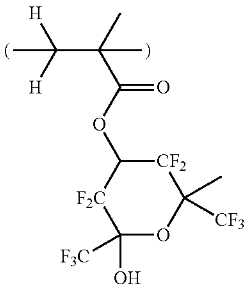
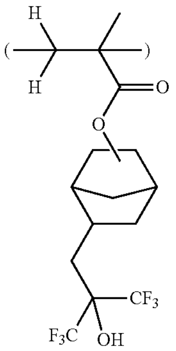
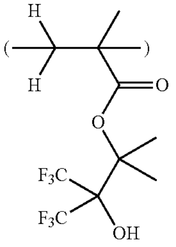
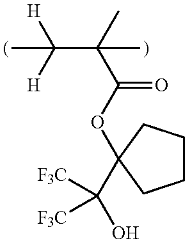
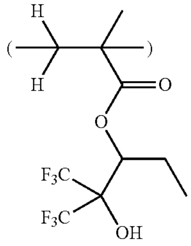
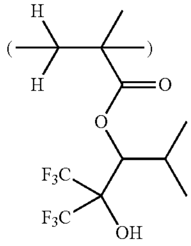
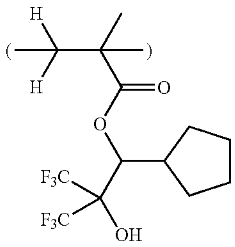
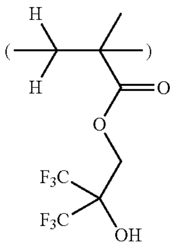

-continued

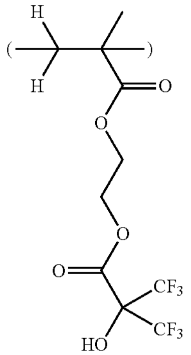
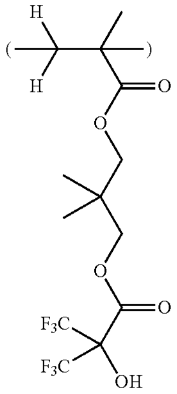
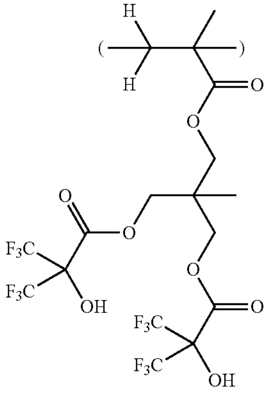
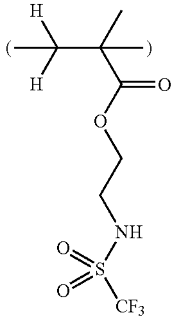
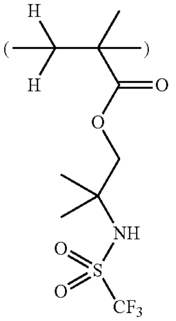

A polymer comprising recurring units of formula (4E) is decomposed under the action of acid to generate a hydroxyl group so that its solubility in various solvents may change. The acid labile group XE may be selected from a variety of such groups. Examples of the acid labile group XE are groups of formulae (L1) to (L4), tertiary alkyl groups of 4 to 20 carbon atoms, trialkylsilyl groups in which each alkyl moiety has 1 to 6 carbon atoms, and oxoalkyl groups of 4 to 20 carbon atoms, like the acid labile group XA mentioned above.

Illustrative examples of the recurring units having formula (4E) are given below, but not limited thereto.

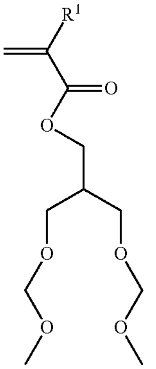
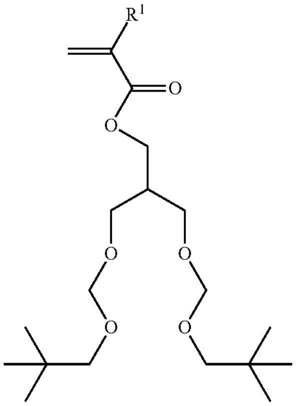
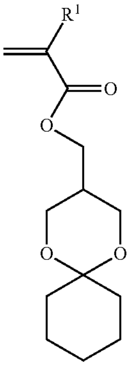
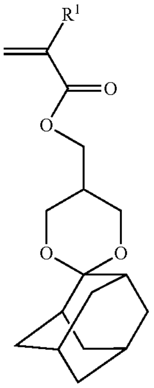
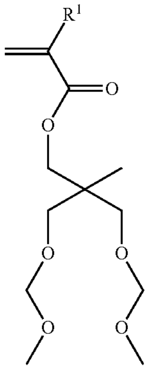
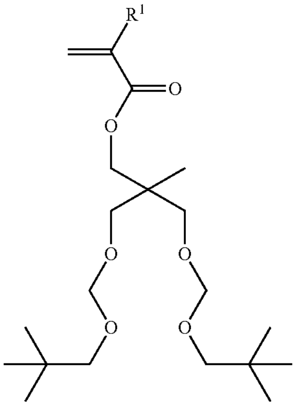
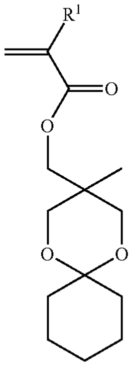
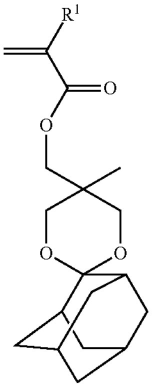
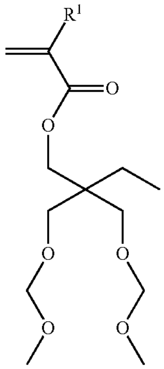
-continued
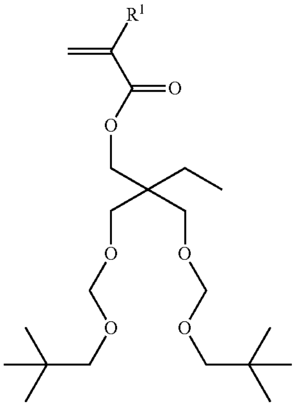
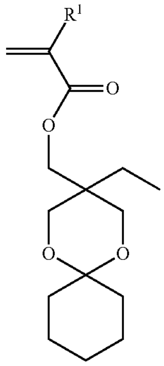
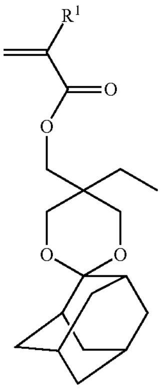
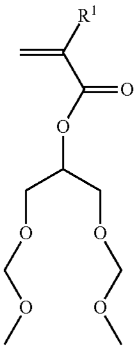
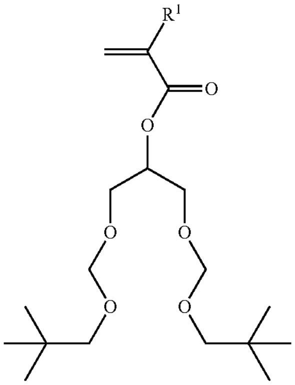
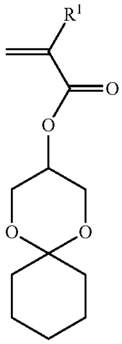
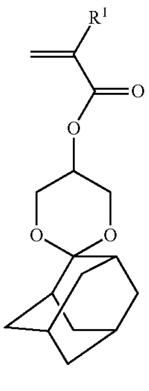
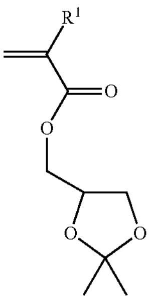
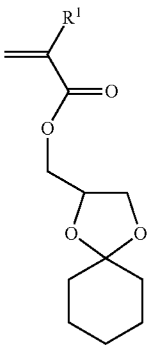

-continued
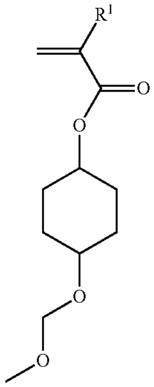
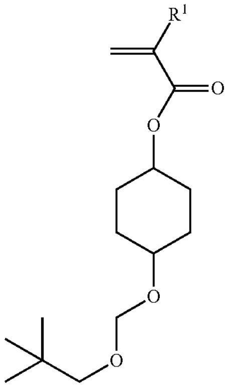
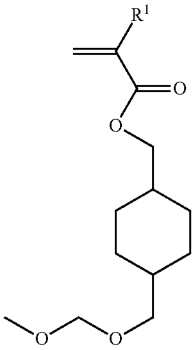
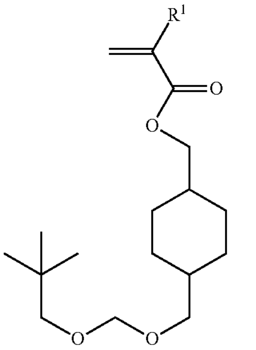
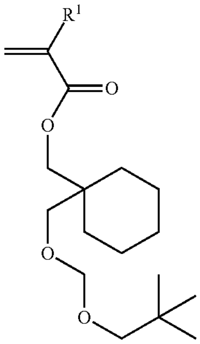
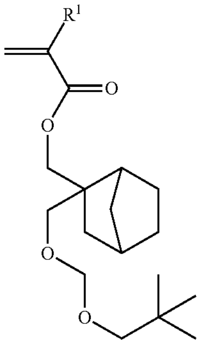
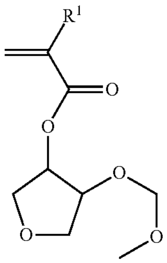
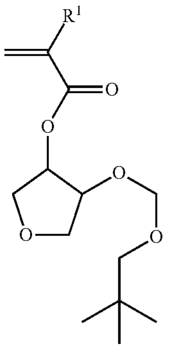
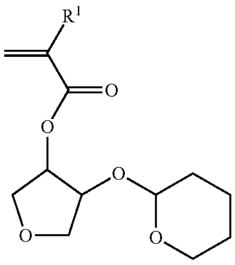
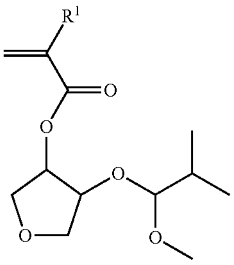
-continued
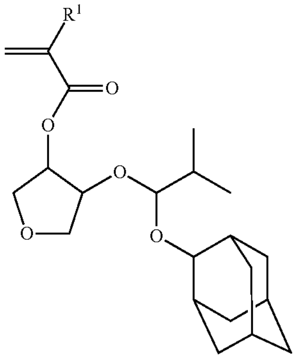
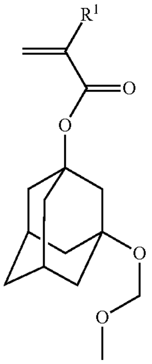
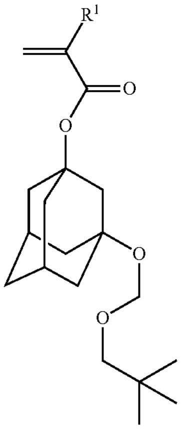
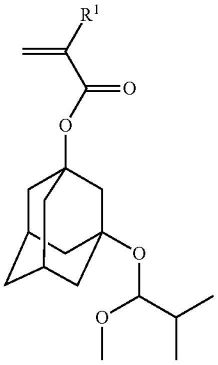
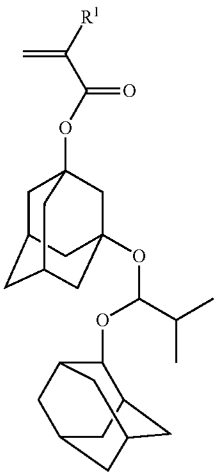
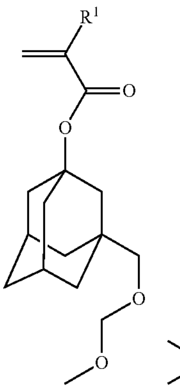
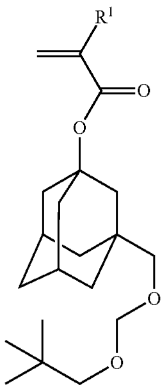
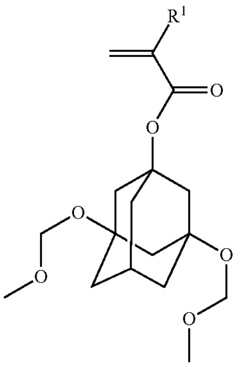
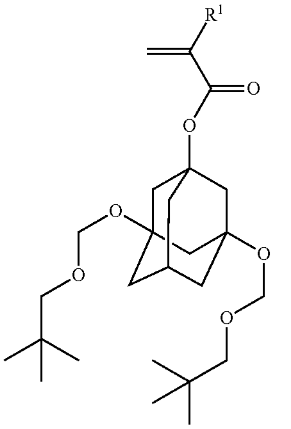

-continued
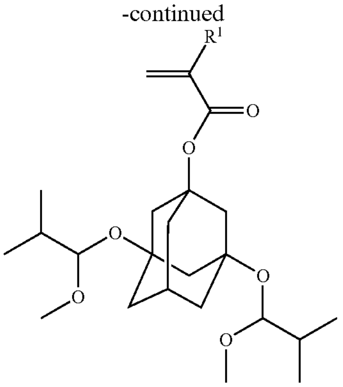
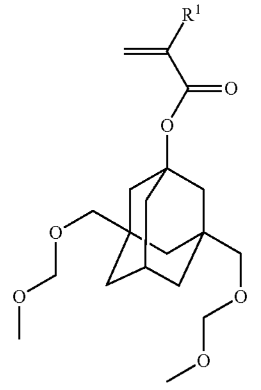
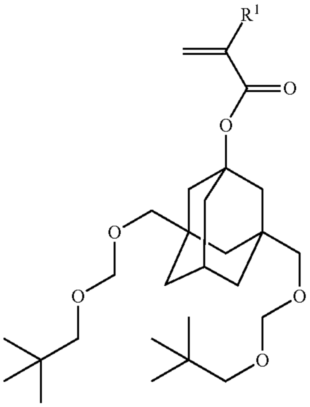
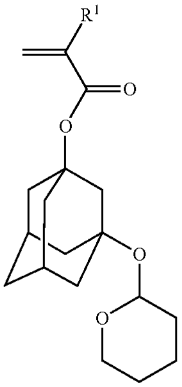
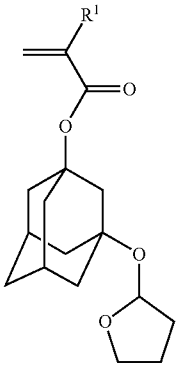
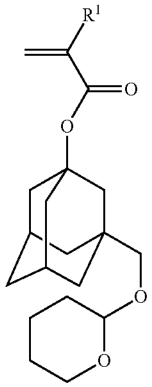
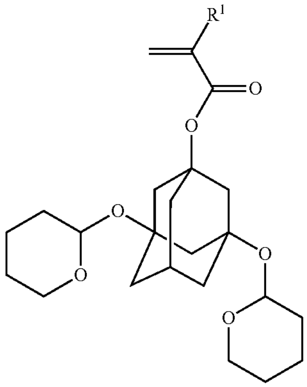
-continued
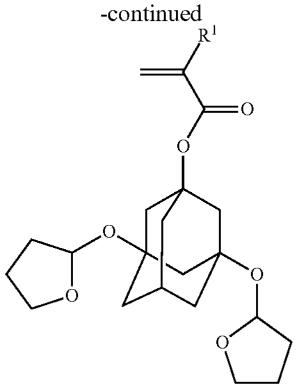
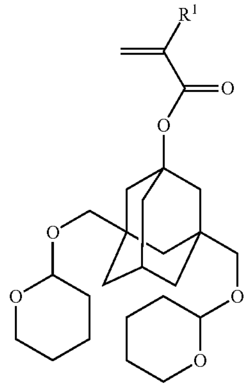
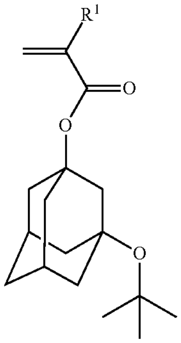
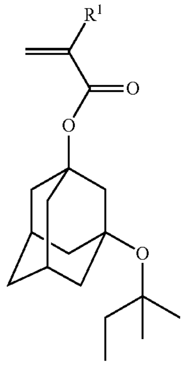
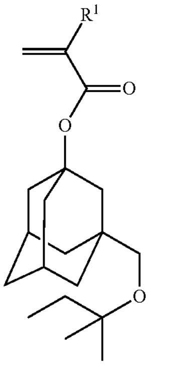
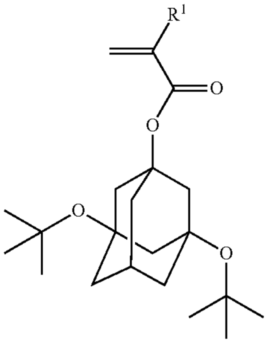
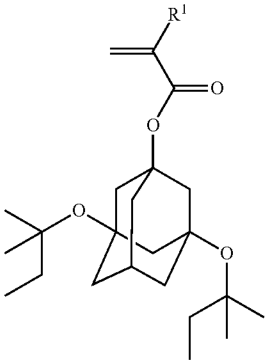

-continued
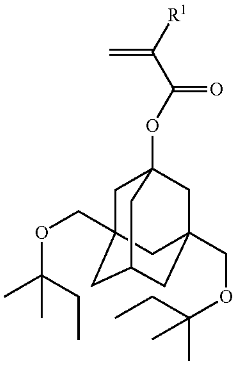
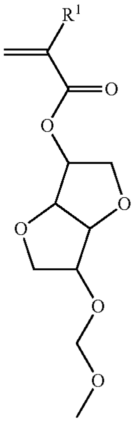
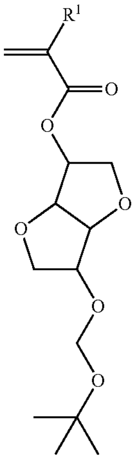
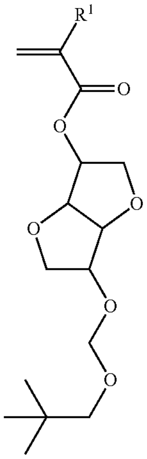
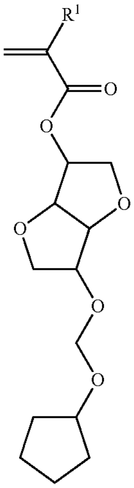
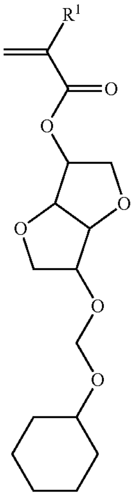
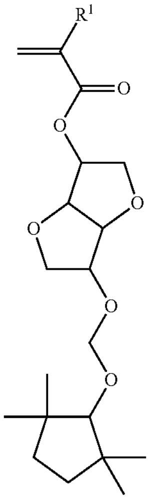
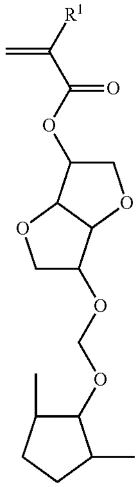
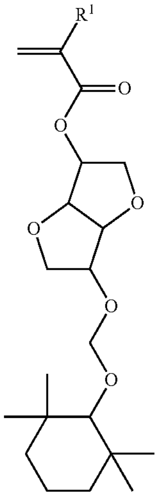
-continued
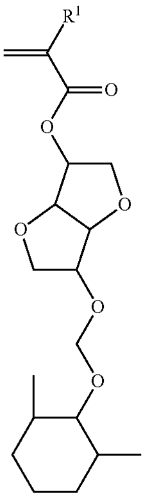
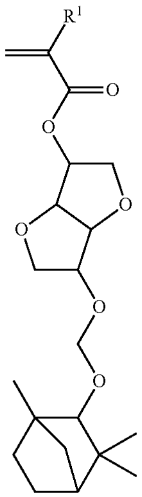
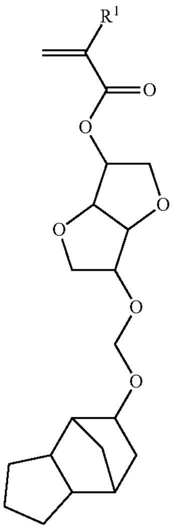
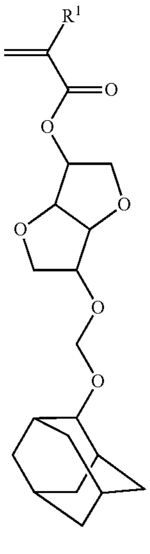
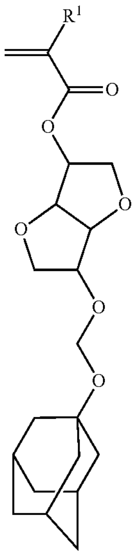
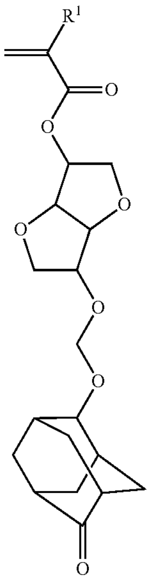
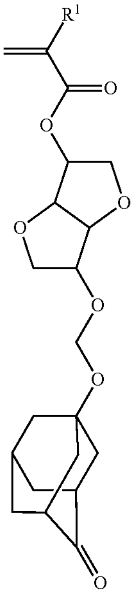
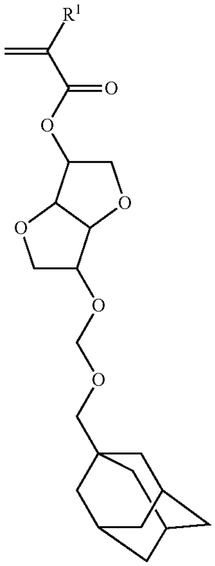
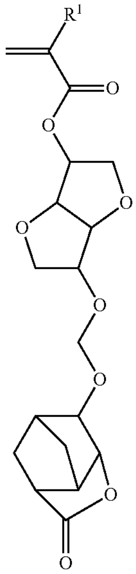

-continued
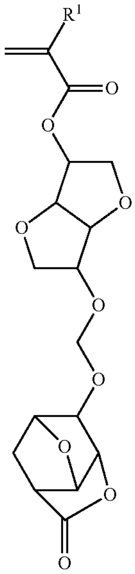
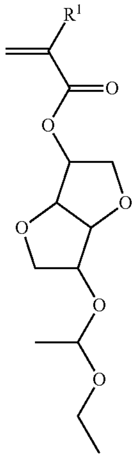
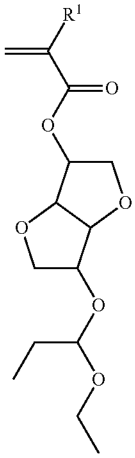
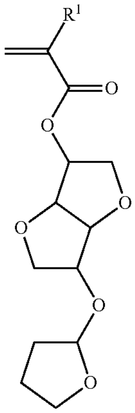
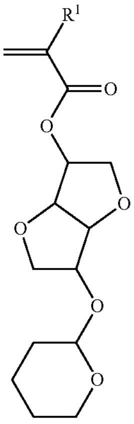
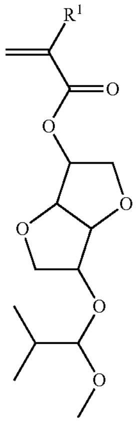
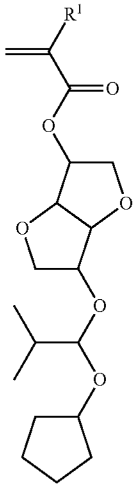
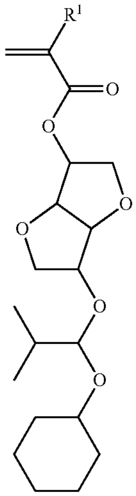
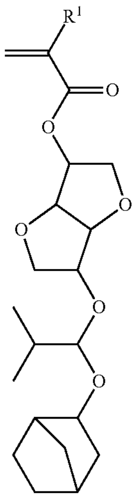
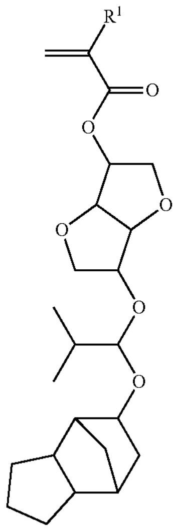
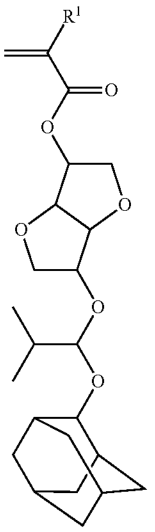
-continued
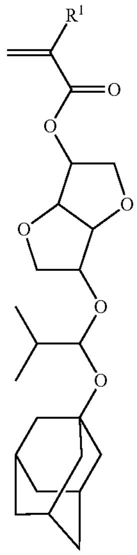
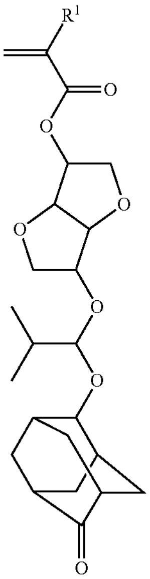
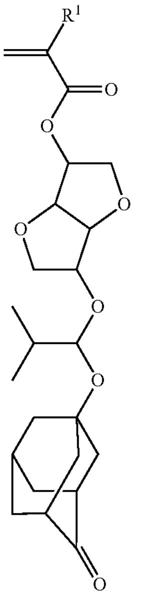
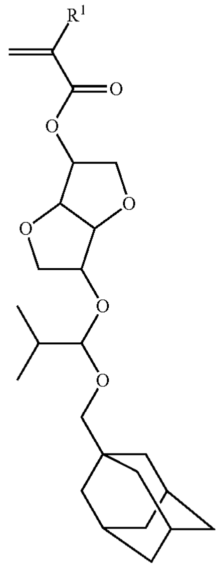
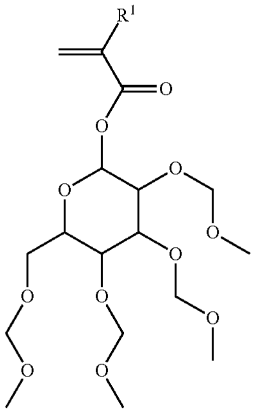
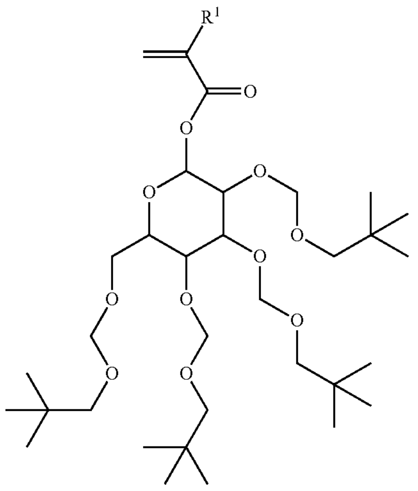

-continued
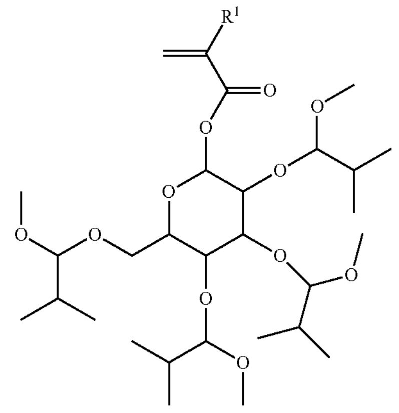
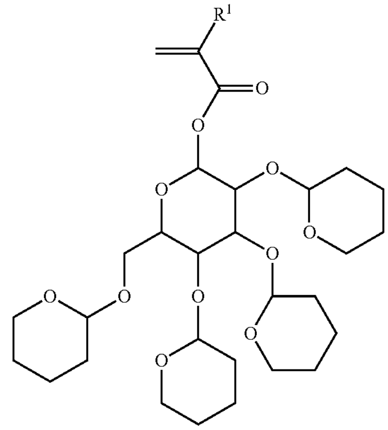
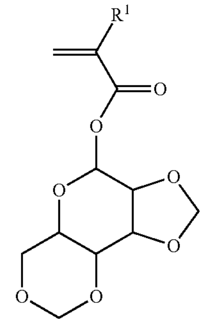
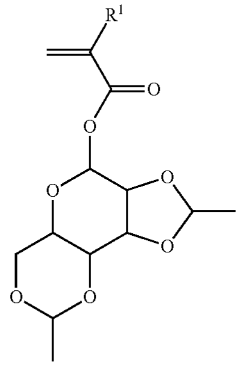
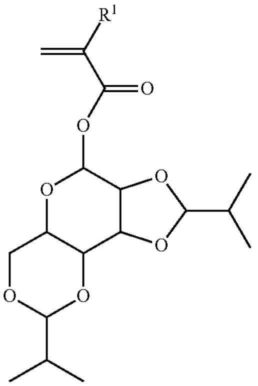
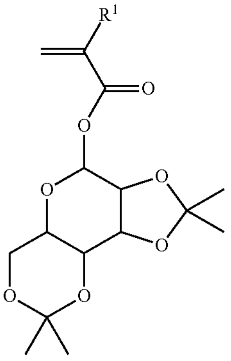
-continued
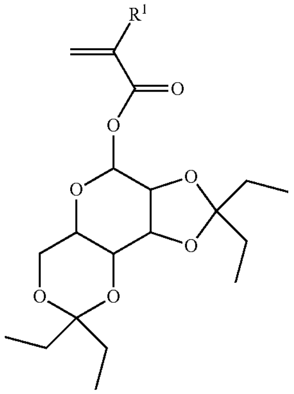
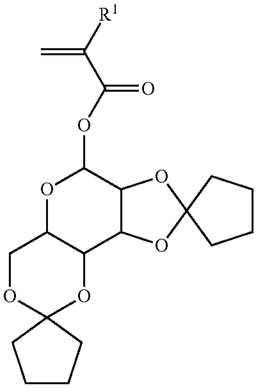
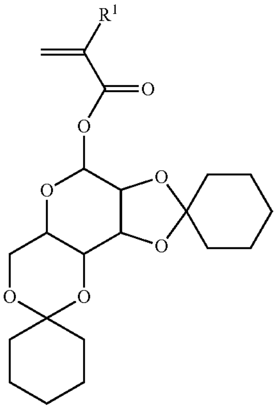
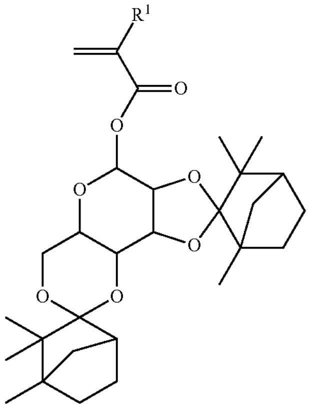
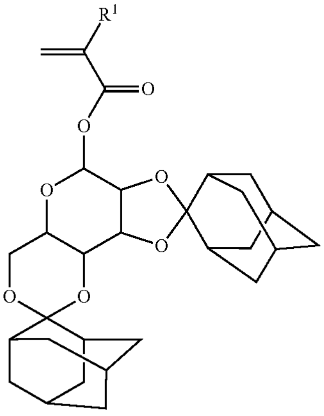

-continued

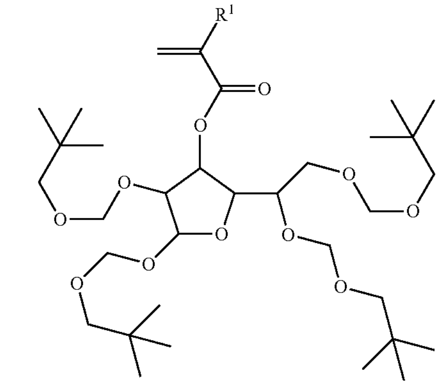

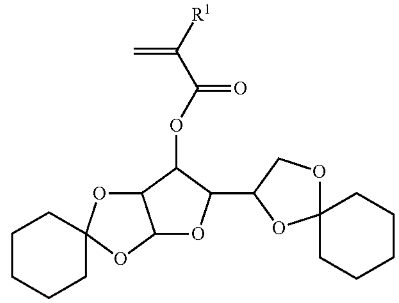

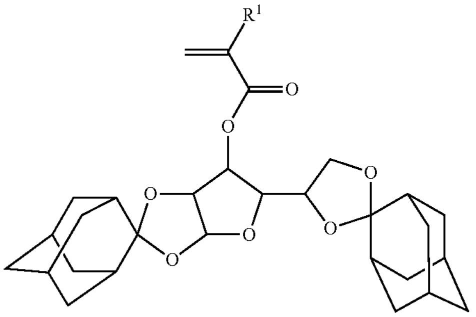

Herein $R^1$ is as defined above.

In a preferred embodiment, the polymer may have further copolymerized therein any of recurring units (f1) to (f3) of sulfonium salt represented by the following general formulae.

(f1)

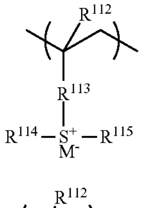

(f2)

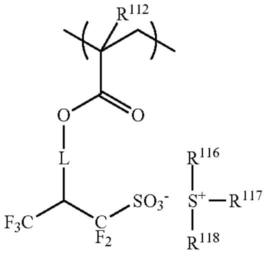

-continued (f3)

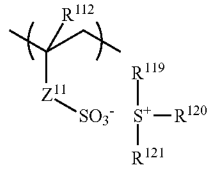

Herein $R^{112}$ is hydrogen or methyl. $R^{113}$ is a single bond, phenylene, or —O—$R^{122}$—, or —C(═O)—$Z^{22}$—$R^{122}$—, wherein $Z^{22}$ is oxygen or NH and $R^{22}$ is a straight $C_1$-$C_6$ or branched or cyclic $C_3$-$C_6$ alkylene group, $C_2$-$C_6$ alkenylene group or phenylene group, which may contain a carbonyl (—CO—), ester (—COO—), ether (—O—), or hydroxyl moiety. L is a single bond or —$Z^{33}$—C(═O)—O—, wherein $Z^{33}$ is a straight $C_1$-$C_{20}$ or branched or cyclic $C_3$-$C_{20}$ divalent hydrocarbon group which may be substituted with or separated by a heteroatom. $Z^{11}$ is a single bond, methylene, ethylene, phenylene, fluorinated phenylene, —O—$R^{123}$— or —C(═O)—$Z^{44}$—$R^{123}$—, wherein $Z^{44}$ is oxygen or NH, and $R^{123}$ is a straight $C_1$-$C_6$ or branched or cyclic $C_3$-$C_6$ alkylene group, $C_2$-$C_6$ alkenylene group or phenylene group, which may contain a carbonyl, ester, ether, or hydroxyl moiety. $M^-$ is a non-nucleophilic counter ion. $R^{114}$, $R^{115}$, $R^{116}$, $R^{117}$, $R^{118}$, $R^{119}$, $R^{120}$, and $R^{121}$ are each independently a straight $C_1$-$C_{20}$ or branched or cyclic $C_3$-$C_{20}$ hydrocarbon group which may be substituted with or separated by a heteroatom.

Examples of the groups $R^{114}$, $R^{115}$, $R^{116}$, $R^{117}$, $R^{118}$, $R^{119}$, $R^{120}$, and $R^{121}$ include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl and adamantyl; alkenyl groups such as vinyl, allyl, propenyl, butenyl, hexenyl and cyclohexenyl; aryl groups such as phenyl, naphthyl, and thienyl; and aralkyl groups such as benzyl, 1-phenylethyl and 2-phenylethyl, with aryl groups being preferred. In the foregoing groups, at least one hydrogen atom may be substituted by a heteroatom such as oxygen, sulfur, nitrogen or halogen, or a heteroatom such as oxygen, sulfur or nitrogen may intervene, whereby a hydroxyl, cyano, carbonyl, ether bond, ester bond, sulfonic acid ester bond, carbonate bond, lactone ring, sultone ring, carboxylic anhydride, or haloalkyl group may form or intervene. Also, $R^{114}$ and $R^{115}$ may bond together to form a ring with the sulfur atom in the formula, or any two or more of $R^{116}$, $R^{117}$, and $R^{118}$, or any two or more of $R^{119}$, $R^{120}$, and $R^{121}$ may bond together to form a ring with the sulfur atom in the formula.

In formula (f2), when L is —$Z^{33}$—C(═O)—O—, $Z^{33}$ is a straight $C_1$-$C_{20}$, branched or cyclic $C_3$-$C_{20}$ divalent hydrocarbon group which may be substituted with or separated by a heteroatom. Examples of the group $Z^{33}$ are shown below, but not limited thereto.

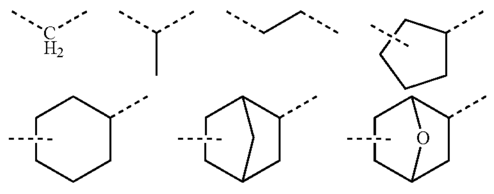

-continued

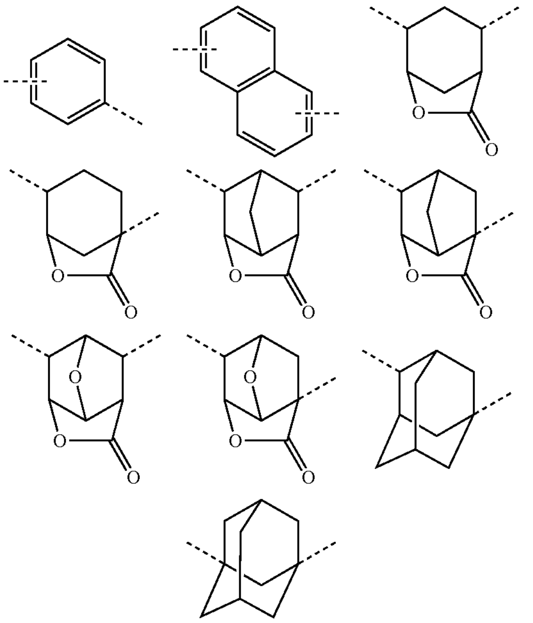

When $R^{114}$ and $R^{115}$ bond together to form a ring with the sulfur atom, or when any two or more of $R^{116}$, $R^{117}$, and $R^{118}$, or any two or more of $R^{119}$, $R^{120}$, and $R^{121}$ bond together to form a ring with the sulfur atom, exemplary rings are shown below.

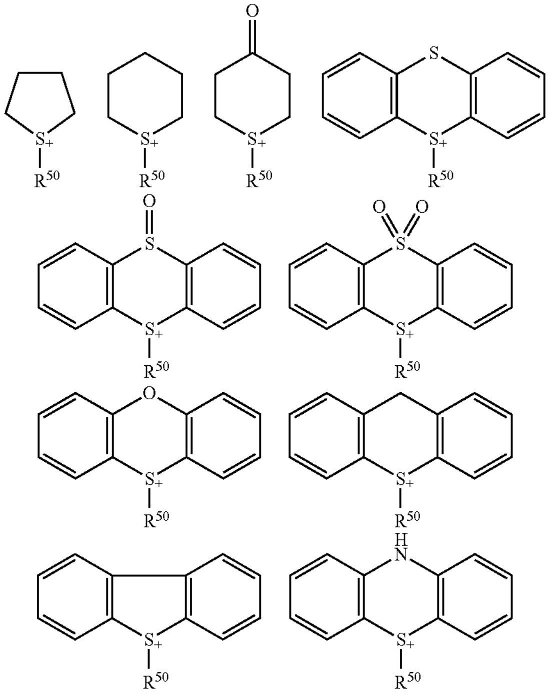

Herein $R^{50}$ is a straight $C_1$-$C_{20}$, branched or cyclic $C_3$-$C_{20}$ divalent hydrocarbon group which may be substituted with or separated by a heteroatom, as represented by $R^{113}$ to $R^{121}$.

Exemplary structures of the sulfonium cation in formulae (f2) and (f3) are shown below, but not limited thereto.

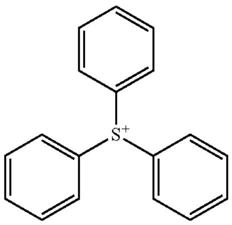

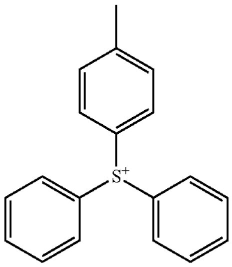

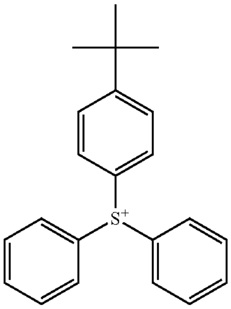

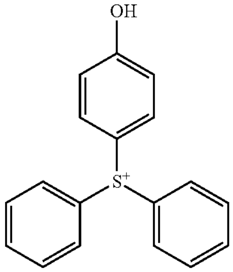

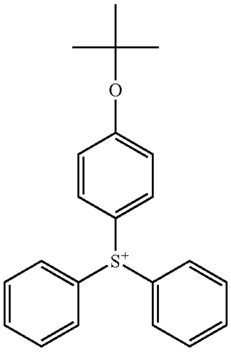

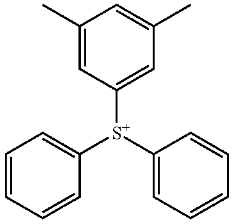

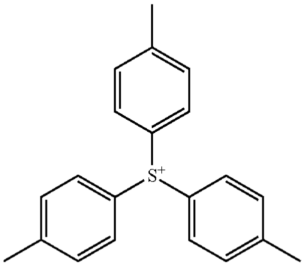

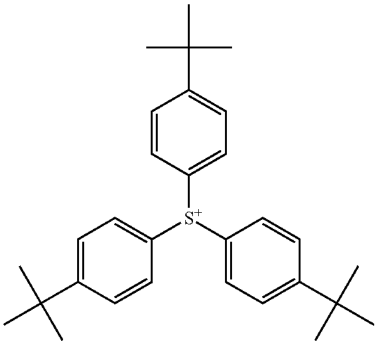

-continued

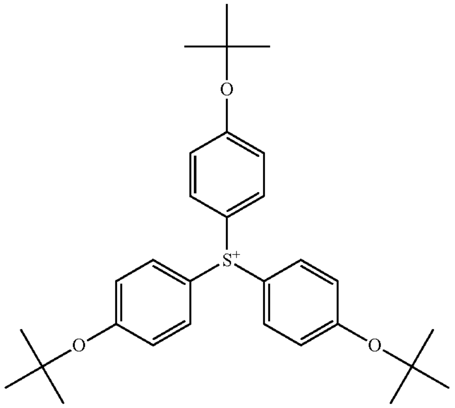

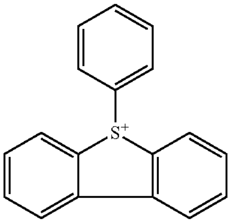

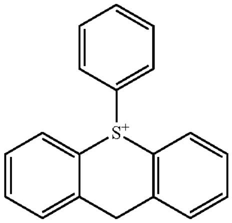

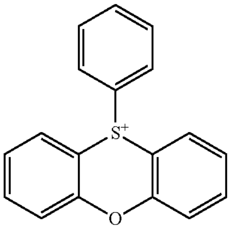

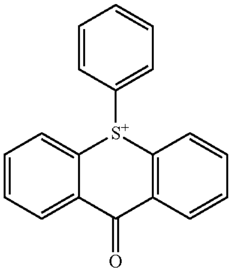

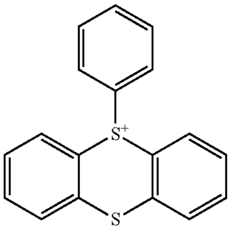

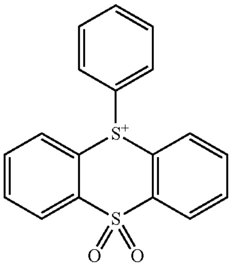

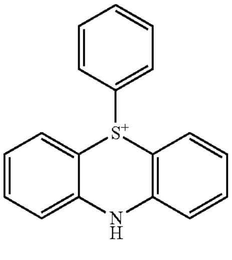

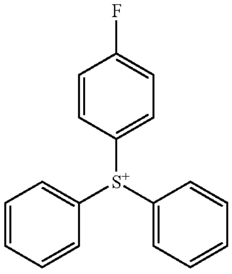

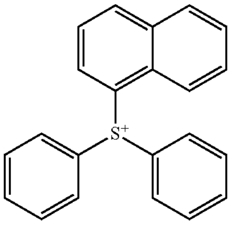

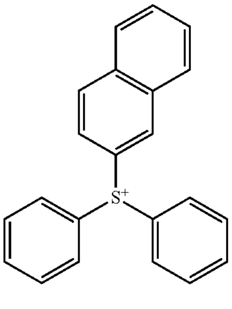

-continued

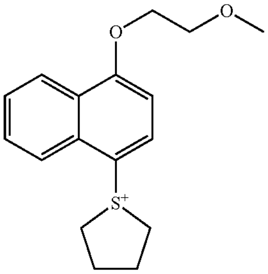

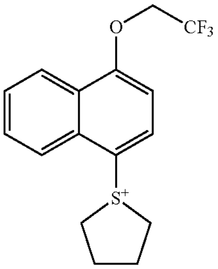

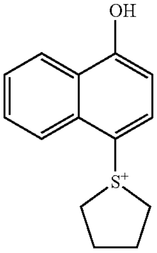

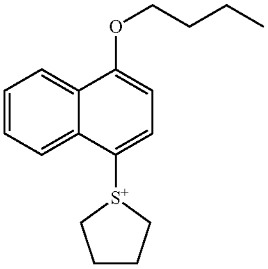

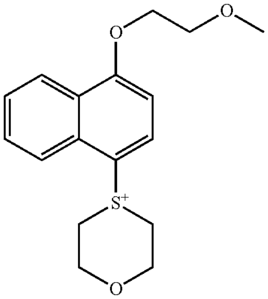

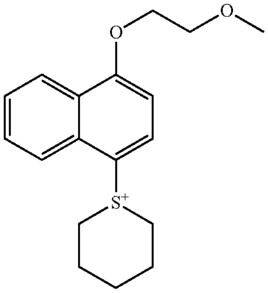

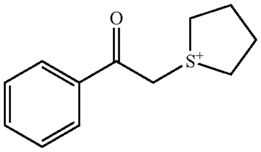

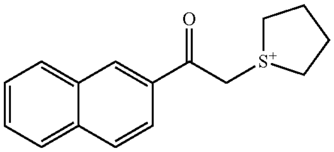

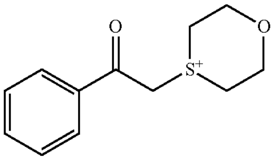

Examples of the non-nucleophilic counter ion represented by $M^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Also included are a sulfonate which is fluorinated at α-position as represented by the general formula (F-1) and a sulfonate which is fluorinated at α- and β-positions as represented by the general formula (F-2).

$$R^{19}-F_2C-SO_3^-$$ (F-1)

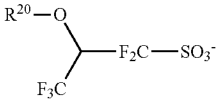

(F-2)

In formula (F-1), $R^{19}$ is hydrogen, or a straight, branched or cyclic $C_1$-$C_{20}$ alkyl group, $C_2$-$C_{20}$ alkenyl group or $C_6$-$C_{20}$ aryl group, which may have an ether, ester, carbonyl moiety, lactone ring or fluorine atom. In formula (F-2), $R^{20}$ is hydrogen, or a straight, branched or cyclic $C_1$-$C_{30}$ alkyl group, acyl group, $C_2$-$C_{20}$ alkenyl group, $C_6$-$C_{20}$ aryl group or aryloxy group, which may have an ether, ester, carbonyl moiety or lactone ring.

Furthermore, recurring units having an oxirane or oxetane ring may be copolymerized. When the inventive polymer further comprising recurring units having an oxirane or oxetane ring copolymerized therein is used in a resist composition subject to organic solvent development, the resist film in the exposed region is crosslinked, from which the insolubilization of the resist film in the developer and an improvement in etch resistance of negative pattern are expectable. Examples of recurring units having an oxirane or oxetane ring are shown below. Note that $R^{41}$ is hydrogen or methyl.

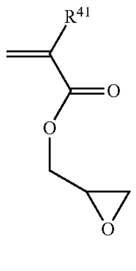
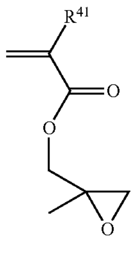
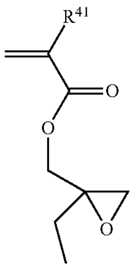
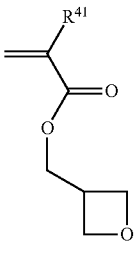

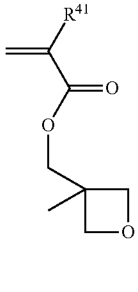
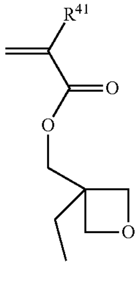
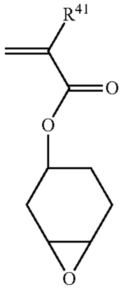
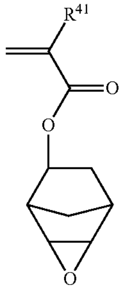

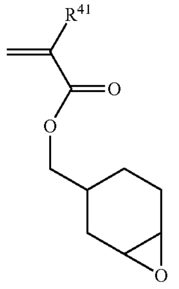
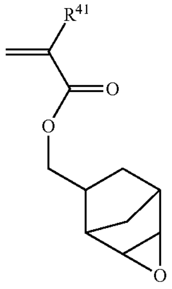
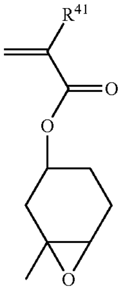

-continued

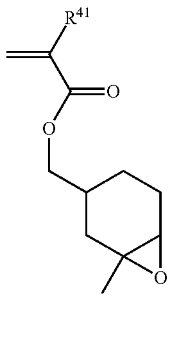
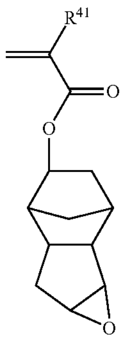
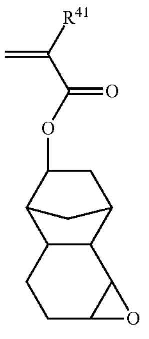

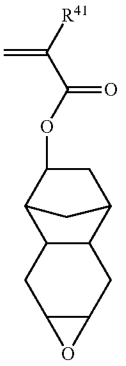
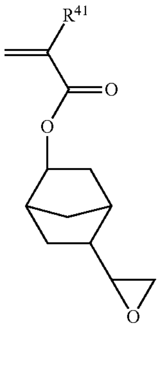
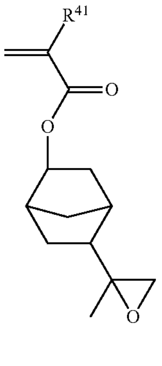

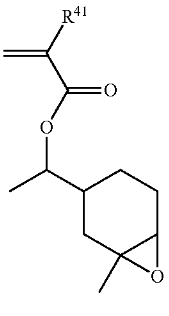
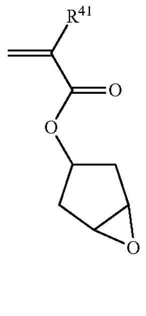
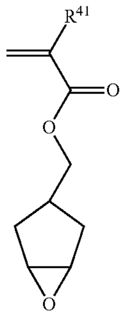

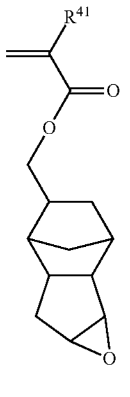
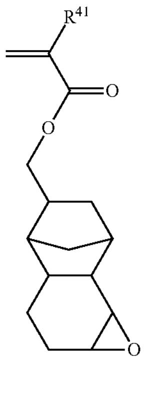
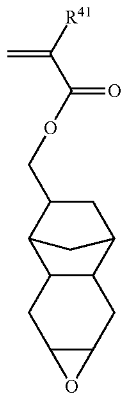

-continued
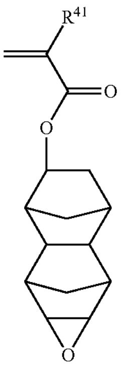
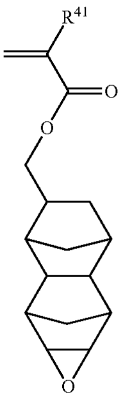
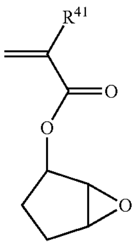
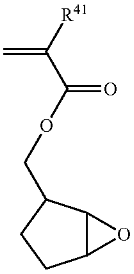
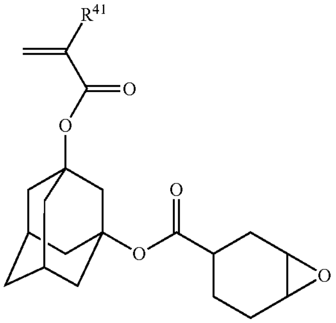
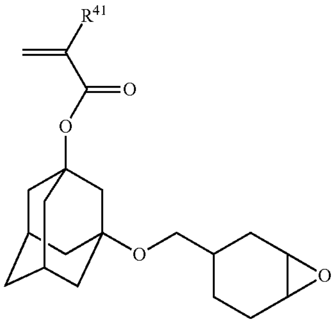
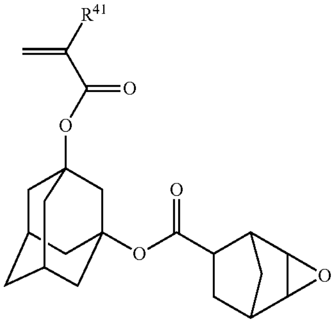
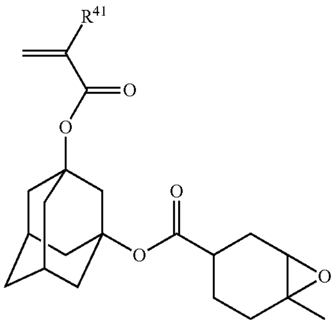
-continued
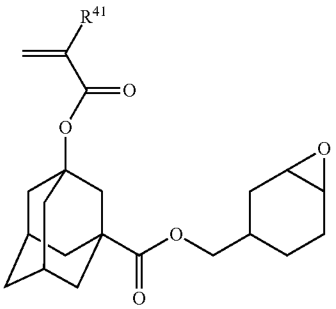
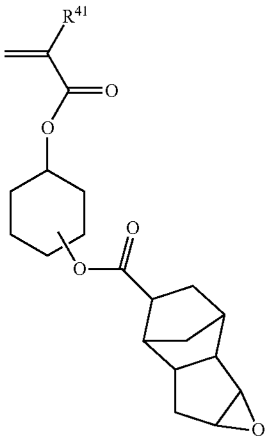
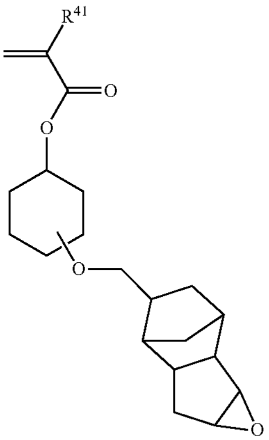
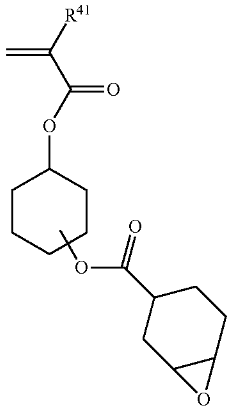
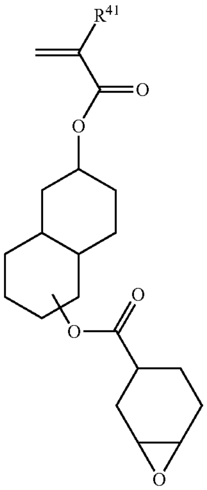
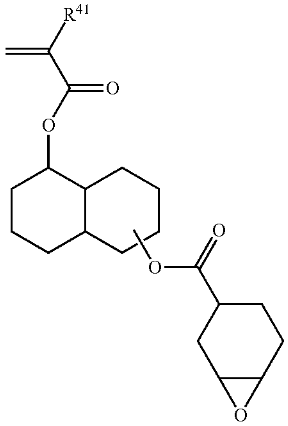
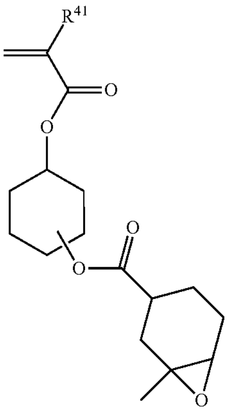

-continued

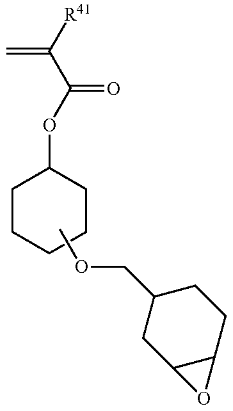

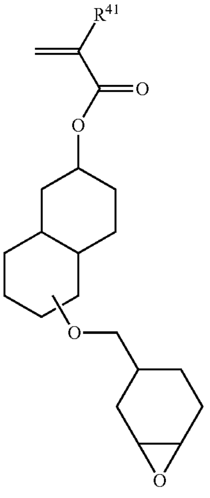

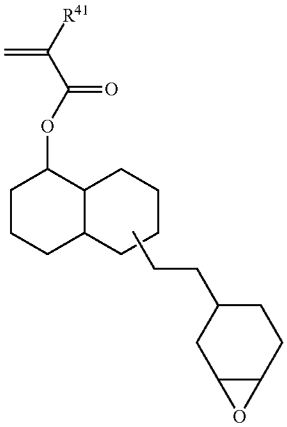

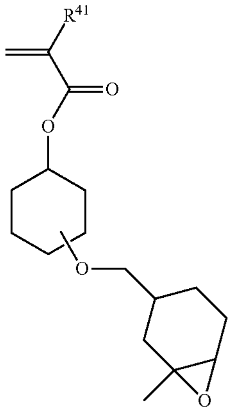

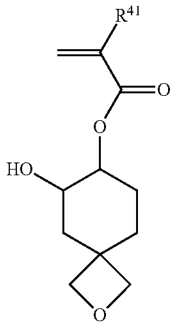

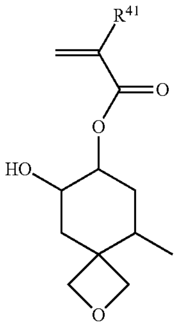

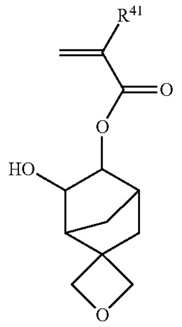

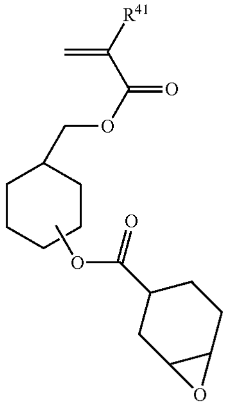

In addition to the foregoing units, the inventive polymer may further comprise recurring units derived from carbonto-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo$[4.4.0.1^{2,5}.1^{7,10}]$dodecene derivatives, unsaturated acid anhydrides such as itaconic anhydride, and other monomers.

The polymer should preferably have a weight average molecular weight (Mw) in the range of 1,000 to 500,000, and more preferably 3,000 to 100,000, as measured versus polystyrene standards by GPC using tetrahydrofuran solvent. Outside the range, there may result an extreme loss of etch resistance, a failure to provide a differential dissolution rate before and after exposure, and a lowering of resolution.

In the polymer, the recurring units derived from the inventive monomer and other monomers are preferably incorporated in the following molar fractions (mol %):

(I) more than 0 mol % to 100 mol %, preferably 5 to 70 mol %, and more preferably 10 to 50 mol % of constituent units of at least one type selected from units (2a) to (2d) derived from monomers of formulae (1a) to (1d);

(II) 0 mol % to less than 100 mol %, preferably 30 to 95 mol %, and more preferably 50 to 90 mol % of constituent units of at least one type selected from units (4A) to (4E);

(III) 0 to 30 mol %, preferably 0 to 20 mol %, and more preferably 0 to 10 mol % of constituent units of at least one type selected from units (f1) to (f3); and (IV) 0 to 80 mol %, preferably 0 to 70 mol %, and more preferably 0 to 50 mol % of constituent units derived from one or more other monomers. Preferably the total of fractions (I) to (IV) is 100 mol %. The inventive polymer is not limited to the above range. When units (f1) to (f3) are incorporated, a fraction of at least 1 mol %, especially at least 2 mol % is preferred. In this case, the fraction (I) and/or fraction (II) may be reduced in accordance with fraction (III).

The inventive polymers may be prepared by copolymerization reaction using the compound having formulae (1a) to (1d) as a first monomer and one or more polymerizable double bond-bearing compounds corresponding to recurring units (4A) to (4E), (f1) to (f3), and other units as second and subsequent monomers. The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 to about 48 hours. Reaction conditions outside the described range may be employed if desired.

When hydroxystyrene or hydroxyvinylnaphthalene is copolymerized, a copolymer may be obtained by dissolving hydroxystyrene or hydroxyvinylnaphthalene and another comonomer(s) in an organic solvent, adding a radical polymerization initiator, and heat polymerization. Alternatively, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

Resist Composition

The polymer is advantageously used as a base resin in a resist composition. Specifically, the polymer is used as a base resin and combined with any desired components including an organic solvent, acid generator, dissolution regulator, basic compound, and surfactant to formulate a resist composition. This resist composition has a very high sensitivity in that the dissolution rate in an organic solvent developer of the polymer in exposed areas is decelerated by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs.

Particularly when an acid generator is included to formulate a chemically amplified resist composition capable of utilizing acid catalyzed reaction, the composition has a higher sensitivity and is further improved in the properties described above. Inclusion of a dissolution regulator may lead to an increased difference in dissolution rate between exposed and unexposed areas and a further improvement in resolution. Addition of a basic compound may be effective in suppressing the diffusion rate of acid in the resist film, achieving a further improvement in resolution. Addition of a surfactant may improve or control the coating characteristics of the resist composition.

The resist composition may include an acid generator in order for the composition to function as a chemically amplified positive or negative resist composition. Typical of the acid generator used herein is a photoacid generator (PAG) capable of generating an acid in response to actinic light or radiation. Preferably the PAG is used in an amount of 0.5 to 30 parts, more preferably 1 to 20 parts by weight per 100 parts by weight of the base resin. The PAG is any compound capable of generating an acid upon exposure to high-energy radiation. The preferred photoacid generators include the sulfonium salts and PAGs described in JP-A 2009-269953 and the PAGs described in JP 3995575. Any sulfonium salt, iodonium salt, sulfonyldiazomethane, N-sulfonyloxyimide, and oxime-O-sulfonate acid generators may be used. These compounds may be used alone or in admixture. Examples of the acid generated by the acid generator include sulfonic acids, imidic acids and methide acids. Of these, sulfonic acids which are fluorinated at α-position are most commonly used. Fluorination at α-position is not essential when the acid labile group used is an acetal group susceptible to deprotection. Where the base polymer having recurring units (f1), (f2) or (f3) of acid generator copolymerized therein is used, the acid generator of addition type is not essential.

The resist composition may comprise an acid generator having the general formula (Z1) or (Z2) as component (Z).

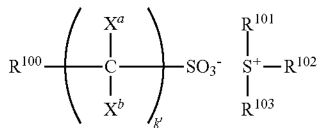

(Z1)

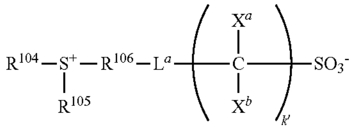

(Z2)

Herein $R^{100}$ is hydrogen, fluorine, or a straight, branched or cyclic $C_1$-$C_{35}$ monovalent hydrocarbon group which may contain a heteroatom. $X^a$ and $X^b$ are each independently hydrogen, fluorine, or trifluoromethyl, k' is an integer of 1 to 4. $R^{101}$, $R^{102}$, and $R^{103}$ are each independently a substituted or unsubstituted, straight or branched alkyl, alkenyl or oxoalkyl group of 1 to 10 carbon atoms, or a substituted or unsubstituted aryl, aralkyl or aryloxoalkyl group of 6 to 18 carbon atoms, or any two or more of $R^{101}$, $R^{102}$, and $R^{103}$ may bond together to form a ring with the sulfur atom. $R^{104}$ and $R^{105}$ are each independently a straight, branched or cyclic $C_1$-$C_{20}$ monovalent hydrocarbon group which may be substituted with or separated by a heteroatom. $R^{106}$ is a straight, branched or cyclic $C_1$-$C_{20}$ divalent hydrocarbon group which may be substituted with or separated by a heteroatom, or any two or more of $R^{104}$, $R^{105}$, and $R^{106}$ may bond together to form a ring with the sulfur atom. $L^a$ is a single bond or a straight, branched or cyclic $C_1$-$C_{20}$ divalent hydrocarbon group which may be substituted with or separated by a heteroatom.

Preferred as component (Z) are acid generators having the general formulae (Z3) and (Z4).

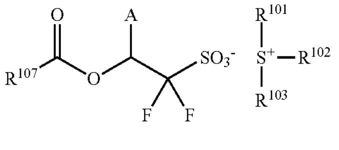

(Z3)

-continued (Z4)

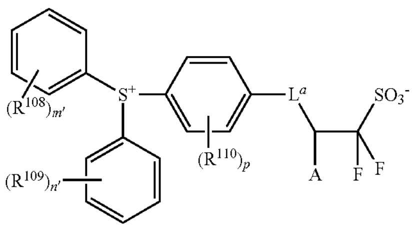

Herein A is hydrogen or trifluoromethyl. $R^{101}$, $R^{102}$, and $R^{103}$ are each independently a substituted or unsubstituted, straight or branched alkyl, alkenyl or oxoalkyl group of 1 to 10 carbon atoms, or a substituted or unsubstituted aryl, aralkyl or aryloxoalkyl group of 6 to 18 carbon atoms, or any two or more of $R^{101}$, $R^{102}$, and $R^{103}$ may bond together to form a ring with the sulfur atom. $R^{107}$ is a straight, branched or cyclic $C_1$-$C_{35}$ monovalent hydrocarbon group which may contain a heteroatom. $R^{108}$, $R^{109}$, and $R^{110}$ are each independently hydrogen or a straight, branched or cyclic $C_1$-$C_{20}$ monovalent hydrocarbon group which may be separated by a heteroatom. Each of m' and n' is an integer of 0 to 5, p is an integer of 0 to 4. $L^a$ is a single bond or a straight, branched or cyclic $C_1$-$C_{20}$ divalent hydrocarbon group which may be substituted with or separated by a heteroatom.

When component (Z) is an acid generator having formula (Z3) or (Z4), preferably formula (Z3) or (Z4) wherein A is trifluoromethyl, a pattern with improved properties, for example, a line-and-space pattern having low roughness (LWR) and improved control of acid diffusion length or a hole pattern having improved roundness and dimensional control can be formed.

Illustrative, non-limiting examples of component (Z) are shown below.

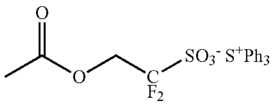

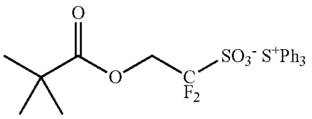

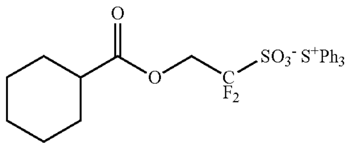

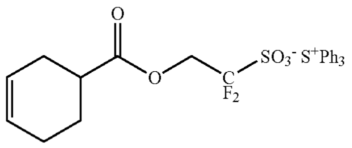

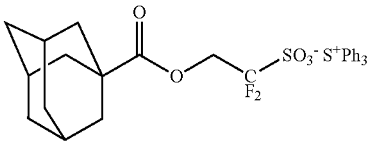

-continued

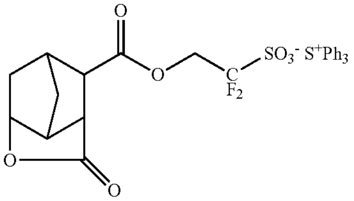

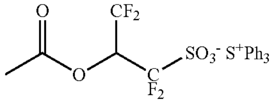

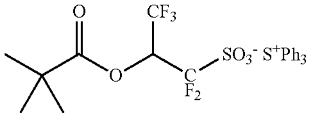

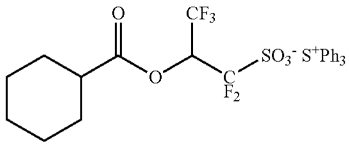

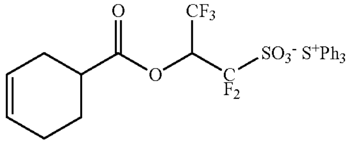

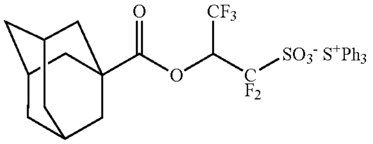

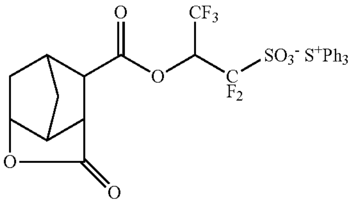

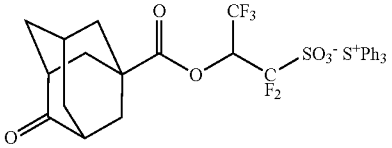

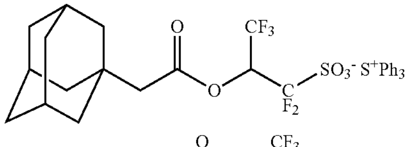

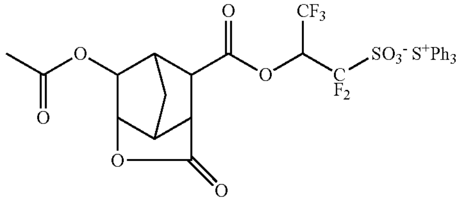

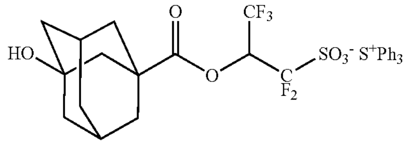

-continued
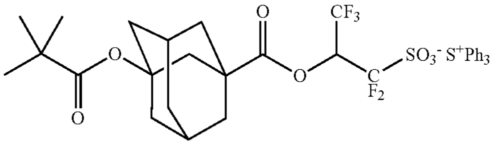
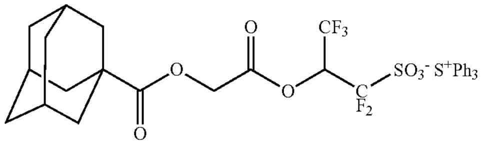
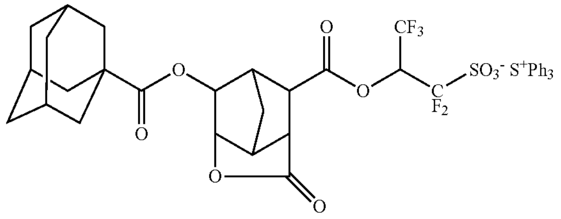
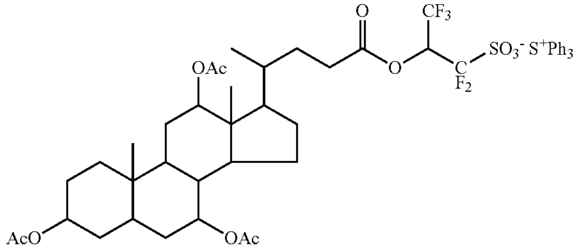
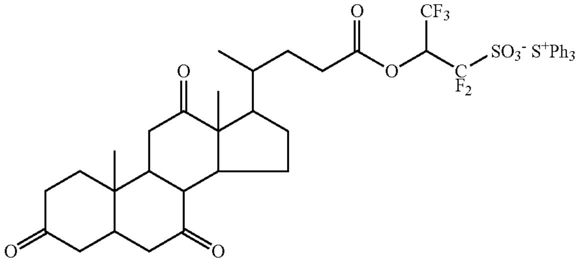
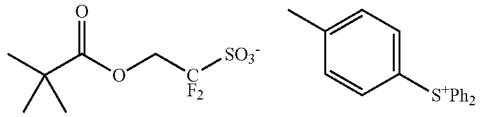
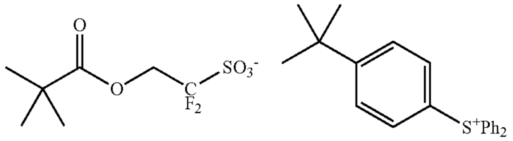
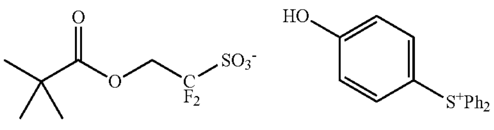
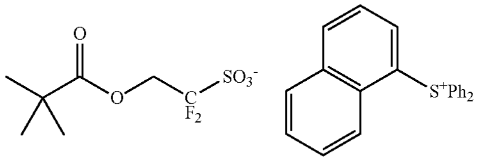
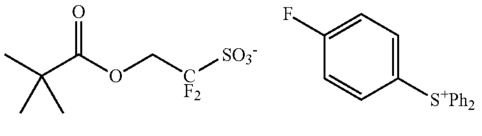
-continued
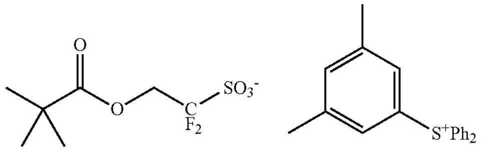
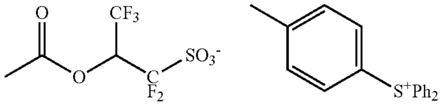
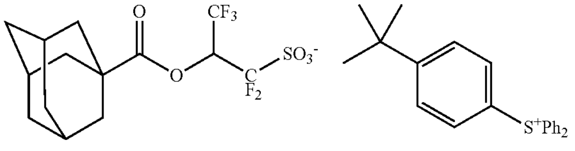
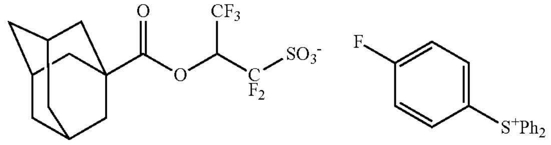
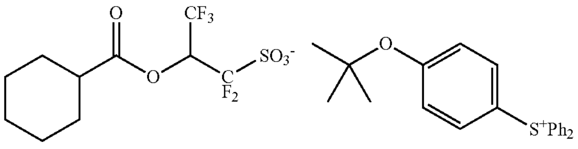
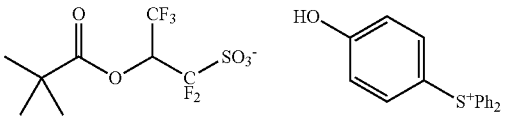
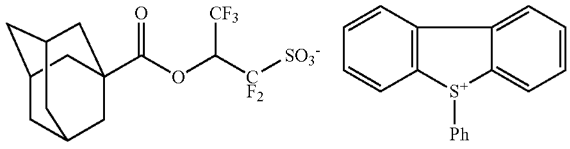
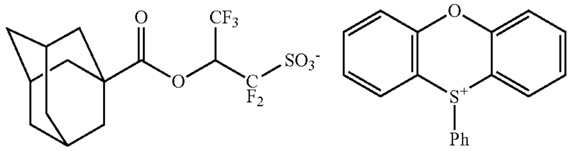
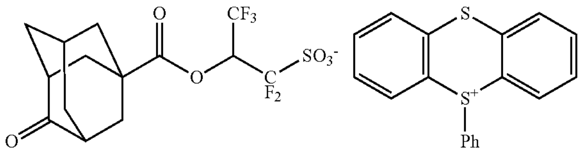
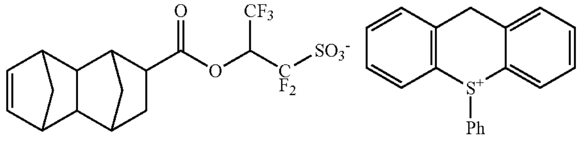
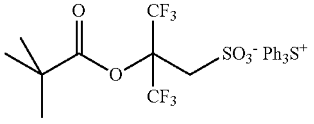
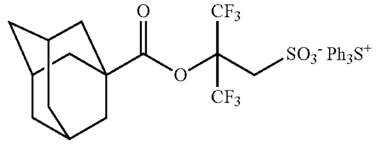

-continued
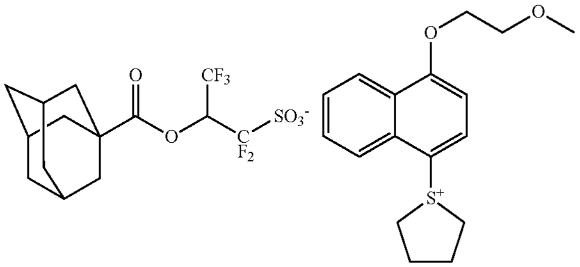
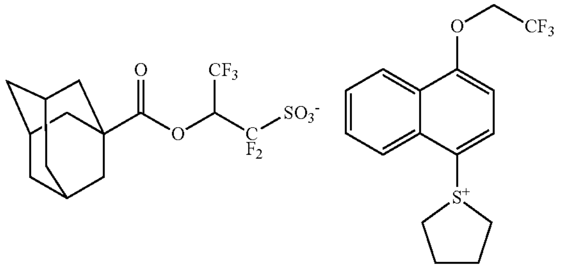
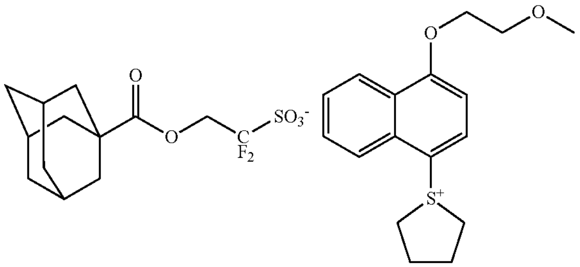
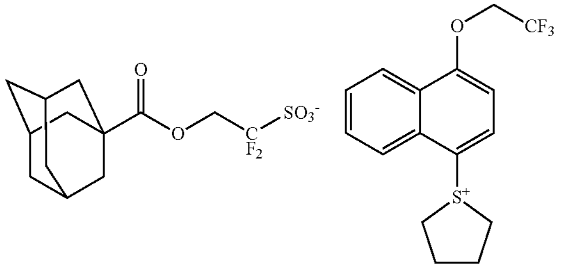
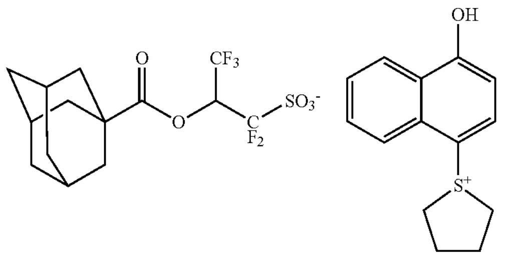
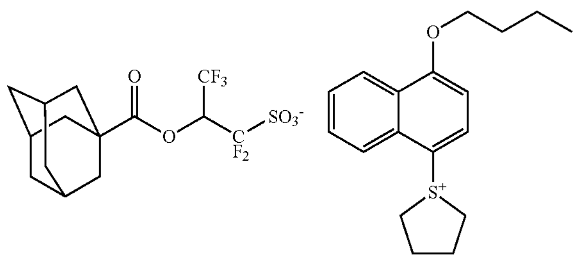
-continued
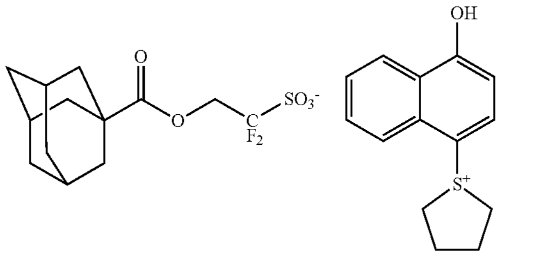
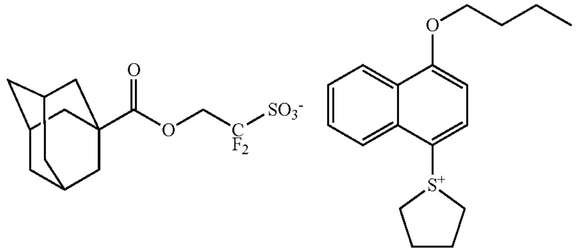
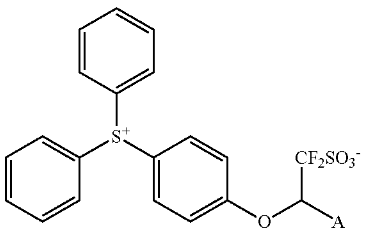
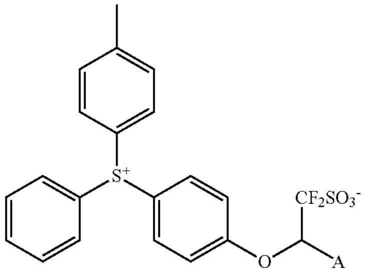
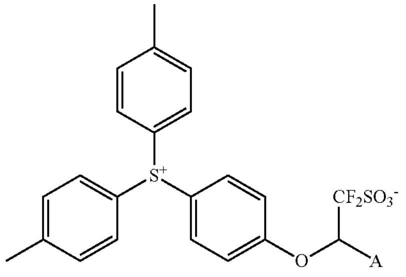
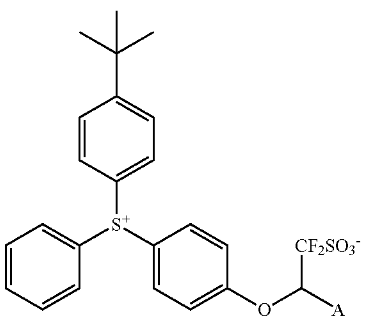

-continued
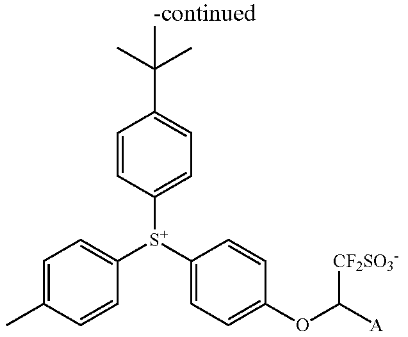
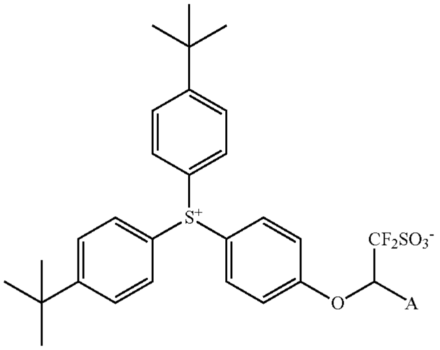
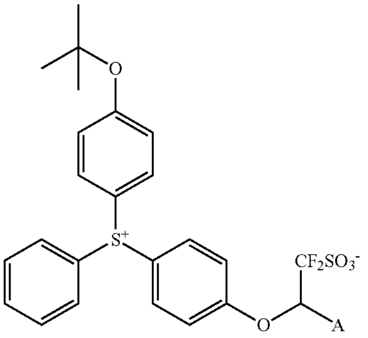
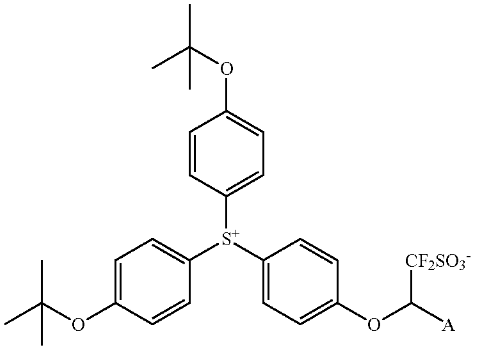
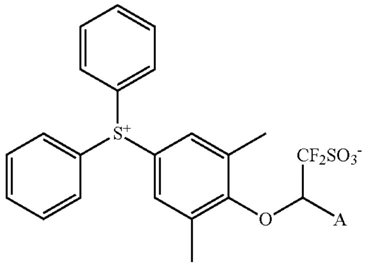
-continued
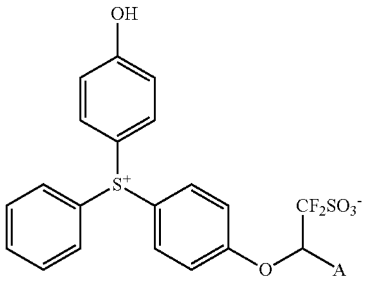
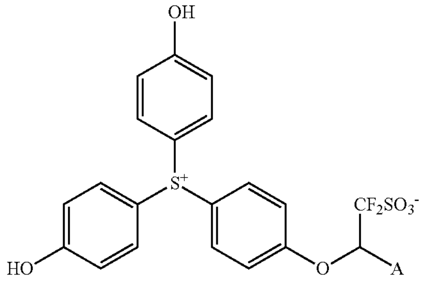
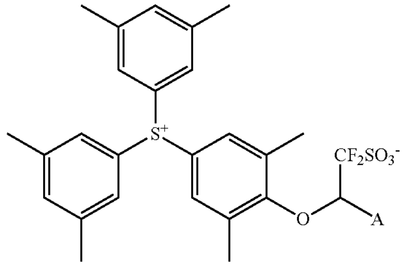
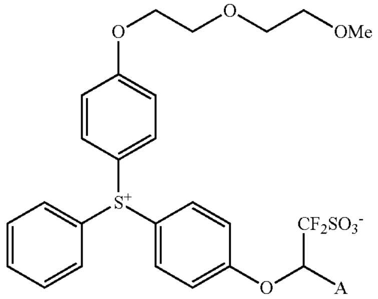
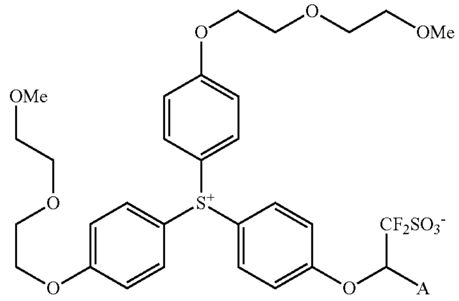

-continued
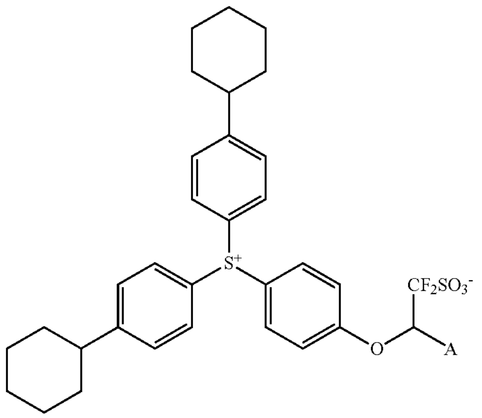
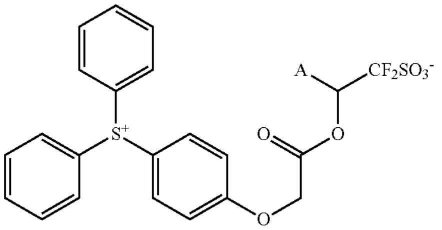
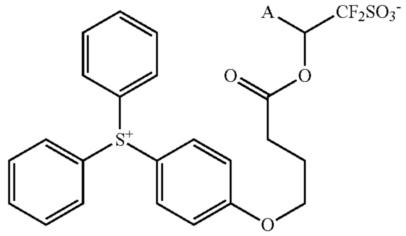
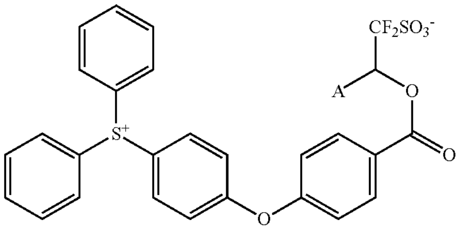
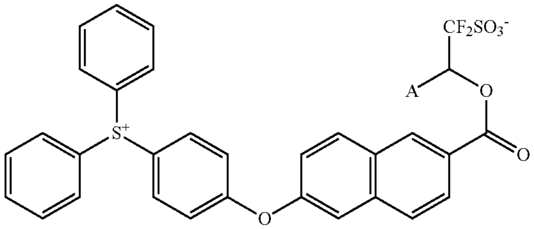
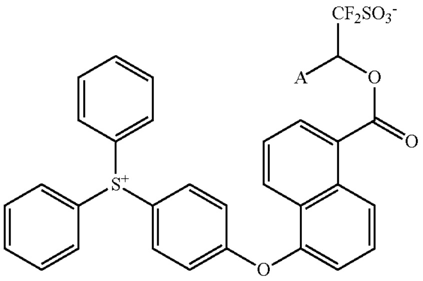
-continued
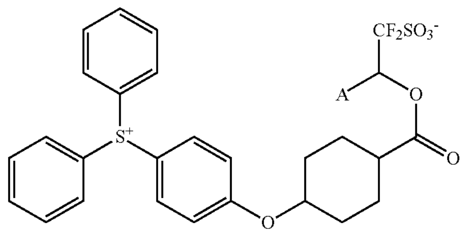
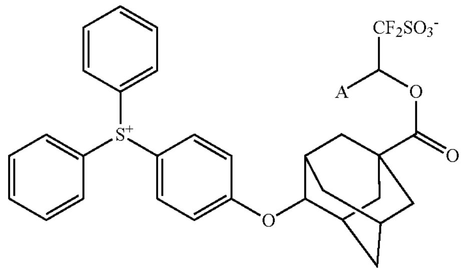
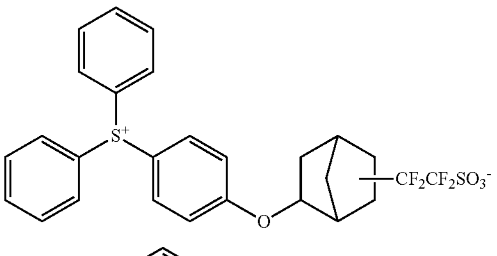
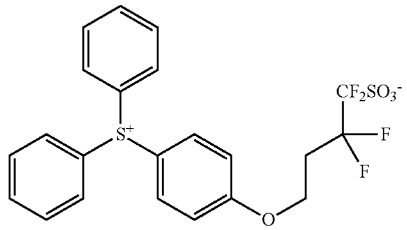
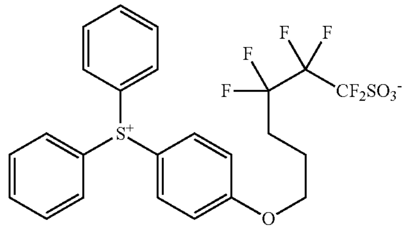
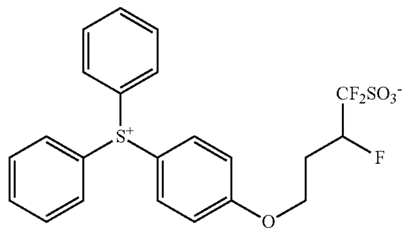
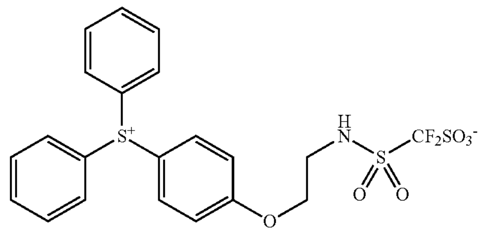

-continued

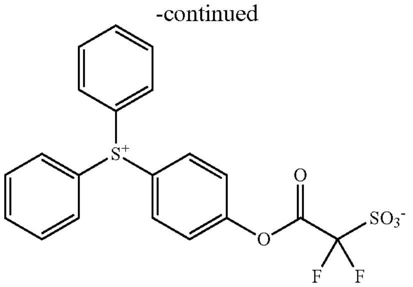

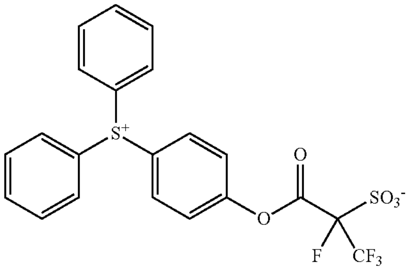

In the above formulae, A is hydrogen or trifluoromethyl.

In addition to the inventive polymer, the resist composition may further comprise at least one component selected from among an organic solvent, basic compound, dissolution regulator, surfactant, and acetylene alcohol.

Suitable organic solvents include those described in JP-A 2008-111103, paragraphs [0144] to [0145] (U.S. Pat. No. 7,537,880), for example, ketones such as cyclohexanone, cyclopentanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

Examples of the basic compound used herein include primary, secondary, and tertiary amine compounds as described in JP-A 2008-111103, paragraphs [0146] to [0164], specifically amine compounds having a hydroxyl, ether, ester, lactone, cyano or sulfonic ester group, and compounds having a carbamate group as described in JP 3790649.

Onium salts such as sulfonium salts, iodonium salts and ammonium salts of sulfonic acids which are not fluorinated at α-position as described in US 2008153030 (JP-A 2008-158339) and similar onium salts of carboxylic acids as described in JP-A 2013-037092 may be used as the quencher. Where an α-position non-fluorinated sulfonic acid salt or carboxylic acid salt and an α-position fluorinated sulfonic acid, imide acid, and methide acid generated by a PAG are co-present, salt exchange occurs to generate an α-position non-fluorinated sulfonic acid or carboxylic acid. Since this α-position non-fluorinated sulfonic acid or carboxylic acid has an insufficient acid strength to induce deprotection reaction to the resist resin, the relevant sulfonium salt, iodonium salt or ammonium salt functions as a quencher. In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed area, further improved focus margin or DOF and satisfactory dimensional control.

When the polarity switch units of formulae (2a) to (2d), (4A) or (4E) are highly reactive with acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Illustrative, non-limiting examples of the α-position non-fluorinated sulfonic acid salt and carboxylic acid salt are given below.

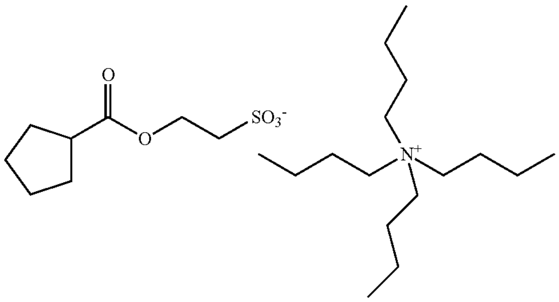

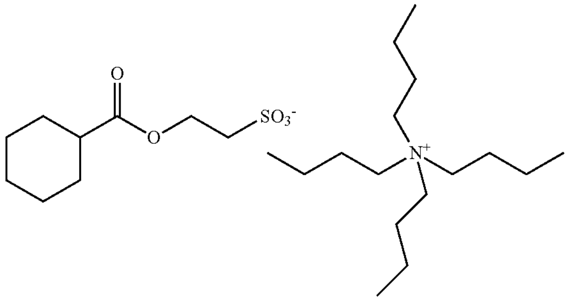

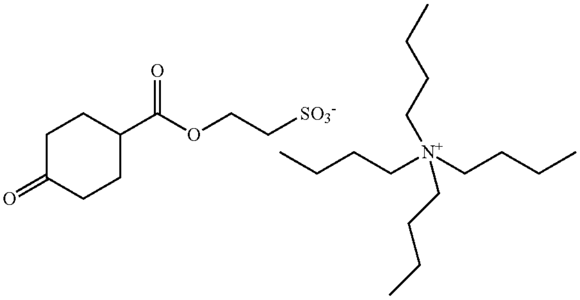

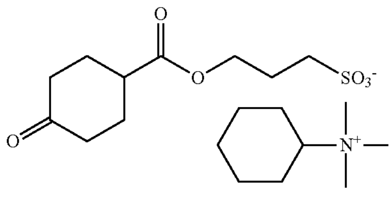

-continued
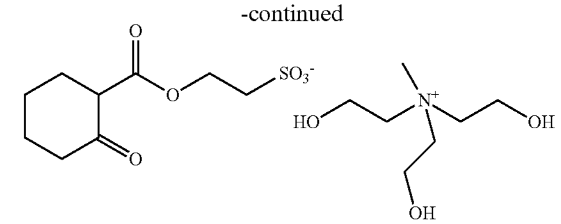
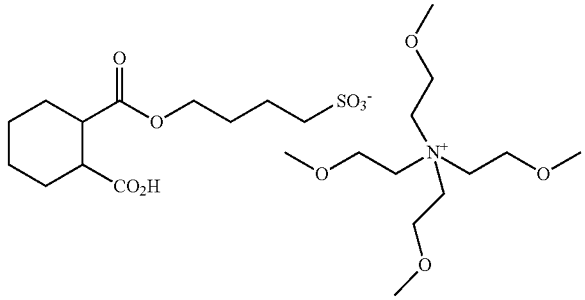
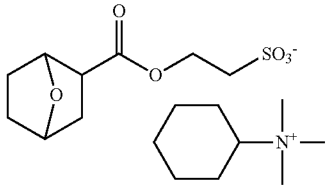
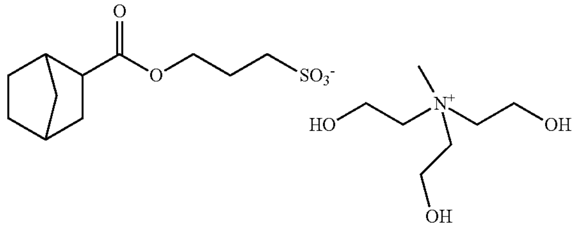
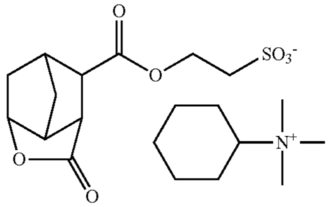
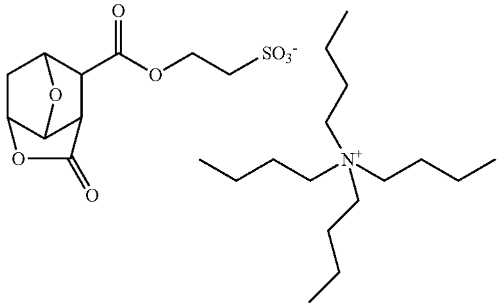
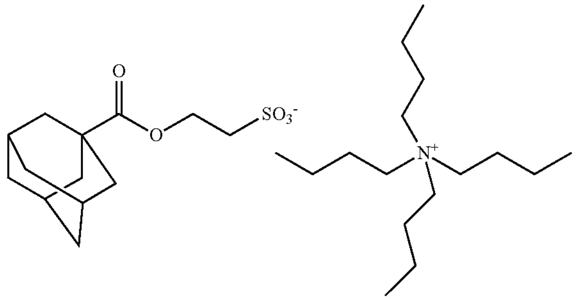
-continued
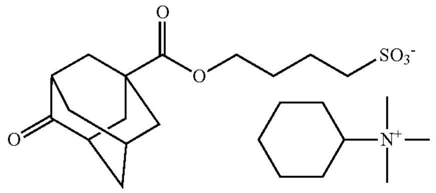
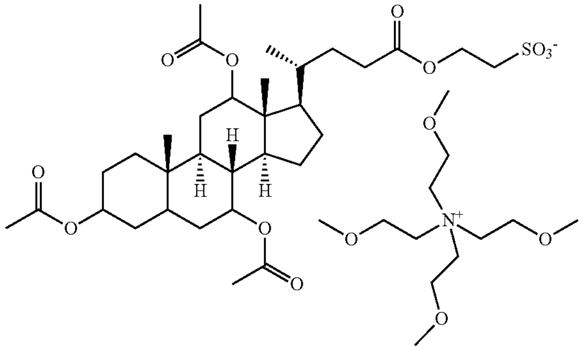
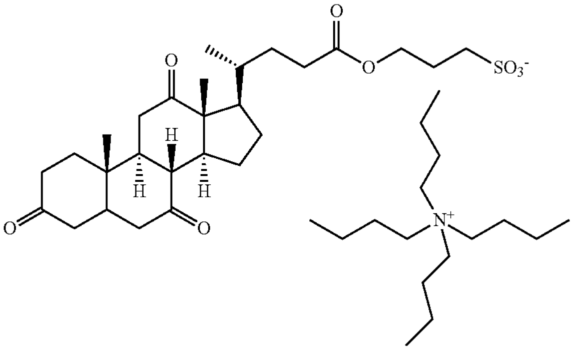
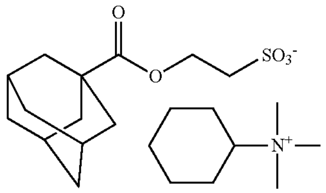
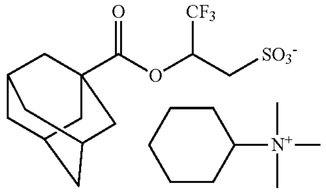
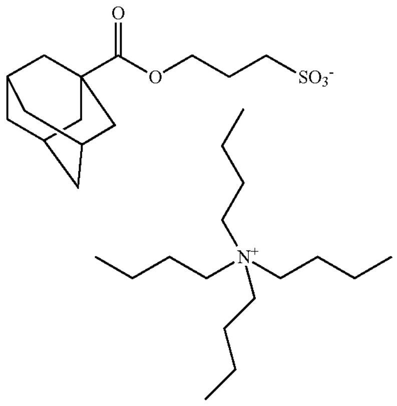

-continued
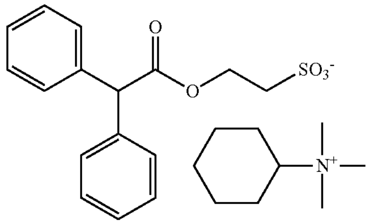
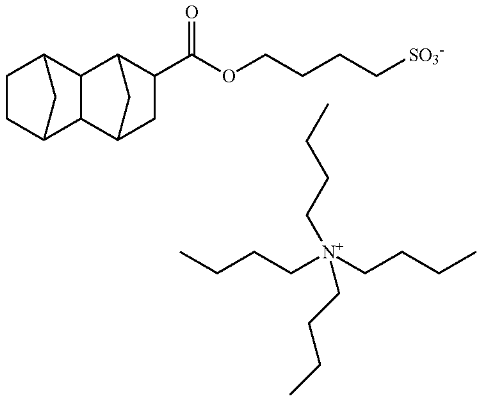
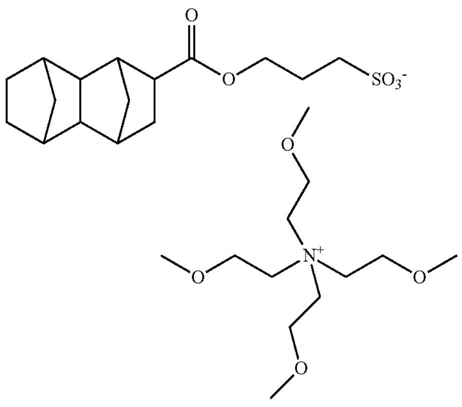
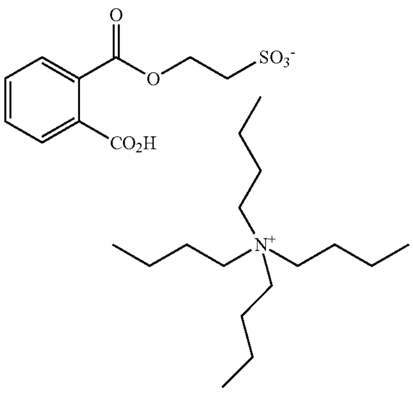
-continued
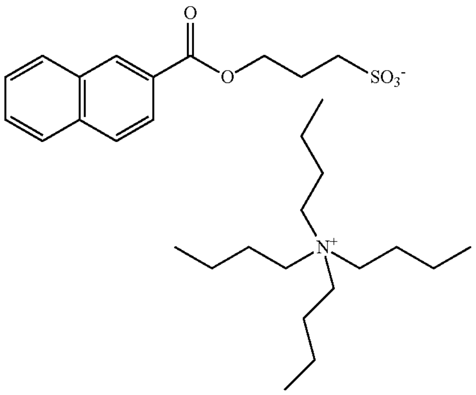
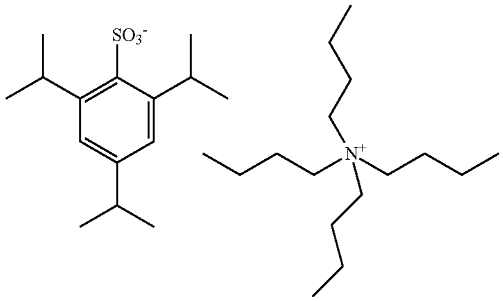
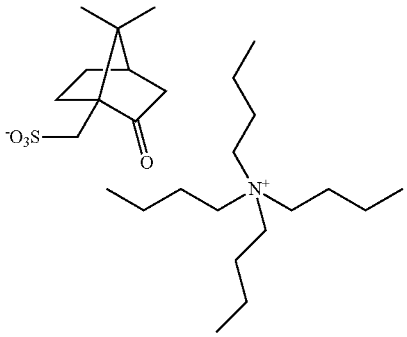
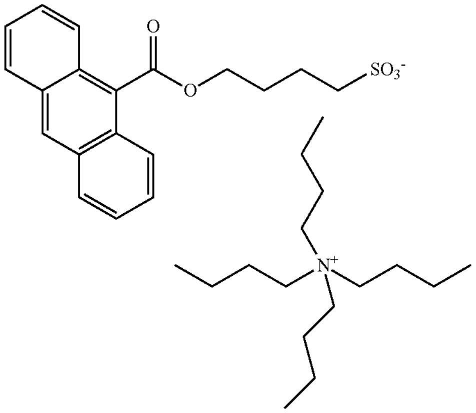
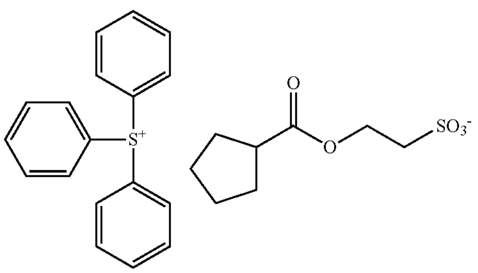

-continued
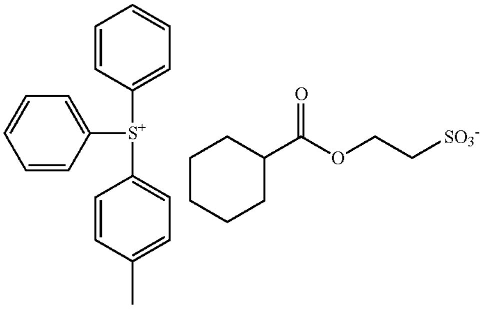
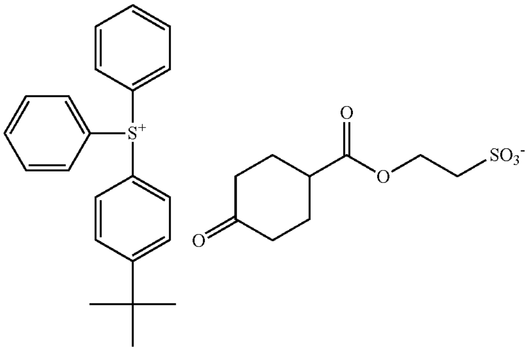
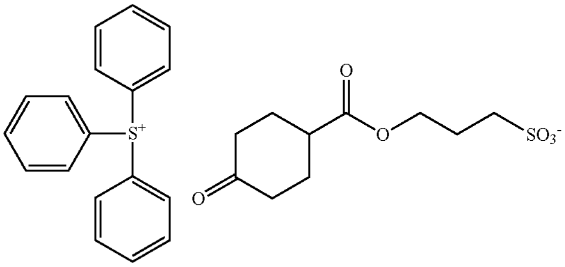
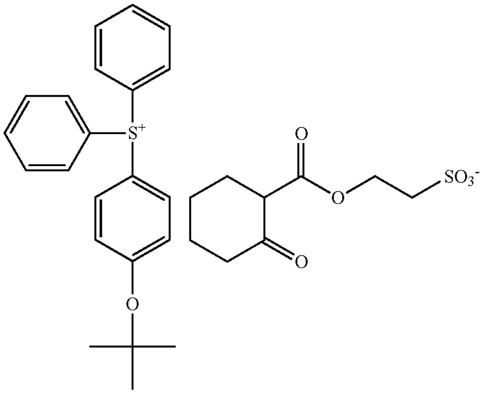
-continued
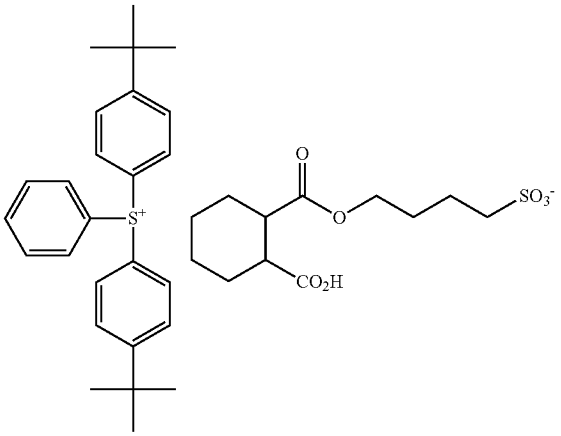
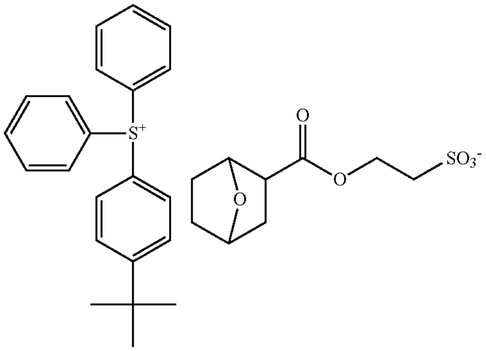
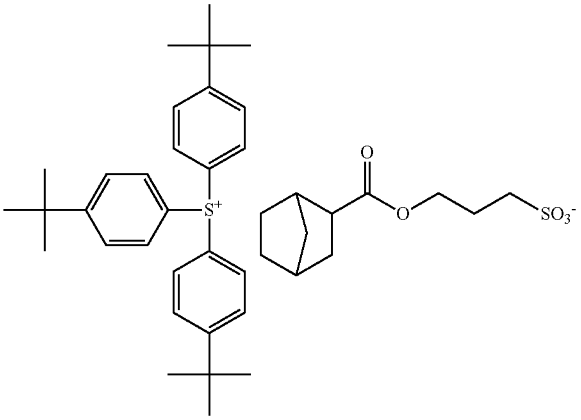
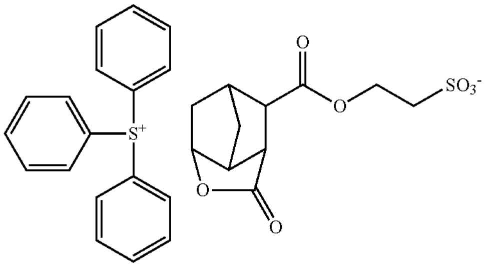

-continued
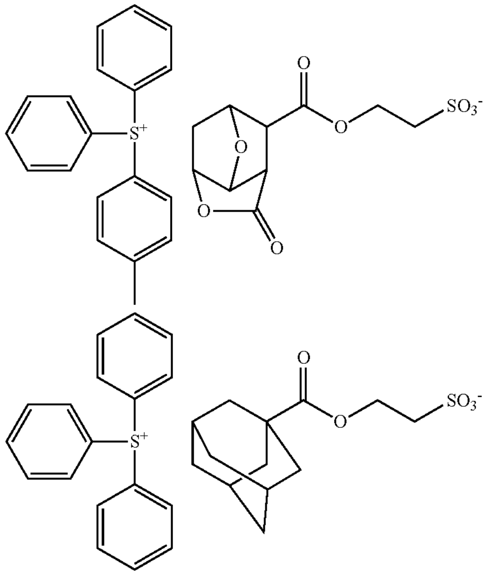
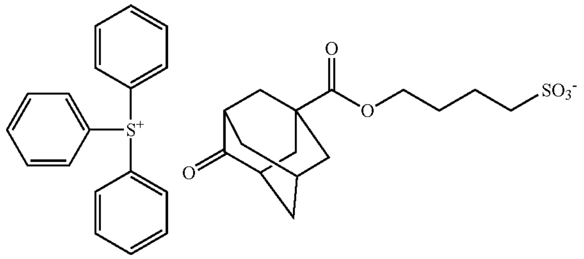
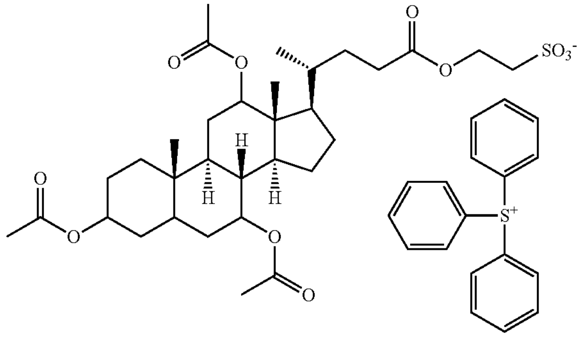
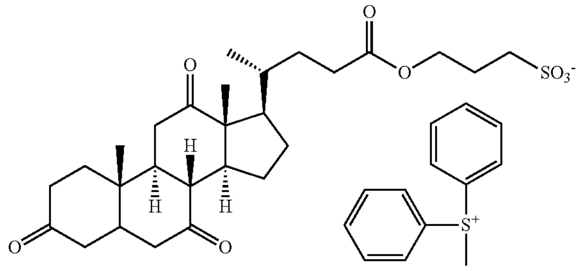
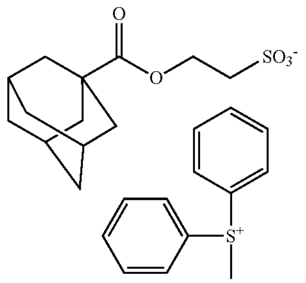
-continued
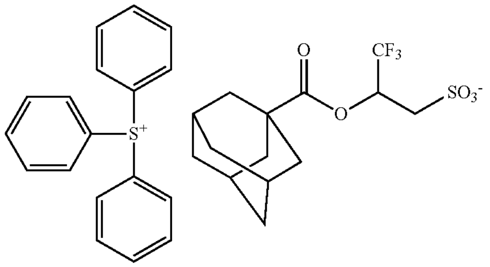
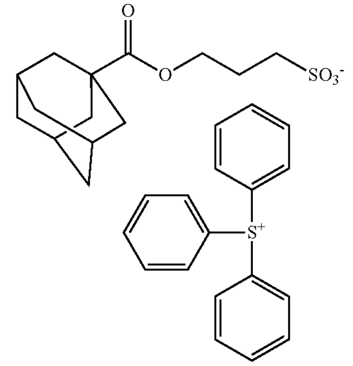
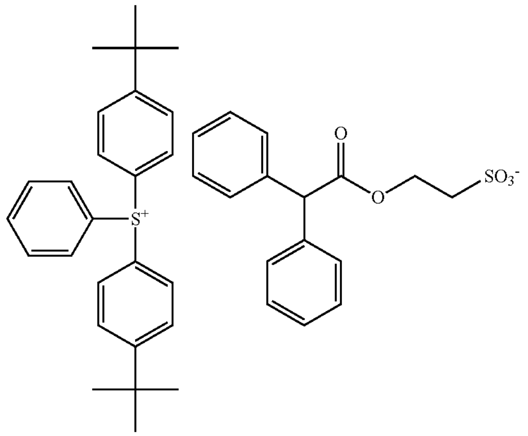
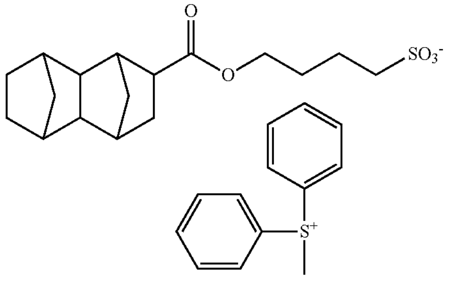
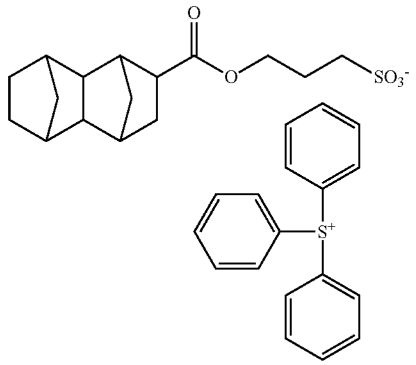

-continued
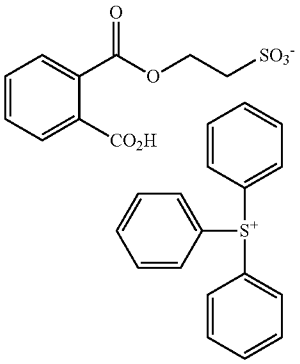
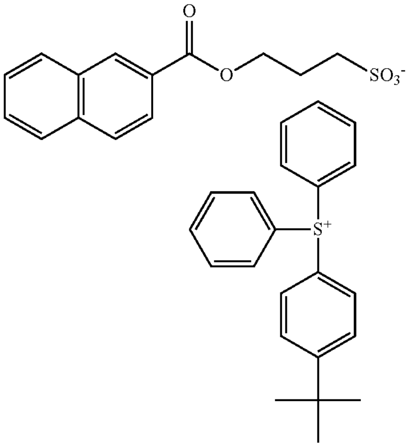
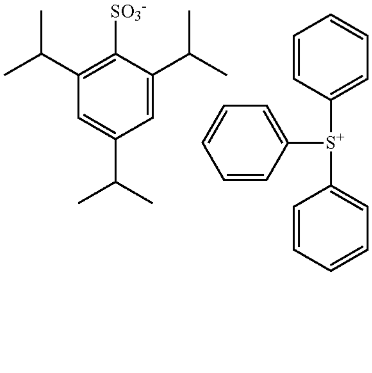
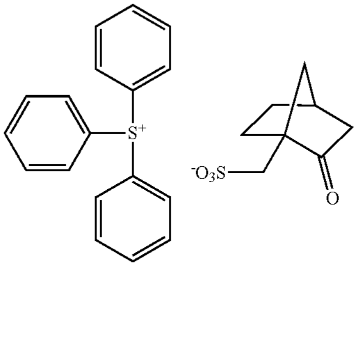
-continued
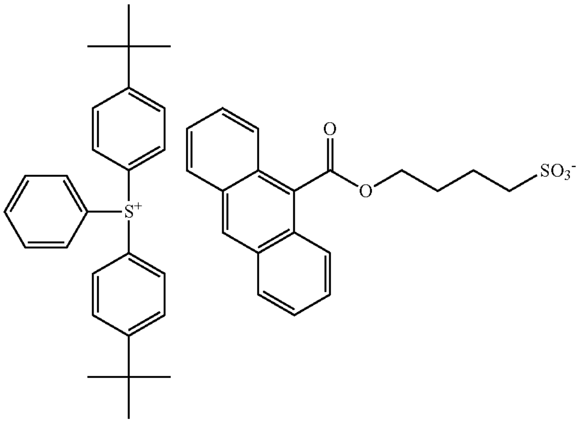
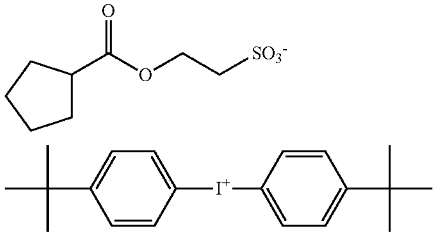
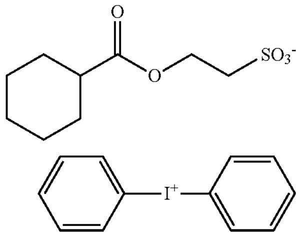
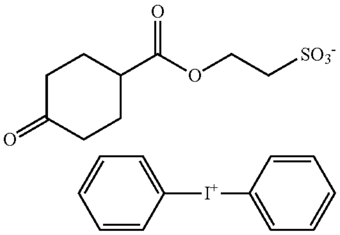
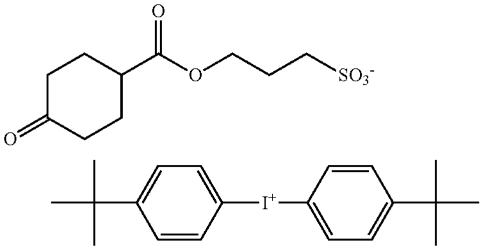
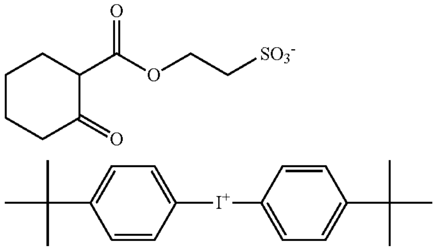

-continued
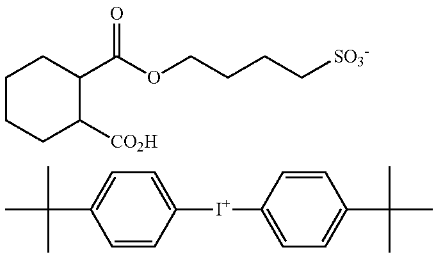
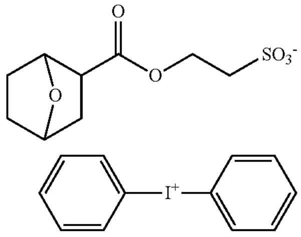
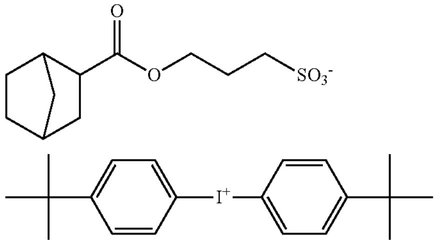
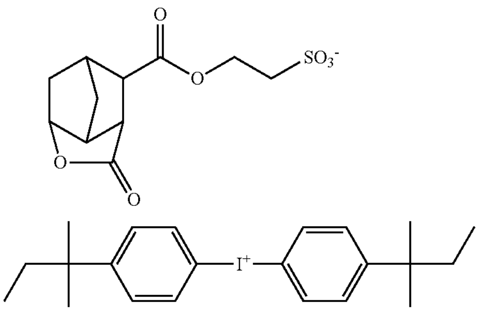
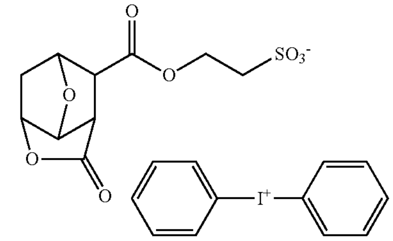
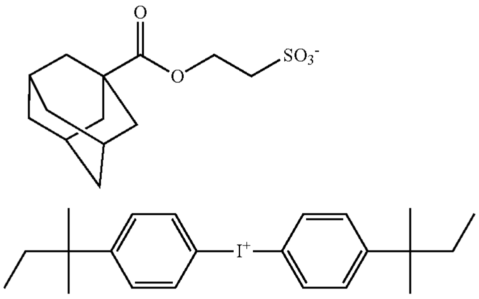
-continued
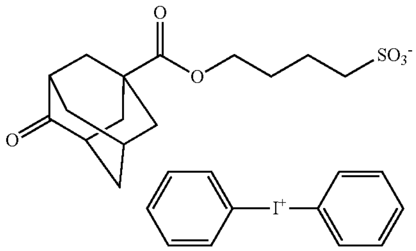
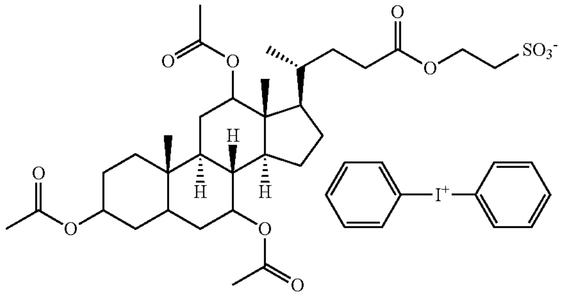
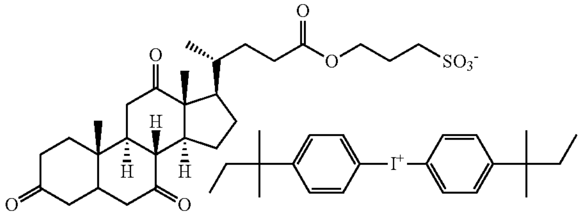
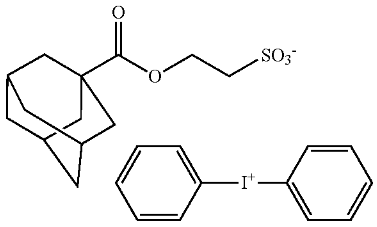
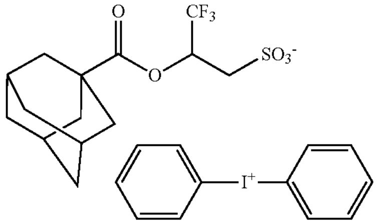
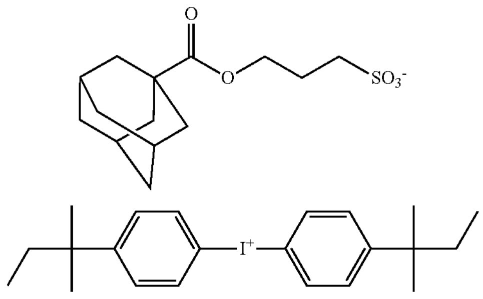

-continued
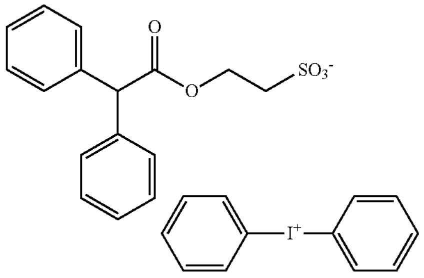
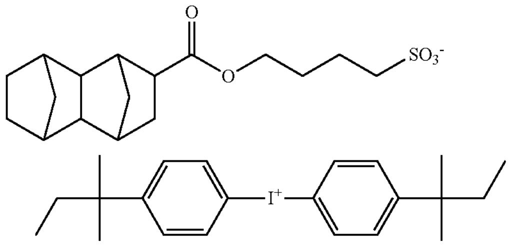
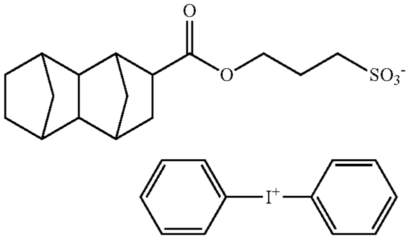
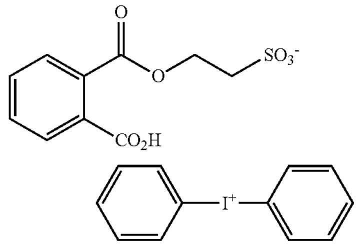
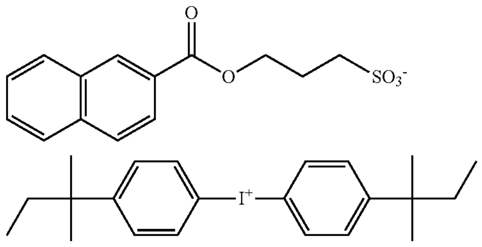
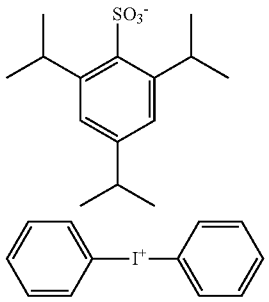
-continued
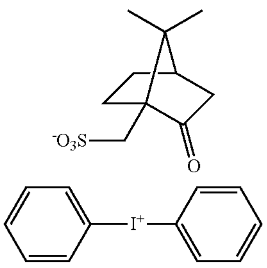
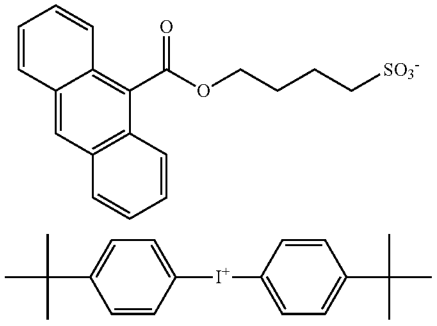
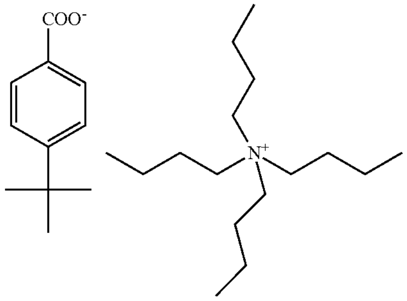
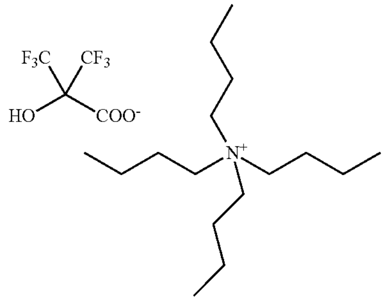
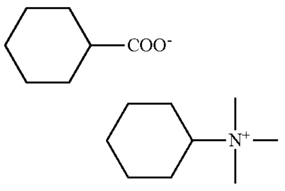
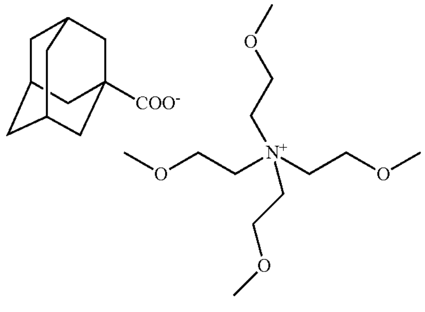

-continued
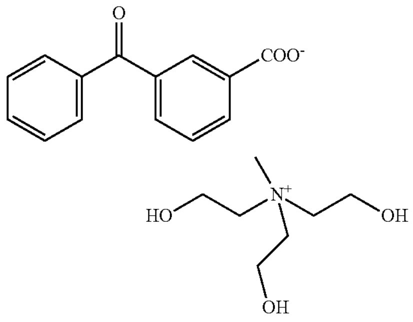
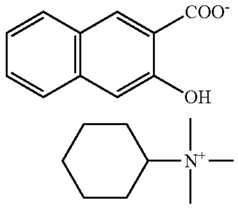
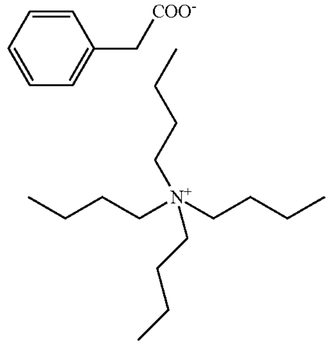
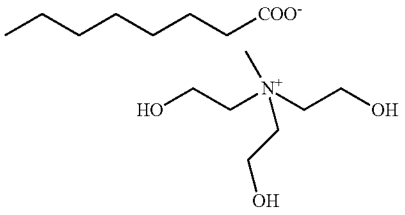
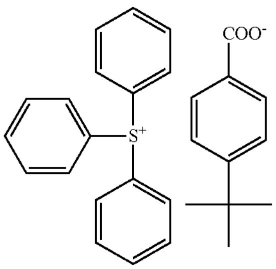
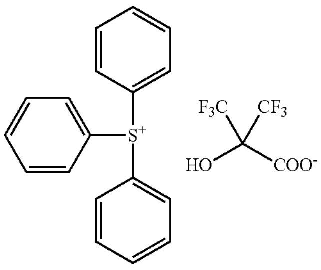
-continued
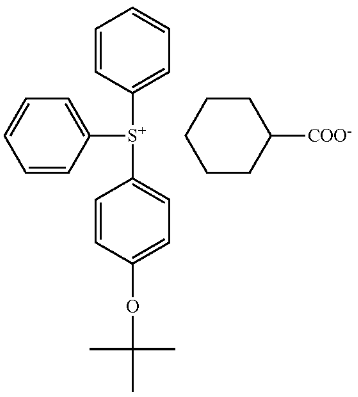
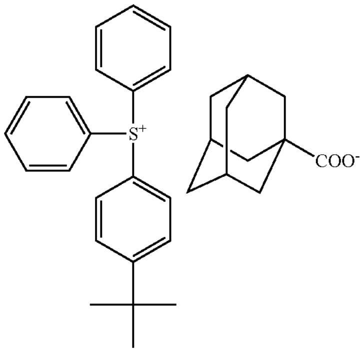
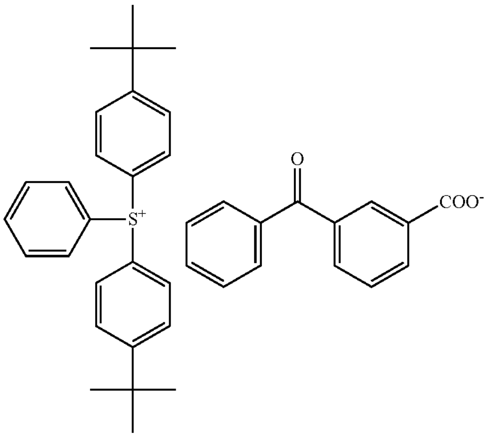
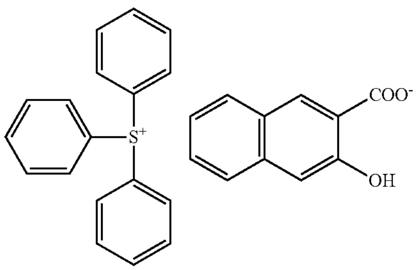

-continued
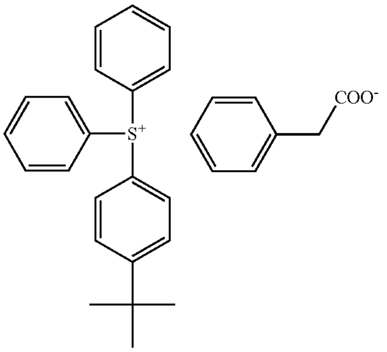
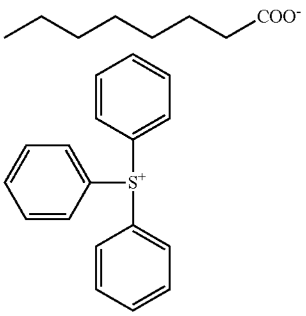
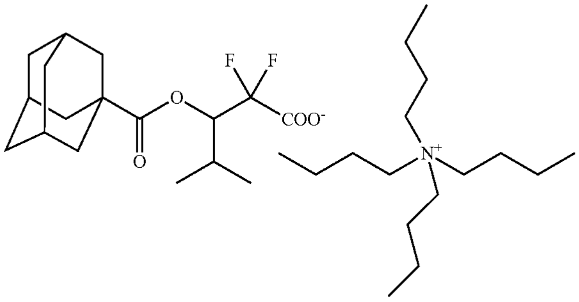
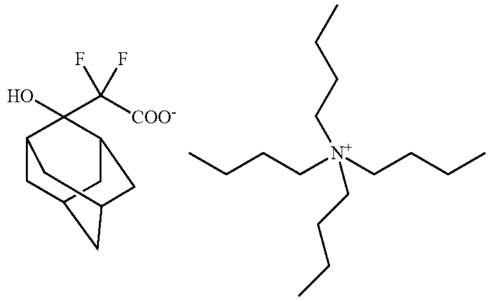
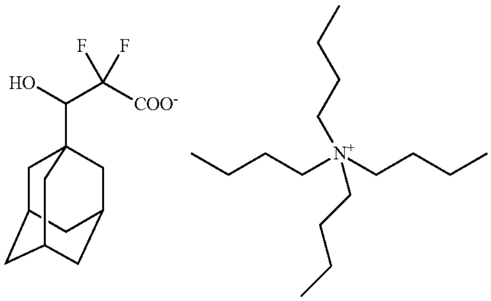
-continued
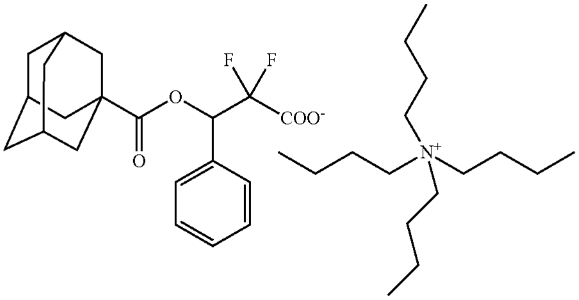
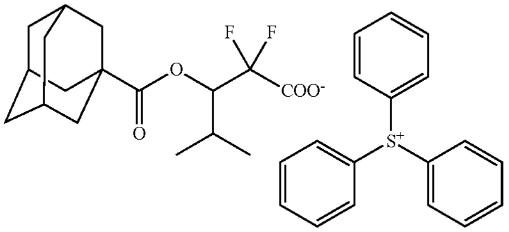
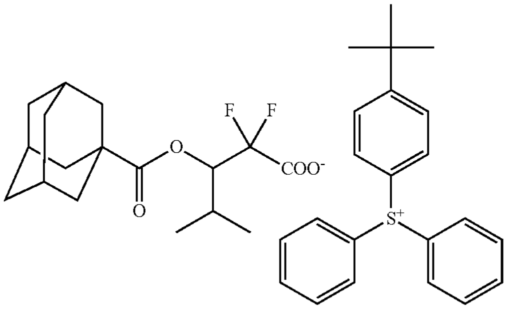
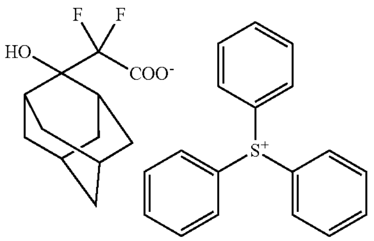
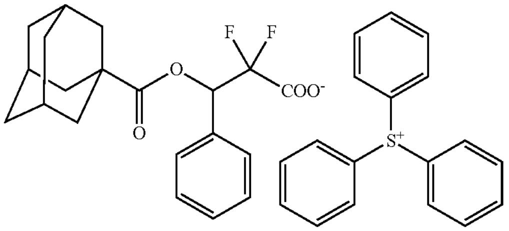
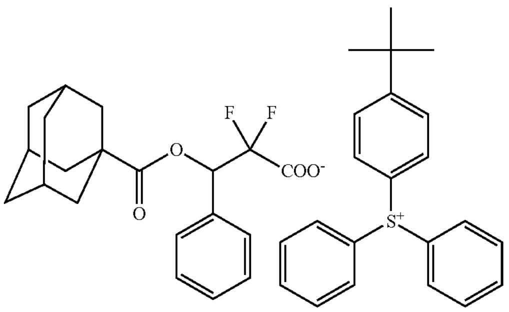

-continued

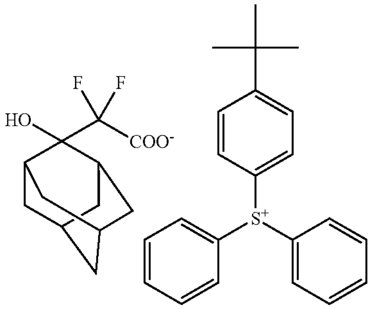

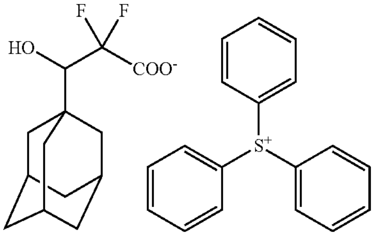

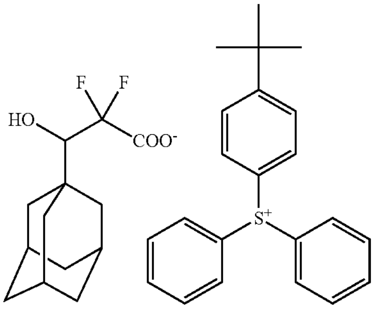

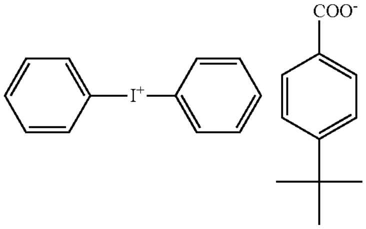

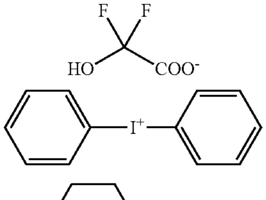

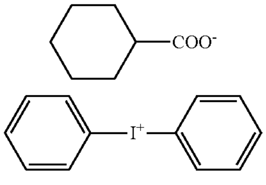

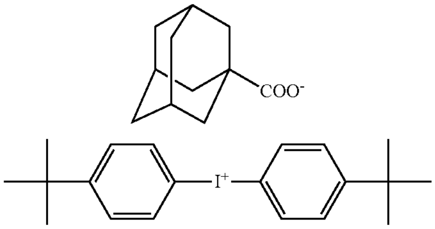

-continued

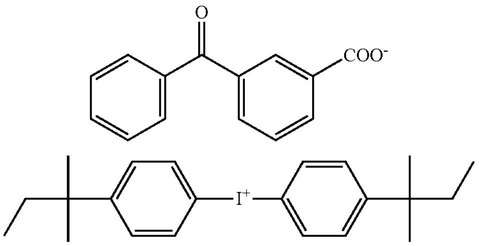

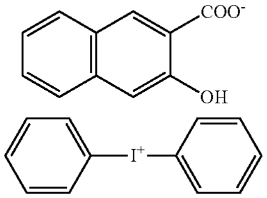

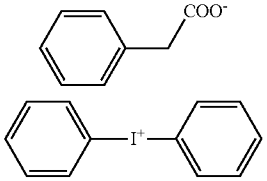

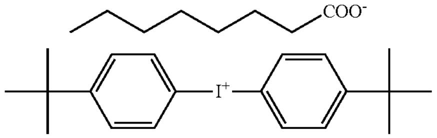

Exemplary surfactants are described in JP-A 2008-111103, paragraphs [0165] to [0166]. Exemplary dissolution regulators are described in JP-A 2008-122932 (US 2008090172), paragraphs [0155] to [0178], and exemplary acetylene alcohols in paragraphs [0179] to [0182].

Notably, an appropriate amount of the organic solvent used is 50 to 10,000 parts, preferably 100 to 5,000 parts by weight, an appropriate amount of the dissolution regulator is 0 to 50 parts, preferably 0 to 40 parts by weight, and an appropriate amount of the basic compound is 0 to 100 parts, preferably 0.001 to 50 parts by weight, per 100 parts by weight of the base resin. Amounts of the surfactant and acetylene alcohol may be determined as appropriate for a particular purpose.

Also a polymeric additive may be added for improving the water repellency on surface of a resist film as spin coated. The water repellency improver may be used in the topcoatless immersion lithography. The water repellency improver has a specific structure with a 1,1,1,3,3,3-hexafluoro-2-propanol residue and is described in JP-A 2007-297590, JP-A 2008-111103, JP-A 2008-122932, JP-A 2012-128067, and JP-A 2013-057836.

Preferred as the polymer for improving water repellency are a homopolymer consisting of fluorinated units, a copolymer consisting of fluorinated units of two or more types, and a copolymer consisting of fluorinated units and other units. Examples of the fluorinated units and other units are shown below, but not limited thereto. Notably $R^{55}$ is hydrogen or methyl.

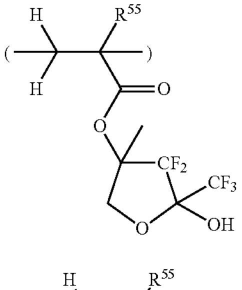
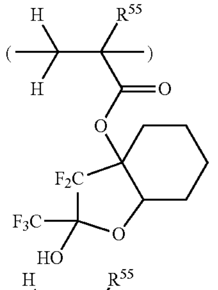
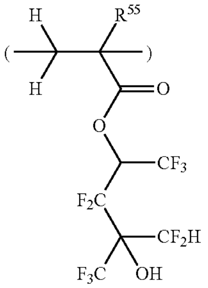
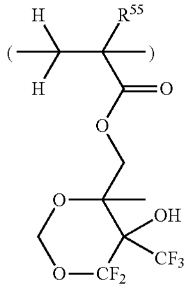
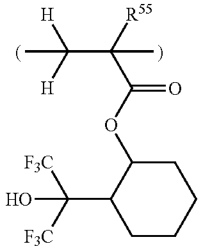
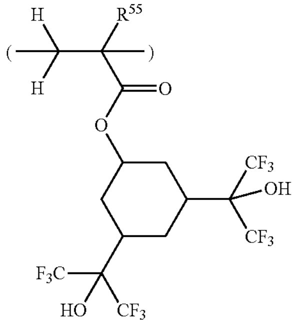
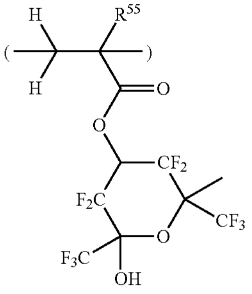
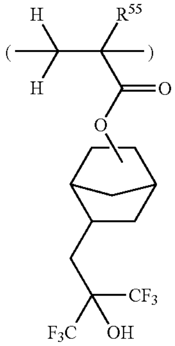
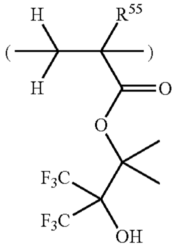
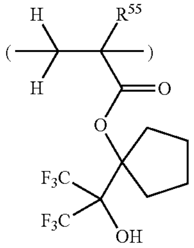
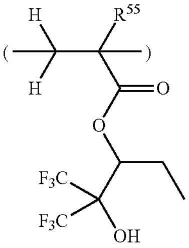
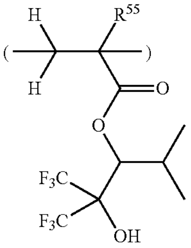
-continued
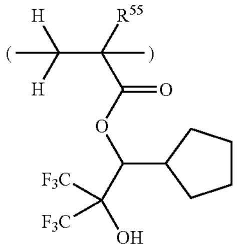
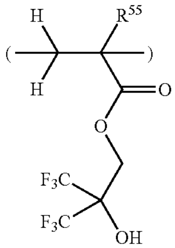
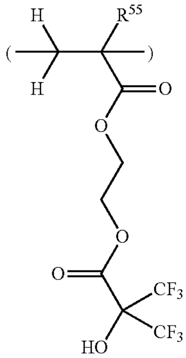
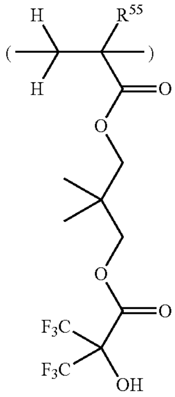
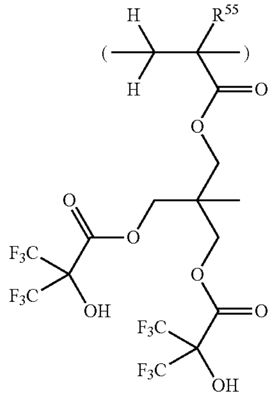
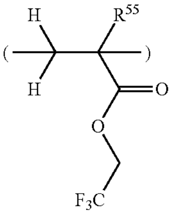
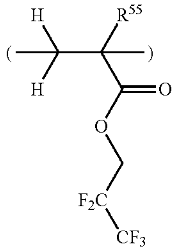
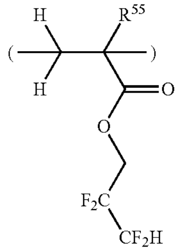
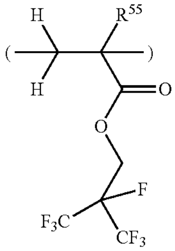
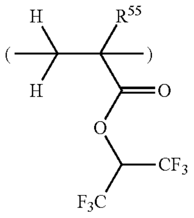
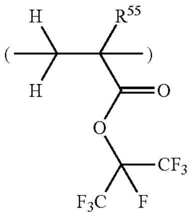

-continued
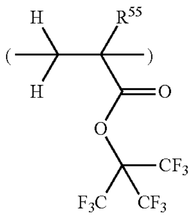
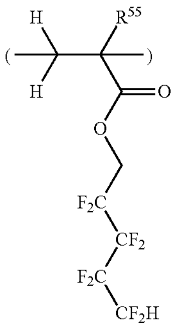
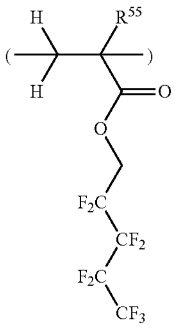
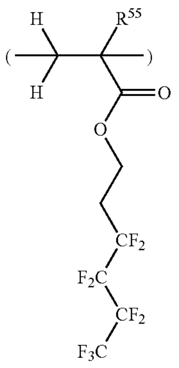
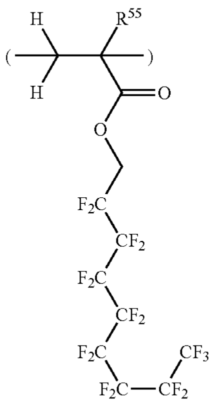
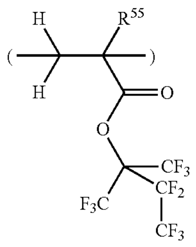
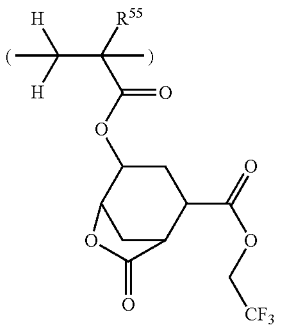
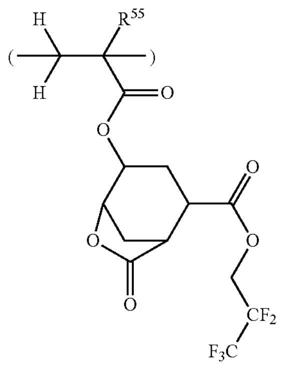
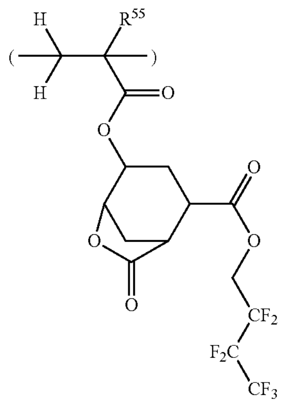
-continued
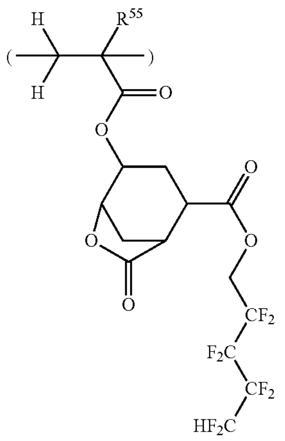
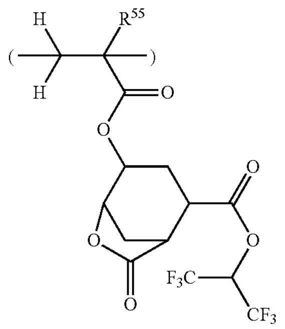
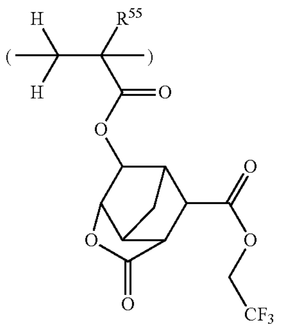
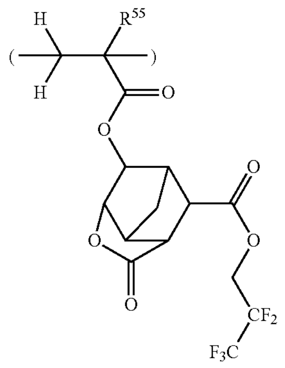
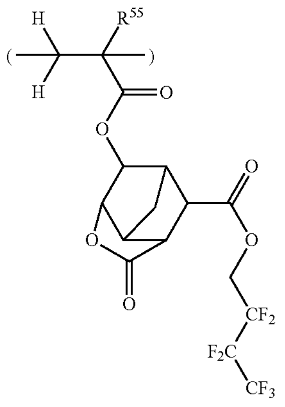
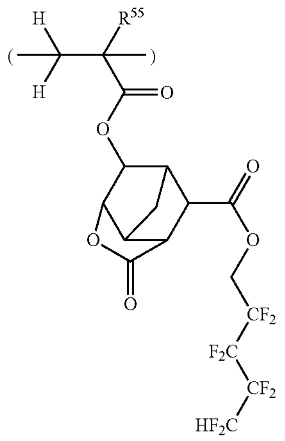
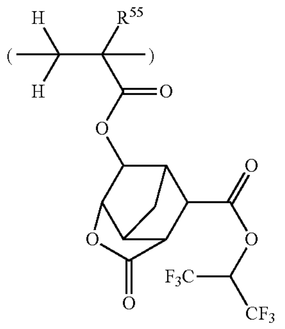
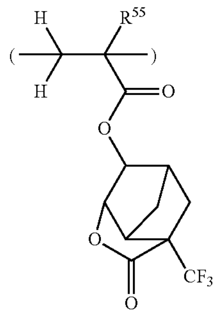

-continued
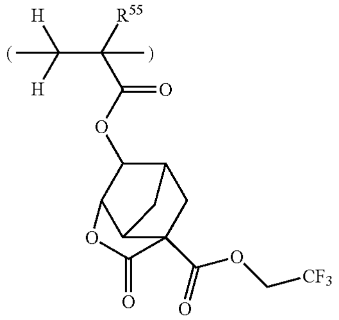
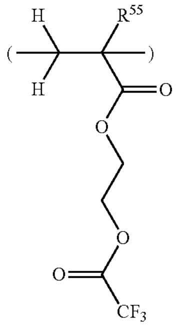
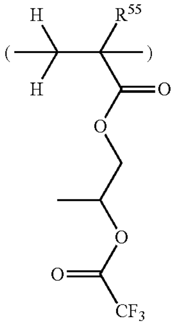
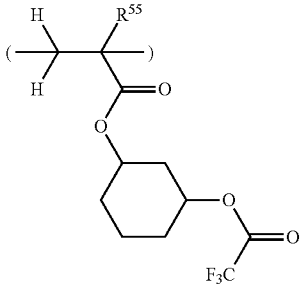
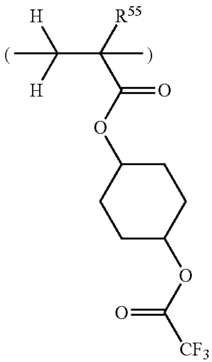
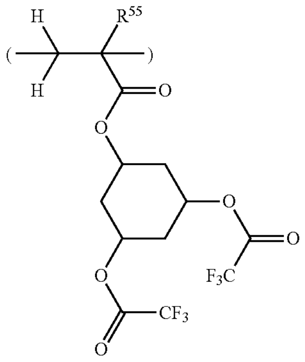
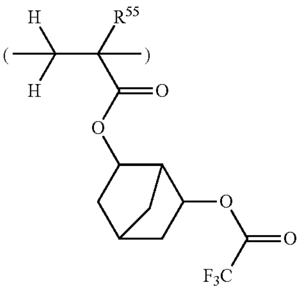
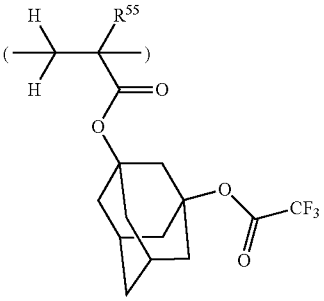
-continued
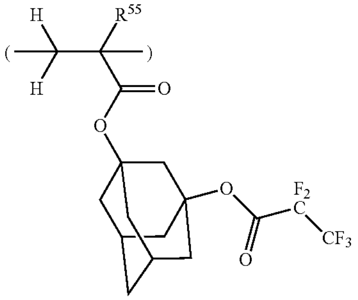
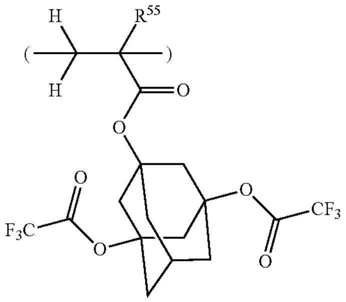
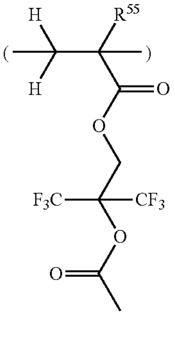
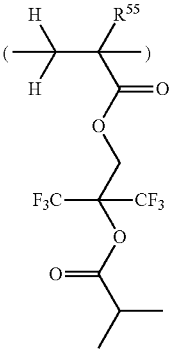
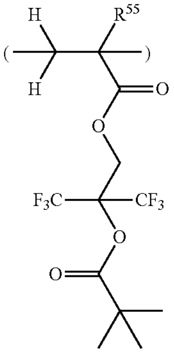
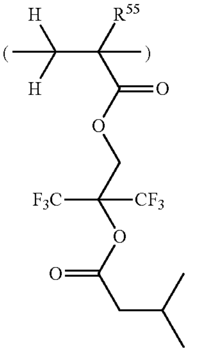
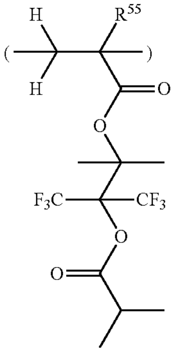
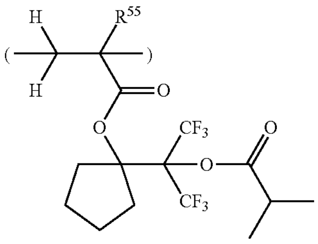

-continued
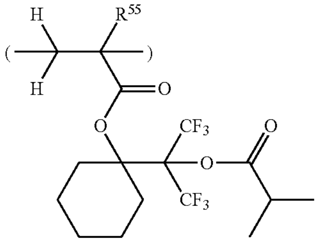
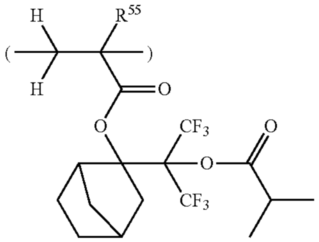
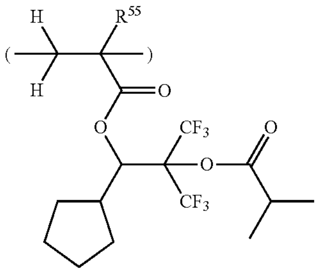
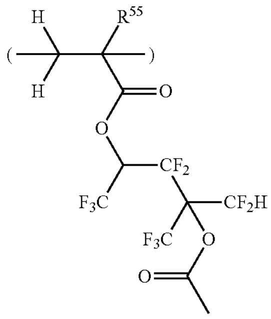
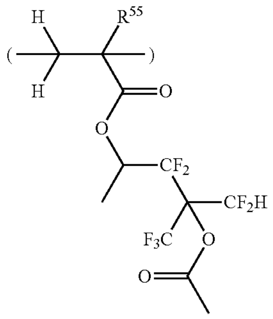
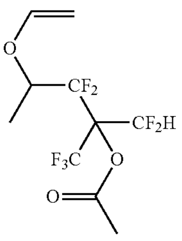
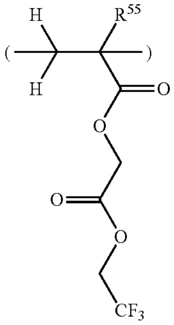
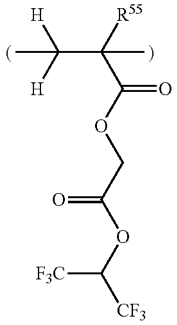
-continued
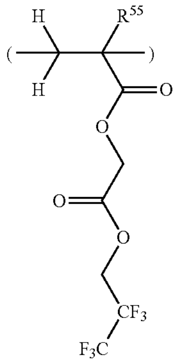
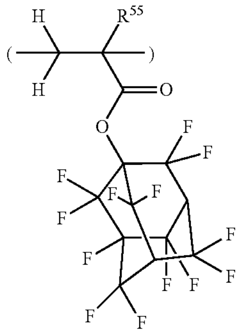
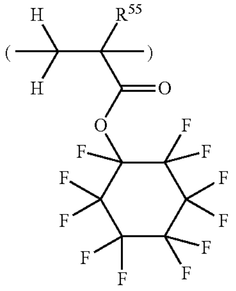
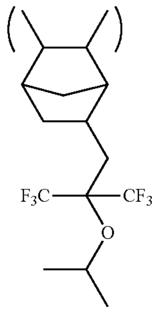
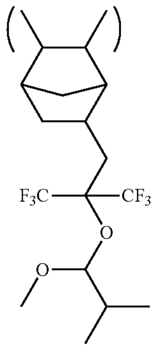
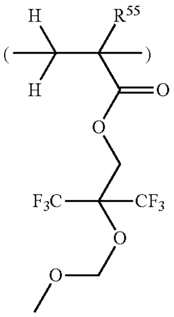
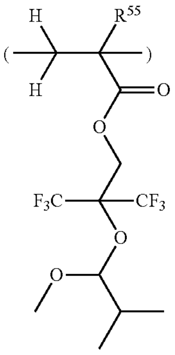
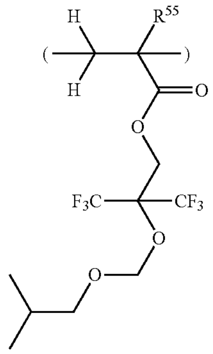
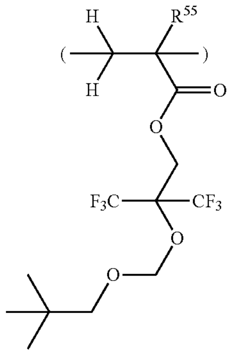

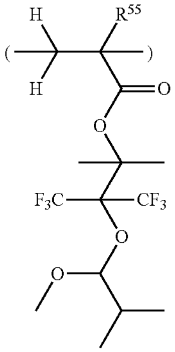
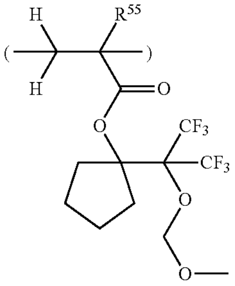
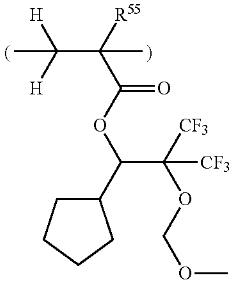
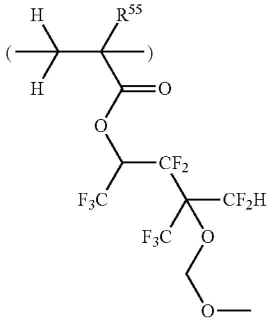
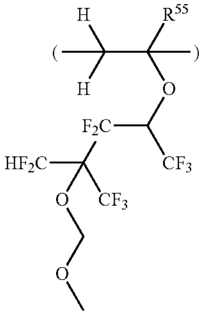
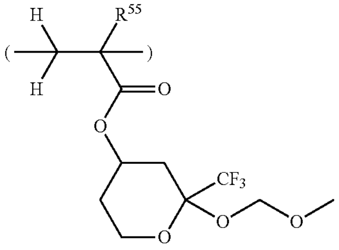
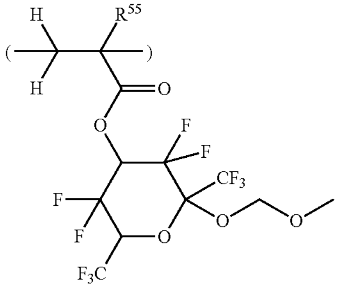
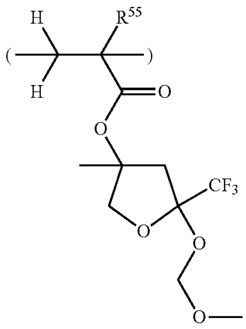
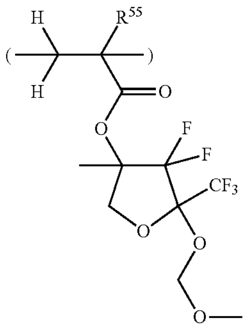
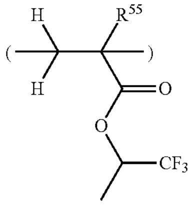
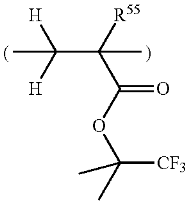
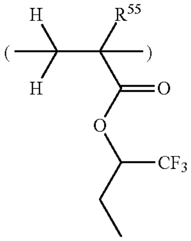
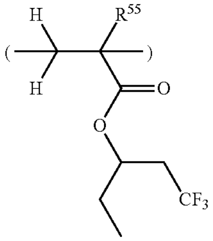
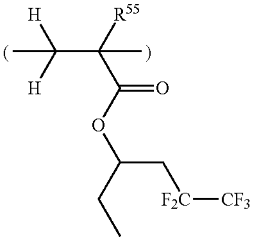
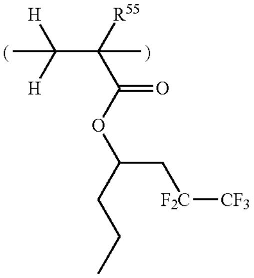
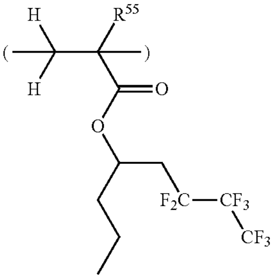
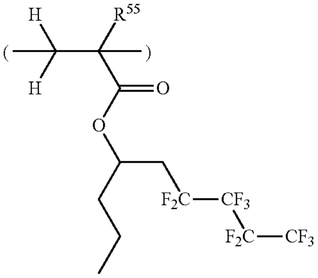
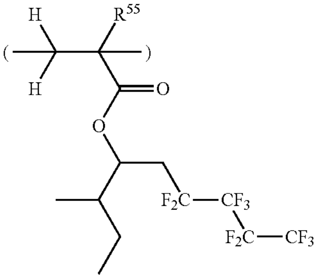

-continued
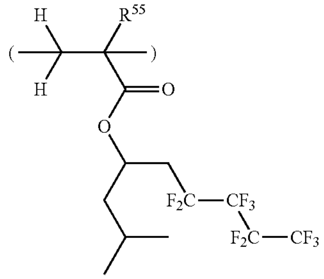
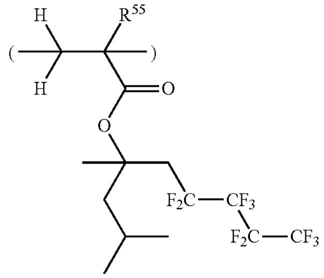
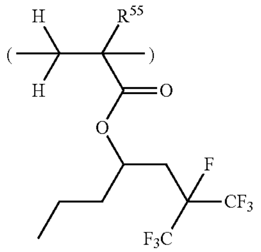
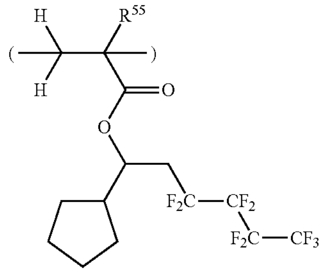
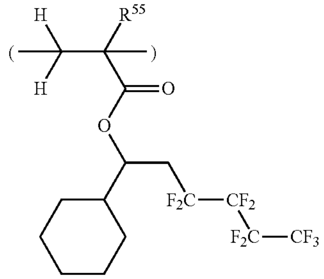
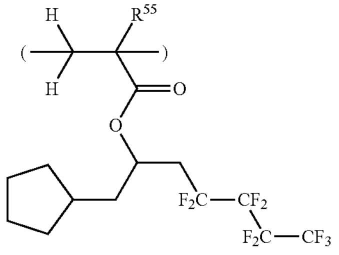
-continued
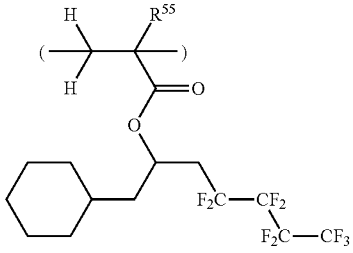
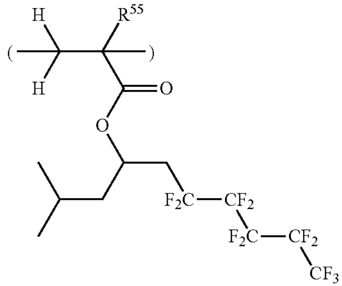
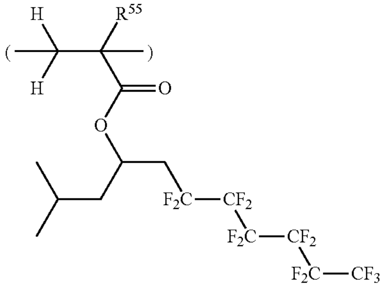
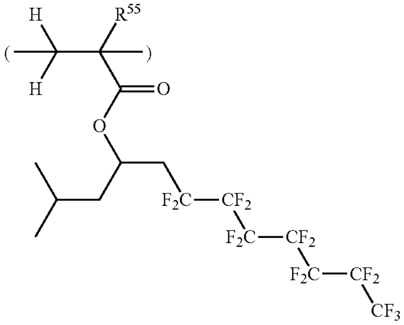
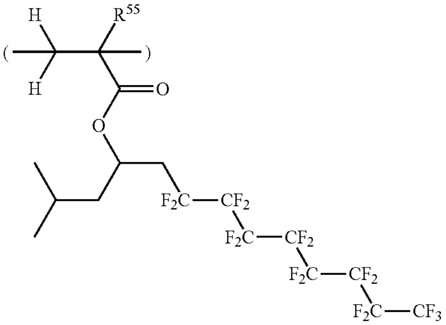
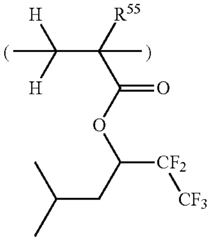
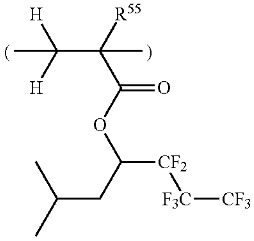

-continued
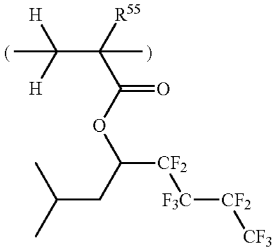
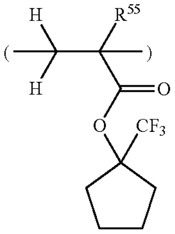
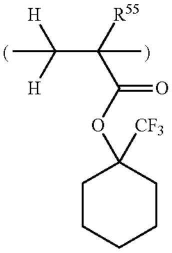
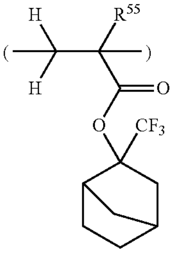
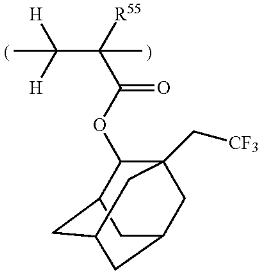
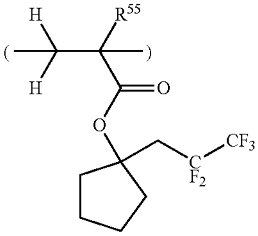
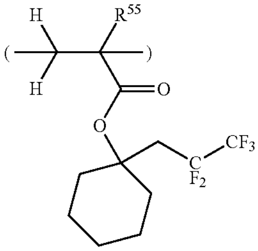
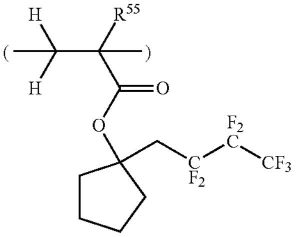
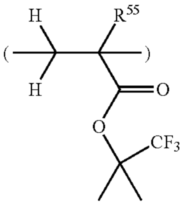
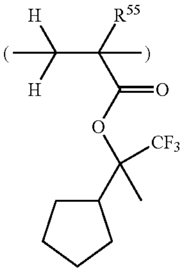
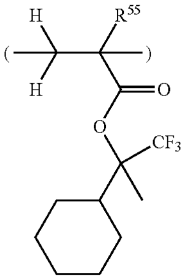
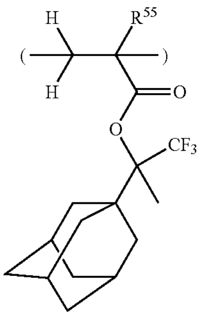
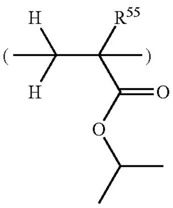
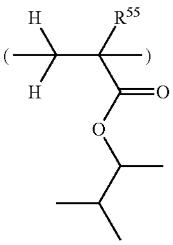
-continued
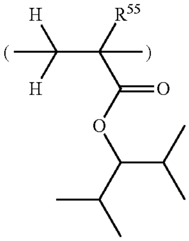
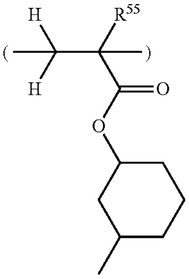
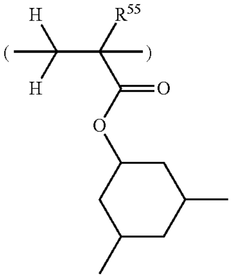
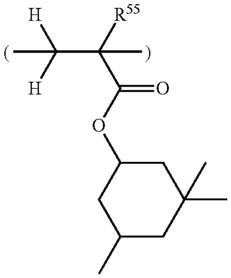
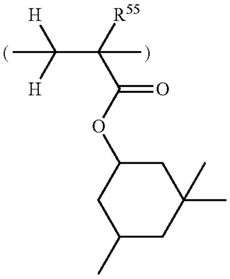
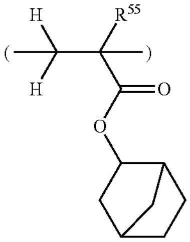
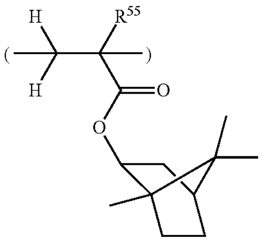
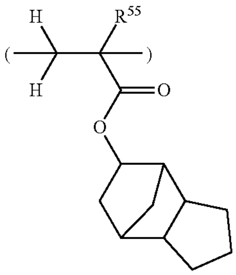
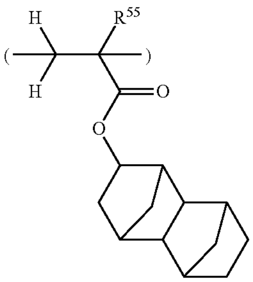
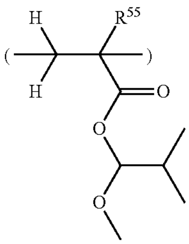
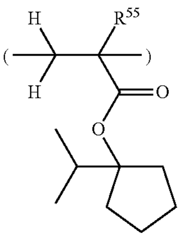
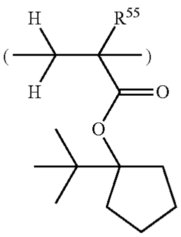
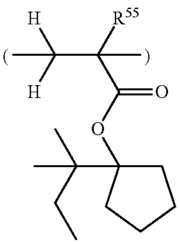

-continued

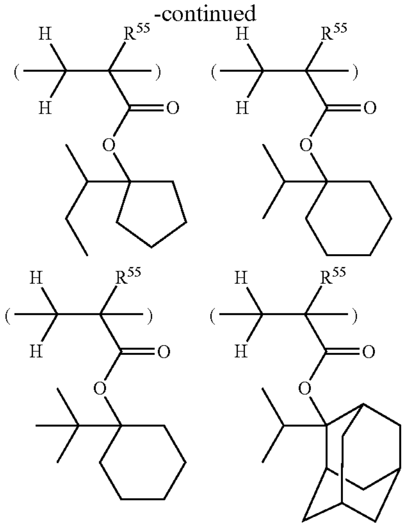

The water repellency improver to be added to the resist composition should be soluble in the organic solvent which is used as the developer to form a negative pattern. The water repellency improver of specific structure with a 1,1,1,3,3,3-hexafluoro-2-propanol residue is well soluble in the developer. A polymer having an amino group or amine salt copolymerized as recurring units may serve as the water repellency improver and is effective for preventing evaporation of acid during PEB, any hole pattern opening failure after development, and bridging of a line-and-space pattern. An appropriate amount of the water repellency improver is 0.1 to 20 parts, preferably 0.5 to 10 parts by weight per 100 parts by weight of the base resin.

While the resist composition is basically composed of the polymer, acid generator, organic solvent, and organic nitrogen-containing compound, other components including a dissolution regulator, acidic compound, stabilizer and dye may be added if desired. Optional other components are added in conventional amounts as long as the benefits of the invention are not compromised.

Process

A further embodiment of the invention is a pattern forming process comprising the steps of applying the resist composition onto a substrate, prebaking to form a resist film, exposing the resist film to high-energy radiation, baking, and developing the exposed resist film in a developer.

The process of forming a positive pattern using an aqueous alkaline solution as developer is well known in the art, for example, from JP-A 2011-231312, paragraphs [0138] to [0146].

Figure 1B:
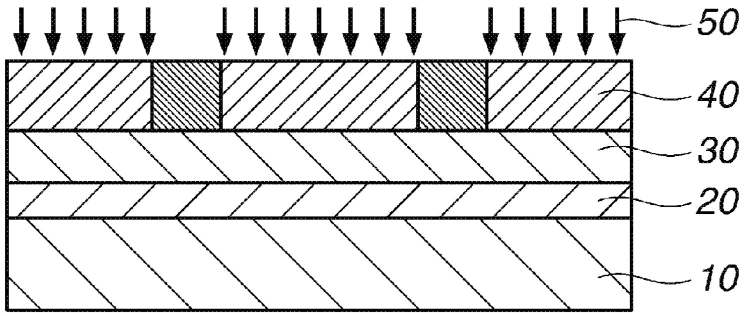
Figure 1C:
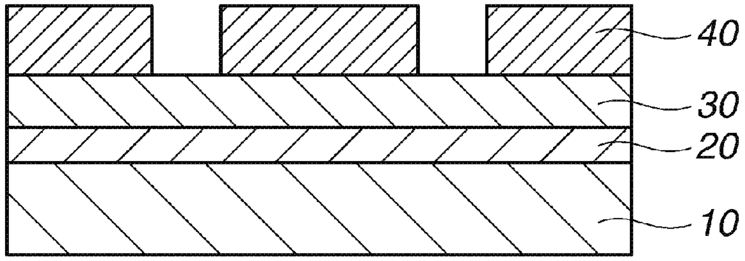

The process of forming a negative pattern using an organic solvent as developer is illustrated in FIGS. 1(A) to 1(C). First, the positive resist composition is coated on a substrate to form a resist film thereon. Specifically, a resist film 40 of a resist composition is formed on a processable substrate 20 disposed on a substrate 10 directly or via an intermediate intervening layer 30 as shown in FIG. 1(A). The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 300 seconds, especially 15 to 200 seconds.

The substrate 10 used herein is generally a silicon substrate. The processable substrate (or target film) 20 used herein includes $SiO_2$, SiN, SiON, SiOC, p-Si, α-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Next comes exposure depicted at 50 in FIG. 1(B). For the exposure, preference is given to high-energy radiation having a wavelength of 140 to 250 nm, EUV having a wavelength of 13.5 nm, electron beam (EB), and especially ArF excimer laser radiation of 193 nm. The exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. The immersion lithography involves prebaking a resist film and exposing the resist film to light through a projection lens, with water introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue. While the protective film must dissolve in the organic solvent developer, the polymer comprising recurring units derived from a monomer having a 1,1,1,3,3,3-hexafluoro-2-propanol residue dissolves in organic solvent developers. In particular, protective film-forming materials having 1,1,1,3,3,3-hexafluoro-2-propanol residues as described in JP-A 2007-025634, 2008-003569, 2008-081716, and 2008-111089 readily dissolve in organic solvent developers.

In the protective film-forming composition, an amine compound or amine salt or a polymer having copolymerized therein recurring units containing an amine group or amine salt may be used. This component is effective for controlling diffusion of the acid generated in the exposed region of the photoresist film to the unexposed region for thereby preventing any hole opening failure. Useful protective film materials having an amine compound added thereto are described in JP-A 2008-003569, and useful protective film materials having an amino group or amine salt copolymerized are described in JP-A 2007-316448. The amine compound or amine salt may be selected from the compounds enumerated as the basic compound to be added to the resist composition. An appropriate amount of the amine compound or amine salt added is 0.01 to 10 parts, preferably 0.02 to 8 parts by weight per 100 parts by weight of the base resin.

After formation of the photoresist film, deionized water rinsing (or post-soaking) may be carried out for extracting the acid generator and the like from the film surface or washing away particles, or after exposure, rinsing (or post-soaking) may be carried out for removing water droplets left on the resist film. If the acid evaporating from the exposed region during PEB deposits on the unexposed region to deprotect the protective group on the surface of the unexposed region, there is a possibility that the surface edges of holes of a hole pattern after development are bridged. Particularly in the case of negative development, regions surrounding the holes receive light so that acid is generated therein. There is a possibility that the holes are not opened if the acid outside the holes evaporates and deposits inside the holes during PEB. Provision of a protective film is effective for preventing evaporation of acid and for avoiding any hole opening failure. A protective film having an amine compound or amine salt added thereto is more effective for preventing acid evaporation. On the other hand, a protective film to which an acid compound such as a carboxyl or sulfo group is added or which is based on a polymer having copolymerized therein monomeric units containing a carboxyl or sulfo group is undesirable because of a potential hole opening failure.

A further embodiment of the invention is a process for forming a pattern by applying a resist composition comprising a polymer comprising recurring units having formula (2a), (2b), (2c) or (2d), an acid generator, and an organic solvent onto a substrate, baking the composition to form a resist film, forming a protective film on the resist film, exposing the resist film to high-energy radiation to define exposed and unexposed regions, baking, and applying an organic solvent developer to the coated substrate to form a negative pattern wherein the unexposed region of resist film and the protective film are dissolved and the exposed region of resist film is not dissolved. The protective film is preferably formed from a composition comprising a polymer bearing a 1,1,1,3,3,3-hexafluoro-2-propanol residue and an amino group or amine salt-containing compound, or a composition comprising a polymer bearing a 1,1,1,3,3,3-hexafluoro-2-propanol residue and having amino group or amine salt-containing recurring units copolymerized, the composition further comprising an alcohol solvent of at least 4 carbon atoms, an ether solvent of 8 to 12 carbon atoms, or a mixture thereof.

With respect to the recurring units having a 1,1,1,3,3,3-hexafluoro-2-propanol residue, those recurring units described above as the water repellency improver are exemplary. The amino group-containing compound may be selected from the exemplary amine compounds to be added to photoresist compositions, as described in JP-A 2008-111103, paragraphs [0146] to [0164]. As the amine salt-containing compound, salts of the foregoing amine compounds with carboxylic acid or sulfonic acid may be used.

Suitable alcohols of at least 4 carbon atoms include 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether.

Exposure is preferably performed in an exposure dose of about 1 to 200 $mJ/cm^2$, more preferably about 10 to 100 $mJ/cm^2$. This is followed by baking (PEB) on a hot plate at 60 to 150° C. for 1 to 5 minutes, preferably at 80 to 120° C. for 1 to 3 minutes.

Thereafter the exposed resist film is developed in a developer consisting of an organic solvent for 0.1 to 3 minutes, preferably 0.5 to 2 minutes by any conventional techniques such as dip, puddle and spray techniques. In this way, the unexposed region of resist film was dissolved away, leaving a negative resist pattern 40 on the substrate 10 as shown in FIG. 1(C). The developer used herein is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable aromatic solvents include toluene, xylene, ethylbenzene, isopropylbenzene, tert-butylbenzene, and mesitylene. The solvents may be used alone or in admixture.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

Like the hole pattern mentioned above, when an isolated space pattern is formed by the positive tone development process in which exposure brings about an increase in solubility in alkaline developer, pattern formation must be done at a lower intensity of incident light than when an isolated line pattern is formed. Thus the intensity contrast of incident light between the unexposed and exposed regions is low. This tends to impose limits on pattern forming abilities such as resolving power, making it difficult to form a resist pattern with high resolution. Unlike the positive tone development process, the negative tone development process in which exposure brings about a reduction in solubility in alkaline developer is believed advantageous for forming an isolated space pattern. Similarly, the negative tone development process using organic solvent developer is believed advantageous for forming an isolated space pattern.

EXAMPLES

Examples of the invention are given below by way of illustration and not by way of limitation. The abbreviation “pbw” is parts by weight. For all polymers, Mw and Mn are determined versus polystyrene standards by GPC using tetrahydrofuran (THF) solvent.

Example 1

A series of hemiacetal compounds were synthesized by the following method.

Example 1-1

Synthesis of Monomer 1

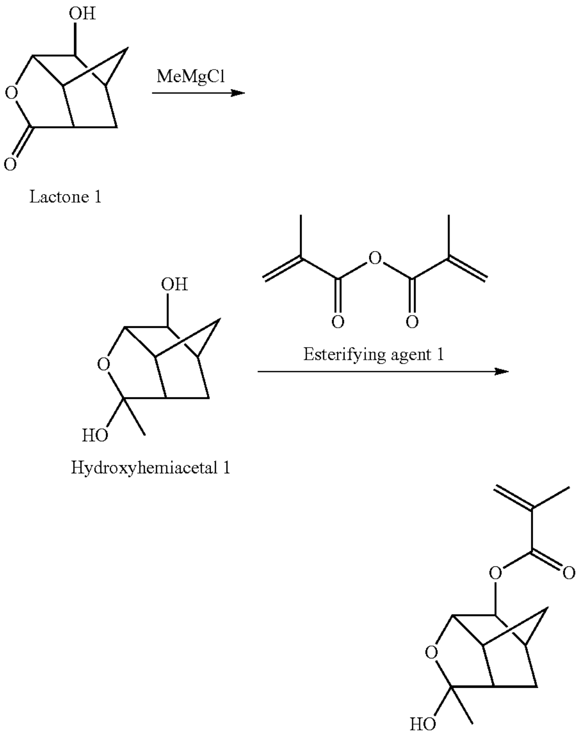

Lactone 1

Hydroxyhemiacetal 1

Monomer 1

Example 1-1-1

Synthesis of Hydroxyhemiacetal 1

In nitrogen atmosphere, 107.9 g of Lactone 1 was dissolved in 1,000 g of THF, after which a solution of 1.0M methylmagnesium chloride in 1,500 mL of THF was added dropwise to the solution at a temperature of −20° C. to 0° C. The reaction solution was stirred at the temperature for 5 hours, after which 1,000 g of 15 wt % ammonium chloride aqueous solution was added dropwise to quench the reaction. This was followed by standard aqueous workup. On recrystallization from an ethyl acetate/n-hexane mixture, Hydroxyhemiacetal 1 was obtained (78.6 g, yield 66%).

IR (D-ATR): ν=3354, 3275, 2998, 2872, 1470, 1455, 1417, 1379, 1341, 1311, 1293, 1245, 1173, 1141, 1122, 1056, 1008, 965, 953, 893, 851 $cm^1$ $^1$H-NMR (600 MHz in DMSO-$d_6$): δ=5.35 (1H, s), 4.60 (1H, d), 3.70 (1H, d), 3.16 (1H, m), 2.93 (1H, t), 1.91-1.95 (2H, m), 1.78 (1H, d), 1.45-1.51 (1H, m), 1.31 (1H, d), 1.26 (3H, s), 1.07 (1H, d) ppm

Example 1-1-2

Synthesis of Monomer 1

A solution of 58.4 g of Hydroxyhemiacetal 1, 48.6 g of triethylamine, and 2.1 g of 4-(dimethylamino)pyridine in 240 g of THF was heated at a temperature of 40-50° C., to which 63.5 g of Esterifying agent 1 was added dropwise. The reaction solution was stirred at 50° C. for 10 hours whereupon it was ice cooled. A saturated sodium hydrogencarbonate aqueous solution was added dropwise thereto to quench the reaction. This was followed by standard aqueous workup. On recrystallization from an ethyl acetate/n-hexane mixture, Monomer 1 was obtained (67.8 g, yield 84%).

IR (D-ATR): ν=3599, 3512, 2961, 2873, 1725, 1480, 1459, 1397, 1367, 1285, 1150, 1032, 995, 970, 937, 845, 772 $cm^1$ $^1$H-NMR (600 MHz in DMSO-$d_6$): δ=5.98 (1H, s), 5.64 (1H, m), 5.58 (1H, s), 4.23 (1H, s), 3.91 (1H, d), 3.07 (1H, t), 2.17 (1H, d), 2.01-2.04 (1H, m), 1.84 (3H, s), 1.73 (1H, d), 1.58-1.63 (1H, m), 1.48 (1H, d), 1.33 (3H, s), 1.24 (1H, dt) ppm

Example 1-2

Synthesis of Monomer 1

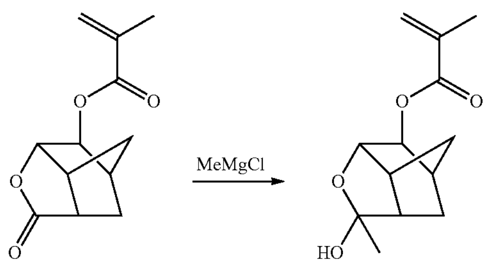

Lactone Monomer 1 Monomer 1

In nitrogen atmosphere, 88.9 g of Lactone Monomer 1 was dissolved in 500 g of THF, after which a solution of 1.0M methylmagnesium chloride in 420 mL of THF was added dropwise to the solution at a temperature of −20° C. to 0° C. The reaction solution was stirred at the temperature for 5 hours, after which 300 g of 15 wt % ammonium chloride aqueous solution was added dropwise to quench the reaction. This was followed by standard aqueous workup. On recrystallization from an ethyl acetate/n-hexane mixture, Monomer 1 was obtained (50.5 g, yield 53%). Physical data of this product were consistent with those of Example 1-1-2.

Example 1-3

Synthesis of Monomer 2

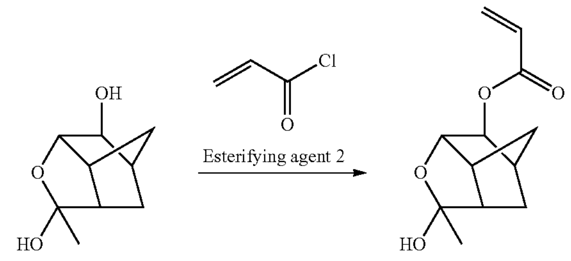

Hydroxyhemiacetal 1 Monomer 2

The same procedure as in Example 1-1-2 was followed aside from using Esterifying agent 2 instead of Esterifying agent 1, obtaining Monomer 2 (yield 81%).

Example 1-4

Synthesis of Monomer 3

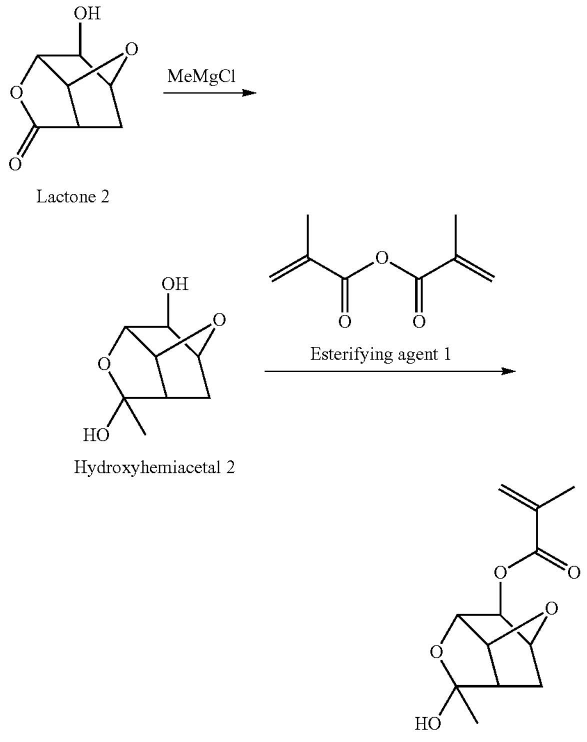

Lactone 2

Hydroxyhemiacetal 2

Monomer 3

Example 1-4-1

Synthesis of Hydroxyhemiacetal 2

The same procedure as in Example 1-1-1 was followed aside from using Lactone 2 instead of Lactone 1, obtaining Hydroxyhemiacetal 2 (yield 59%).

Example 1-4-2

Synthesis of Monomer 3

The same procedure as in Example 1-1-2 was followed aside from using Hydroxyhemiacetal 2 instead of Hydroxyhemiacetal 1, obtaining Monomer 3 (yield 81%).

IR (D-ATR): ν=3369, 3046, 2994, 1711, 1633, 1458, 1405, 1386, 1303, 1284, 1164, 1052, 1022, 997, 976, 962, 937, 918, 880, 840 $cm^{-1}$ $^1$H-NMR (600 MHz in DMSO-$d_6$): δ=5.99 (1H, s), 5.95 (1H, s), 5.67 (1H, t), 5.24 (1H, t), 4.41 (1H, m), 4.01 (1H, dt), 2.16-2.20 (1H, m), 1.85 (3H, s), 1.70-1.78 (1H, m), 1.54 (1H, dt), 1.36 (3H, s) ppm

Example 1-5

Synthesis of Monomer 4

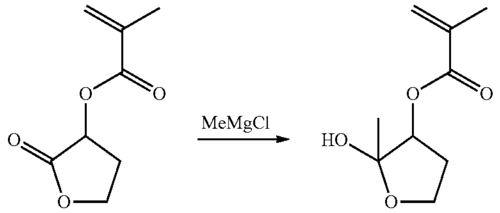

Lactone Monomer 2 Monomer 4

In nitrogen atmosphere, 170.2 g of Lactone Monomer 2 was dissolved in 800 g of THF, to which a solution of 1.0M methylmagnesium chloride in 1100 mL of THF was added dropwise at a temperature of −20° C. to 0° C. The reaction solution was stirred at the temperature for 5 hours, after which 1,200 g of 15 wt % ammonium chloride aqueous solution was added dropwise to quench the reaction. This was followed by standard aqueous workup and vacuum distillation for purification, obtaining Monomer 4 (89.4 g, yield 48%).

IR (D-ATR): ν=3469, 2961, 2929, 2895, 1791, 1717, 1637, 1452, 1404, 1381, 1354, 1317, 1297, 1161, 1116, 1087, 1017, 946, 863, 815, 651, 619, 585, 576, 555 $cm^{-1}$ $^1$H-NMR (600 MHz in DMSO-$d_6$): δ=6.01 (1H, s), 5.68 (1H, s), 4.90 (1H, dd), 4.68 (1H, brs), 3.85 (2H, m), 2.41 (1H, dddd), 1.89 (3H, s), 1.79 (1H, dddd), 1.29 (3H, s) ppm

Example 1-6

Synthesis of Monomer 5

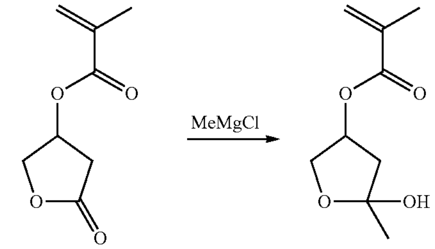

Lactone Monomer 3    Monomer 5

The same procedure as in Example 1-5 was followed aside from using Lactone Monomer 3 instead of Lactone Monomer 2, obtaining Monomer 5 (yield 41%).

Example 1-7

Synthesis of Monomer 6

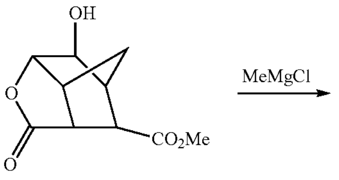

Lactone 3

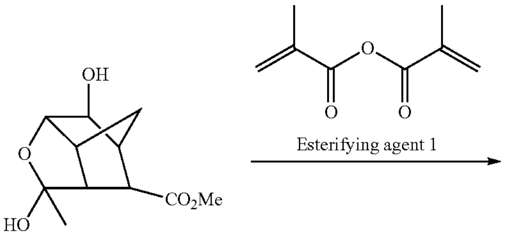

Hydroxyhemiacetal 3

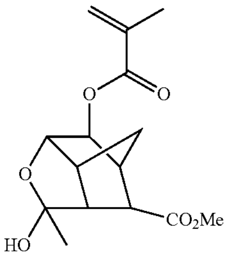

Monomer 6

Example 1-7-1

Synthesis of Hydroxyhemiacetal 3

The same procedure as in Example 1-1-1 was followed aside from using Lactone 3 instead of Lactone 1, obtaining Hydroxyhemiacetal 3 (yield 61%).

Example 1-7-2

Synthesis of Monomer 6

The same procedure as in Example 1-1-2 was followed aside from using Hydroxyhemiacetal 3 instead of Hydroxyhemiacetal 1, obtaining Monomer 6 (yield 73%).

IR (D-ATR): ν=3375, 2977, 2963, 1728, 1713, 1639, 1454, 1438, 1386, 1322, 1301, 1279, 1267, 1176, 1149, 1093, 1017, 943, 911, 879, 812 $cm^{-1}$ $^1$H-NMR (600 MHz in DMSO-$d_6$): δ=6.00 (1H, s), 5.81 (1H, s), 5.66 (1H, t), 4.30 (1H, s), 3.96 (1H, d), 3.63 (3H, s), 3.12 (1H, t), 2.52 (1H, s), 2.49 (overlap with $H_2O$ peak, 1H, m), 2.34 (1H, t), 1.85 (3H, s), 1.72 (1H, d), 1.56 (1H, d), 1.39 (3H, s) ppm

Example 1-8

Synthesis of Monomer 7

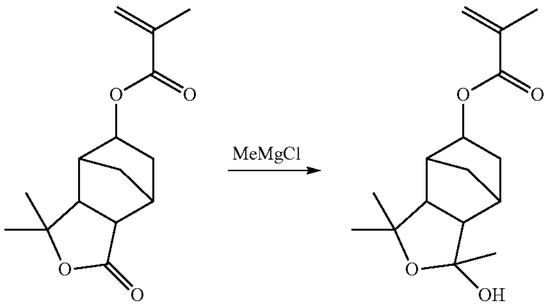

Lactone Monomer 4    Monomer 7

The same procedure as in Example 1-2 was followed aside from using Lactone Monomer 4 instead of Lactone Monomer 1, obtaining Monomer 7 (yield 45%).

IR (D-ATR): ν=3453, 2973, 2944, 1704, 1636, 1384, 1372, 1334, 1325, 1303, 1270, 1178, 1160, 1132, 1093, 982, 958, 937, 900 $cm^{-1}$ $^1$H-NMR (600 MHz in DMSO-$d_6$): δ=5.97 (1H, m), 5.63 (1H, t), 5.26 (1H, s), 4.51 (1H, dd), 2.21 (2H, m), 2.11 (1H, d), 1.90 (1H, d), 1.84 (3H, s), 1.65-1.71 (1H, m), 1.29-1.35 (6H, m), 1.22 (3H, s), 1.07 (3H, s) ppm

Example 1-9

Synthesis of Monomer 8

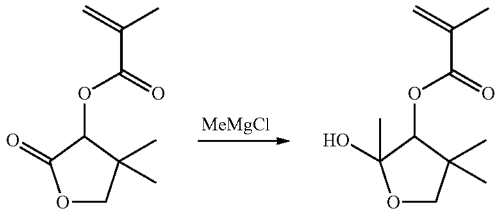

Lactone Monomer 5    Monomer 8

The same procedure as in Example 1-5 was followed aside from using Lactone Monomer 5 instead of Lactone Monomer 2, obtaining Monomer 8 (yield 51%).

Example 1-10

Synthesis of Monomer 9

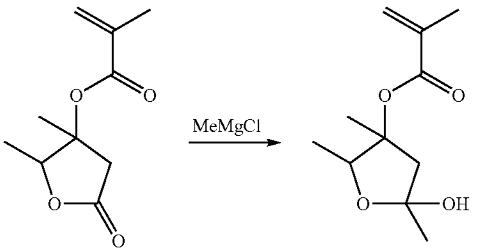

Lactone Monomer 6 Monomer 9

The same procedure as in Example 1-5 was followed aside from using Lactone Monomer 6 instead of Lactone Monomer 2, obtaining Monomer 9 (yield 44%).

Example 1-11

Synthesis of Monomer 10

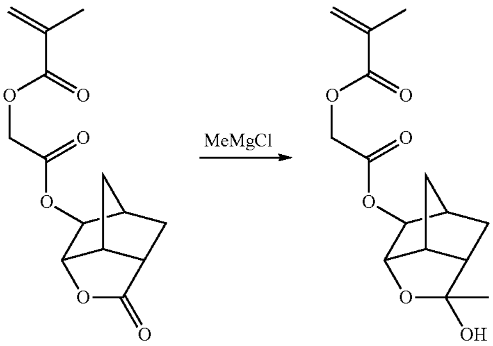

Lactone Monomer 7 Monomer 10

The same procedure as in Example 1-2 was followed aside from using Lactone Monomer 7 instead of Lactone Monomer 1, obtaining Monomer 10 (yield 40%).

Example 1-12

Synthesis of Monomer 11

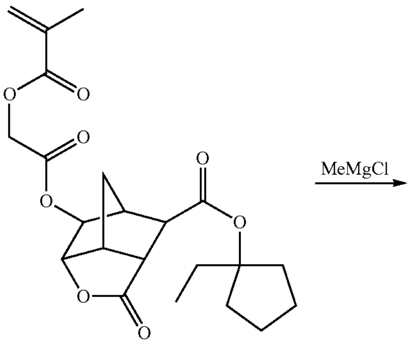

Lactone Monomer 8

-continued

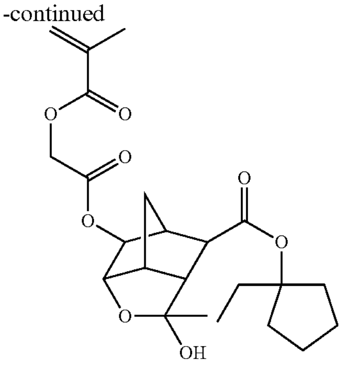

Monomer 11

The same procedure as in Example 1-2 was followed aside from using Lactone Monomer 8 instead of Lactone Monomer 1, obtaining Monomer 11 (yield 54%).

Example 1-13

Synthesis of Monomer 12

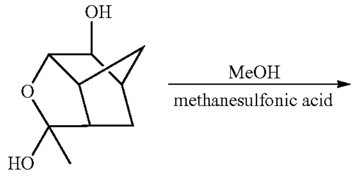

Hydroxyhemiacetal 1

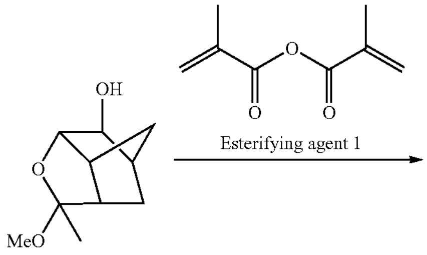

Hydroxyacetal 1

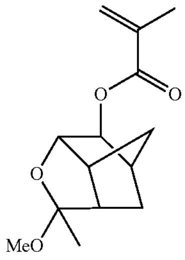

Monomer 12

Example 1-13-1

Synthesis of Hydroxyacetal 1

To a solution of 133.5 g of Hydroxyhemiacetal 1 (obtained in Example 1-1-1) in 871 g of methanol, 4.4 g of methanesulfonic acid was added. The reaction solution was stirred at room temperature for 8 hours. The solution was ice cooled, after which 8.8 g of triethylamine was added dropwise to quench the reaction. The reaction solution was concentrated by distilling off methanol. This was followed by standard aqueous workup and recrystallization from an ethyl acetate/diisopropyl ether mixture, obtaining Hydroxyacetal 1 (127.2 g, yield 88%).

IR (D-ATR): ν=3446, 2991, 2973, 2941, 2927, 1466, 1380, 1322, 1279, 1178, 1150, 1126, 1078, 1063, 1029, 1002, 939, 854, 826 $cm^{-1}$ $^1$H-NMR (600 MHz in DMSO-$d_6$, for only main isomer): δ=4.67 (1H, d), 3.72 (1H, d), 3.22 (1H, app t), 3.06 (3H, s), 2.79-2.83 (1H, m), 2.00-2.04 (1H, m), 1.95 (1H, d), 1.77 (1H, dd), 1.48-1.54 (1H, m), 1.32 (1H, dd), 1.23 (3H, s), 1.11-1.15 (1H, m) ppm

Example 1-13-2

Synthesis of Monomer 12

The same procedure as in Example 1-1-2 was followed aside from using Hydroxyacetal 1 instead of Hydroxyhemiacetal 1, obtaining Monomer 12 (yield 87%).

boiling point: 69° C./10 Pa

IR (D-ATR): ν=2962, 2883, 2827, 1717, 1637, 1452, 1380, 1326, 1307, 1292, 1163, 1144, 1122, 1074, 1029, 1016, 990, 939, 862, 828 $cm^{-1}$ $^1$H-NMR (600 MHz in DMSO-$d_6$, for only main isomer): δ=5.99 (1H, s), 5.65 (1H, m), 4.30 (1H, s), 3.93 (1H, d), 3.09 (3H, s), 2.95 (1H, t), 2.20 (1H, d), 2.11 (1H, m), 1.84 (3H, s), 1.72 (1H, d), 1.62-1.67 (1H, m), 1.50 (1H, d), 1.30 (4H, m) ppm

Example 1-14

Synthesis of Monomer 13

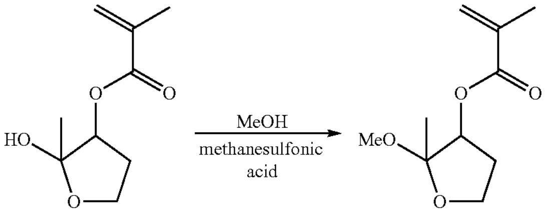

Monomer 4 Monomer 13

The same procedure as in Example 1-13-1 was followed aside from using Monomer 4 instead of Hydroxyhemiacetal 1, obtaining Monomer 13 (yield 87%).

boiling point: 50° C./20 Pa

IR (D-ATR): ν=2993, 2955, 2895, 1721, 1638, 1442, 1404, 1380, 1323, 1295, 1165, 1102, 1054, 1018, 944, 863, 814, 652, 582 $cm^{-1}$ $^1$H-NMR (600 MHz in DMSO-$d_6$, for only main isomer): δ=6.04 (1H, s), 5.70 (1H, s), 4.95 (1H, dd), 3.95 (1H, ddd), 3.70 (1H, ddd), 3.12 (3H, s), 2.39 (1H, dddd), 1.87 (3H, s), 1.82 (1H, dddd), 1.25 (3H, s) ppm

Example 1-15

Synthesis of Monomer 14

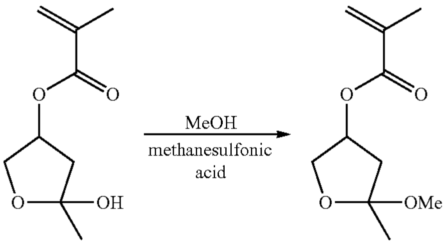

Monomer 5 Monomer 14

The same procedure as in Example 1-13-1 was followed aside from using Monomer 5 instead of Hydroxyhemiacetal 1, obtaining Monomer 14 (yield 82%).

Example 1-16

Synthesis of Monomer 15

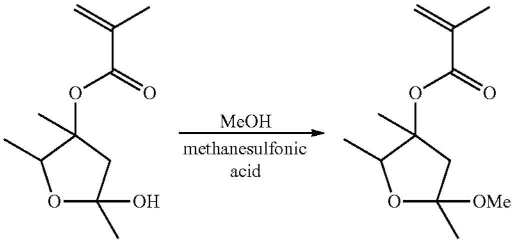

Monomer 9 Monomer 15

The same procedure as in Example 1-13-1 was followed aside from using Monomer 9 instead of Hydroxyhemiacetal 1, obtaining Monomer 15 (yield 90%).

Example 1-17

Synthesis of Monomer 16

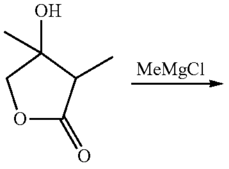

Lactone 4

-continued

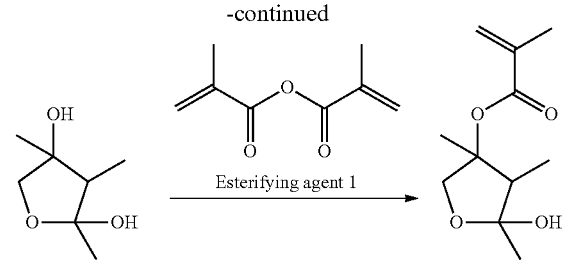

Hydroxyhemiacetal 4

Monomer 16

Example 1-17-1

Synthesis of Hydroxyhemiacetal 4

The same procedure as in Example 1-1-1 was followed aside from using Lactone 4 instead of Lactone 1, obtaining Hydroxyhemiacetal 4 (yield 48%).

Example 1-17-2

Synthesis of Monomer 16

The same procedure as in Example 1-1-2 was followed aside from using Hydroxyhemiacetal 4 instead of Hydroxyhemiacetal 1, obtaining Monomer 16 (yield 83%).

Example 1-18

Synthesis of Monomer 17

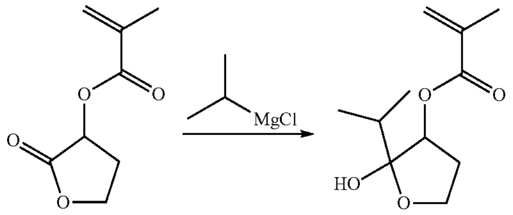

Lactone Monomer 2

Monomer 17

The same procedure as in Example 1-5 was followed aside from using a THF solution of 1.0M isopropylmagnesium chloride instead of the THF solution of 1.0M methylmagnesium chloride, obtaining Monomer 17 (yield 42%).

Example 1-19

Synthesis of Monomer 18

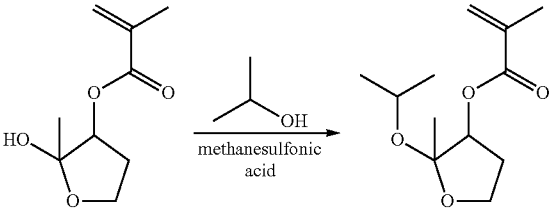

Monomer 4

Monomer 18

The same procedure as in Example 1-13-1 was followed aside from using Monomer 4 instead of Hydroxyhemiacetal 1 and isopropyl alcohol instead of methanol, obtaining Monomer 18 (yield 77%).

Example 1-20

Synthesis of Monomer 19

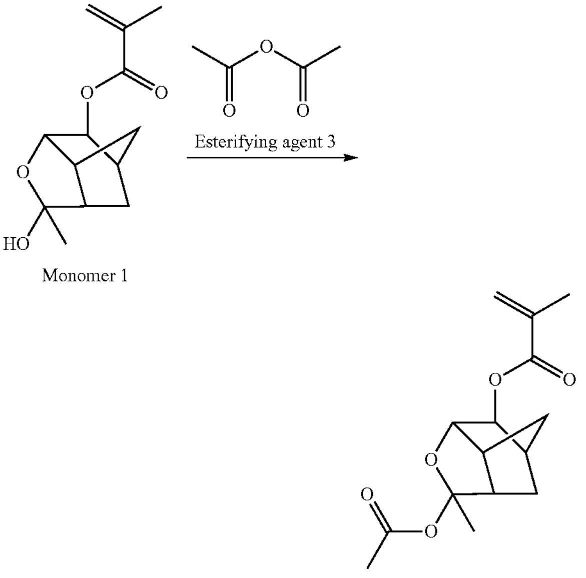

Monomer 1

Monomer 19

The same procedure as in Example 1-1-2 was followed aside from using Monomer 1 instead of Hydroxyhemiacetal 1 and Esterifying agent 3 instead of Esterifying agent 1, obtaining Monomer 19 (yield 76%).

Example 1-21

Synthesis of Monomer 20

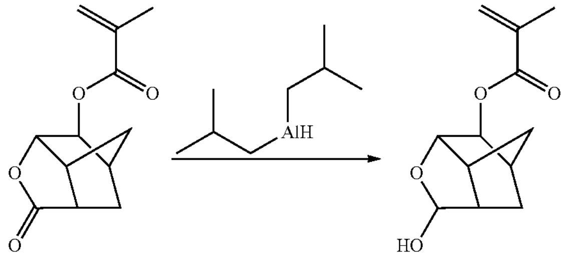

Lactone Monomer 1

Monomer 20

The same procedure as in Example 1-1-2 was followed aside from using diisobutylaluminum hydride instead of the THF solution of 1.0M methylmagnesium chloride, obtaining Monomer 20 (yield 71%).

Example 1-22

Synthesis of Monomer 21

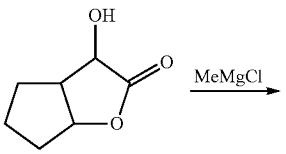

Lactone 5

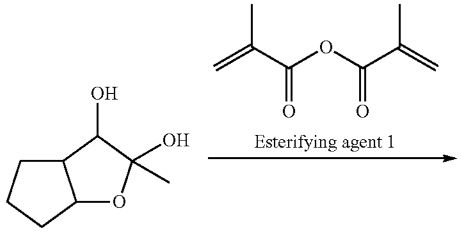

Hydroxyhemiacetal 5

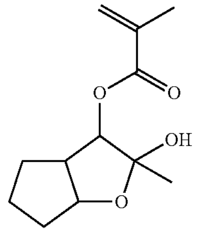

Monomer 21

Example 1-22-1

Synthesis of Hydroxyhemiacetal 5

The same procedure as in Example 1-1-1 was followed aside from using Lactone 5 instead of Lactone 1, obtaining Hydroxyhemiacetal 5 (yield 54%).

Example 1-22-2

Synthesis of Monomer 21

The same procedure as in Example 1-1-2 was followed aside from using Hydroxyhemiacetal 5 instead of Hydroxyhemiacetal 1, obtaining Monomer 21 (yield 86%).

Example 1-23

Synthesis of Monomer 13

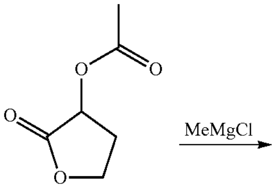

Lactone 6

-continued

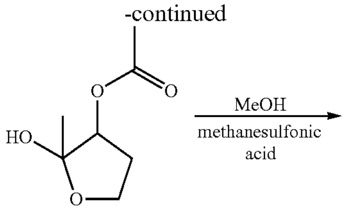

Hemiacetal 1

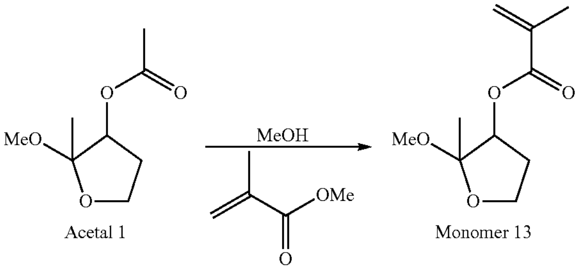

Acetal 1

Monomer 13

Example 1-23-1

Synthesis of Hemiacetal 1

The same procedure as in Example 1-1-1 was followed aside from using Lactone 6 instead of Lactone 1, obtaining Hemiacetal 1 (yield 67%).

Example 1-23-2

Synthesis of Acetal 1

The same procedure as in Example 1-13-1 was followed aside from using Hemiacetal 1 instead of Hydroxyhemiacetal 1, obtaining Acetal 1 (yield 89%).

Example 1-23-3

Synthesis of Monomer 13

A reactor equipped with a distilling head was charged with 17.4 g of Acetal 1 (obtained in Example 1-23-2) and 0.3 g of titanium(IV) isopropoxide. With stirring, the mixture was heated at 70° C. Methanol, 10 g, was added dropwise to the mixture over 2 hours while methyl acetate formed was distilled off. The reaction mixture was stirred and heated to reflux for 3 hours, after which the excess methanol was distilled off. To the residue was added 10.5 g of methyl methacrylate. With stirring, the mixture was heated to reflux while methanol formed was distilled off. The mixture was continuously stirred for 2 hours, after which it was distilled under a reduced pressure, obtaining Monomer 13 (yield 84%). Its physical data were consistent with those of Example 1-14.

Example 1-24

Synthesis of Monomer 22

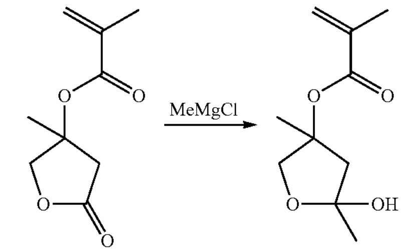

Lactone Monomer 9

Monomer 22

The same procedure as in Example 1-5 was followed aside from using Lactone Monomer 9 instead of Lactone Monomer 2, obtaining Monomer 22 (yield 38%).

Example 1-25

Synthesis of Monomer 23

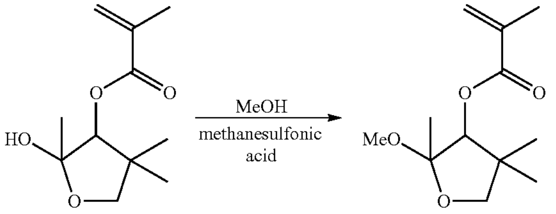

Monomer 8

Monomer 23

The same procedure as in Example 1-13-1 was followed aside from using Monomer 8 instead of Hydroxyhemiacetal 1, obtaining Monomer 23 (yield 92%).

boiling point: 42° C./7 Pa

IR (D-ATR): ν=2966, 2877, 2830, 1723, 1638, 1466, 1403, 1380, 1320, 1297, 1160, 1100, 1070, 1030, 944, 864, 814, 650, 614, 576, 553 $cm^{-1}$ $^1$H-NMR (600 MHz in DMSO-$d_6$, for only main isomer): δ=6.09 (1H, s), 5.73 (1H, s), 4.77 (1H, s), 3.57 (1H, d), 3.50 (1H, d), 3.12 (3H, s), 1.90 (3H, s), 1.21 (3H, s), 1.12 (3H, s), 0.92 (3H, s) ppm Monomer 1

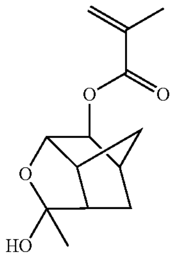

-continued

Monomer 2

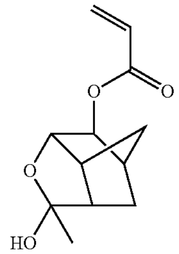

Monomer 3

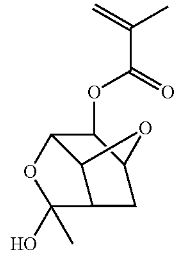

Monomer 4

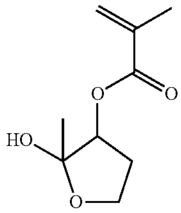

Monomer 5

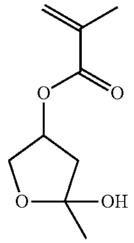

Monomer 6

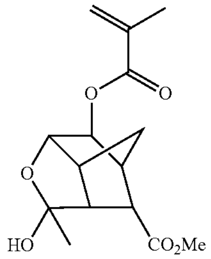

Monome 7

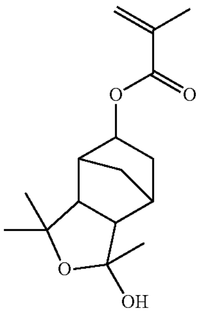

-continued
Monomer 8
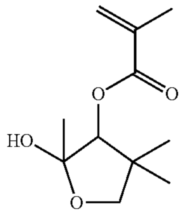
Monomer 9
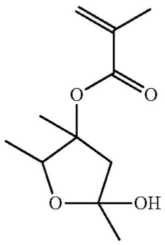
Monomer 10
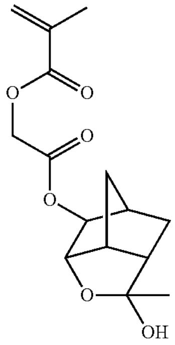
Monomer 11
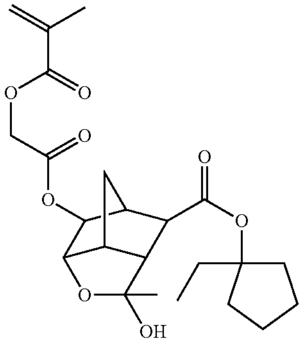
Monomer 12
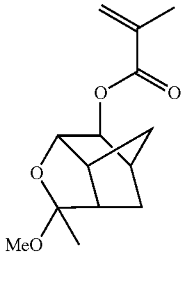
-continued
Monomer 13
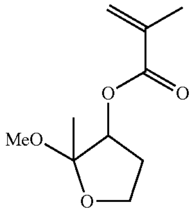
Monomer 14
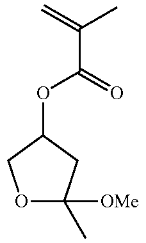
Monomer 15
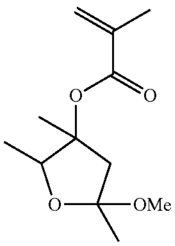
Monomer 16
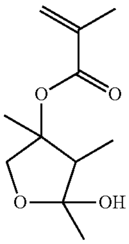
Monomer 17
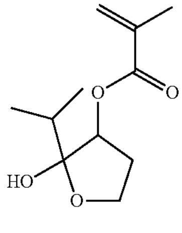
Monomer 18
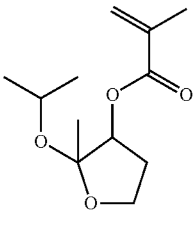

-continued

Monomer 19

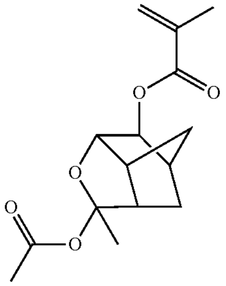

Monomer 20

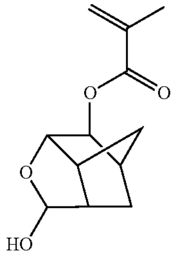

Monomer 21

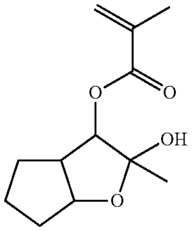

Monomer 22

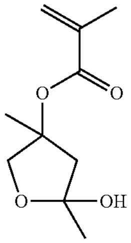

Monomer 23

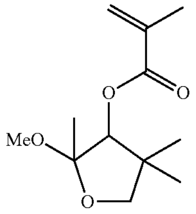

Example 2

A series of polymers were synthesized by the following method.

Example 2-1

Synthesis of Resist Polymer 1

In nitrogen atmosphere, 22.7 g of Monomer 1, 5.6 g of 3-hydroxyadamantyl methacrylate, 21.7 g of 1-ethylcyclopentyl methacrylate, and 2.7 g of dimethyl 2,2'-azobisisobutyrate were dissolved in 120 g of methyl ethyl ketone to form a monomer solution. In nitrogen atmosphere, 30 g of methyl ethyl ketone was stirred and heated at 80° C., to which the monomer solution was added dropwise over 4 hours. After the completion of dropwise addition, the reaction solution was stirred at 80° C. for 2 hours. The solution was cooled to room temperature and then added dropwise to 500 g of n-hexane for precipitation. The solid precipitate was collected by filtration and vacuum dried at 50° C. for 20 hours, obtaining a polymer in white powder solid form, designated Resist Polymer 1. Amount 46.4 g, yield 93%. The polymer was analyzed for composition and Mw.

Resist Polymer 1

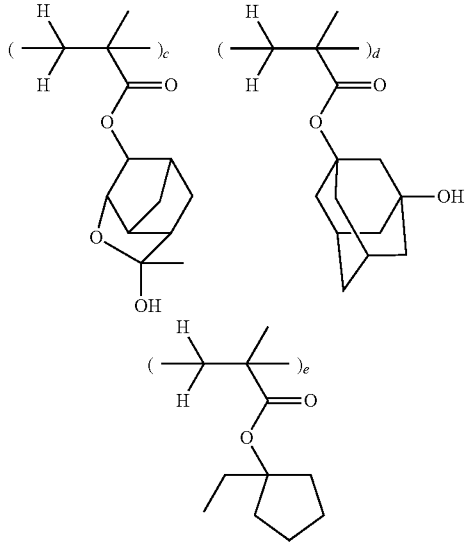

(c = 0.40, d = 0.10, e = 50, Mw = 7,600)

Examples 2-2 to 2-18 & Comparative Examples 1-1 to 1-4

Resist Polymers 2 to 18 & Comparative Polymers 1 to 4

Resist Polymers 2 to 18 and Comparative Polymers 1 to 4 were prepared by the same procedure as in Example 2-1 except that the type and amount of monomers were changed. A ratio of units incorporated in a polymer is computed on a molar basis.

Resist Polymer 2

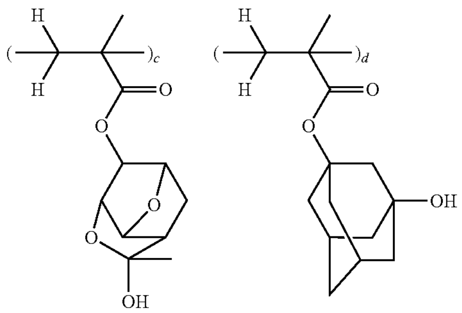

-continued
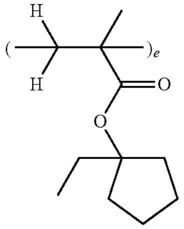
(c = 0.40, d = 0.10, e = 0.50, Mw = 7,800)
Resist Polymer 3
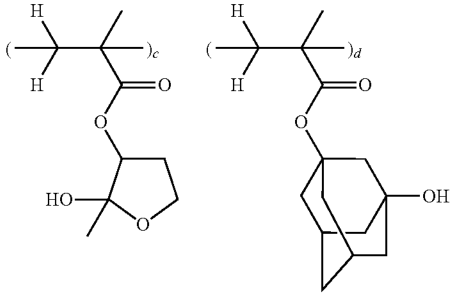
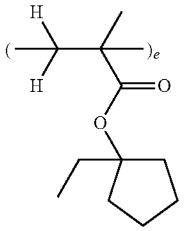
(c = 0.40, d = 0.10, e = 0.50, Mw = 7,000)
Resist Polymer 4
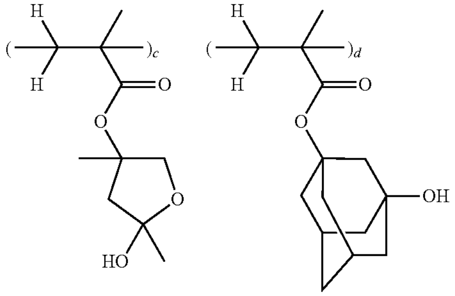
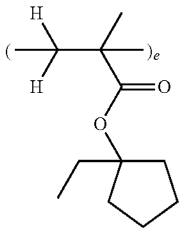
(c = 0.40, d = 0.10, e = 0.50, Mw = 7,100)
-continued
Resist Polymer 5
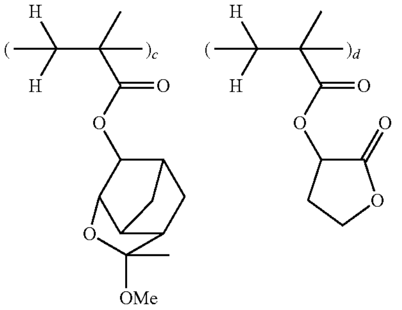
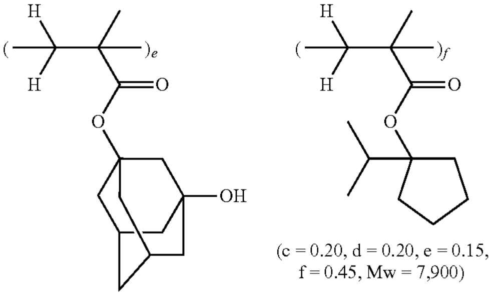
(c = 0.20, d = 0.20, e = 0.15, f = 0.45, Mw = 7,900)
Resist Polymer 6
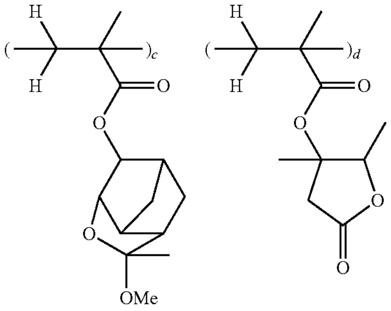
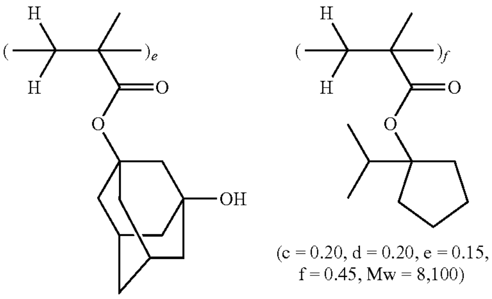
(c = 0.20, d = 0.20, e = 0.15, f = 0.45, Mw = 8,100)
Resist Polymer 7
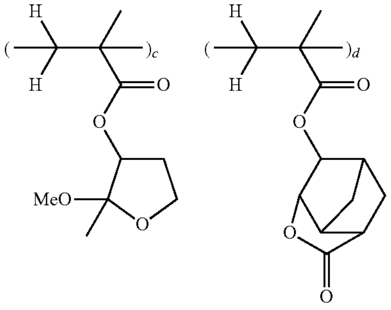

-continued
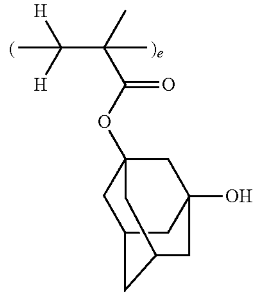
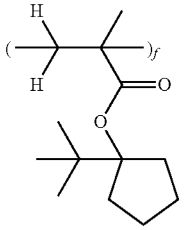
(c = 0.20, d = 0.20, e = 0.15, f = 0.45, Mw = 7,800)
Resist Polymer 8
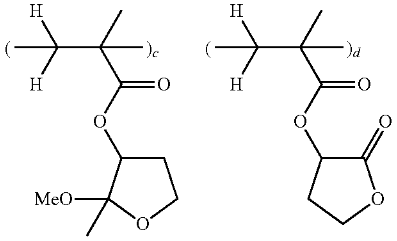
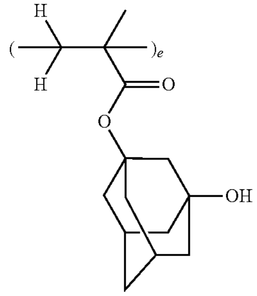
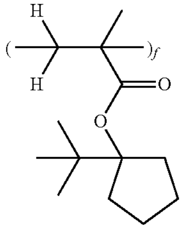
(c = 0.20, d = 0.20, e = 0.15, f = 0.45, Mw = 7,600)
Resist Polymer 9
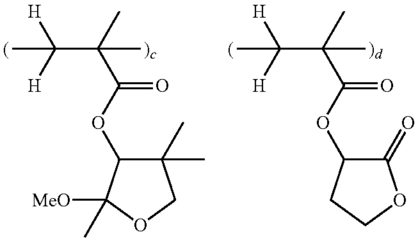
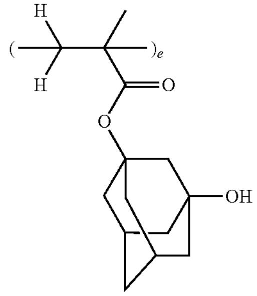
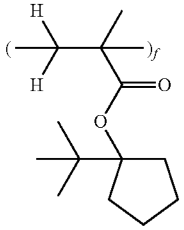
(c = 0.20, d = 0.20, e = 0.15, f = 0.45, Mw = 7,700)
Resist Polymer 10
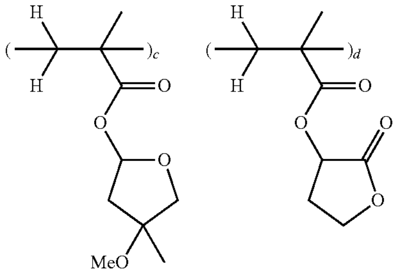
-continued
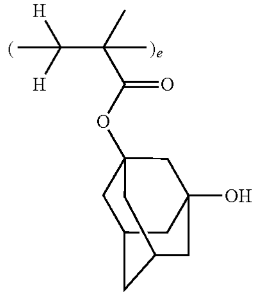
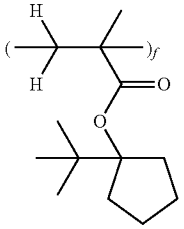
(c = 0.20, d = 0.20, e = 0.15, f = 0.45, Mw = 7,600)
Resist Polymer 11
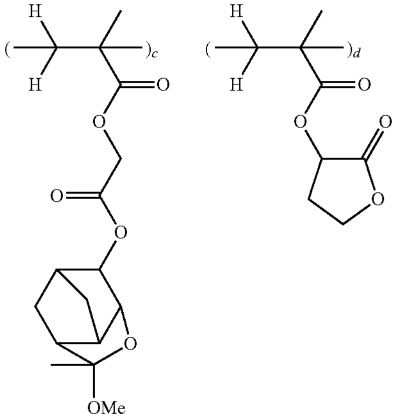
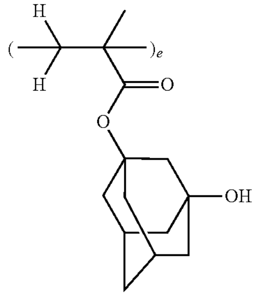
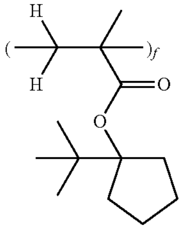
(c = 0.20, d = 0.20, e = 0.15, f = 0.45, Mw = 8,000)
Resist Polymer 12
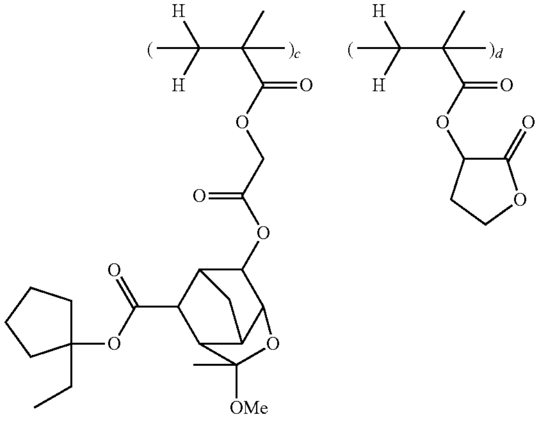

-continued
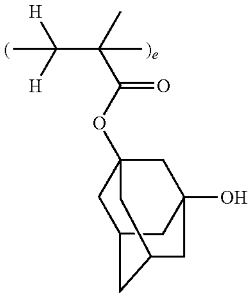
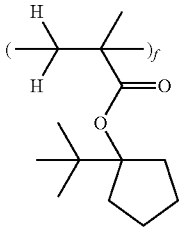
(c = 0.20, d = 0.20, e = 0.15, f = 0.45, Mw = 8,200)
Resist Polymer 13
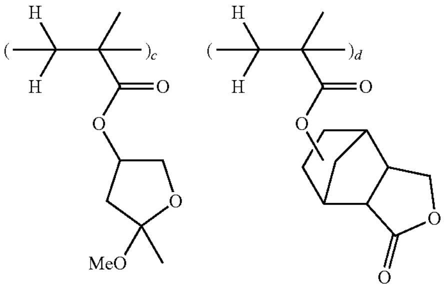
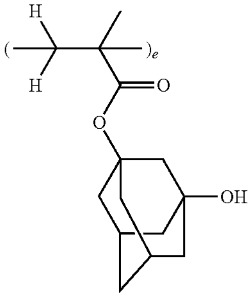
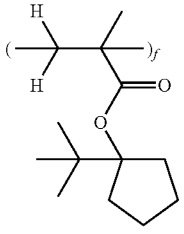
(c = 0.20, d = 0.20, e = 0.15, f = 0.45, Mw = 7,800)
Resist Polymer 14
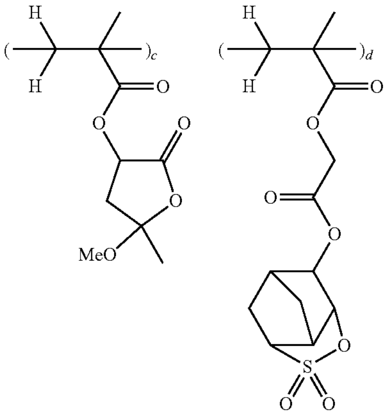
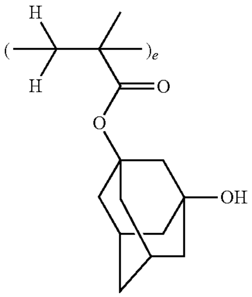
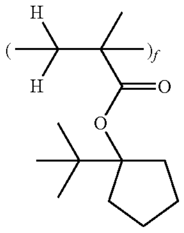
(c = 0.20, d = 0.20, e = 0.15, f = 0.45, Mw = 7,900)
-continued
Resist Polymer 15
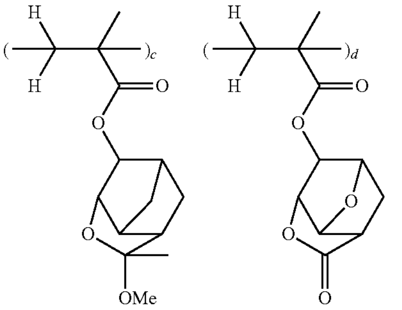
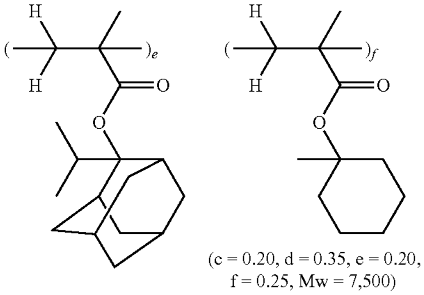
(c = 0.20, d = 0.35, e = 0.20, f = 0.25, Mw = 7,500)
Resist Polymer 16
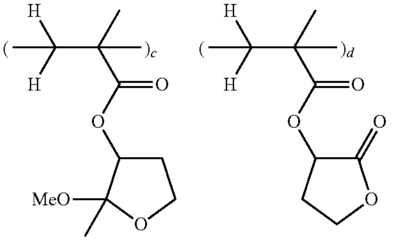
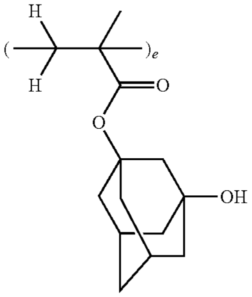
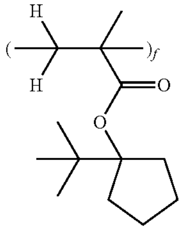
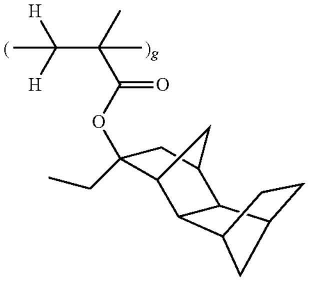
(c = 0.20, d = 0.20, e = 0.15, f = 0.25, g = 0.20, Mw = 7,900)

-continued
Resist Polymer 17
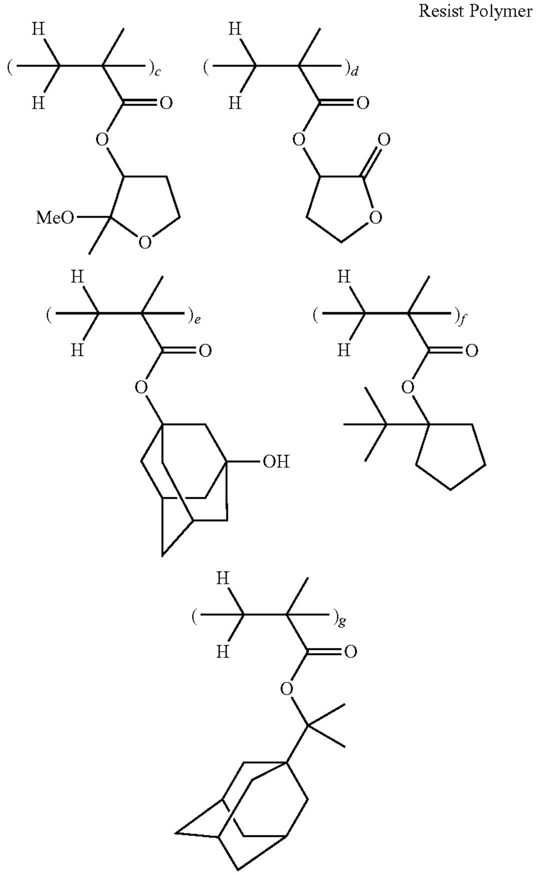
(c = 0.20, d = 0.20, e = 0.15, f = 0.30, g = 0.15, Mw = 7,800)
Resist Polymer 18
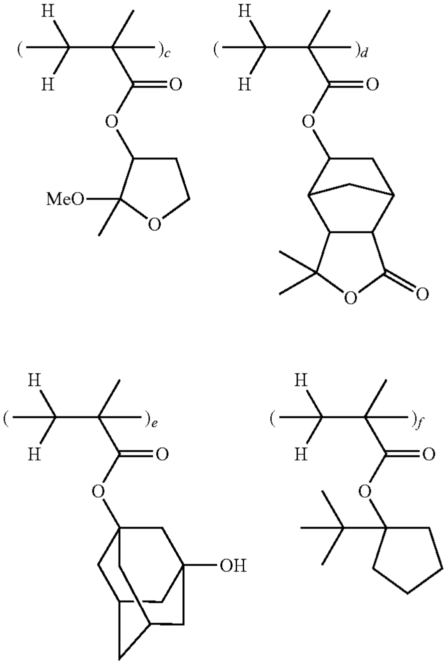
-continued
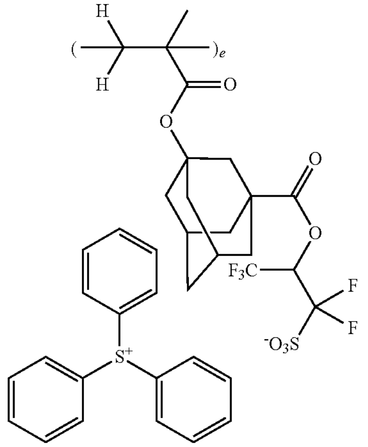
(c = 0.20, d = 0.20, e = 0.10, f = 0.45, g = 0.05, Mw = 8,500)
Comparative Polymer 1
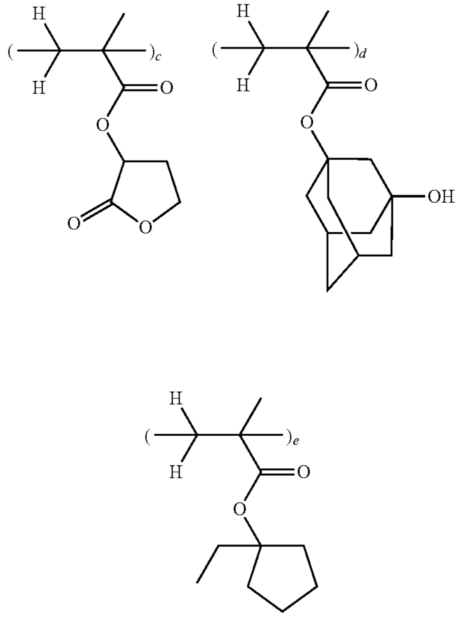
(c = 0.40, d = 0.10, e = 0.50, Mw = 6,800)
Comparative Polymer 2
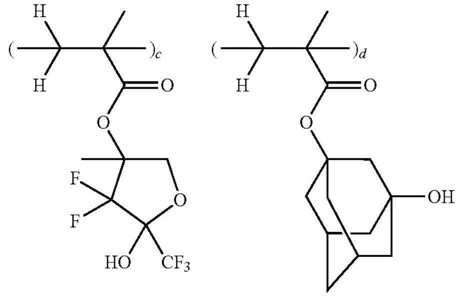

-continued

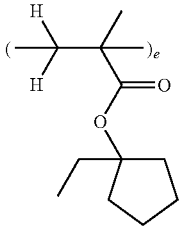

(c = 0.40, d = 0.10, e = 0.50, Mw = 7,400)

Comparative Polymer 3

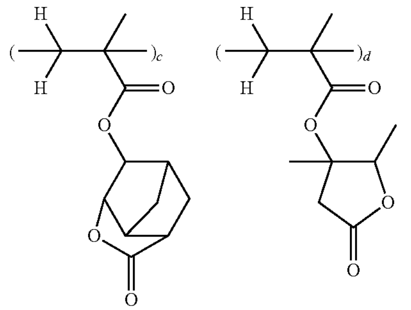

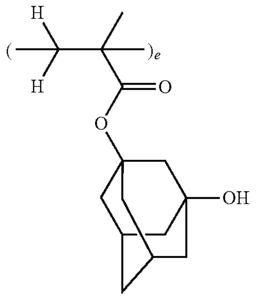

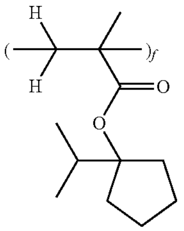

(c = 0.20, d = 0.20, e = 0.15, f = 0.45,Mw = 8,000)

Comparative Polymer 4

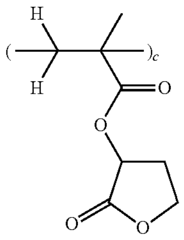

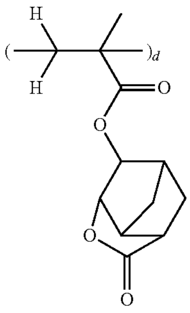

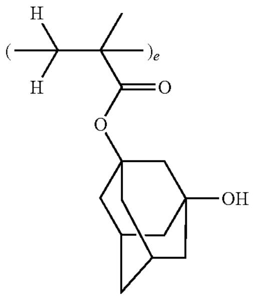

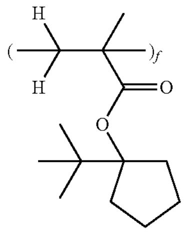

(c = 0.20, d = 0.20, e = 0.15, f = 0.45, Mw = 7,800)

Examples 3-1 to 3-26 and Comparative Examples 2-1 to 2-4

Preparation of Resist Composition

Resist compositions R-1 to R-26 and Comparative Resist compositions R-27 to R-30 in solution form were prepared by dissolving a polymer (Resist Polymers 1 to 18 or Comparative Polymers 1 to 4) as base resin, acid generator, quencher, and water-repellent polymer in a solvent in accordance with the formulation of Table 1 and filtering through a Teflon® filter with a pore size of 0.2 μm. The solvent contained 0.01 wt % of surfactant KH-20 (Asahi Glass Co., Ltd.). The acid generator (PAG-1 to 3), quencher (Q-1 to 3), water-repellent polymer (SF-1, 2), and solvent used herein are identified below.

Acid generator: PAG-1 to 3 shown below

PAG-1

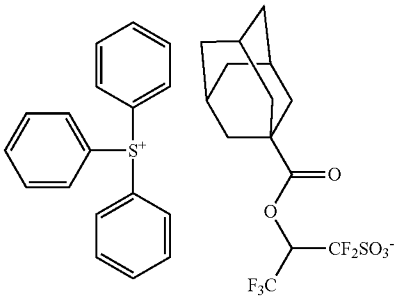

PAG-2

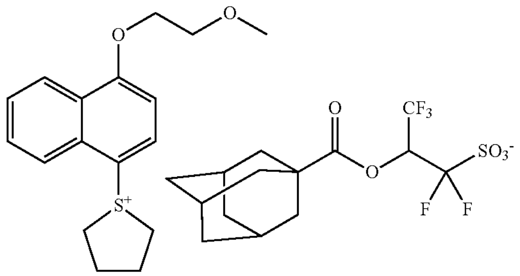

PAG-3

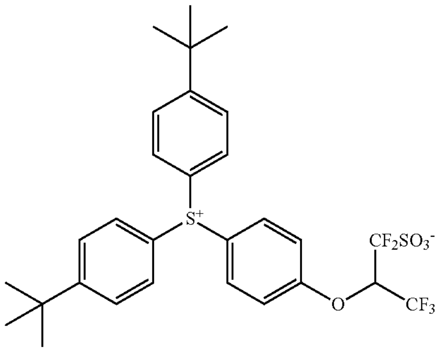

Quencher: Q-1 to 3 shown below

Q-1

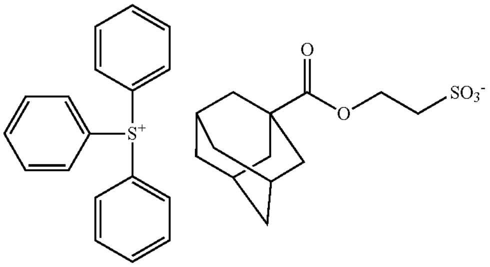

Q-2

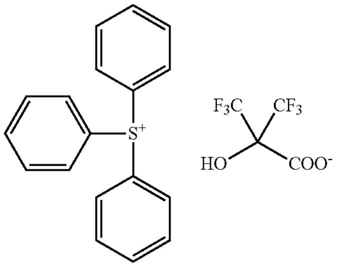

Q-3

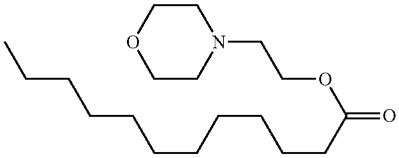

Water-repellent polymer: SF-1 and 2 shown below

SF-1

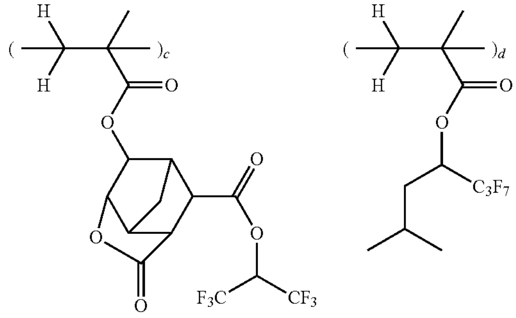

(c = 0.50, d = 0.50, Mw = 7,500)

SF-2

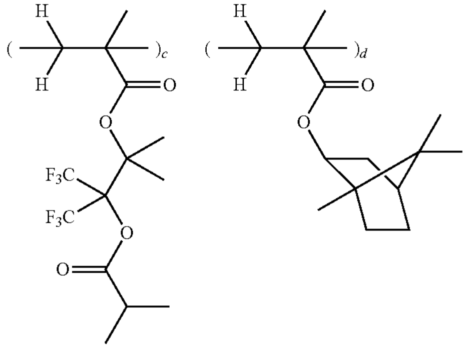

(c = 0.40, d = 0.60, Mw = 9,000)

Solvent 1: PGMEA (1-methyl-2-methoxyethyl acetate)
Solvent 2: GBL (γ-butyrolactone)

TABLE 1

| | | Resist | Resin (pbw) | Acid generator (pbw) | Water-repellent polymer (pbw) | Quencher (pbw) | Solvent 1 (pbw) | Solvent 2 (pbw) |
|---|---|---|---|---|---|---|---|---|
| Example | 3-1 | R-1 | Resist Polymer 7 (100) | PAG-1 (8.0) | SF-1 (6.0) | Q-1 (1.5) | PGMEA (2,000) | GBL (500) |
| | 3-2 | R-2 | Resist Polymer 7 (100) | PAG-2 (8.0) | SF-1 (6.0) | Q-1 (1.5) | PGMEA (2,000) | GBL (500) |
| | 3-3 | R-3 | Resist Polymer 7 (100) | PAG-3 (8.0) | SF-1 (6.0) | Q-1 (1.5) | PGMEA (2,000) | GBL (500) |
| | 3-4 | R-4 | Resist Polymer 8 (100) | PAG-3 (8.0) | SF-1 (6.0) | Q-1 (1.5) | PGMEA (2,000) | GBL (500) |
| | 3-5 | R-5 | Resist Polymer 8 (100) | PAG-3 (8.0) | SF-1 (6.0) | Q-2 (1.5) | PGMEA (2,000) | GBL (500) |
| | 3-6 | R-6 | Resist Polymer 8 (100) | PAG-3 (8.0) | SF-1 (6.0) | Q-3 (1.5) | PGMEA (2,000) | GBL (500) |
| | 3-7 | R-7 | Resist Polymer 6 (100) | PAG-1 (8.0) | SF-1 (6.0) | Q-1 (1.5) | PGMEA (2,000) | GBL (500) |
| | 3-8 | R-8 | Resist Polymer 6 (100) | PAG-1 (8.0) | SF-2 (6.0) | Q-1 (1.5) | PGMEA (2,000) | GBL (500) |
| | 3-9 | R-9 | Resist Polymer 1 (100) | PAG-3 (8.0) | SF-2 (6.0) | Q-2 (1.5) | PGMEA (2,000) | GBL (500) |
| | 3-10 | R-10 | Resist Polymer 2 (100) | PAG-3 (8.0) | SF-2 (6.0) | Q-2 (1.5) | PGMEA (2,000) | GBL (500) |
| | 3-11 | R-11 | Resist Polymer 3 (100) | PAG-3 (8.0) | SF-2 (6.0) | Q-2 (1.5) | PGMEA (2,000) | GBL (500) |
| | 3-12 | R-12 | Resist Polymer 4 (100) | PAG-3 (8.0) | SF-2 (6.0) | Q-2 (1.5) | PGMEA (2,000) | GBL (500) |
| | 3-13 | R-13 | Resist Polymer 5 (100) | PAG-3 (8.0) | SF-2 (6.0) | Q-2 (1.5) | PGMEA (2,000) | GBL (500) |
| | 3-14 | R-14 | Resist Polymer 6 (100) | PAG-3 (8.0) | SF-2 (6.0) | Q-2 (1.5) | PGMEA (2,000) | GBL (500) |

TABLE 1-continued

| | | Resist | Resin (pbw) | Acid generator (pbw) | Water-repellent polymer (pbw) | Quencher (pbw) | Solvent 1 (pbw) | Solvent 2 (pbw) |
|---|---|---|---|---|---|---|---|---|
| | 3-15 | R-15 | Resist Polymer 7 (100) | PAG-3 (8.0) | SF-2 (6.0) | Q-2 (1.5) | PGMEA (2,000) | GBL (500) |
| | 3-16 | R-16 | Resist Polymer 8 (100) | PAG-3 (8.0) | SF-2 (6.0) | Q-2 (1.5) | PGMEA (2,000) | GBL (500) |
| | 3-17 | R-17 | Resist Polymer 9 (100) | PAG-3 (8.0) | SF-2 (6.0) | Q-2 (1.5) | PGMEA (2,000) | GBL (500) |
| | 3-18 | R-18 | Resist Polymer 10 (100) | PAG-3 (8.0) | SF-2 (6.0) | Q-2 (1.5) | PGMEA (2,000) | GBL (500) |
| | 3-19 | R-19 | Resist Polymer 11 (100) | PAG-3 (8.0) | SF-2 (6.0) | Q-2 (1.5) | PGMEA (2,000) | GBL (500) |
| | 3-20 | R-20 | Resist Polymer 12 (100) | PAG-3 (8.0) | SF-2 (6.0) | Q-2 (1.5) | PGMEA (2,000) | GBL (500) |
| | 3-21 | R-21 | Resist Polymer 13 (100) | PAG-3 (8.0) | SF-2 (6.0) | Q-2 (1.5) | PGMEA (2,000) | GBL (500) |
| | 3-22 | R-22 | Resist Polymer 14 (100) | PAG-3 (8.0) | SF-2 (6.0) | Q-2 (1.5) | PGMEA (2,000) | GBL (500) |
| | 3-23 | R-23 | Resist Polymer 15 (100) | PAG-3 (8.0) | SF-2 (6.0) | Q-2 (1.5) | PGMEA (2,000) | GBL (500) |
| | 3-24 | R-24 | Resist Polymer 16 (100) | PAG-3 (8.0) | SF-2 (6.0) | Q-2 (1.5) | PGMEA (2,000) | GBL (500) |
| | 3-25 | R-25 | Resist Polymer 17 (100) | PAG-3 (8.0) | SF-2 (6.0) | Q-2 (1.5) | PGMEA (2,000) | GBL (500) |
| | 3-26 | R-26 | Resist Polymer 18 (100) | — | SF-2 (6.0) | Q-2 (1.5) | PGMEA (2,000) | GBL (500) |
| Comparative Example | 2-1 | R-27 | Comparative Polymer 1 (100) | PAG-3 (8.0) | SF-2 (6.0) | Q-2 (1.5) | PGMEA (2,000) | GBL (500) |
| | 2-2 | R-28 | Comparative Polymer 2 (100) | PAG-3 (8.0) | SF-2 (6.0) | Q-2 (1.5) | PGMEA (2,000) | GBL (500) |
| | 2-3 | R-29 | Comparative Polymer 3 (100) | PAG-3 (8.0) | SF-2 (6.0) | Q-2 (1.5) | PGMEA (2,000) | GBL (500) |
| | 2-4 | R-30 | Comparative Polymer 4 (100) | PAG-3 (8.0) | SF-2 (6.0) | Q-2 (1.5) | PGMEA (2,000) | GBL (500) |

Examples 4-1 to 4-26 and Comparative Examples 3-1 to 3-4

ArF Lithography Patterning Test: Evaluation of Hole Pattern

On a silicon wafer, a spin-on carbon film ODL-50 (Shin-Etsu Chemical Co., Ltd.) having a carbon content of 100 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-1 to R-26) or comparative resist composition (R-27 to R-30) shown in Table 1 was spin coated, then baked on a hot plate at 100° C. for 60 seconds to form a resist film of 90 nm thick.

Using an ArF excimer laser immersion lithography scanner NSR-610C (Nikon Corp., NA 1.30, σ 0.9/0.72, cross-pole opening 35 deg., azimuthally polarized illumination), exposure was performed through a mask bearing a hole pattern having a hole diameter of 55 nm and a pitch of 100 nm (after reduction projection) in a varying dose. After the exposure, the wafer was baked (PEB) at the temperature shown in Table 2 for 60 seconds and developed in a developer. Specifically, the developer shown in Table 2 was injected from a development nozzle while the wafer was spun at 30 rpm for 3 seconds, which was followed by stationary puddle development for 27 seconds. The wafer was rinsed with 4-methyl-2-pentanol, spin dried, and baked at 100° C. for 20 seconds to evaporate off the rinse liquid. In this way, a pattern of holes with a diameter of 50 nm was obtained.

Mask Error Factor (MEF)

At the exposure dose corresponding to a hole pattern with diameter 50 nm, a hole pattern having a pitch of 100 nm was printed through a mask pattern providing a hole pattern size of 53 nm, 54 nm, 56 nm or 57 nm (after reduction projection). The hole pattern was observed under TDSEM (CG-4000 by Hitachi High-Technologies Ltd.), and the diameter of holes was measured. A straight line was drawn by plotting the hole pattern size (nm) after reduction projection on the abscissa and the diameter of holes in the resist film via each mask pattern on the ordinate, before the slope of the straight line was determined and reported as MEF. A value of MEF closer to unity (1) indicates better mask reproduction. The results are shown in Table 2.

TABLE 2

| | | Resist | PEB temp. (° C.) | Dose ($mJ/cm^2$) | Developer | MEF (nm) |
|---|---|---|---|---|---|---|
| Example | 4-1 | R-1 | 90 | 29 | 2-heptanone | 3.2 |
| | 4-2 | R-2 | 90 | 31 | 2-heptanone | 3.4 |
| | 4-3 | R-3 | 90 | 32 | 2-heptanone | 3.0 |
| | 4-4 | R-4 | 90 | 31 | 2-heptanone | 3.2 |
| | 4-5 | R-5 | 90 | 32 | 2-heptanone | 3.2 |
| | 4-6 | R-6 | 90 | 35 | 2-heptanone | 3.1 |
| | 4-7 | R-7 | 95 | 28 | n-butyl acetate | 3.1 |
| | 4-8 | R-8 | 95 | 31 | n-butyl acetate | 3.3 |
| | 4-9 | R-9 | 100 | 33 | n-butyl acetate | 3.2 |
| | 4-10 | R-10 | 100 | 31 | n-butyl acetate | 3.3 |
| | 4-11 | R-11 | 100 | 30 | n-butyl acetate | 3.3 |
| | 4-12 | R-12 | 100 | 30 | n-butyl acetate | 3.1 |
| | 4-13 | R-13 | 95 | 29 | n-butyl acetate | 2.9 |
| | 4-14 | R-14 | 95 | 30 | n-butyl acetate | 2.8 |
| | 4-15 | R-15 | 90 | 29 | n-butyl acetate | 3.0 |
| | 4-16 | R-16 | 90 | 28 | n-butyl acetate | 3.2 |

TABLE 2-continued

| | | Resist | PEB temp. (° C.) | Dose (mJ/cm$^2$) | Developer | MEF (nm) |
|---|---|---|---|---|---|---|
| | 4-17 | R-17 | 90 | 29 | n-butyl acetate | 3.1 |
| | 4-18 | R-18 | 90 | 28 | n-butyl acetate | 3.3 |
| | 4-19 | R-19 | 90 | 29 | n-butyl acetate | 3.4 |
| | 4-20 | R-20 | 90 | 27 | n-butyl acetate | 3.5 |
| | 4-21 | R-21 | 90 | 30 | n-butyl acetate | 3.0 |
| | 4-22 | R-22 | 90 | 31 | n-butyl acetate | 3.3 |
| | 4-23 | R-23 | 95 | 30 | n-butyl acetate | 3.4 |
| | 4-24 | R-24 | 90 | 32 | n-butyl acetate | 3.3 |
| | 4-25 | R-25 | 90 | 33 | n-butyl acetate | 3.2 |
| | 4-26 | R-26 | 90 | 27 | n-butyl acetate | 2.9 |
| Comparative Example | 3-1 | R-27 | 100 | 36 | n-butyl acetate | 4.1 |
| | 3-2 | R-28 | 100 | 35 | n-butyl acetate | 5.8 |
| | 3-3 | R-29 | 95 | 34 | n-butyl acetate | 3.9 |
| | 3-4 | R-30 | 90 | 35 | n-butyl acetate | 3.8 |

It is evident from Table 2 that the resist compositions within the scope of the invention are effective for forming negative patterns via organic solvent development, the patterns having improved MEF.

Examples 5-1 to 5-4 and Comparative Examples 4-1 to 4-2

Etch Resistance Test

On a silicon wafer which had been surface treated in hexamethyldisilazane (HMDS) gas phase at 90° C. for 60 seconds, the resist solution (R-11, R-14, R-15, R-16) or comparative resist solution (R-29, R-30) in Table 1 was spin-coated and baked (PAB) on a hot plate at 100° C. for 60 seconds to form a resist film of 100 nm thick. Using an ArF excimer laser scanner (NSR-307E by Nikon Corp., NA 0.85), the entire surface of the wafer was subjected to open-frame exposure. The exposure dose was set to 50 mJ/cm$^2$ so that the PAG might generate sufficient acid to induce deprotection reaction. This was followed by bake (PEB) at 120° C. for 60 seconds for converting the base resin in the resist film to the deprotected state. The portion where the base resin is deprotected corresponds to the insoluble region in negative tone development. A reduction of resist film thickness by exposure and PEB was determined and divided by the initial film thickness, with the result being reported as PEB shrinkage (%).

Further, the resist film was developed for 30 seconds using butyl acetate as developer. The thickness of the resist film after development was measured. A dissolution rate (nm/sec) was computed from a difference between the film thickness after PEB and the film thickness after development. A lower PEB shrinkage or lower dissolution rate is preferable in that a film thickness necessary for dry etching is retained, or the initial film thickness can be reduced, which is advantageous in terms of resolution. The results are shown in Table 3.

TABLE 3

| | | Resist | PEB shrinkage (%) | Dissolution rate (nm/sec) |
|---|---|---|---|---|
| Example | 5-1 | R-11 | 8 | 0.12 |
| | 5-2 | R-14 | 10 | 0.13 |
| | 5-3 | R-15 | 13 | 0.15 |
| | 5-4 | R-16 | 12 | 0.16 |

TABLE 3-continued

| | | Resist | PEB shrinkage (%) | Dissolution rate (nm/sec) |
|---|---|---|---|---|
| Comparative Example | 4-1 | R-29 | 23 | 0.22 |
| | 4-2 | R-30 | 25 | 0.23 |

It is evident from Table 3 that the resist compositions within the scope of the invention show a low PEB shrinkage, indicating that a resist film of sufficient thickness is retained after development.

Japanese Patent Application No. 2015-026066 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units of at least one type selected from the general formulae (2a) to (2d):

(2a)

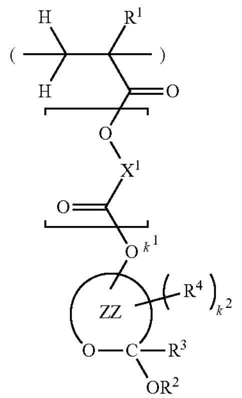

(2b)

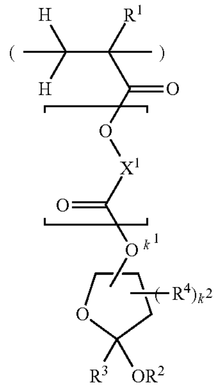

-continued (2c)

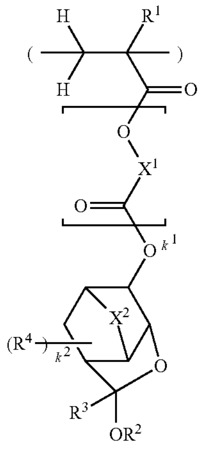

(2d)

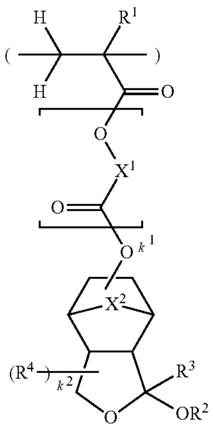

wherein $R^1$ is hydrogen, methyl or trifluoromethyl, $R^2$ is methyl, $R^3$ and $R^4$ are each independently hydrogen or a straight, branched or cyclic, $C_1$-$C_{15}$ monovalent hydrocarbon group in which any constituent —$CH_2$— may be replaced by —O— or —C(═O)—, $X^1$ is a straight, branched or cyclic, $C_1$-$C_{15}$ divalent hydrocarbon group in which a constituent —$CH_2$— may be replaced by —O— or —C(═O)—, $X^2$ is —$CH_2$— or —O—, the ring ZZ designates a non-aromatic mono- or polycyclic ring of 4 to 20 carbon atoms having a hemiacetal structure, $k^1$ is 0 or 1, and $k^2$ is an integer of 0 to 3.

2. The polymer of claim 1, further comprising recurring units of at least one type selected from the general formulae (4A) to (4E):

(4A)

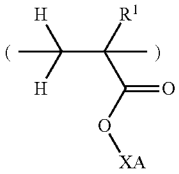

-continued (4B)

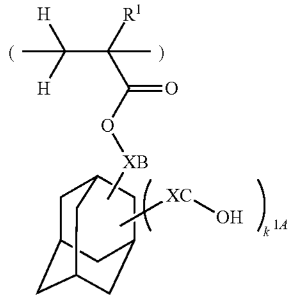

(4C)

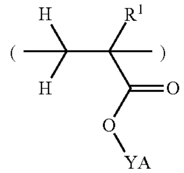

(4D)

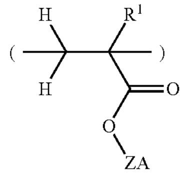

(4E)

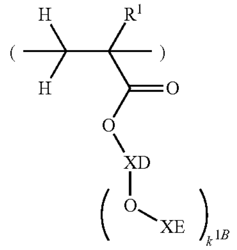

wherein $R^1$ is as defined above, XA is an acid labile group, XB and XC are each independently a single bond or a straight or branched, $C_1$-$C_4$ divalent hydrocarbon group, XD is a straight, branched or cyclic, $C_1$-$C_{16}$ di- to pentavalent aliphatic hydrocarbon group in which a constituent —$CH_2$— may be replaced by —O— or —C(═O)—, XE is an acid labile group, YA is a substituent group of lactone, sultone or carbonate structure, ZA is hydrogen, a $C_1$-$C_{15}$ fluoroalkyl group or a $C_1$-$C_{15}$ fluoroalcohol-containing group, $k^{1A}$ is an integer of 1 to 3, and $k^{1B}$ is an integer of 1 to 4.

3. The polymer of claim 1, further comprising recurring units of at least one type selected from sulfonium salt units (f1) to (f3) represented by the following general formula:

(f1)

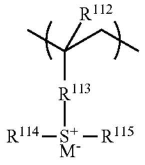

(f2)

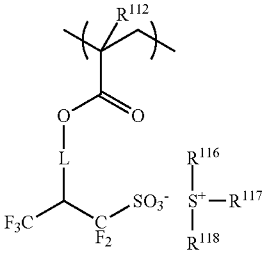

(f3)

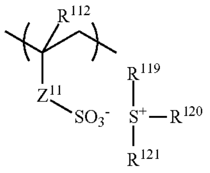

wherein $R^{112}$ is hydrogen or methyl; $R^{113}$ is a single bond, phenylene, —O—$R^{122}$—, or —C(═O)—$Z^{22}$—$R^{122}$—, $Z^{22}$ is oxygen or NH, $R^{122}$ is a straight $C_1$-$C_6$ or branched or cyclic $C_3$-$C_6$ alkylene group, $C_2$-$C_6$ alkenylene group or phenylene group, which may contain a carbonyl (—CO—), ester (—COO—), ether (—O—), or hydroxyl moiety; L is a single bond or —$Z^{33}$—C(═O)—O—, $Z^{33}$ is a straight $C_1$-$C_{20}$ or branched or cyclic $C_3$-$C_{20}$ divalent hydrocarbon group which may be substituted with or separated by a heteroatom, $Z^{11}$ is a single bond, methylene, ethylene, phenylene, fluorinated phenylene, —O—$R^{123}$— or —C(═O)—$Z^{44}$—$R^{123}$—, $Z^{44}$ is oxygen or NH, $R^{123}$ is a straight $C_1$-$C_6$ or branched or cyclic $C_3$-$C_6$ alkylene group, $C_2$-$C_6$ alkenylene group or phenylene group, which may contain a carbonyl, ester, ether, or hydroxyl moiety; $M^-$ is a non-nucleophilic counter ion; $R^{114}$, $R^{115}$, $R^{116}$, $R^{117}$, $R^{118}$, $R^{119}$, $R^{120}$, and $R^{121}$ are each independently a straight $C_1$-$C_{20}$ or branched or cyclic $C_3$-$C_{20}$ hydrocarbon group which may be substituted with or separated by a heteroatom.

4. A resist composition comprising a base resin containing the polymer of claim 3, and an organic solvent.

5. A resist composition comprising a base resin containing the polymer of claim 1, an acid generator, and an organic solvent.

6. The polymer of claim 1 wherein the ring ZZ is a non-aromatic mono- or polycyclic ring selected from the group consisting of the following formulae:

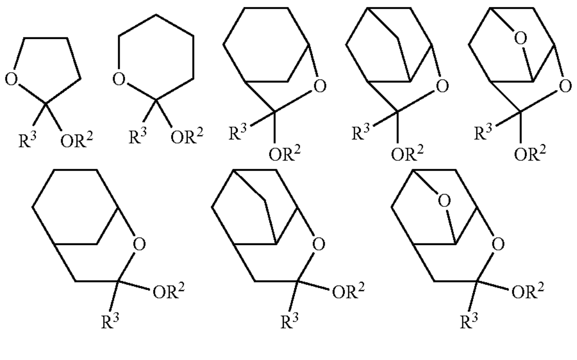

-continued

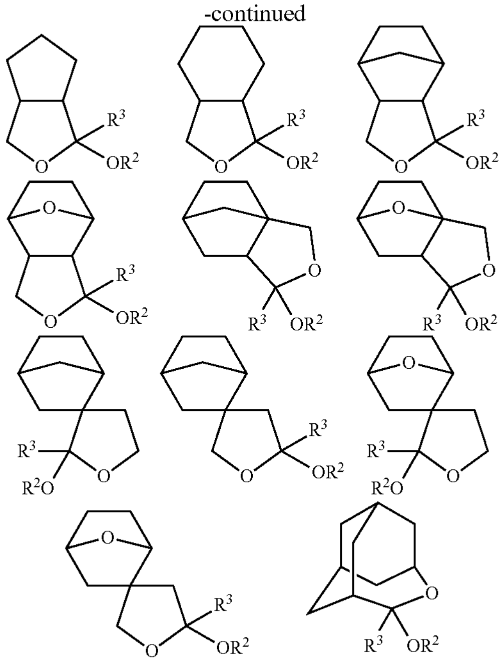

wherein $R^2$ and $R^3$ are as defined above.

7. A polymer comprising recurring units of at least one type selected from the general formulae (2c) and (2d):

(2c)

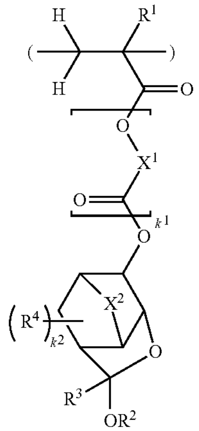

(2d)

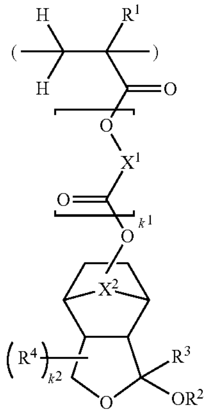

wherein $R^1$ is hydrogen, methyl or trifluoromethyl, $R^2$ to $R^4$ are each independently a straight, branched or cyclic, $C_1$-$C_{15}$ monovalent hydrocarbon group in which any constituent —$CH_2$— may be replaced by —O— or —C(═O)—, $X^1$ is a straight, branched or cyclic, $C_1$-$C_{15}$ divalent hydrocarbon group in which a constituent —$CH_2$— may be replaced by —O— or —C(═O)—, $X^2$ is —$CH_2$— or —O—, the ring ZZ designates a non-aromatic mono- or polycyclic ring of 4 to 20 carbon atoms having a hemiacetal structure, $k^1$ is 0 or 1, and $k^2$ is an integer of 0 to 3.

8. The polymer of claim 7, further comprising recurring units of at least one type selected from the general formulae (4A) to (4E):

(4A)

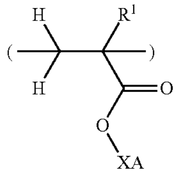

(4B)

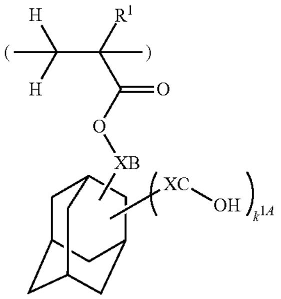

(4C)

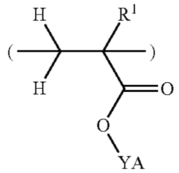

(4D)

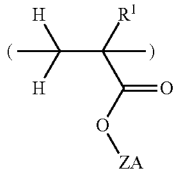

(4E)

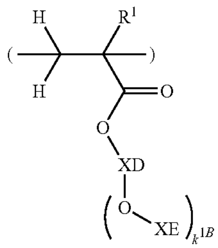

wherein $R^1$ is as defined above, XA is an acid labile group, XB and XC are each independently a single bond or a straight or branched, $C_1$-$C_4$ divalent hydrocarbon group, XD is a straight, branched or cyclic, $C_1$-$C_{16}$ di- to pentavalent aliphatic hydrocarbon group in which a constituent —$CH_2$— may be replaced by —O— or —C(═O)—, XE is an acid labile group, YA is a substituent group of lactone, sultone or carbonate structure, ZA is hydrogen, a $C_1$-$C_{15}$ fluoroalkyl group or a $C_1$-$C_{15}$ fluoroalcohol-containing group, $k^{1A}$ is an integer of 1 to 3, and $k^{1B}$ is an integer of 1 to 4.

9. The polymer of claim 7, further comprising recurring units of at least one type selected from sulfonium salt units (f1) to (f3) represented by the following general formula:

(f1)

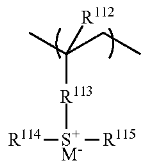

(f2)

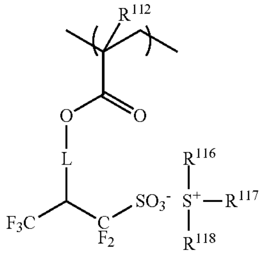

(f3)

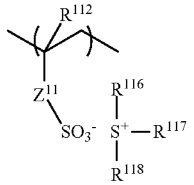

wherein $R^{112}$ is hydrogen or methyl; $R^{113}$ is a single bond, phenylene, —O—$R^{122}$—, or —C(═O)—$Z^{22}$—$R^{122}$—, $Z^{22}$ is oxygen or NH, $R^{122}$ is a straight $C_1$-$C_6$ or branched or cyclic $C_3$-$C_6$ alkylene group, $C_2$-$C_6$ alkenylene group or phenylene group, which may contain a carbonyl (—CO—), ester (—COO—), ether (—O—), or hydroxyl moiety; L is a single bond or —$Z^{33}$—C(═O)—O—, $Z^{33}$ is a straight $C_1$-$C_{20}$ or branched or cyclic $C_3$-$C_{20}$ divalent hydrocarbon group which may be substituted with or separated by a heteroatom, $Z^{11}$ is a single bond, methylene, ethylene, phenylene, fluorinated phenylene, —O—$R^{123}$— or —C(═O)—$Z^{44}$—$R^{123}$—, $Z^{44}$ is oxygen or NH, $R^{123}$ is a straight $C_1$-$C_6$ or branched or cyclic $C_3$-$C_6$ alkylene group, $C_2$-$C_6$ alkenylene group or phenylene group, which may contain a carbonyl, ester, ether, or hydroxyl moiety; $M^-$ is a non-nucleophilic counter ion; $R^{114}$, $R^{115}$, $R^{116}$, $R^{117}$, $R^{118}$, $R^{119}$, $R^{120}$, and $R^{121}$ are each independently a straight $C_1$-$C_{20}$ or branched or cyclic $C_3$-$C_{20}$ hydrocarbon group which may be substituted with or separated by a heteroatom.

10. A resist composition comprising a base resin containing the polymer of claim 9, and an organic solvent.

11. A resist composition comprising a base resin containing the polymer of claim 7, an acid generator, and an organic solvent.

* * * * *